US011186842B2

(12) United States Patent
Borodovsky et al.

(10) Patent No.: US 11,186,842 B2
(45) Date of Patent: Nov. 30, 2021

(54) COMPLEMENT COMPONENT IRNA COMPOSITIONS AND METHODS OF USE THEREOF

(71) Applicant: Alnylam Pharmaceuticals, Inc., Cambridge, MA (US)

(72) Inventors: Anna Borodovsky, Melrose, MA (US); Brian Bettencourt, Groton, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/574,158

(22) Filed: Sep. 18, 2019

(65) Prior Publication Data

US 2020/0263183 A1 Aug. 20, 2020

Related U.S. Application Data

(60) Division of application No. 15/176,231, filed on Jun. 8, 2016, now Pat. No. 10,465,194, which is a continuation of application No. PCT/US2014/069951, filed on Dec. 12, 2014.

(60) Provisional application No. 61/915,210, filed on Dec. 12, 2013.

(51) Int. Cl.

| | |
|---|---|
| ***C12N 15/11*** | (2006.01) |
| ***C12N 15/113*** | (2010.01) |
| ***A61K 38/12*** | (2006.01) |
| ***A61K 31/713*** | (2006.01) |
| ***A61K 39/395*** | (2006.01) |
| ***C07K 16/18*** | (2006.01) |

(52) U.S. Cl.

CPC ........ *C12N 15/1137* (2013.01); *A61K 31/713* (2013.01); *A61K 38/12* (2013.01); *A61K 39/3955* (2013.01); *C07K 16/18* (2013.01); *C12N 15/111* (2013.01); *C12N 15/1138* (2013.01); *C12N 2310/14* (2013.01); *C12N 2310/315* (2013.01); *C12N 2310/321* (2013.01); *C12N 2310/343* (2013.01); *C12N 2310/346* (2013.01); *C12N 2310/351* (2013.01); *C12N 2320/51* (2013.01); *C12Y 304/21047* (2013.01); *Y02A 50/30* (2018.01)

(58) Field of Classification Search

CPC ................ A61K 31/713; C12N 15/113; C12N 2310/11; C12N 2310/14; C12N 2310/343; C12N 2310/346; C12N 15/111

See application file for complete search history.

(56) References Cited

U.S. PATENT DOCUMENTS

| | | | | |
|---|---|---|---|---|
| 10,465,194 | B2 | 11/2019 | Borodovsky et al. | |
| 2007/0088154 | A1 | 4/2007 | Khvorova et al. | |
| 2007/0123484 | A1 | 5/2007 | Bhat | |
| 2008/0113351 | A1 | 5/2008 | Naito et al. | |
| 2009/0239814 | A1 | 9/2009 | Manoharan et al. | |
| 2009/0306178 | A1* | 12/2009 | Bhat .................... | C12N 15/113 514/44 A |
| 2016/0222389 | A1 | 8/2016 | Grossman | |
| 2020/0263183 | A1 | 8/2020 | Borodovsky et al. | |

FOREIGN PATENT DOCUMENTS

| | | | | |
|---|---|---|---|---|
| EP | 1752536 A1 | 2/2007 | | |
| WO | WO-2006/047673 A2 | 5/2006 | | |
| WO | WO-2007/064846 A2 | 6/2007 | | |
| WO | WO-2007/089375 A2 | 8/2007 | | |
| WO | WO-2008/036841 A2 | 3/2008 | | |
| WO | WO-2012/037254 A1 | 3/2012 | | |
| WO | WO-2013/067076 A2 | 5/2013 | | |
| WO | WO-2013/074974 A2 | 5/2013 | | |
| WO | WO-2014107763 A1 * | 7/2014 | ........... | C12N 15/113 |
| WO | WO-2015/038939 A2 | 3/2015 | | |
| WO | WO-2015/089368 A2 | 6/2015 | | |
| WO | WO-2017/040078 A1 | 3/2017 | | |
| WO | WO-2019/089922 A1 | 5/2019 | | |

OTHER PUBLICATIONS

U.S. Appl. No. 15/176,231, filed Jun. 8, 2016, U.S. Pat. No. 10,465,194, Nov. 5, 2019, US20160298124, Granted.

U.S. Appl. No. 16/574,158, filed Sep. 18, 2019, US 20200263183, Published.

U.S. Appl. No. 16/760,593, filed Apr. 30, 2020, Pending.

PCT/US2018/058705, Nov. 1, 2018, WO 2019/089922.

Bora et al., Complement activation via alternative pathway is critical in the development of laser-induced choroidal neovascularization: role of factor B and factor H. J Immunol. Aug. 1, 2006;177(3):1872-8.

Borodovsky et al., Development of RNAi Therapeutics Targeting the Complement Pathway. Blood. 2013;122(21)2471.

Cheng et al., [Effect of C5-siRNA silencing receptor C5 on myocardial ischemia injury in rats]. Nan Fang Yi Ke Da Xue Xue Bao. Jun. 2010;30(6):1486-8.

International Search Report and Written Opinion for Application No. PCT/US2014/069951, dated Jul. 6, 2015.

Zheng et al., "Preventing Renal Ischemia-Reperfusion Injury Using Small Interfering RNA by Targeting Complement 3 Gene," American Journal of Transplantation 2006; 6: 2099-2108.

(Continued)

*Primary Examiner* — Dana H Shin

(74) *Attorney, Agent, or Firm* — McCarter & English, LLP; Maria Laccotripe Zacharakis; Deborah L. Nagle

(57) ABSTRACT

The invention relates to iRNA, e.g., double-stranded ribonucleic acid (dsRNA), compositions targeting the complement factor B (CFB) gene, the complement component C3 gene, and the complement component C9 gene and methods of using such iRNA, e.g., dsRNA, compositions to inhibit expression of CFB, C9 and/or C3 and to treat subjects having a complement component-associated disease, e.g., paroxysmal nocturnal hemoglobinuria and atypical hemolytic uremic syndrome.

18 Claims, 3 Drawing Sheets

Specification includes a Sequence Listing.

(56) References Cited

OTHER PUBLICATIONS

Zheng et al., "Protection of Renal Ischemia Injury using Combination Gene Silencing of Complement 3 and Caspase 3 Genes," *Transplantation* 2006;82: 1781-1786.
Reynolds et al., "Rational siRNA design for RNA interference," Nature Biotechnology, vol. 22, pp. 326-330, 2004.
International Search Report and Written Opinion from PCT/US2018/058705, dated Mar. 1, 2019.

* cited by examiner

SEQUENCE LISTING

<160> NUMBER OF SEQ ID NOS: 492

<210> SEQ ID NO 1
<211> LENGTH: 2646

<212> TYPE: DNA
<213> ORGANISM: Homo sapiens

<400> SEQUENCE: 1
gacttctgca gtttctgttt ccttgactgg cagctcagcg gggccctccc gcttggatgt 60
tccgggaaag tgatgtgggt aggacaggcg gggcgagccg caggtgccag aacacagatt 120
gtataaaagg ctgggggctg gtggggagca ggggaaggga atgtgaccag gtctaggtct 180
ggagtttcag cttggacact gagccaagca gacaagcaaa gcaagccagg acacaccatc 240
ctgccccagg cccagcttct ctcctgcctt ccaacgccat ggggagcaat ctcagccccc 300
aactctgcct gatgcccttt atcttgggcc tcttgtctgg aggtgtgacc accactccat 360
ggtctttggc ccggccccag ggatcctgct ctctggaggg ggtagagatc aaaggcggct 420
ccttccgact tctccaagag ggccaggcac tggagtacgt gtgtccttct ggcttctacc 480
cgtaccctgt gcagacacgt acctgcagat ctacggggtc ctggagcacc ctgaagactc 540
aagaccaaaa gactgtcagg aaggcagagt gcagagcaat ccactgtcca agaccacacg 600
acttcgagaa cggggaatac tggccccggt ctccctacta caatgtgagt gatgagatct 660
ctttccactg ctatgacggt tacactctcc ggggctctgc caatcgcacc tgccaagtga 720
atggccgatg gagtgggcag acagcgatct gtgacaacgg agcggggtac tgctccaacc 780
cgggcatccc cattggcaca aggaaggtgg gcagccagta ccgccttgaa gacagcgtca 840
cctaccactg cagccggggg cttaccctgc gtggctccca gcggcgaacg tgtcaggaag 900
gtggctcttg gagcgggacg gagccttcct gccaagactc cttcatgtac gacacccctc 960
aagaggtggc cgaagctttc ctgtcttccc tgacagagac catagaagga gtcgatgctg 1020
aggatgggca cggcccaggg gaacaacaga agcggaagat cgtcctggac ccttcaggct 1080
ccatgaacat ctacctggtg ctagatggat cagacagcat tggggccagc aacttcacag 1140
gagccaaaaa gtgtctagtc aacttaattg agaaggtggc aagttatggt gtgaagccaa 1200
gatatggtct agtgacatat gccacatacc ccaaaatttg ggtcaaagtg tctgaagcag 1260
acagcagtaa tgcagactgg gtcacgaagc agctcaatga aatcaattat gaagaccaca 1320
agttgaagtc agggactaac accaagaagg ccctccaggc agtgtacagc atgatgagct 1380
ggccagatga cgtccctcct gaaggctgga accgcacccg ccatgtcatc atcctcatga 1440
ctgatggatt gcacaacatg ggcggggacc caattactgt cattgatgag atccgggact 1500
tgctatacat tggcaaggat cgcaaaaacc caagggagga ttatctggat gtctatgtgt 1560
ttggggtcgg gcctttggtg aaccaagtga acatcaatgc tttggcttcc aagaaagaca 1620
atgagcaaca tgtgttcaaa gtcaaggata tggaaaacct ggaagatgtt ttctaccaaa 1680
tgatcgatga aagccagtct ctgagtctct gtggcatggt ttgggaacac aggaagggta 1740
ccgattacca caagcaacca tggcaggcca agatctcagt cattcgccct tcaaagggac 1800
acgagagctg tatgggggct gtggtgtctg agtactttgt gctgacagca gcacattgtt 1860
tcactgtgga tgacaaggaa cactcaatca aggtcagcgt aggaggggag aagcgggacc 1920
tggagataga agtagtccta tttcacccca actacaacat taatgggaaa aaagaagcag 1980
gaattcctga attttatgac tatgacgttg ccctgatcaa gctcaagaat aagctgaaat 2040
atggccagac tatcaggccc atttgtctcc cctgcaccga gggaacaact cgagctttga 2100
ggcttcctcc aactaccact tgccagcaac aaaaggaaga gctgctccct gcacaggata 2160
tcaaagctct gtttgtgtct gaggaggaga aaaagctgac tcggaaggag gtctacatca 2220

```
agaatgggga taagaaaggc agctgtgaga gagatgctca atatgcccca ggctatgaca   2280

aagtcaagga catctcagag gtggtcaccc ctcggttcct ttgtactgga ggagtgagtc   2340

cctatgctga ccccaatact tgcagaggtg attctggcgg ccccttgata gttcacaaga   2400

gaagtcgttt cattcaagtt ggtgtaatca gctggggagt agtggatgtc tgcaaaaacc   2460

agaagcggca aaagcaggta cctgctcacg cccgagactt tcacatcaac ctctttcaag   2520

tgctgccctg gctgaaggag aaactccaag atgaggattt gggttttcta taaggggttt   2580

cctgctggac aggggcgtgg gattgaatta aaacagctgc gacaacaaaa aaaaaaaaaa   2640

aaaaaa                                                              2646


<210> SEQ ID NO 2
<211> LENGTH: 2767
<212> TYPE: DNA
<213> ORGANISM: Mus musculus

<400> SEQUENCE: 2

gctccatcac acagtccatg gaaagactga tcttttaaat tgggggtagt ggaggtggtg     60

gtctgtgctt gttaggaggg gtctgggggc taagagggag ctttgaaagg gaagttctgg    120

cccttggtca gtcaagggtg gggctcacat agtttctgtt tcctcagttg gcagttcagc    180

tggggccctc cttcatgaat gttccgggaa gcagtggctg cgtgcgcagg gtaggctggc    240

caggctgcag atgccagagc agattgcata aaaggttagg ggacagtggg aaaggggtgt    300

agccagatcc agcatttggg tttcagtttg gacaggaggt caaataggca cccagagtga    360

cctggagagg gctttgggcc actggactct ctggtgcttt ccatgacaat ggagagcccc    420

cagctctgcc tcgtcctctt ggtcttaggc ttctcctctg gaggtgtgag cgcaactcca    480

gtgcttgagg cccggcccca agtctcctgc tctctggagg gagtagagat caaaggcggc    540

tcctttcaac ttctccaagg cggtcaggcc ctggagtacc tatgtccctc tggcttctac    600

ccataccccg tgcagactcg aacctgcaga tccacaggct cctggagcga cctgcagacc    660

cgagaccaaa agattgtcca gaaggcggaa tgcagagcaa tacgctgccc acgaccgcag    720

gactttgaaa atggggaatt ctggccccgg tccccccttct acaacctgag tgaccagatt    780

tcttttcaat gctatgatgg ttacgttctc cggggctctg ctaatcgcac ctgccaagag    840

aatggccggt gggatgggca aacagcaatt tgtgatgatg gagctggata ctgtcccaat    900

cccggtattc ctattgggac aaggaaggtg ggtagccaat accgccttga agacattgtt    960

acttaccact gcagccgggg acttgtcctg cgtggctccc agaagcgaaa gtgtcaagaa   1020

ggtggctcat ggagtgggac agagccttcc tgccaagatt ccttcatgta tgacagccct   1080

caagaagtgg ccgaagcatt cctatcctcc ctgacagaga ccatcgaagg agccgatgct   1140

gaggatgggc acagcccagg agaacagcag aagaggaaga ttgtcctaga cccctcgggc   1200

tccatgaata tctacctggt gctagatgga tcagacagca tcggaagcag caacttcaca   1260

ggggctaagc ggtgcctcac caacttgatt gagaaggtgg cgagttacgg ggtgaggcca   1320

cgatatggtc tcctgacata tgctacagtc cccaaagtgt tggtcagagt gtctgatgag   1380

aggagtagcg atgccgactg ggtcacagag aagctcaacc aaatcagtta tgaagaccac   1440

aagctgaagt cagggaccaa caccaagagg gctctccagg ctgtgtatag catgatgagc   1500

tgggcagggg atgccccgcc tgaaggctgg aatagaaccc gccatgtcat catcattatg   1560

actgatggct tgcacaacat gggtggaaac cctgtcactg tcattcagga catccgagcc   1620

ttgctggaca tcggcaggga tcccaaaaat cccagggagg attacctgga tgtgtatgtg   1680
```

```
tttggggtcg ggcctctggt ggactccgtg aacatcaatg ccttagcttc caaaaaggac   1740

aatgagcatc atgtgtttaa agtcaaggat atggaagacc tggagaatgt tttctaccaa   1800

atgattgatg aaaccaaatc tctgagtctc tgtggcatgg tgtgggagca taaaaaaggc   1860

aacgattatc ataagcaacc atggcaagcc aagatctcag tcactcgccc tctgaaagga   1920

catgagacct gtatgggggc cgtggtgtct gagtacttcg tgctgacagc agcgcactgc   1980

ttcatggtgg atgatcagaa acattccatc aaggtcagcg tgggggtca gaggcgggac   2040

ctggagattg aagaggtcct gttccacccc aaatacaata ttaatgggaa aaaggcagaa   2100

gggatccctg agttctatga ttatgatgtg gccctagtca agctcaagaa caagctcaag   2160

tatggccaga ctctcaggcc catctgtctc cctgcacgg agggaaccac acgagccttg   2220

aggcttcctc agacagccac ctgcaagcag cacaaggaac agttgctccc tgtgaaggat   2280

gtcaaagctc tgtttgtatc tgagcaaggg aagagcctga ctcggaagga ggtgtacatc   2340

aagaatgggg acaagaaagc cagttgtgag agagatgcta caaaggccca aggctatgag   2400

aaggtcaaag atgcctctga ggtggtcact ccacggttcc tctgcacagg aggggtggat   2460

ccctatgctg accccaacac atgcaaagga gattccgggg gccctctcat tgttcacaag   2520

agaagccgct tcattcaagt tggtgtgatt agctggggag tagtagatgt ctgcagagac   2580

cagaggcggc aacagctggt accctcttat gcccgggact tccacatcaa cctcttccag   2640

gtgctgccct ggctaaagga caagctcaaa gatgaggatt tgggttttct ataaagagct   2700

tcctgcaggg agagtgtgag gacagattaa agcagttaca ataacaaaaa aaaaaaaaaa   2760

aaaaaaa                                                               2767
```

<210> SEQ ID NO 3
<211> LENGTH: 2763
<212> TYPE: DNA
<213> ORGANISM: Mus musculus

<400> SEQUENCE: 3

```
gctccatcac acagtccatg gaaagactga tcttttaaat tgggggtagt ggaggtggtg     60

gtctgtgctt gttaggaggg gtctgggggc taagagggag ctttgaaagg gaagttctgg    120

cccttggtca gtcaagggtg gggctcacat agtttctgtt tcctcagttg gcagttcagc    180

tggggccctc cttcatgaat gttccgggaa gcagtggctg cgtgcgcagg gtaggctggc    240

caggctgcag atgccagagc agattgcata aaaggttagg ggacagtggg aaaggggtgt    300

agccagatcc agcatttggg tttcagtttg gacaggaggt caaataggca cccagagtga    360

cctggagagg gctttgggcc actggactct ctggtgcttt ccatgacaat ggagagcccc    420

cagctctgcc tcgtcctctt ggtcttaggc ttctcctctg gaggtgtgag cgcaactcca    480

gtgcttgagg cccggcccca agtctcctgc tctctggagg gagtagagat caaaggcggc    540

tcctttcaac ttctccaagg cggtcaggcc ctggagtacc tatgtccctc tggcttctac    600

ccataccccg tgcagactcg aacctgcaga tccacaggct cctggagcga cctgcagacc    660

cgagaccaaa agattgtcca gaaggcggaa tgcagagcaa tacgctgccc acgaccgcag    720

gactttgaaa atggggaatt ctggccccgg tccccccttct acaacctgag tgaccagatt    780

tcttttcaat gctatgatgg ttacgttctc cggggctctg ctaatcgcac ctgccaagag    840

aatggccggt gggatgggca aacagcaatt tgtgatgatg gagctggata ctgtcccaat    900

cccggtattc ctattgggac aaggaaggtg ggtagccaat accgccttga agacattgtt    960
```

-continued

```
acttaccact gcagccgggg acttgtcctg cgtggctccc agaagcgaaa gtgtcaagaa   1020

ggtggctcat ggagtgggac agagccttcc tgccaagatt ccttcatgta tgacagccct   1080

caagaagtgg ccgaagcatt cctatcctcc ctgacagaga ccatcgaagg agccgatgct   1140

gaggatgggc acagcccagg agaacagcag aagaggaaga ttgtcctaga cccctcgggc   1200

tccatgaata tctacctggt gctagatgga tcagacagca tcggaagcag caacttcaca   1260

ggggctaagc ggtgcctcac caacttgatt gagaaggtgg cgagttacgg ggtgaggcca   1320

cgatatggtc tcctgacata tgctacagtc cccaaagtgt tggtcagagt gtctgatgag   1380

aggagtagcg atgccgactg ggtcacagag aagctcaacc aaatcagtta tgaagaccac   1440

aagctgaagt cagggaccaa caccaagagg gctctccagg ctgtgtatag catgatgagc   1500

tgggcagggg atgccccgcc tgaaggctgg aatagaaccc gccatgtcat catcattatg   1560

actgatggct tgcacaacat gggtggaaac cctgtcactg tcattcagga catccgagcc   1620

ttgctggaca tcggcaggga tcccaaaaat cccagggagg attacctgga tgtgtatgtg   1680

tttggggtcg ggcctctggt ggactccgtg aacatcaatg ccttagcttc caaaaaggac   1740

aatgagcatc atgtgtttaa agtcaaggat atggaagacc tggagaatgt tttctaccaa   1800

atgattgatg aaaccaaatc tctgagtctc tgtggcatgg tgtgggagca taaaaaaggc   1860

aacgattatc ataagcaacc atggcaagcc aagatctcag tcactcgccc tctgaaagga   1920

catgagacct gtatgggggc cgtggtgtct gagtacttcg tgctgacagc agcgcactgc   1980

ttcatggtgg atgatcagaa acattccatc aaggtcagcg tgggggggtca gaggcgggac   2040

ctggagattg aagaggtcct gttccacccc aaatacaata ttaatgggaa aaaggcagaa   2100

gggatccctg agttctatga ttatgatgtg gccctagtca agctcaagaa caagctcaag   2160

tatggccaga ctctcaggcc catctgtctc ccctgcacgg agggaaccac acgagccttg   2220

aggcttcctc agacagccac ctgcaagcag cacaaggaac agttgctccc tgtgaaggat   2280

gtcaaagctc tgtttgtatc tgagcaaggg aagagcctga ctcggaagga ggtgtacatc   2340

aagaatgggg acaagccagt tgtgagagag atgctacaaa ggcccaaggc tatgagaagg   2400

tcaaagatgc ctctgaggtg gtcactccac ggttcctctg cacaggaggg gtggatccct   2460

atgctgaccc caacacatgc aaaggagatt ccgggggccc tctcattgtt cacaagagaa   2520

gccgcttcat tcaagttggt gtgattagct ggggagtagt agatgtctgc agagaccaga   2580

ggcggcaaca gctggtaccc tcttatgccc gggacttcca catcaacctc ttccaggtgc   2640

tgccctggct aaaggacaag ctcaaagatg aggatttggg ttttctataa agagcttcct   2700

gcagggagag tgtgaggaca gattaaagca gttacaataa caaaaaaaaa aaaaaaaaaa   2760

aaa                                                                 2763
```

<210> SEQ ID NO 4
<211> LENGTH: 2573
<212> TYPE: DNA
<213> ORGANISM: Rattus norvegicus

<400> SEQUENCE: 4

```
cagcaggggc cctccttcat gaatgttccg ggaagcagcg tctgtgcagg gtaggttggc     60

caggctgcag gtgccagagc agattgcata aaaggttagg ggccggtggg aaaggggtgt    120

agccagatcc agcactggag tttcagtctg gacagcaagt caagtagcca cccagagtga    180

actggaaagg gcttttggcc acgggctttc catgacaatg gagggtcccc agctctgctt    240

agtcctcttg gtcttaggcc tctcctccgg aggtgtgagc gcaactccag tgcttgaggc    300
```

```
ccggccccag gtctcttgct ctctggaggg agtagagatc aaaggcggct ccttccaact    360
tctccaagac ggtcaggccc tggagtacct gtgtccctct ggcttctacc cataccctgt    420
gcagactcga acctgcaaat ccacaggctc ctggagtgtc ctccagaccc gggaccaaaa    480
gattgtcaag aaggcagaat gcagagcaat acgctgccca cgaccacagg actttgaaaa    540
tggggagttc tggccccggt ccccctacta caacctgagt gatcagattt cttttcaatg    600
ctatgatggc tacactctcc ggggctctgc taatcgcacc tgccaagaga atggccggtg    660
ggatgggcaa acagcaatct gtgatgatgg agcgggatac tgtcccaacc cgggtattcc    720
tattgggaca aggaaggtgg gaagccagta ccgtcttgaa gacactgtca cttaccactg    780
tagtcgggga cttgtcctac gtggctccca gcagcgaagg tgccaggaag gtggctcgtg    840
gagtgggaca gagccttcct gccaagattc cttcatgtac gacagccctc aagaggtggc    900
cgaagcattt ctatcctccc tgacagagac catcgaagga gcagatgcgg aggatgggca    960
cagcccaggg gaacagcaga agaggaagat tatcctggac ccctcgggct ccatgaatat   1020
ctacatggtg ctggatggat ccgacagcat cggggccagc aacttcacag ggccaagcg    1080
gtgtctcgcc aacttgattg agaaggtggc gagttatggg gtgaagccaa gatacggtct   1140
agtgacatat gccacagtcc ccaaagtctt ggtcagagtg tctgaggaga ggagtagtga   1200
tgccgactgg gtcacagaga agctcaacca aatcagttat gaagaccaca agctgaagtc   1260
agggaccaac accaagaagg ctctccaggc tgtatacagc atgatgagct ggccagggga   1320
tgctccgcct gaaggctgga atcgaacccg ccacgtcatc atcatcatga ctgatggctt   1380
gcacaacatg ggtggagacc ctgtcactgt cattgaggac atccgagact tgctggatat   1440
tggcagggat cgcaaaaatc cccgggagga ttatttggat gtgtatgtgt ttggggtcgg   1500
gcctctggtg gaccctgtga acatcaatgc cttggcttcc aaaaagaaca atgagcagca   1560
tgtgttcaag gtcaaggaca tggaggatct ggagaacgtc ttctacaaaa tgatcgatga   1620
aaccaaatct ctgggtctct gtggcatggt gtgggagcat cagaaaggcg gtgattatta   1680
caagcaacca tggcaagcca agatctcagt cactcgtcct ctgaaaggac atgagaactg   1740
tatgggggcc gtggtgtccg agtacttcgt gctgacagca gcgcattgct tcacagtgga   1800
agatcagaaa cactccatca aggtcaacgt ggaggggaaa aggcgggacc tggagattga   1860
agaggtcctg ttccacccta attacgacat caatgggaaa aaggcagaag gaatctctga   1920
gttctatgac tatgatgttg ccctcatcaa gctcaagacc aagctgaagt acagccagac   1980
tctcaggccc atctgtctcc cctgcacaga gggaaccacc cgagccttgc ggcttcctca   2040
gacagccacc tgcaaacagc acaaggaaga gttgctccct atgaaggacg tcaaagctct   2100
gtttgtatcc gaggaaggga agaagctgac ccggaaggag gtgtacatca agaatgggga   2160
aaagaaagcc agttgtgaga gagatgctac aaaggcccaa ggctatgaga aggtcaaagt   2220
tgcctctgag gtggtcaccc ccaggttcct gtgcaccgga ggggtagatc cctatgctga   2280
ccccaacaca tgcaaaggag actccggggg ccctctcatt gttcacaaga gaagccgctt   2340
cattcaagtt ggtgtgatca gctggggagt agtggatgtc tgcaaagacc cgaggcggca   2400
acagttggtg ccctcctatg cccgggactt ccacatcaat ctcttccagg tgctgccctg   2460
gctaaaggag aagctcaaag acgaggactt gggtttctta taaggagctt cctgctggga   2520
gggtgagggc agattaaagc agctacaata caaatacaaa aaaaaaaaaa aaa          2573
```

<210> SEQ ID NO 5

<211> LENGTH: 2334
<212> TYPE: DNA
<213> ORGANISM: Pan troglodytes

<400> SEQUENCE: 5
cccaggccca gcttctctcc tgccttccaa cgccatgggg agcaatctca gcccccaact 60
ctgcctgatg cccttcatct tgggcctctt gtctggaggt gtgaccacca ctccatggcc 120
tttggcccag ccccaggaat cctgctctct ggagggggta gagatcaaag gcggctcctt 180
ccgacttctc caagagggcc aggcactgga gtacgtgtgt ccttctggct tctacccgta 240
ccctgtgcag acacgtacct gcagatctac ggggtcctgg agcaccctga agactcaagt 300
ccaaaagact gtcaggaagg cagagtgcag agcaatccac tgtccaagac cacacgactt 360
cgagaacggg gaatactggc cccggtctcc ctactacaat gtgagtgatg agatctcttt 420
ccactgctat gacggttaca ctctccgggg ctctgccaat cgcacctgcc aagtgaatgg 480
ccggtggagt gggcagacag cgatctgtga caacggagcg gggtactgct ccaacccggg 540
catccccatt ggcacaagga aggtgggcag ccagtaccgc cttgaagaca gcgtcaccta 600
ccactgcagc cgggggctta ccctgcgtgg ctcccagcgg cgaacgtgtc aggaaggtgg 660
ctcttggagc gggacggagc cttcttgcca agactccttc atgtacgaca cccctcaaga 720
ggtggccgaa gctttcctgt cttccctgac agagaccata gaaggagtcg atgctgagga 780
tgggcacggc ccaggggaac aacagaagcg gaagatcgtc ctggaccctt caggctccat 840
gaacatctac ctggtgctag atggatcaga cagcattggg gccagcaact tcacaggagc 900
caaaaagtgt ctagtcaact taattgagaa ggtggcaagt tatggtgtga agccaagata 960
tggtctagtg acatatgcca cacaccccaa aatttgggtc aaagtgtctg atccagacag 1020
cagtaatgca gactgggtca cgaagcagct caatgaaatc aattatgaag accacaagtt 1080
gaagtcaggg actaacacca agaaggccct ccaggcagtg tacagcatga tgagctggcc 1140
agatgacatc cctcctgaag gctggaaccg cacccgccat gtcatcatcc tcatgactga 1200
tggattgcac aacatgggcg gggacccaat tactgtcatt gatgagatcc gggacttgct 1260
atacattggc aaggatcgca aaaacccaag ggaggattat ctggatgtct atgtgtttgg 1320
ggtcgggcct ttggtgaacc aagtgaacat caatgctttg gcttccaaga aagacaatga 1380
gcaacatgtg ttcaaagtca aggatatgga aaacctggaa gatgttttct accaaatgat 1440
tgatgaaagc cagtctctga gtctctgtgg catggtttgg gaacacagga agggtaccga 1500
ttaccacaag caaccatggc aagccaagat ctcagtcatt cgcccttcaa agggacacga 1560
gagctgtatg gggctgtgg tgtctgagta ctttgtgctg acagcagcac actgtttcac 1620
tgtggatgac aaggaacact caatcaaggt cagcgtagga ggggagaagc gggacctgga 1680
gatagaagta gtcctatttc accccaacta caacattaat gggaaaaaag cagcaggaat 1740
tcctgaattt tatgactatg acgttgccct gatcaagctc aagaataagc tgaaatatgg 1800
ccagactatc aggcccattt gtctccccctg caccgaggga acaactcgag ctttgaggct 1860
tcctccaact accacttgcc agcaacaaaa ggaagagctg ctccctgcac aggatatcaa 1920
agctctgttt gtgtctgagg aggagaaaaa gctgactcgg aaggaggtct acatcaagaa 1980
tggggataag aaaggcagct gtgagagaga tgctcaatat gccccaggct atgacaaagt 2040
caaggacatc tcagaggtgg tcacccctcg gttcctttgt actggaggag tgagtcccta 2100
tgctgacccc aatacttgca gaggtgattc tggcggcccc ttgatagttc acaaaagaag 2160
tcgtttcatt caagttggtg taatcagctg ggagtagtg gatgtctgca aaaaccagaa 2220
gcggcaaaag caggtacctg ctcacgcccg agactttcac atcaacctct ttcaagtgct 2280
gccctggctg aaggagaaac tccaagatga ggatttgggt tttctataag gggt 2334

<210> SEQ ID NO 6
<211> LENGTH: 5101
<212> TYPE: DNA
<213> ORGANISM: Homo sapiens

<400> SEQUENCE: 6
cactcctccc catcctctcc ctctgtccct ctgtccctct gaccctgcac tgtcccagca 60
ccatgggacc cacctcaggt cccagcctgc tgctcctgct actaacccac ctccccctgg 120
ctctggggag tcccatgtac tctatcatca cccccaacat cttgcggctg gagagcgagg 180
agaccatggt gctggaggcc cacgacgcgc aaggggatgt tccagtcact gttactgtcc 240
acgacttccc aggcaaaaaa ctagtgctgt ccagtgagaa gactgtgctg acccctgcca 300
ccaaccacat gggcaacgtc accttcacga tcccagccaa cagggagttc aagtcagaaa 360
aggggcgcaa caagttcgtg accgtgcagg ccaccttcgg gacccaagtg gtggagaagg 420
tggtgctggt cagcctgcag agcgggtacc tcttcatcca gacagacaag accatctaca 480
cccctggctc cacagttctc tatcggatct tcaccgtcaa ccacaagctg ctacccgtgg 540
gccggacggt catggtcaac attgagaacc cggaaggcat cccggtcaag caggactcct 600
tgtcttctca gaaccagctt ggcgtcttgc ccttgtcttg ggacattccg gaactcgtca 660
acatgggcca gtggaagatc cgagcctact atgaaaactc accacagcag gtcttctcca 720
ctgagtttga ggtgaaggag tacgtgctgc ccagtttcga ggtcatagtg gagcctacag 780
agaaattcta ctacatctat aacgagaagg gcctggaggt caccatcacc gccaggttcc 840
tctacgggaa gaaagtggag ggaactgcct ttgtcatctt cgggatccag gatggcgaac 900
agaggatttc cctgcctgaa tccctcaagc gcattccgat tgaggatggc tcgggggagg 960
ttgtgctgag ccggaaggta ctgctggacg gggtgcagaa cccccgagca gaagacctgg 1020
tggggaagtc tttgtacgtg tctgccaccg tcatcttgca ctcaggcagt gacatggtgc 1080
aggcagagcg cagcgggatc cccatcgtga cctctcccta ccagatccac ttcaccaaga 1140
cacccaagta cttcaaacca ggaatgccct ttgacctcat ggtgttcgtg acgaaccctg 1200
atggctctcc agcctaccga gtccccgtgg cagtccaggg cgaggacact gtgcagtctc 1260
taacccaggg agatggcgtg gccaaactca gcatcaacac acaccccagc cagaagccct 1320
tgagcatcac ggtgcgcacg aagaagcagg agctctcgga ggcagagcag gctaccagga 1380
ccatgcaggc tctgccctac agcaccgtgg gcaactccaa caattacctg catctctcag 1440
tgctacgtac agagctcaga cccggggaga ccctcaacgt caacttcctc ctgcgaatgg 1500
accgcgccca cgaggccaag atccgctact acacctacct gatcatgaac aagggcaggc 1560
tgttgaaggc gggacgccag gtgcgagagc ccggccagga cctggtggtg ctgcccctgt 1620
ccatcaccac cgacttcatc ccttccttcc gcctggtggc gtactacacg ctgatcggtg 1680
ccagcggcca gagggaggtg gtggccgact ccgtgtgggt ggacgtcaag gactcctgcg 1740
tgggctcgct ggtggtaaaa agcggccagt cagaagaccg gcagcctgta cctgggcagc 1800
agatgaccct gaagatagag ggtgaccacg gggcccgggt ggtactggtg gccgtggaca 1860
agggcgtgtt cgtgctgaat aagaagaaca aactgacgca gagtaagatc tgggacgtgg 1920
tggagaaggc agacatcggc tgcaccccgg gcagtgggaa ggattacgcc ggtgtcttct 1980

```
ccgacgcagg gctgaccttc acgagcagca gtggccagca gaccgcccag agggcagaac   2040
ttcagtgccc gcagccagcc gcccgccgac gccgttccgt gcagctcacg gagaagcgaa   2100
tggacaaagt cggcaagtac cccaaggagc tgcgcaagtg ctgcgaggac ggcatgcggg   2160
agaaccccat gaggttctcg tgccagcgcc ggacccgttt catctccctg ggcgaggcgt   2220
gcaagaaggt cttcctggac tgctgcaact acatcacaga gctgcggcgg cagcacgcgc   2280
gggccagcca cctgggcctg gccaggagta acctggatga ggacatcatt gcagaagaga   2340
acatcgtttc ccgaagtgag ttcccagaga gctggctgtg gaacgttgag gacttgaaag   2400
agccaccgaa aaatggaatc tctacgaagc tcatgaatat atttttgaaa gactccatca   2460
ccacgtggga gattctggct gtgagcatgt cggacaagaa agggatctgt gtggcagacc   2520
ccttcgaggt cacagtaatg caggacttct tcatcgacct gcggctaccc tactctgttg   2580
ttcgaaacga gcaggtggaa atccgagccg ttctctacaa ttaccggcag aaccaagagc   2640
tcaaggtgag ggtggaacta ctccacaatc cagccttctg cagcctggcc accaccaaga   2700
ggcgtcacca gcagaccgta accatccccc ccaagtcctc gttgtccgtt ccatatgtca   2760
tcgtgccgct aaagaccggc ctgcaggaag tggaagtcaa ggctgctgtc taccatcatt   2820
tcatcagtga cggtgtcagg aagtccctga aggtcgtgcc ggaaggaatc agaatgaaca   2880
aaactgtggc tgttcgcacc ctggatccag aacgcctggg ccgtgaagga gtgcagaaag   2940
aggacatccc acctgcagac ctcagtgacc aagtcccgga caccgagtct gagaccagaa   3000
ttctcctgca agggacccca gtggcccaga tgacagagga tgccgtcgac gcggaacggc   3060
tgaagcacct cattgtgacc ccctcgggct gcggggaaca gaacatgatc ggcatgacgc   3120
ccacggtcat cgctgtgcat tacctggatg aaacggagca gtgggagaag ttcggcctag   3180
agaagcggca gggggccttg gagctcatca agaaggggta cacccagcag ctggccttca   3240
gacaacccag ctctgccttt gcggccttcg tgaaacgggc acccagcacc tggctgaccg   3300
cctacgtggt caaggtcttc tctctggctg tcaacctcat cgccatcgac tcccaagtcc   3360
tctgcggggc tgttaaatgg ctgatcctgg agaagcagaa gcccgacggg gtcttccagg   3420
aggatgcgcc cgtgatacac caagaaatga ttggtggatt acggaacaac aacgagaaag   3480
acatggccct cacggccttt gttctcatct cgctgcagga ggctaaagat atttgcgagg   3540
agcaggtcaa cagcctgcca ggcagcatca ctaaagcagg agacttcctt gaagccaact   3600
acatgaacct acagagatcc tacactgtgg ccattgctgg ctatgctctg gcccagatgg   3660
gcaggctgaa ggggcctctt cttaacaaat ttctgaccac agccaaagat aagaaccgct   3720
gggaggaccc tggtaagcag ctctacaacg tggaggccac atcctatgcc ctcttggccc   3780
tactgcagct aaaagacttt gactttgtgc ctcccgtcgt gcgttggctc aatgaacaga   3840
gatactacgg tggtggctat ggctctaccc aggccacctt catggtgttc caagccttgg   3900
ctcaatacca aaaggacgcc cctgaccacc aggaactgaa ccttgatgtg tccctccaac   3960
tgcccagccg cagctccaag atcacccacc gtatccactg ggaatctgcc agcctcctgc   4020
gatcagaaga gaccaaggaa aatgagggtt tcacagtcac agctgaagga aaaggccaag   4080
gcaccttgtc ggtggtgaca atgtaccatg ctaaggccaa agatcaactc acctgtaata   4140
aattcgacct caaggtcacc ataaaaccag caccggaaac agaaaagagg cctcaggatg   4200
ccaagaacac tatgatcctt gagatctgta ccaggtaccg gggagaccag gatgccacta   4260
tgtctatatt ggacatatcc atgatgactg gctttgctcc agacacagat gacctgaagc   4320
agctggccaa tggtgttgac agatacatct ccaagtatga gctggacaaa gccttctccg   4380
```

```
ataggaacac cctcatcatc tacctggaca aggtctcaca ctctgaggat gactgtctag   4440

ctttcaaagt tcaccaatac tttaatgtag agcttatcca gcctggagca gtcaaggtct   4500

acgcctatta caacctggag gaaagctgta cccggttcta ccatccggaa aaggaggatg   4560

gaaagctgaa caagctctgc cgtgatgaac tgtgccgctg tgctgaggag aattgcttca   4620

tacaaaagtc ggatgacaag gtcaccctgg aagaacggct ggacaaggcc tgtgagccag   4680

gagtggacta tgtgtacaag acccgactgg tcaaggttca gctgtccaat gactttgacg   4740

agtacatcat ggccattgag cagaccatca agtcaggctc ggatgaggtg caggttggac   4800

agcagcgcac gttcatcagc cccatcaagt gcagagaagc cctgaagctg gaggagaaga   4860

aacactacct catgtggggt ctctcctccg atttctgggg agagaagccc aacctcagct   4920

acatcatcgg gaaggacact tgggtggagc actggcccga ggaggacgaa tgccaagacg   4980

aagagaacca gaaacaatgc caggacctcg gcgccttcac cgagagcatg gttgtctttg   5040

ggtgccccaa ctgaccacac ccccattccc ccactccaga taaagcttca gttatatctc   5100

a                                                                   5101
```

<210> SEQ ID NO 7
<211> LENGTH: 5147
<212> TYPE: DNA
<213> ORGANISM: Mus musculus

<400> SEQUENCE: 7

```
agagaggaga gccatataaa gagccagcgg ctacagcccc agctcgcctc tgcccacccc     60

tgccccttac cccttcattc cttccacctt tttccttcac tatgggacca gcttcagggt    120

cccagctact agtgctactg ctgctgttgg ccagctcccc attagctctg gggatcccca    180

tgtattccat cattactccc aatgtcctac ggctggagag cgaagagacc atcgtactgg    240

aggcccacga tgctcagggt gacatcccag tcacagtcac tgtgcaagac ttcctaaaga    300

ggcaagtgct gaccagtgag aagacagtgt tgacaggagc cagtggacat ctgagaagcg    360

tctccatcaa gattccagcc agtaaggaat tcaactcaga taaggagggg cacaagtacg    420

tgacagtggt ggcaaacttc ggggaaacgg tggtggagaa agcagtgatg gtaagcttcc    480

agagtgggta cctcttcatc cagacagaca agaccatcta cacccctggc tccactgtct    540

tatatcggat cttcactgtg gacaacaacc tactgcccgt gggcaagaca gtcgtcatcc    600

tcattgagac ccccgatggc attcctgtca agagagacat tctgtcttcc aacaaccaac    660

acggcatctt gcctttgtct tggaacattc ctgaactggt caacatgggg cagtggaaga    720

tccgagcctt ttacgaacat gcgccgaagc agatcttctc cgcagagttt gaggtgaagg    780

aatacgtgct gcccagtttt gaggtccggg tggagcccac agagacattt tattacatcg    840

atgacccaaa tggcctggaa gtttccatca tagccaagtt cctgtacggg aaaaacgtgg    900

acgggacagc cttcgtgatt tttggggtcc aggatggcga taagaagatt tctctggccc    960

actccctcac gcgcgtagtg attgaggatg gtgtggggga tgcagtgctg acccggaagg   1020

tgctgatgga gggggtacgg ccttccaacg ccgacgccct ggtggggaag tccctgtatg   1080

tctccgtcac tgtcatcctg cactcaggta gtgacatggt agaggcagag cgcagtggga   1140

tcccgattgt cacttccccg taccagatcc acttcaccaa gacacccaaa ttcttcaagc   1200

cagccatgcc ctttgacctc atggtgttcg tgaccaaccc cgatggctct ccggccagca   1260

aagtgctggt ggtcactcag ggatctaatg caaaggctct cacccaagat gatggcgtgg   1320
```

-continued

```
ccaagctaag catcaacaca cccaacagcc gccaacccct gaccatcaca gtccgcacca   1380
agaaggacac tctcccagaa tcacggcagg ccaccaagac aatggaggcc catccctaca   1440
gcactatgca caactccaac aactacctac acttgtcagt gtcacgaatg gagctcaagc   1500
cggggggacaa cctcaatgtc aacttccacc tgcgcacaga cccaggccat gaggccaaga   1560
tccgatacta cacctacctg gttatgaaca aggggaagct cctgaaggca ggccgccagg   1620
ttcgggagcc tggccaggac ctggtggtct tgtccctgcc catcactcca gagtttattc   1680
cttcatttcg cctggtggct tactacaccc tgattggagc tagtggccag agggaggtgg   1740
tggctgactc tgtgtgggtg gatgtgaagg attcctgtat tggcacgctg gtggtgaagg   1800
gtgacccaag agataaccat ctcgcacctg ggcaacaaac gacactcagg attgaaggaa   1860
accagggggc ccgagtgggg ctagtggctg tggacaaggg agtgtttgtg ctgaacaaga   1920
agaacaaact cacacagagc aagatctggg atgtggtaga gaaggcagac attggctgca   1980
ccccaggcag tgggaagaac tatgctggtg tcttcatgga tgcaggcctg gccttcaaga   2040
caagccaagg actgcagact gaacagagag cagatcttga gtgcaccaag ccagcagccc   2100
gccgccgtcg ctcagtacag ttgatggaaa gaaggatgga caaagctggt cagtacactg   2160
acaagggtct tcggaagtgt tgtgaggatg gtatgcggga tatccctatg agatacagct   2220
gccagcgccg ggcacgcctc atcacccagg gcgagaactg cataaaggcc ttcatagact   2280
gctgcaacca catcaccaag ctgcgtgaac aacacagaag agaccacgtg ctgggcctgg   2340
ccaggagtga attggaggaa gacataattc cagaagaaga tattatctct agaagccact   2400
tcccacagag ctggttgtgg accatagaag agttgaaaga accagagaaa aatggaatct   2460
ctacgaaggt catgaacatc tttctcaaag attccatcac cacctgggag attctggcag   2520
tgagcttgtc agacaagaaa gggatctgtg tggcagaccc ctatgagatc agagtgatgc   2580
aggacttctt cattgacctg cggctgccct actctgtagt gcgcaacgaa caggtggaga   2640
tcagagctgt gctcttcaac taccgtgaac aggaggaact taaggtgagg gtggaactgt   2700
tgcataatcc agccttctgc agcatggcca ccgccaagaa tcgctacttc cagaccatca   2760
aaatccctcc caagtcctcg gtggctgtac cgtatgtcat tgtcccctg aagatcggcc   2820
aacaagaggt ggaggtcaag gctgctgtct tcaatcactt catcagtgat ggtgtcaaga   2880
agacactgaa ggtcgtgcca gaaggaatga gaatcaacaa aactgtggcc atccatacac   2940
tggacccaga gaagctcggt caagggggag tgcagaaggt ggatgtgcct gccgcagacc   3000
ttagcgacca agtgccagac acagactctg agaccagaat tatcctgcaa gggagcccgg   3060
tggttcagat ggctgaagat gctgtggacg gggagcggct gaaacacctg atcgtgaccc   3120
ccgcaggctg tggggaacag aacatgattg gcatgacacc aacagtcatt gcggtacact   3180
acctggacca gaccgaacag tgggagaagt tcggcataga gaagaggcaa gaggccctgg   3240
agctcatcaa gaaagggtac acccagcagc tggccttcaa acagcccagc tctgcctatg   3300
ctgccttcaa caaccggccc cccagcacct ggctgacagc ctacgtggtc aaggtcttct   3360
ctctagctgc caacctcatc gccatcgact ctcacgtcct gtgtggggct gttaaatggt   3420
tgattctgga gaaacagaag ccggatggtg tctttcagga ggatgggccc gtgattcacc   3480
aagaaatgat tggtggcttc cggaacgcca aggaggcaga tgtgtcactc acagccttcg   3540
tcctcatcgc actgcaggaa gccagggaca tctgtgaggg gcaggtcaat agccttcctg   3600
ggagcatcaa caaggcaggg gagtatattg aagccagtta catgaacctg cagagaccat   3660
acacagtggc cattgctggg tatgccctgg ccctgatgaa caaactggag gaaccttacc   3720
```

-continued

```
tcggcaagtt tctgaacaca gccaaagatc ggaaccgctg ggaggagcct gaccagcagc   3780

tctacaacgt agaggccaca tcctacgccc tcctggccct gctgctgctg aaagactttg   3840

actctgtgcc ccctgtagtg cgctggctca atgagcaaag atactacgga ggcggctatg   3900

gctccaccca ggctaccttc atggtattcc aagccttggc ccaatatcaa acagatgtcc   3960

ctgaccataa ggacttgaac atggatgtgt ccttccacct ccccagccgt agctctgcaa   4020

ccacgtttcg cctgctctgg gaaaatggca acctcctgcg atcggaagag accaagcaaa   4080

atgaggcctt ctctctaaca gccaaaggaa aaggccgagg cacattgtcg gtggtggcag   4140

tgtatcatgc caaactcaaa agcaaagtca cctgcaagaa gtttgacctc agggtcagca   4200

taagaccagc ccctgagaca gccaagaagc ccgaggaagc caagaatacc atgttccttg   4260

aaatctgcac caagtacttg ggagatgtgg acgccactat gtccatcctg gacatctcca   4320

tgatgactgg ctttgctcca gacacaaagg acctggaact gctggcctct ggagtagata   4380

gatacatctc caagtacgag atgaacaaag ccttctccaa caagaacacc ctcatcatct   4440

acctagaaaa gatttcacac accgaagaag actgcctgac cttcaaagtt caccagtact   4500

ttaatgtggg acttatccag cccgggtcgg tcaaggtcta ctcctattac aacctcgagg   4560

aatcatgcac ccggttctat catccagaga aggacgatgg gatgctcagc aagctgtgcc   4620

acagtgaaat gtgccggtgt gctgaagaga actgcttcat gcaacagtca caggagaaga   4680

tcaacctgaa tgtccggcta gacaaggctt gtgagcccgg agtcgactat gtgtacaaga   4740

ccgagctaac caacatagag ctgttggatg attttgatga gtacaccatg accatccagc   4800

aggtcatcaa gtcaggctca gatgaggtgc aggcagggca gcaacgcaag ttcatcagcc   4860

acatcaagtg cagaaacgcc ctgaagctgc agaaagggaa gaagtacctc atgtggggcc   4920

tctcctctga cctctgggga gaaaagccca acaccagcta catcattggg aaggacacgt   4980

gggtggagca ctggcctgag gcagaagaat gccaggatca gaagtaccag aaacagtgcg   5040

aagaacttgg ggcattcaca gaatctatgg tggtttatgg ttgtcccaac tgactacagc   5100

ccagccctct aataaagctt cagttgtatt tcaaaaaaaa aaaaaaa                 5147
```

<210> SEQ ID NO 8
<211> LENGTH: 5091
<212> TYPE: DNA
<213> ORGANISM: Rattus norvegicus

<400> SEQUENCE: 8

```
ctaccccttta ccccctcactc cttccacctt tgtcctttac catgggaccc acgtcagggt    60

cccagctact agtgctactg ctgctgttgg ccagctccct gctagctctg gggagcccca   120

tgtactccat cattactccc aatgtcctgc ggctggagag tgaagagact ttcatactag   180

aggcccatga tgctcagggt gatgtcccag tcactgtcac tgtgcaagac ttcctaaaga   240

agcaagtgct gaccagtgag aagacagtgt tgacaggagc cactggacat ctgaacaggg   300

tctccatcaa gattccagcc agtaaggaat tcaatgcaga taaggggcac aagtacgtga   360

cagtggtggc aaacttcggg gcaacagtgg tggagaaagc ggtgctagta agctttcaga   420

gtggttacct cttcatccag acagacaaga ccatctacac cccaggctcc actgttttct   480

atcggatctt cactgtggac aacaacctat tgcctgtggg caagacagtc gtcatcgtca   540

ttgagacccc ggacggcgtt cccatcaaga gagacattct atcttcccac aaccaatatg   600

gcatcttgcc tttgtcttgg aacattccag aactggtcaa catggggcag tggaagatcc   660
```

-continued

```
gagccttcta tgaacatgca ccaaagcaga ccttctctgc agagtttgag gtgaaggaat    720
acgtgctgcc cagtttcgaa gtcctggtgg agcctacaga gaaattttat tacatcgatg    780
acccaaaggg cctggaagtt tccatcacag ccagattcct gtatgggaag aacgtggacg    840
ggacagcttt cgtgatcttt ggggtccagg atgaggataa gaagatttct ctggcccagt    900
ccctcacccg cgtgctgatc gaggatggtt caggggaggc agtgctcagc cgaaaagtgc    960
tgatggacgg ggtacggccc tccagcccag aagccctagt ggggaagtcc ctgtacgtct   1020
ctgtcactgt tatcctgcac tcaggtagcg acatggtaga ggcagagcgc agtgggatcc   1080
caattgtcac ttccccgtac cagatccact tcaccaagac acccaaattc ttcaagccag   1140
ccatgccttt cgacctcatg gtgtttgtga ccaaccctga tggctctcca gcccgcagag   1200
tgccagtagt cactcaggga tccgacgcgc aggctctcac ccaggatgat ggtgtggcca   1260
agctgagcgt caacacaccc aacaaccgcc aacccctgac tatcacggtc cgcaccaaga   1320
aggagggtat cccggacgcg cggcaggcca ccaggacgat gcaggcccag ccctacagca   1380
ctatgcacaa ttccaacaac tacctgcact tgtcagtgtc tcgggtggag ctcaagcctg   1440
gggacaacct caatgtcaac ttccacctgc gcacggacgc tggccaagag gccaagatcc   1500
gatactacac ctatctggtt atgaacaagg ggaagttact gaaggcaggc cgtcaggttc   1560
gggagcctgg ccaggacctg gtggtcttgt cactgcccat cactccagaa tttatacctt   1620
ccttccgcct ggtggcttac tacaccctga ttggagctaa tggccaaagg gaggtggtgg   1680
ccgactcagt gtgggtggat gtgaaggact cctgtgtagg cacgctggtg gtgaaaggtg   1740
acccaagaga taaccgacag cccgcgcctg ggcatcaaac gacactaagg atcgagggga   1800
accaggggc ccgagtgggg ctagtggctg tggacaaggg ggtgtttgtg ctgaacaaga   1860
agaacaaact cacacagagc aagatctggg atgtagtaga gaaggcagac attggctgca   1920
ccccaggcag tgggaagaac tatgcgggtg tcttcatgga tgctggcctg accttcaaga   1980
caaaccaagg cctgcagact gatcagagag aagatcctga gtgcgccaag ccagctgccc   2040
gccgccgtcg ctcagtgcag ttgatggaaa ggaggatgga caaagctggt cagtacaccg   2100
acaagggtct gcggaagtgt tgtgaggatg gcatgcgtga tatccctatg aagtacagct   2160
gccagcgccg ggctcgcctc atcacccagg gcgagagctg cctgaaggcc ttcatggact   2220
gctgcaacta tatcaccaag cttcgtgagc agcacagaag agaccatgtg ctgggcctgg   2280
ccaggagtga tgtggatgaa gacataatcc cagaagaaga tattatctct agaagccact   2340
tcccagagag ctggttgtgg accatagaag agttgaaaga accagagaaa aatggaatct   2400
ctacgaaggt catgaacatc tttctcaaag attccatcac cacctgggag attctggcag   2460
tgagcttgtc cgacaagaaa gggatctgtg tggcagaccc ctatgagatc acagtgatgc   2520
aggacttctt cattgacctg cgactgccct actctgtggt gcgcaatgaa caggtggaga   2580
tcagagctgt gctcttcaat taccgtgaac aggagaaact taaggtaagg gtggaactgt   2640
tgcataaccc agccttctgc agcatggcca ctgccaagaa gcggtactac cagaccatcg   2700
aaatccctcc caagtcctct gtggctgtgc cttatgtcat tgtccccttg aagatcggcc   2760
tccaggaggt ggaggtcaag gccgccgtct tcaaccactt catcagtgat ggtgtcaaga   2820
agatactgaa ggtcgtgcca gaaggaatga gagtcaacaa aactgtggct gtccgtacac   2880
tggatccaga acacctcggt caagggggag tgcagaggga ggatgtacct gcagcagacc   2940
tcagtgacca agtgccagac acagattctg agaccagaat tctcctgcaa gggaccccgg   3000
tggctcagat ggccgaggac gctgtggacg gggagcggct gaaacacctg atcgtgaccc   3060
```

```
cctctggctg tggggagcag aacatgattg gcatgacacc cacggtcatt gcagtacact   3120

atctggatca gaccgaacag tgggagaaat tcggcctaga gaagaggcaa gaagctctgg   3180

agctcatcaa gaaagggtac acccagcagc tggctttcaa acagcccagc tctgcctatg   3240

ctgccttcaa caaccggcct cccagcacct ggctgacagc ctatgtggtc aaggtcttct   3300

ctctggctgc caacctcatc gccatcgact ctcaggtcct gtgtggggct gtcaaatggc   3360

tgattctgga gaaacagaag ccagatggtg tctttcagga ggacggacca gtgattcacc   3420

aagaaatgat tggtggcttc cggaacacca aggaggcaga tgtgtcgctt acagcctttg   3480

tcctcatcgc actgcaggaa gccagagata tctgtgaggg gcaggtcaac agccttcccg   3540

ggagcatcaa caaggcaggg gagtatcttg aagccagtta cctgaacctg cagagaccat   3600

acacagtagc cattgctggg tatgccctgg ccctgatgaa caaactggag gaaccttacc   3660

tcaccaagtt tctgaacaca gccaaagatc ggaaccgctg ggaggagcct ggccagcagc   3720

tctacaatgt ggaggccacc tcctacgccc tcctggccct gctgctgctg aaagactttg   3780

actctgtgcc tcctgtggtg cgctggctca acgagcaaag atactacgga ggtggctatg   3840

gctccacgca ggctaccttc atggtattcc aagccttggc tcaataccaa acagatgtcc   3900

ctgaccacaa ggacttgaac atggatgtgt ccctccacct ccccagccgc agctccccaa   3960

ctgtgtttcg cctgctatgg gaaagtggca gtctcctgag atcagaagag accaagcaga   4020

atgagggctt ttctctgaca gccaaaggaa aaggccaagg cacactgtcg gtggtgacag   4080

tgtatcacgc caaagtcaaa ggcaaagcca cctgcaagaa gtttgacctc agggtcacca   4140

taaaaccagc ccctgagaca gccaagaagc cccaggatgc caagagttct atgatccttg   4200

acatctgcac caggtacttg ggagacgtgg atgctactat gtccatcctg gacatctcca   4260

tgatgactgg ctttattcca gacacaaacg acctggaact gctgagctct ggagtagaca   4320

gatacatttc caagtatgag atggacaaag ccttctccaa caagaacacc ctcatcatct   4380

acctagaaaa gatctcacac tccgaagaag actgcctgtc cttcaaagtc caccagttct   4440

ttaacgtggg acttatccag ccggggtcgg tcaaggtcta ctcctactac aatctagagg   4500

agtcatgcac ccggttctat catccggaga aggacgatgg aatgctgagc aagctgtgcc   4560

acaatgaaat gtgccgctgt gcagaggaga actgcttcat gcatcagtca caggatcagg   4620

tcagcctgaa tgaacgacta gacaaggctt gtgagcctgg agtggactac gtgtacaaga   4680

ccaagctaac gacgatagag ctgtcggatg attttgatga gtacatcatg accatcgagc   4740

aggtcatcaa gtcaggctca gatgaggtgc aggcaggtca ggaacgaagg ttcatcagcc   4800

acgtcaagtg cagaaacgcc ctaaagctgc agaaagggaa gcagtacctc atgtggggcc   4860

tctcctccga cctctgggga gaaaagccca ataccagcta catcattggg aaggacacgt   4920

gggtggagca ctggcccgag gcagaggaat gtcaggatca gaagaaccag aaacagtgcg   4980

aagacctcgg ggcattcaca gaaacaatgg tggttttcgg ctgccccaac tgaccacaac   5040

ctccaataaa gcttcagttg tattttaccc atcaaaaaaa aaaaaaaaaa a            5091
```

<210> SEQ ID NO 9
<211> LENGTH: 2693
<212> TYPE: DNA
<213> ORGANISM: Homo sapiens

<400> SEQUENCE: 9

```
gcttgttccc tgtcctctgg ccctttgcaa ataaatgcct taccagacct gccctgccac     60
```

```
cccactcgca gccacccagc aagagcagca tgtcagcctg ccggagcttt gcagttgcaa    120
tctgcatttt agaaataagc atcctcacag cacagtacac gaccagttat gacccagagc    180
taacagaaag cagtggctct gcatcacaca tagactgcag aatgagcccc tggagtgaat    240
ggtcacaatg cgatccttgt ctcagacaaa tgtttcgttc aagaagcatt gaggtctttg    300
gacaatttaa tgggaaaaga tgcaccgacg ctgtgggaga cagacgacag tgtgtgccca    360
cagagccctg tgaggatgct gaggatgact gcggaaatga ctttcaatgc agtacaggca    420
gatgcataaa gatgcgactt cggtgtaatg gtgacaatga ctgcggagac ttttcagatg    480
aggatgattg tgaaagtgag ccccgtcccc cctgcagaga cagagtggta gaagagtctg    540
agctggcacg aacagcaggc tatgggatca acattttagg gatggatccc ctaagcacac    600
cttttgacaa tgagttctac aatggactct gtaaccggga tcgggatgga aacactctga    660
catactaccg aagaccttgg aacgtggctt ctttgatcta tgaaaccaaa ggcgagaaaa    720
atttcagaac cgaacattac gaagaacaaa ttgaagcatt taaaagtatc atccaagaga    780
agacatcaaa ttttaatgca gctatatctc taaaatttac acccactgaa acaaataaag    840
ctgaacaatg ttgtgaggaa acagcctcct caatttcttt acatggcaag ggtagttttc    900
ggttttcata ttccaaaaat gaaacttacc aactattttt gtcatattct tcaaagaagg    960
aaaaaatgtt tctgcatgtg aaaggagaaa ttcatctggg aagatttgta atgagaaatc   1020
gcgatgttgt gctcacaaca acttttgtgg atgatataaa agctttgcca actacctatg   1080
aaaagggaga atattttgcc tttttggaaa cctatggaac tcactacagt agctctgggt   1140
ctctaggagg actctatgaa ctaatatatg ttttggataa agcttccatg aagcggaaag   1200
gtgttgaact aaaagacata aagagatgcc ttgggtatca tctggatgta tctctggctt   1260
tctctgaaat ctctgttgga gctgaattta ataaagatga ttgtgtaaag aggggagagg   1320
gtagagctgt aaacatcacc agtgaaaacc tcatagatga tgttgtttca ctcataagag   1380
gtggaaccag aaaatatgca tttgaactga aagaaaagct tctccgagga accgtgattg   1440
atgtgactga ctttgtcaac tgggcctctt ccataaatga tgctcctgtt ctcattagtc   1500
aaaaactgtc tcctatatat aatctggttc cagtgaaaat gaaaaatgca cacctaaaga   1560
aacaaaactt ggaaagagcc attgaagact atatcaatga atttagtgta agaaaatgcc   1620
acacatgcca aaatggaggt acagtgattc taatggatgg aaagtgtttg tgtgcctgcc   1680
cattcaaatt tgagggaatt gcctgtgaaa tcagtaaaca aaaaatttct gaaggattgc   1740
cagccctaga gttccccaat gaaaaataga gctgttggct tctctgagct ccagtggaag   1800
aagaaaacac tagtaccttc agatcctacc cctgaagata atcttagctg ccaagtaaat   1860
agcaacatgc ttcatgaaaa tcctaccaac ctctgaagtc tcttctctct taggtctata   1920
attttttttt aaatttttct tccttaaact cctgtgatgt ttccattttt tgttccctaa   1980
tgagaagtca acagtgaaat acgccagaac tgctttatcc cacggaaaat gccaatctct   2040
tctaaaaaaa aacaaaatta aattaaaaac agaatgttgg tttaaaaaac ttcaaagtaa   2100
ttttcaaacg gctttgtatg gttaacatat tctgccaggt ccatgaccac acgtctgtac   2160
catgcaattt aactcttatt tacattgtta tgtttagttt ggttatttgc ttaggtgtgc   2220
atacattcat tcagcaaatg ctgagcacca gccacgtgca cagcagttgc ttttactagt   2280
cttagctcta cgatttaaat ccatgtgtcc aagggggaaa acatattata tttgtaacca   2340
aaaactacta gtttaccaga ggactgaagg gagataaaga ggagttggtt aatgggtaca   2400
aaaatccagt tagatgaaag gaataatata gatagtgttc agtagcagaa tagaatgaac   2460
```

ataaactatt agtttaaatt atgtgaaatt ccttctattt gatcatattt tacaagaaaa 2520
aacatcaatt ttatatagtc caacttaata cctagcctta tgagttgtat aaggtaaggt 2580
tacctacctg agaagctgat taacattggt tgtacaatct tattcattag agaacatggt 2640
gcttagggtc tgagaccttt tgaaaggtct gagaactctt taaaaaaagg aaa 2693

<210> SEQ ID NO 10
<211> LENGTH: 1767
<212> TYPE: DNA
<213> ORGANISM: Mus musculus

<400> SEQUENCE: 10
actgcccctt gtcctccggc tgcaaaggaa tgctttgcaa gcctccaggg ctccccagga 60
ggagcagcat ggcctcaggc atggccatca ccttagccct tgccatcttt gccttgggtg 120
tcaatgcaca gatgccaata cccgtttcca gagaagaaca agaacaacac tatcccatac 180
cgatagactg cagaatgagc ccatggagca attggtcaga gtgtgatcct tgcctcaaac 240
aaaggtttcg ctcaagaagc attttagcct tcggacagtt taatgggaaa agctgtgttg 300
atgttttggg agacagacaa ggctgtgaac ccacccagga gtgtgaagag atacaggaaa 360
actgtggaaa tgactttcag tgtgagacag gcaggtgcat aaagaggaga cttctgtgta 420
atggtgacaa cgactgtgga gattattctg atgagaatga ctgtgacgat gacccacgca 480
ccccatgccg tgaccgagta gcggaagaat cagagctggg actaacagca ggctatggga 540
tcaacatctt agggatggag cccctgagaa caccttttga caatgagttc tacaacggac 600
tctgtgaccg ggtacgagac gaaaagacat actatcgcaa accttggaat gtagtttctc 660
tgatctatga aaccaaggct gataaaagtt tcagaactga gaactatgac gaacacttgg 720
aagtattcaa agccatcaac cgagagaaga cctcgaattt taatgcagat tttgccctaa 780
aattttcagc caccgaagta cctgaaaagg gagctgggga agtctcccca gcagaacact 840
cttcaaaacc tacaaacatt tcagctaaat ttaaattttc atatttcatg ggaaaaaatt 900
ttcgaagact atcatcttat ttttcgcagt cgaaaaagat gtttgtgcac ttgagaggag 960
tggtccaact ggggagattt gtaatgagga atcgggatgt tgtgctgagg tcaactttcc 1020
tggatgatgt aaaagctcta ccaacttcct atgaaaaggg agaatatttt ggatttttgg 1080
aaacctatgg gactcactac agtacctctg ggtccctggg aggacaatat gaaattgtct 1140
atgtcttgga taaagcttcc atgaaagaga aaggtgttga cctgaatgat gtaaaacatt 1200
gtcttggatt taatatggat ttacgtattc ctctacaaga cgacttaaag gatgcatcag 1260
tcacagcaag tgttaatgcg gatggttgca taaagacaga taatgggaaa actgtaaaca 1320
tcacccgcga taacatcata gatgatgtca tttcattcat aagaggaggg actagggagc 1380
aagcaattct cctgaaagag aagattctca gaggagacaa gacatttgat aagactgact 1440
tcgccaactg ggcctcgtcc ctggcaaacg ctccagctct catcagtcaa agaatgtccc 1500
ctatatataa tctcattcct ttgaaaataa aagatgcata cataaagaag caaaatttgg 1560
aaaaggctgt tgaagactat atagatgaat tcagtactaa aaggtgctac ccatgtctaa 1620
atggaggtac tataattctt ctggatgggc agtgcctgtg ctcctgccca atgatgttta 1680
ggggaatggc ctgcgaaatc catcaaaaaa tatagccttc aggaaacaaa gcaaaccctg 1740
gttcacatgg aagggggaaa aaaaaag 1767

<210> SEQ ID NO 11

<211> LENGTH: 2083
<212> TYPE: DNA
<213> ORGANISM: Rattus norvegicus

<400> SEQUENCE: 11
ggttgcaaag aaatgcttct caggactcca gggctgccta ggaggagcgg catggcctca 60
ggcgtgacca tcaccctagc cattgcaatc tttgccttgg agatcaatgc acaggcccca 120
gagcccactc cccgggaaga gccatcagca gacgccctcc taccaataga ctgcagaatg 180
agcacatgga gtcagtggtc acagtgtgat ccttgcctca aacaaaggtt tcgctcaaga 240
agcatggaag tctttggaca gtttcaggga aaaagctgtg ctgatgcttt gggagacaga 300
caacattgtg aacccactca ggagtgtgaa gaggtacagg aaaactgtgg gaatgacttt 360
cagtgtgaaa caggcaggtg cataaagagg aaacttctgt gtaatggtga caacgactgt 420
ggagattttt ctgatgagag tgactgtgaa agtgacccgc gcctcccgtg ccgtgaccgg 480
gtggtagaag aatcggaact gggacgaaca gcaggatatg ggatcaacat cttagggatg 540
gatcccctgg gcacgccttt tgacaatgag ttctacaatg gactctgtga ccgggtacgg 600
gacggaaaca ctttgacata ctatcgcaaa ccttggaacg tagcatttct ggcctatgaa 660
accaaggctg acaaaaattt cagaactgag aattatgaag aacagtttga aatgttcaaa 720
accatcgtcc gagacaggac cacgagtttt aatgctaatt tagctctaaa attcacaatc 780
actgaagcac ctataaaaaa agttggagtt gatgaagtca gcccagaaaa aaactcttca 840
aagcctaaag actcttctgt tgattttcaa ttttcatatt tcaagaaaga aaattttcaa 900
cgattgtcat cctacttgtc acagacgaaa aagatgtttc tgcacgtgag aggaatgatt 960
caactgggga gatttgtcat gaggaatcgg ggcgttatgc tgacgacaac tttcctggat 1020
gatgtaaagg ctttaccagt ttcctatgaa aagggcgaat attttgggtt tttggagact 1080
tatgggactc actacagtag ctctgggtcc ctgggagggc tctacgaact gatctatgtc 1140
ttggataaag cttccatgaa agagaaaggt gttgaactca gcgacgtaaa gcggtgtctt 1200
gggtttaacc tggatgtttc tctatatacg cctctacaaa ctgccttaga aggaccatca 1260
ttgacagcca atgttaatca cagtgattgc ttaaagacag gggatggtaa agtagtaaac 1320
atcagccgcg atcacatcat agatgatgtt atttcattca taagaggagg gaccaggaag 1380
caagcagttc tcctgaaaga gaagcttctc agaggagcca agacgattga tgtgaacgac 1440
ttcatcaact gggcctcatc cttggatgac gctccagctc tcattagtca aaaactgtcc 1500
cctatctata atctcattcc tttgacaatg aaagatgcat acgcaaagaa acagaatatg 1560
gaaaaggcta ttgaagacta tgttaatgaa ttcagtgcta gaaagtgcta cccatgtcaa 1620
aacggaggca cagcaattct tctggatgga cagtgcatgt gctcctgcac aatcaagttt 1680
aaggggattg cctgcgaaat cagtaaacaa agatagcctt caggaaacaa agcaaaacct 1740
ggttcacatg gaaggtggaa aaaaggacaa aaaaagaaga agagagagga gagagaagag 1800
agagagaaaa gaaaaaaccc caggactttc caacttagca tcctacccta gagcgaatcc 1860
tcactgccaa gtagaaagca gcttgcttca tggaaatcct accaacctct gatgtcgtct 1920
ctgtttcagg tctacagtgc ctttctcccc tctttaatgc ctataatgct tccatttttt 1980
tttttatccc taatgaagaa tcggcagtga gatatgccag gactgccttt tcccacaggc 2040
aatgccaatc tctcgctaat aaaacagagt taaattaaaa aca 2083

<210> SEQ ID NO 12
<211> LENGTH: 2646

-continued

<212> TYPE: DNA
<213> ORGANISM: Homo sapiens

<400> SEQUENCE: 12
tttttttttt tttttttttt gttgtcgcag ctgttttaat tcaatcccac gcccctgtcc 60
agcaggaaac cccttataga aaacccaaat cctcatcttg gagtttctcc ttcagccagg 120
gcagcacttg aaagaggttg atgtgaaagt ctcgggcgtg agcaggtacc tgcttttgcc 180
gcttctggtt tttgcagaca tccactactc cccagctgat tacaccaact tgaatgaaac 240
gacttctctt gtgaactatc aaggggccgc cagaatcacc tctgcaagta ttggggtcag 300
catagggact cactcctcca gtacaaagga accgaggggt gaccacctct gagatgtcct 360
tgactttgtc atagcctggg gcatattgag catctctctc acagctgcct ttcttatccc 420
cattcttgat gtagacctcc ttccgagtca gctttttctc ctcctcagac acaaacagag 480
ctttgatatc ctgtgcaggg agcagctctt ccttttgttg ctggcaagtg gtagttggag 540
gaagcctcaa agctcgagtt gttccctcgg tgcaggggag acaaatgggc ctgatagtct 600
ggccatattt cagcttattc ttgagcttga tcagggcaac gtcatagtca taaaattcag 660
gaattcctgc ttcttttttc ccattaatgt tgtagttggg gtgaaatagg actacttcta 720
tctccaggtc ccgcttctcc cctcctacgc tgaccttgat tgagtgttcc ttgtcatcca 780
cagtgaaaca atgtgctgct gtcagcacaa agtactcaga caccacagcc cccatacagc 840
tctcgtgtcc ctttgaaggg cgaatgactg agatcttggc ctgccatggt tgcttgtggt 900
aatcggtacc cttcctgtgt tcccaaacca tgccacagag actcagagac tggctttcat 960
cgatcatttg gtagaaaaca tcttccaggt tttccatatc cttgactttg aacacatgtt 1020
gctcattgtc tttcttggaa gccaaagcat tgatgttcac ttggttcacc aaaggcccga 1080
ccccaaacac atagacatcc agataatcct cccttgggtt tttgcgatcc ttgccaatgt 1140
atagcaagtc ccggatctca tcaatgacag taattgggtc cccgcccatg ttgtgcaatc 1200
catcagtcat gaggatgatg acatggcggg tgcggttcca gccttcagga gggacgtcat 1260
ctggccagct catcatgctg tacactgcct ggagggcctt cttggtgtta gtccctgact 1320
tcaacttgtg gtcttcataa ttgatttcat tgagctgctt cgtgacccag tctgcattac 1380
tgctgtctgc ttcagacact ttgacccaaa ttttggggta tgtggcatat gtcactagac 1440
catatcttgg cttcacacca taacttgcca ccttctcaat taagttgact agacactttt 1500
tggctcctgt gaagttgctg gccccaatgc tgtctgatcc atctagcacc aggtagatgt 1560
tcatggagcc tgaagggtcc aggacgatct tccgcttctg ttgttcccct gggccgtgcc 1620
catcctcagc atcgactcct tctatggtct ctgtcaggga agacaggaaa gcttcggcca 1680
cctcttgagg ggtgtcgtac atgaaggagt cttggcagga aggctccgtc ccgctccaag 1740
agccaccttc ctgacacgtt cgccgctggg agccacgcag ggtaagcccc cggctgcagt 1800
ggtaggtgac gctgtcttca aggcggtact ggctgcccac cttccttgtg ccaatgggga 1860
tgcccgggtt ggagcagtac cccgctccgt tgtcacagat cgctgtctgc ccactccatc 1920
ggccattcac ttggcaggtg cgattggcag agccccggag agtgtaaccg tcatagcagt 1980
ggaaagagat ctcatcactc acattgtagt agggagaccg gggccagtat tccccgttct 2040
cgaagtcgtg tggtcttgga cagtggattg ctctgcactc tgccttcctg acagtctttt 2100
ggtcttgagt cttcagggtg ctccaggacc ccgtagatct gcaggtacgt gtctgcacag 2160
ggtacgggta gaagccagaa ggacacacgt actccagtgc ctggccctct tggagaagtc 2220

```
ggaaggagcc gcctttgatc tctacccccct ccagagagca ggatccctgg ggccgggcca   2280

aagaccatgg agtggtggtc acacctccag acaagaggcc caagataaag ggcatcaggc   2340

agagttgggg gctgagattg ctccccatgg cgttggaagg caggagagaa gctgggcctg   2400

gggcaggatg gtgtgtcctg gcttgctttg cttgtctgct tggctcagtg tccaagctga   2460

aactccagac ctagacctgg tcacattccc ttcccctgct ccccaccagc cccagcctt   2520

ttatacaatc tgtgttctgg cacctgcggc tcgccccgcc tgtcctaccc acatcacttt   2580

cccggaacat ccaagcggga gggccccgct gagctgccag tcaaggaaac agaaactgca   2640

gaagtc                                                              2646


<210> SEQ ID NO 13
<211> LENGTH: 2767
<212> TYPE: DNA
<213> ORGANISM: Mus musculus

<400> SEQUENCE: 13

ttttttttt ttttttttt ttgttattgt aactgcttta atctgtcctc acactctccc     60

tgcaggaagc tctttataga aaacccaaat cctcatcttt gagcttgtcc tttagccagg    120

gcagcacctg gaagaggttg atgtggaagt cccgggcata agagggtacc agctgttgcc    180

gcctctggtc tctgcagaca tctactactc cccagctaat cacaccaact tgaatgaagc    240

ggcttctctt gtgaacaatg agagggcccc cggaatctcc tttgcatgtg ttggggtcag    300

catagggatc cacccctcct gtgcagagga accgtggagt gaccacctca gaggcatctt    360

tgaccttctc atagccttgg gcctttgtag catctctctc acaactggct ttcttgtccc    420

cattcttgat gtacacctcc ttccgagtca ggctcttccc ttgctcagat acaaacagag    480

ctttgacatc cttcacaggg agcaactgtt ccttgtgctg cttgcaggtg gctgtctgag    540

gaagcctcaa ggctcgtgtg gttccctccg tgcaggggag acagatgggc ctgagagtct    600

ggccatactt gagcttgttc ttgagcttga ctagggccac atcataatca tagaactcag    660

ggatcccttc tgccttttc ccattaatat tgtatttggg gtggaacagg acctcttcaa    720

tctccaggtc ccgcctctga cccccacgc tgaccttgat ggaatgtttc tgatcatcca    780

ccatgaagca gtgcgctgct gtcagcacga agtactcaga caccacggcc cccatacagg    840

tctcatgtcc tttcagaggg cgagtgactg agatcttggc ttgccatggt tgcttatgat    900

aatcgttgcc ttttttatgc tcccacacca tgccacagag actcagagat ttggtttcat    960

caatcatttg gtagaaaaca ttctccaggt cttccatatc cttgacttta aacacatgat   1020

gctcattgtc ctttttggaa gctaaggcat tgatgttcac ggagtccacc agaggcccga   1080

ccccaaacac atacacatcc aggtaatcct ccctgggatt tttgggatcc ctgccgatgt   1140

ccagcaaggc tcggatgtcc tgaatgacag tgacagggtt tccacccatg ttgtgcaagc   1200

catcagtcat aatgatgatg acatggcggg ttctattcca gccttcaggc ggggcatccc   1260

ctgcccagct catcatgcta tacacagcct ggagagccct cttggtgttg gtccctgact   1320

tcagcttgtg gtcttcataa ctgatttggt tgagcttctc tgtgacccag tcggcatcgc   1380

tactcctctc atcagacact ctgaccaaca ctttggggac tgtagcatat gtcaggagac   1440

catatcgtgg cctcaccccg taactcgcca ccttctcaat caagttggtg aggcaccgct   1500

tagcccctgt gaagttgctg cttccgatgc tgtctgatcc atctagcacc aggtagatat   1560

tcatggagcc cgaggggtct aggacaatct tcctcttctg ctgttctcct gggctgtgcc   1620

catcctcagc atcggctcct tcgatggtct ctgtcaggga ggataggaat gcttcggcca   1680
```

```
cttcttgagg gctgtcatac atgaaggaat cttggcagga aggctctgtc ccactccatg   1740

agccaccttc ttgacacttt cgcttctggg agccacgcag gacaagtccc cggctgcagt   1800

ggtaagtaac aatgtcttca aggcggtatt ggctacccac cttccttgtc ccaataggaa   1860

taccgggatt gggacagtat ccagctccat catcacaaat tgctgtttgc ccatccccacc   1920

ggccattctc ttggcaggtg cgattagcag agccccggag aacgtaacca tcatagcatt   1980

gaaaagaaat ctggtcactc aggttgtaga agggggaccg gggccagaat tccccatttt   2040

caaagtcctg cggtcgtggg cagcgtattg ctctgcattc cgccttctgg acaatctttt   2100

ggtctcgggt ctgcaggtcg ctccaggagc ctgtggatct gcaggttcga gtctgcacgg   2160

ggtatgggta gaagccagag ggacataggt actccagggc ctgaccgcct tggagaagtt   2220

gaaaggagcc gcctttgatc tctactccct ccagagagca ggagacttgg ggccgggcct   2280

caagcactgg agttgcgctc acacctccag aggagaagcc taagaccaag aggacgaggc   2340

agagctgggg gctctccatt gtcatggaaa gcaccagaga gtccagtggc ccaaagccct   2400

ctccaggtca ctctgggtgc ctatttgacc tcctgtccaa actgaaaccc aaatgctgga   2460

tctggctaca ccccttttccc actgtcccct aacctttttat gcaatctgct ctggcatctg   2520

cagcctggcc agcctaccct gcgcacgcag ccactgcttc ccggaacatt catgaaggag   2580

ggccccagct gaactgccaa ctgaggaaac agaaactatg tgagccccac ccttgactga   2640

ccaagggcca gaacttccct ttcaaagctc cctcttagcc cccagacccc tcctaacaag   2700

cacagaccac cacctccact acccccaatt taaaagatca gtctttccat ggactgtgtg   2760

atggagc                                                             2767
```

<210> SEQ ID NO 14
<211> LENGTH: 2763
<212> TYPE: DNA
<213> ORGANISM: Mus musculus

<400> SEQUENCE: 14

```
tttttttttt tttttttttt ttgttattgt aactgcttta atctgtcctc acactctccc     60

tgcaggaagc tctttataga aaacccaaat cctcatcttt gagcttgtcc tttagccagg    120

gcagcacctg gaagaggttg atgtggaagt cccgggcata agagggtacc agctgttgcc    180

gcctctggtc tctgcagaca tctactactc cccagctaat cacaccaact tgaatgaagc    240

ggcttctctt gtgaacaatg agagggcccc cggaatctcc tttgcatgtg ttggggtcag    300

catagggatc cacccctcct gtgcagagga accgtggagt gaccacctca gaggcatctt    360

tgaccttctc atagccttgg gcctttgtag catctctctc acaactggct tgtccccatt    420

cttgatgtac acctccttcc gagtcaggct cttcccttgc tcagatacaa acagagcttt    480

gacatccttc acagggagca actgttcctt gtgctgcttg caggtggctg tctgaggaag    540

cctcaaggct cgtgtggttc cctccgtgca ggggagacag atgggcctga gagtctggcc    600

atacttgagc ttgttcttga gcttgactag ggccacatca taatcataga actcagggat    660

cccttctgcc tttttcccat taatattgta tttggggtgg aacaggacct cttcaatctc    720

caggtcccgc ctctgacccc ccacgctgac cttgatggaa tgtttctgat catccaccat    780

gaagcagtgc gctgctgtca gcacgaagta ctcagacacc acggccccca tacaggtctc    840

atgtcctttc agagggcgag tgactgagat cttggcttgc catggttgct tatgataatc    900

gttgcctttt ttatgctccc acaccatgcc acagagactc agagatttgg tttcatcaat    960
```

-continued

```
catttggtag aaaacattct ccaggtcttc catatccttg actttaaaca catgatgctc   1020
attgtccttt ttggaagcta aggcattgat gttcacggag tccaccagag gcccgacccc   1080
aaacacatac acatccaggt aatcctccct gggatttttg ggatccctgc cgatgtccag   1140
caaggctcgg atgtcctgaa tgacagtgac agggtttcca cccatgttgt gcaagccatc   1200
agtcataatg atgatgacat ggcgggttct attccagcct tcaggcgggg catcccctgc   1260
ccagctcatc atgctataca cagcctggag agccctcttg gtgttggtcc ctgacttcag   1320
cttgtggtct tcataactga tttggttgag cttctctgtg acccagtcgg catcgctact   1380
cctctcatca gacactctga ccaacacttt ggggactgta gcatatgtca ggagaccata   1440
tcgtggcctc accccgtaac tcgccacctt ctcaatcaag ttggtgaggc accgcttagc   1500
ccctgtgaag ttgctgcttc cgatgctgtc tgatccatct agcaccaggt agatattcat   1560
ggagcccgag gggtctagga caatcttcct cttctgctgt tctcctgggc tgtgcccatc   1620
ctcagcatcg gctccttcga tggtctctgt cagggaggat aggaatgctt cggccacttc   1680
ttgagggctg tcatacatga aggaatcttg gcaggaaggc tctgtcccac tccatgagcc   1740
accttcttga cactttcgct tctgggagcc acgcaggaca agtccccggc tgcagtggta   1800
agtaacaatg tcttcaaggc ggtattggct acccaccttc cttgtcccaa taggaatacc   1860
gggattggga cagtatccag ctccatcatc acaaattgct gtttgcccat cccaccggcc   1920
attctcttgg caggtgcgat tagcagagcc ccggagaacg taaccatcat agcattgaaa   1980
agaaatctgg tcactcaggt tgtagaaggg ggaccggggc cagaattccc cattttcaaa   2040
gtcctgcggt cgtgggcagc gtattgctct gcattccgcc ttctggacaa tcttttggtc   2100
tcgggtctgc aggtcgctcc aggagcctgt ggatctgcag gttcgagtct gcacggggta   2160
tgggtagaag ccagagggac ataggtactc cagggcctga ccgccttgga gaagttgaaa   2220
ggagccgcct ttgatctcta ctccctccag agagcaggag acttggggcc gggcctcaag   2280
cactggagtt gcgctcacac ctccagagga gaagcctaag accaagagga cgaggcagag   2340
ctgggggctc tccattgtca tggaaagcac cagagagtcc agtggcccaa agccctctcc   2400
aggtcactct gggtgcctat ttgacctcct gtccaaactg aaacccaaat gctggatctg   2460
gctacacccc tttcccactg tcccctaacc ttttatgcaa tctgctctgg catctgcagc   2520
ctggccagcc taccctgcgc acgcagccac tgcttcccgg aacattcatg aaggagggcc   2580
ccagctgaac tgccaactga ggaaacagaa actatgtgag ccccaccctt gactgaccaa   2640
gggccagaac ttccctttca aagctccctc ttagccccca gacccctcct aacaagcaca   2700
gaccaccacc tccactaccc ccaatttaaa agatcagtct ttccatggac tgtgtgatgg   2760
agc                                                                 2763
```

<210> SEQ ID NO 15
<211> LENGTH: 2573
<212> TYPE: DNA
<213> ORGANISM: Rattus norvegicus

<400> SEQUENCE: 15

```
tttttttttt ttttttgtat ttgtattgta gctgctttaa tctgccctca ccctcccagc     60
aggaagctcc ttataagaaa cccaagtcct cgtctttgag cttctccttt agccagggca    120
gcacctggaa gagattgatg tggaagtccc gggcatagga gggcaccaac tgttgccgcc    180
tcgggtcttt gcagacatcc actactcccc agctgatcac accaacttga atgaagcggc    240
ttctcttgtg aacaatgaga gggcccccgg agtctccttt gcatgtgttg gggtcagcat    300
```

```
agggatctac ccctccggtg cacaggaacc tgggggtgac cacctcagag gcaactttga    360
ccttctcata gccttgggcc tttgtagcat ctctctcaca actggctttc ttttccccat    420
tcttgatgta cacctccttc cgggtcagct tcttcccttc ctcggataca aacagagctt    480
tgacgtcctt catagggagc aactcttcct tgtgctgttt gcaggtggct gtctgaggaa    540
gccgcaaggc tcgggtggtt ccctctgtgc aggggagaca gatgggcctg agagtctggc    600
tgtacttcag cttggtcttg agcttgatga gggcaacatc atagtcatag aactcagaga    660
ttccttctgc ctttttccca ttgatgtcgt aattagggtg gaacaggacc tcttcaatct    720
ccaggtcccg ccttttcccc tccacgttga ccttgatgga gtgtttctga tcttccactg    780
tgaagcaatg cgctgctgtc agcacgaagt actcggacac cacggccccc atacagttct    840
catgtccttt cagaggacga gtgactgaga tcttggcttg ccatggttgc ttgtaataat    900
caccgccttt ctgatgctcc cacaccatgc cacagagacc cagagatttg gtttcatcga    960
tcattttgta gaagacgttc tccagatcct ccatgtcctt gaccttgaac acatgctgct   1020
cattgttctt tttggaagcc aaggcattga tgttcacagg gtccaccaga ggcccgaccc   1080
caaacacata cacatccaaa taatcctccc ggggattttt gcgatccctg ccaatatcca   1140
gcaagtctcg gatgtcctca atgacagtga cagggtctcc acccatgttg tgcaagccat   1200
cagtcatgat gatgatgacg tggcgggttc gattccagcc ttcaggcgga gcatcccctg   1260
gccagctcat catgctgtat acagcctgga gagccttctt ggtgttggtc cctgacttca   1320
gcttgtggtc ttcataactg atttggttga gcttctctgt gacccagtcg gcatcactac   1380
tcctctcctc agacactctg accaagactt tggggactgt ggcatatgtc actagaccgt   1440
atcttggctt caccccataa ctcgccacct tctcaatcaa gttggcgaga caccgcttgg   1500
cccctgtgaa gttgctggcc ccgatgctgt cggatccatc cagcaccatg tagatattca   1560
tggagcccga ggggtccagg ataatcttcc tcttctgctg ttcccctggg ctgtgcccat   1620
cctccgcatc tgctccttcg atggtctctg tcagggagga tagaaatgct tcggccacct   1680
cttgagggct gtcgtacatg aaggaatctt ggcaggaagg ctctgtccca ctccacgagc   1740
caccttcctg gcaccttcgc tgctgggagc cacgtaggac aagtccccga ctacagtggt   1800
aagtgacagt gtcttcaaga cggtactggc ttcccacctt ccttgtccca ataggaatac   1860
ccgggttggg acagtatccc gctccatcat cacagattgc tgtttgccca tcccaccggc   1920
cattctcttg gcaggtgcga ttagcagagc cccggagagt gtagccatca tagcattgaa   1980
aagaaatctg atcactcagg ttgtagtagg gggaccgggg ccagaactcc ccattttcaa   2040
agtcctgtgg tcgtgggcag cgtattgctc tgcattctgc cttcttgaca atcttttggt   2100
cccgggtctg gaggacactc caggagcctg tggatttgca ggttcgagtc tgcacagggt   2160
atgggtagaa gccagaggga cacaggtact ccagggcctg accgtcttgg agaagttgga   2220
aggagccgcc tttgatctct actccctcca gagagcaaga gacctggggc cgggcctcaa   2280
gcactggagt tgcgctcaca cctccggagg agaggcctaa gaccaagagg actaagcaga   2340
gctggggacc ctccattgtc atggaaagcc cgtggccaaa agccctttcc agttcactct   2400
gggtggctac ttgacttgct gtccagactg aaactccagt gctggatctg gctacacccc   2460
tttcccaccg gcccctaacc ttttatgcaa tctgctctgg cacctgcagc ctggccaacc   2520
taccctgcac agacgctgct tcccggaaca ttcatgaagg agggcccctg ctg          2573
```

<210> SEQ ID NO 16

<211> LENGTH: 2334
<212> TYPE: DNA
<213> ORGANISM: Pan troglodytes

<400> SEQUENCE: 16
accccttata gaaaacccaa atcctcatct tggagtttct ccttcagcca gggcagcact 60
tgaaagaggt tgatgtgaaa gtctcgggcg tgagcaggta cctgcttttg ccgcttctgg 120
tttttgcaga catccactac tccccagctg attacaccaa cttgaatgaa acgacttctt 180
ttgtgaacta tcaaggggcc gccagaatca cctctgcaag tattggggtc agcataggga 240
ctcactcctc cagtacaaag gaaccgaggg gtgaccacct ctgagatgtc cttgactttg 300
tcatagcctg gggcatattg agcatctctc tcacagctgc ctttcttatc cccattcttg 360
atgtagacct ccttccgagt cagctttttc tcctcctcag acacaaacag agctttgata 420
tcctgtgcag ggagcagctc ttccttttgt tgctggcaag tggtagttgg aggaagcctc 480
aaagctcgag ttgttccctc ggtgcagggg agacaaatgg gcctgatagt ctggccatat 540
ttcagcttat tcttgagctt gatcagggca acgtcatagt cataaaattc aggaattcct 600
gctgcttttt tcccattaat gttgtagttg gggtgaaata ggactacttc tatctccagg 660
tcccgcttct cccctcctac gctgaccttg attgagtgtt ccttgtcatc cacagtgaaa 720
cagtgtgctg ctgtcagcac aaagtactca gacaccacag cccccataca gctctcgtgt 780
ccctttgaag ggcgaatgac tgagatcttg gcttgccatg gttgcttgtg gtaatcggta 840
cccttcctgt gttcccaaac catgccacag agactcagag actggctttc atcaatcatt 900
tggtagaaaa catcttccag gttttccata tccttgactt tgaacacatg ttgctcattg 960
tctttcttgg aagccaaagc attgatgttc acttggttca ccaaaggccc gaccccaaac 1020
acatagacat ccagataatc ctcccttggg tttttgcgat ccttgccaat gtatagcaag 1080
tcccggatct catcaatgac agtaattggg tccccgccca tgttgtgcaa tccatcagtc 1140
atgaggatga tgacatggcg ggtgcggttc cagccttcag gagggatgtc atctggccag 1200
ctcatcatgc tgtacactgc ctggagggcc ttcttggtgt tagtccctga cttcaacttg 1260
tggtcttcat aattgatttc attgagctgc ttcgtgaccc agtctgcatt actgctgtct 1320
ggatcagaca ctttgaccca aattttgggg tgtgtggcat atgtcactag accatatctt 1380
ggcttcacac cataacttgc caccttctca attaagttga ctagacactt tttggctcct 1440
gtgaagttgc tggccccaat gctgtctgat ccatctagca ccaggtagat gttcatggag 1500
cctgaagggt ccaggacgat cttccgcttc tgttgttccc ctgggccgtg cccatcctca 1560
gcatcgactc cttctatggt ctctgtcagg gaagacagga aagcttcggc cacctcttga 1620
ggggtgtcgt acatgaagga gtcttggcaa gaaggctccg tcccgctcca agagccacct 1680
tcctgacacg ttcgccgctg ggagccacgc agggtaagcc cccggctgca gtggtaggtg 1740
acgctgtctt caaggcggta ctggctgccc accttccttg tgccaatggg gatgcccggg 1800
ttggagcagt accccgctcc gttgtcacag atcgctgtct gcccactcca ccggccattc 1860
acttggcagg tgcgattggc agagccccgg agagtgtaac cgtcatagca gtggaaagag 1920
atctcatcac tcacattgta gtagggagac cggggccagt attccccgtt ctcgaagtcg 1980
tgtggtcttg gacagtggat tgctctgcac tctgccttcc tgacagtctt ttggacttga 2040
gtcttcaggg tgctccagga ccccgtagat ctgcaggtac gtgtctgcac agggtacggg 2100
tagaagccag aaggacacac gtactccagt gcctggccct cttggagaag tcggaaggag 2160
ccgcctttga tctctacccc ctccagagag caggattcct ggggctgggc caaaggccat 2220
ggagtggtgg tcacacctcc agacaagagg cccaagatga agggcatcag gcagagttgg 2280
gggctgagat tgctccccat ggcgttggaa ggcaggagag aagctgggcc tggg 2334

<210> SEQ ID NO 17
<211> LENGTH: 5101
<212> TYPE: DNA
<213> ORGANISM: Homo sapiens

<400> SEQUENCE: 17
tgagatataa ctgaagcttt atctggagtg ggggaatggg ggtgtggtca gttggggcac 60
ccaaagacaa ccatgctctc ggtgaaggcg ccgaggtcct ggcattgttt ctggttctct 120
tcgtcttggc attcgtcctc ctcgggccag tgctccaccc aagtgtcctt cccgatgatg 180
tagctgaggt tgggcttctc tccccagaaa tcggaggaga gaccccacat gaggtagtgt 240
ttcttctcct ccagcttcag ggcttctctg cacttgatgg ggctgatgaa cgtgcgctgc 300
tgtccaacct gcacctcatc cgagcctgac ttgatggtct gctcaatggc catgatgtac 360
tcgtcaaagt cattggacag ctgaaccttg accagtcggg tcttgtacac atagtccact 420
cctggctcac aggccttgtc cagccgttct tccagggtga ccttgtcatc cgacttttgt 480
atgaagcaat tctcctcagc acagcggcac agttcatcac ggcagagctt gttcagcttt 540
ccatcctcct tttccggatg gtagaaccgg gtacagcttt cctccaggtt gtaataggcg 600
tagaccttga ctgctccagg ctggataagc tctacattaa agtattggtg aactttgaaa 660
gctagacagt catcctcaga gtgtgagacc ttgtccaggt agatgatgag ggtgttccta 720
tcggagaagg ctttgtccag ctcatacttg gagatgtatc tgtcaacacc attggccagc 780
tgcttcaggt catctgtgtc tggagcaaag ccagtcatca tggatatgtc caatatagac 840
atagtggcat cctggtctcc ccggtacctg gtacagatct caaggatcat agtgttcttg 900
gcatcctgag gcctcttttc tgtttccggt gctggtttta tggtgacctt gaggtcgaat 960
ttattacagg tgagttgatc tttggcctta gcatggtaca ttgtcaccac cgacaaggtg 1020
ccttggcctt ttccttcagc tgtgactgtg aaaccctcat tttccttggt ctcttctgat 1080
cgcaggaggc tggcagattc ccagtggata cggtgggtga tcttggagct gcggctgggc 1140
agttggaggg acacatcaag gttcagttcc tggtggtcag gggcgtcctt ttggtattga 1200
gccaaggctt ggaacaccat gaaggtggcc tgggtagagc catagccacc accgtagtat 1260
ctctgttcat tgagccaacg cacgacggga ggcacaaagt caaagtcttt tagctgcagt 1320
agggccaaga gggcatagga tgtggcctcc acgttgtaga gctgcttacc agggtcctcc 1380
cagcggttct tatctttggc tgtggtcaga aatttgttaa gaagaggccc cttcagcctg 1440
cccatctggg ccagagcata gccagcaatg gccacagtgt aggatctctg taggttcatg 1500
tagttggctt caaggaagtc tcctgcttta gtgatgctgc ctggcaggct gttgacctgc 1560
tcctcgcaaa tatctttagc ctcctgcagc gagatgagaa caaaggccgt gagggccatg 1620
tctttctcgt tgttgttccg taatccacca atcatttctt ggtgtatcac gggcgcatcc 1680
tcctggaaga ccccgtcggg cttctgcttc tccaggatca gccatttaac agccccgcag 1740
aggacttggg agtcgatggc gatgaggttg acagccagag agaagacctt gaccacgtag 1800
gcggtcagcc aggtgctggg tgcccgtttc acgaaggccg caaaggcaga gctgggttgt 1860
ctgaaggcca gctgctgggt gtaccccttc ttgatgagct ccaaggcccc ctgccgcttc 1920
tctaggccga acttctccca ctgctccgtt tcatccaggt aatgcacagc gatgaccgtg 1980

-continued

```
ggcgtcatgc cgatcatgtt ctgttccccg cagcccgagg gggtcacaat gaggtgcttc   2040
agccgttccg cgtcgacggc atcctctgtc atctgggcca ctggggtccc ttgcaggaga   2100
attctggtct cagactcggt gtccgggact tggtcactga ggtctgcagg tgggatgtcc   2160
tctttctgca ctccttcacg gcccaggcgt tctggatcca gggtgcgaac agccacagtt   2220
ttgttcattc tgattccttc cggcacgacc ttcagggact tcctgacacc gtcactgatg   2280
aaatgatggt agacagcagc cttgacttcc acttcctgca ggccggtctt tagcggcacg   2340
atgacatatg gaacggacaa cgaggacttg ggggggatgg ttacggtctg ctggtgacgc   2400
ctcttggtgg tggccaggct gcagaaggct ggattgtgga gtagttccac cctcaccttg   2460
agctcttggt tctgccggta attgtagaga acggctcgga tttccacctg ctcgtttcga   2520
acaacagagt agggtagccg caggtcgatg aagaagtcct gcattactgt gacctcgaag   2580
gggtctgcca cacagatccc tttcttgtcc gacatgctca cagccagaat ctcccacgtg   2640
gtgatggagt ctttcaaaaa tatattcatg agcttcgtag agattccatt tttcggtggc   2700
tctttcaagt cctcaacgtt ccacagccag ctctctggga actcacttcg ggaaacgatg   2760
ttctcttctg caatgatgtc ctcatccagg ttactcctgg ccaggcccag gtggctggcc   2820
cgcgcgtgct gccgccgcag ctctgtgatg tagttgcagc agtccaggaa gaccttcttg   2880
cacgcctcgc ccagggagat gaaacgggtc cggcgctggc acgagaacct catggggttc   2940
tcccgcatgc cgtcctcgca gcacttgcgc agctccttgg ggtacttgcc gactttgtcc   3000
attcgcttct ccgtgagctg cacggaacgg cgtcggcggg cggctggctg cgggcactga   3060
agttctgccc tctgggcggt ctgctggcca ctgctgctcg tgaaggtcag ccctgcgtcg   3120
gagaagacac cggcgtaatc cttcccactg cccggggtgc agccgatgtc tgccttctcc   3180
accacgtccc agatcttact ctgcgtcagt ttgttcttct tattcagcac gaacacgccc   3240
ttgtccacgg ccaccagtac cacccgggcc ccgtggtcac cctctatctt cagggtcatc   3300
tgctgcccag gtacaggctg ccggtcttct gactggccgc tttttaccac cagcgagccc   3360
acgcaggagt ccttgacgtc cacccacacg gagtcggcca ccacctccct ctggccgctg   3420
gcaccgatca gcgtgtagta cgccaccagg cggaaggaag ggatgaagtc ggtggtgatg   3480
gacaggggca gcaccaccag gtcctggccg ggctctcgca cctggcgtcc cgccttcaac   3540
agcctgccct tgttcatgat caggtaggtg tagtagcgga tcttggcctc gtgggcgcgg   3600
tccattcgca ggaggaagtt gacgttgagg gtctccccgg gtctgagctc tgtacgtagc   3660
actgagagat gcaggtaatt gttggagttg cccacggtgc tgtagggcag agcctgcatg   3720
gtcctggtag cctgctctgc ctccgagagc tcctgcttct tcgtgcgcac cgtgatgctc   3780
aagggcttct ggctggggtg tgtgttgatg ctgagtttgg ccacgccatc tccctgggtt   3840
agagactgca cagtgtcctc gccctggact gccacgggga ctcggtaggc tggagagcca   3900
tcagggttcg tcacgaacac catgaggtca aagggcattc ctggtttgaa gtacttgggt   3960
gtcttggtga agtggatctg gtagggagag gtcacgatgg ggatcccgct gcgctctgcc   4020
tgcaccatgt cactgcctga gtgcaagatg acggtggcag acacgtacaa agacttcccc   4080
accaggtctt ctgctcgggg gttctgcacc ccgtccagca gtaccttccg gctcagcaca   4140
acctcccccg agccatcctc aatcggaatg cgcttgaggg attcaggcag ggaaatcctc   4200
tgttcgccat cctggatccc gaagatgaca aaggcagttc cctccacttt cttcccgtag   4260
aggaacctgg cggtgatggt gacctccagg cccttctcgt tatagatgta gtagaatttc   4320
tctgtaggct ccactatgac ctcgaaactg ggcagcacgt actccttcac ctcaaactca   4380
```

```
gtggagaaga cctgctgtgg tgagttttca tagtaggctc ggatcttcca ctggcccatg   4440

ttgacgagtt ccggaatgtc ccaagacaag ggcaagacgc caagctggtt ctgagaagac   4500

aaggagtcct gcttgaccgg gatgccttcc gggttctcaa tgttgaccat gaccgtccgg   4560

cccacgggta gcagcttgtg gttgacggtg aagatccgat agagaactgt ggagccaggg   4620

gtgtagatgg tcttgtctgt ctggatgaag aggtacccgc tctgcaggct gaccagcacc   4680

accttctcca ccacttgggt cccgaaggtg gcctgcacgg tcacgaactt gttgcgcccc   4740

ttttctgact tgaactccct gttggctggg atcgtgaagg tgacgttgcc catgtggttg   4800

gtggcagggg tcagcacagt cttctcactg gacagcacta gttttttgcc tgggaagtcg   4860

tggacagtaa cagtgactgg aacatcccct tgcgcgtcgt gggcctccag caccatggtc   4920

tcctcgctct ccagccgcaa gatgttgggg gtgatgatag agtacatggg actccccaga   4980

gccaggggga ggtgggttag tagcaggagc agcaggctgg gacctgaggt gggtcccatg   5040

gtgctgggac agtgcagggt cagagggaca gagggacaga gggagaggat ggggaggagt   5100

g                                                                  5101
```

<210> SEQ ID NO 18
<211> LENGTH: 5147
<212> TYPE: DNA
<213> ORGANISM: Mus musculus

<400> SEQUENCE: 18

```
tttttttttt tttttgaaat acaactgaag ctttattaga gggctgggct gtagtcagtt     60

gggacaacca taaaccacca tagattctgt gaatgcccca agttcttcgc actgtttctg    120

gtacttctga tcctggcatt cttctgcctc aggccagtgc tccacccacg tgtccttccc    180

aatgatgtag ctggtgttgg gcttttctcc ccagaggtca gaggagaggc cccacatgag    240

gtacttcttc cctttctgca gcttcagggc gtttctgcac ttgatgtggc tgatgaactt    300

gcgttgctgc cctgcctgca cctcatctga gcctgacttg atgacctgct ggatggtcat    360

ggtgtactca tcaaaatcat ccaacagctc tatgttggtt agctcggtct tgtacacata    420

gtcgactccg ggctcacaag ccttgtctag ccggacattc aggttgatct tctcctgtga    480

ctgttgcatg aagcagttct cttcagcaca ccggcacatt tcactgtggc acagcttgct    540

gagcatccca tcgtccttct ctggatgata gaaccgggtg catgattcct cgaggttgta    600

ataggagtag accttgaccg acccgggctg gataagtccc acattaaagt actggtgaac    660

tttgaaggtc aggcagtctt cttcggtgtg tgaaatcttt tctaggtaga tgatgagggt    720

gttcttgttg gagaaggctt tgttcatctc gtacttggag atgtatctat ctactccaga    780

ggccagcagt tccaggtcct ttgtgtctgg agcaaagcca gtcatcatgg agatgtccag    840

gatggacata gtggcgtcca catctcccaa gtacttggtg cagatttcaa ggaacatggt    900

attcttggct tcctcgggct tcttggctgt ctcaggggct ggtcttatgc tgaccctgag    960

gtcaaacttc ttgcaggtga ctttgctttt gagtttggca tgatacactg ccaccaccga   1020

caatgtgcct cggccttttc ctttggctgt tagagagaag gcctcatttt gcttggtctc   1080

ttccgatcgc aggaggttgc cattttccca gagcaggcga aacgtggttg cagagctacg   1140

gctggggagg tggaaggaca catccatgtt caagtcctta tggtcaggga catctgtttg   1200

atattgggcc aaggcttgga ataccatgaa ggtagcctgg gtggagccat agccgcctcc   1260

gtagtatctt tgctcattga gccagcgcac tacagggggc acagagtcaa agtctttcag   1320
```

-continued cagcagcagg gccaggaggg cgtaggatgt ggcctctacg ttgtagagct gctggtcagg 1380
ctcctcccag cggttccgat ctttggctgt gttcagaaac ttgccgaggt aaggttcctc 1440
cagtttgttc atcagggcca gggcataccc agcaatggcc actgtgtatg gtctctgcag 1500
gttcatgtaa ctggcttcaa tatactcccc tgccttgttg atgctcccag gaaggctatt 1560
gacctgcccc tcacagatgt ccctggcttc ctgcagtgcg atgaggacga aggctgtgag 1620
tgacacatct gcctccttgg cgttccggaa gccaccaatc atttcttggt gaatcacggg 1680
cccatcctcc tgaaagacac catccggctt ctgtttctcc agaatcaacc atttaacagc 1740
cccacacagg acgtgagagt cgatggcgat gaggttggca gctagagaga agaccttgac 1800
cacgtaggct gtcagccagg tgctgggggg ccggttgttg aaggcagcat aggcagagct 1860
gggctgtttg aaggccagct gctgggtgta ccctttcttg atgagctcca gggcctcttg 1920
cctcttctct atgccgaact tctcccactg ttcggtctgg tccaggtagt gtaccgcaat 1980
gactgttggt gtcatgccaa tcatgttctg ttccccacag cctgcggggg tcacgatcag 2040
gtgtttcagc cgctccccgt ccacagcatc ttcagccatc tgaaccaccg ggctcccttg 2100
caggataatt ctggtctcag agtctgtgtc tggcacttgg tcgctaaggt ctgcggcagg 2160
cacatccacc ttctgcactc cccctgacc gagcttctct gggtccagtg tatggatggc 2220
cacagttttg ttgattctca ttccttctgg cacgaccttc agtgtcttct tgacaccatc 2280
actgatgaag tgattgaaga cagcagcctt gacctccacc tcttgttggc cgatcttcaa 2340
ggggacaatg acatacggta cagccaccga ggacttggga gggattttga tggtctggaa 2400
gtagcgattc ttggcggtgg ccatgctgca gaaggctgga ttatgcaaca gttccaccct 2460
caccttaagt tcctcctgtt cacggtagtt gaagagcaca gctctgatct ccacctgttc 2520
gttgcgcact acagagtagg gcagccgcag gtcaatgaag aagtcctgca tcactctgat 2580
ctcatagggg tctgccacac agatcccttt cttgtctgac aagctcactg ccagaatctc 2640
ccaggtggtg atggaatctt tgagaaagat gttcatgacc ttcgtagaga ttccattttt 2700
ctctggttct ttcaactctt ctatggtcca caaccagctc tgtgggaagt ggcttctaga 2760
gataatatct tcttctggaa ttatgtcttc ctccaattca ctcctggcca ggcccagcac 2820
gtggtctctt ctgtgttgtt cacgcagctt ggtgatgtgg ttgcagcagt ctatgaaggc 2880
ctttatgcag ttctcgccct gggtgatgag gcgtgcccgg cgctggcagc tgtatctcat 2940
agggatatcc cgcataccat cctcacaaca cttccgaaga cccttgtcag tgtactgacc 3000
agctttgtcc atccttcttt ccatcaactg tactgagcga cggcggcggg ctgctggctt 3060
ggtgcactca agatctgctc tctgttcagt ctgcagtcct tggcttgtct tgaaggccag 3120
gcctgcatcc atgaagacac cagcatagtt cttcccactg cctggggtgc agccaatgtc 3180
tgccttctct accacatccc agatcttgct ctgtgtgagt ttgttcttct tgttcagcac 3240
aaacactccc ttgtccacag ccactagccc cactcgggcc ccctggtttc cttcaatcct 3300
gagtgtcgtt tgttgcccag gtgcgagatg gttatctctt gggtcaccct tcaccaccag 3360
cgtgccaata caggaatcct tcacatccac ccacacagag tcagccacca cctccctctg 3420
gccactagct ccaatcaggg tgtagtaagc caccaggcga aatgaaggaa taaactctgg 3480
agtgatgggc agggacaaga ccaccaggtc ctggccaggc tcccgaacct ggcggcctgc 3540
cttcaggagc ttccccttgt tcataaccag gtaggtgtag tatcggatct tggcctcatg 3600
gcctgggtct gtgcgcaggt ggaagttgac attgaggttg tcccccggct tgagctccat 3660
tcgtgacact gacaagtgta ggtagttgtt ggagttgtgc atagtgctgt agggatgggc 3720

```
ctccattgtc ttggtggcct gccgtgattc tgggagagtg tccttcttgg tgcggactgt   3780

gatggtcagg ggttggcggc tgttgggtgt gttgatgctt agcttggcca cgccatcatc   3840

ttgggtgaga gcctttgcat tagatccctg agtgaccacc agcactttgc tggccggaga   3900

gccatcgggg ttggtcacga acaccatgag gtcaaagggc atggctggct tgaagaattt   3960

gggtgtcttg gtgaagtgga tctggtacgg ggaagtgaca atcgggatcc cactgcgctc   4020

tgcctctacc atgtcactac ctgagtgcag gatgacagtg acggagacat acagggactt   4080

ccccaccagg gcgtcggcgt tggaaggccg tacccccctcc atcagcacct tccgggtcag   4140

cactgcatcc cccacaccat cctcaatcac tacgcgcgtg agggagtggg ccagagaaat   4200

cttcttatcg ccatcctgga ccccaaaaat cacgaaggct gtcccgtcca cgtttttccc   4260

gtacaggaac ttggctatga tggaaacttc caggccattt gggtcatcga tgtaataaaa   4320

tgtctctgtg ggctccaccc ggacctcaaa actgggcagc acgtattcct tcacctcaaa   4380

ctctgcggag aagatctgct tcggcgcatg ttcgtaaaag gctcggatct tccactgccc   4440

catgttgacc agttcaggaa tgttccaaga caaaggcaag atgccgtgtt ggttgttgga   4500

agacagaatg tctctcttga caggaatgcc atcgggggtc tcaatgagga tgacgactgt   4560

cttgcccacg ggcagtaggt tgttgtccac agtgaagatc cgatataaga cagtggagcc   4620

aggggtgtag atggtcttgt ctgtctggat gaagaggtac ccactctgga agcttaccat   4680

cactgctttc tccaccaccg tttccccgaa gtttgccacc actgtcacgt acttgtgccc   4740

ctccttatct gagttgaatt ccttactggc tggaatcttg atggagacgc ttctcagatg   4800

tccactggct cctgtcaaca ctgtcttctc actggtcagc acttgcctct ttaggaagtc   4860

ttgcacagtg actgtgactg ggatgtcacc ctgagcatcg tgggcctcca gtacgatggt   4920

ctcttcgctc tccagccgta ggacattggg agtaatgatg gaatacatgg ggatccccag   4980

agctaatggg gagctggcca acagcagcag tagcactagt agctgggacc ctgaagctgg   5040

tcccatagtg aaggaaaaag gtggaaggaa tgaaggggta aggggcaggg gtgggcagag   5100

gcgagctggg gctgtagccg ctggctcttt atatggctct cctctct                5147
```

```
<210> SEQ ID NO 19
<211> LENGTH: 5091
<212> TYPE: DNA
<213> ORGANISM: Rattus norvegicus

<400> SEQUENCE: 19

ttttttttt tttttttga tgggtaaaat acaactgaag ctttattgga ggttgtggtc     60

agttggggca gccgaaaacc accattgttt ctgtgaatgc cccgaggtct tcgcactgtt    120

tctggttctt ctgatcctga cattcctctg cctcgggcca gtgctccacc cacgtgtcct    180

tcccaatgat gtagctggta ttgggctttt ctccccagag gtcggaggag aggccccaca    240

tgaggtactg cttccctttc tgcagcttta gggcgtttct gcacttgacg tggctgatga    300

accttcgttc ctgacctgcc tgcacctcat ctgagcctga cttgatgacc tgctcgatgg    360

tcatgatgta ctcatcaaaa tcatccgaca gctctatcgt cgttagcttg gtcttgtaca    420

cgtagtccac tccaggctca caagccttgt ctagtcgttc attcaggctg acctgatcct    480

gtgactgatg catgaagcag ttctcctctg cacagcggca catttcattg tggcacagct    540

tgctcagcat tccatcgtcc ttctccggat gatagaaccg ggtgcatgac tcctctagat    600

tgtagtagga gtagaccttg accgaccccg gctggataag tcccacgtta aagaactggt    660
```

-continued

```
ggactttgaa ggacaggcag tcttcttcgg agtgtgagat cttttctagg tagatgatga    720
gggtgttctt gttggagaag gctttgtcca tctcatactt ggaaatgtat ctgtctactc    780
cagagctcag cagttccagg tcgtttgtgt ctggaataaa gccagtcatc atggagatgt    840
ccaggatgga catagtagca tccacgtctc ccaagtacct ggtgcagatg tcaaggatca    900
tagaactctt ggcatcctgg ggcttcttgg ctgtctcagg ggctggtttt atggtgaccc    960
tgaggtcaaa cttcttgcag gtggctttgc ctttgacttt ggcgtgatac actgtcacca   1020
ccgacagtgt gccttggcct tttcctttgg ctgtcagaga aaagccctca ttctgcttgg   1080
tctcttctga tctcaggaga ctgccacttt cccatagcag gcgaaacaca gttggggagc   1140
tgcggctggg gaggtggagg gacacatcca tgttcaagtc cttgtggtca gggacatctg   1200
tttggtattg agccaaggct tggaatacca tgaaggtagc ctgcgtggag ccatagccac   1260
ctccgtagta tctttgctcg ttgagccagc gcaccacagg aggcacagag tcaaagtctt   1320
tcagcagcag cagggccagg agggcgtagg aggtggcctc cacattgtag agctgctggc   1380
caggctcctc ccagcggttc cgatctttgg ctgtgttcag aaacttggtg aggtaaggtt   1440
cctccagttt gttcatcagg gccagggcat acccagcaat ggctactgtg tatggtctct   1500
gcaggttcag gtaactggct tcaagatact cccctgcctt gttgatgctc ccgggaaggc   1560
tgttgacctg cccctcacag atatctctgg cttcctgcag tgcgatgagg acaaaggctg   1620
taagcgacac atctgcctcc ttggtgttcc ggaagccacc aatcatttct tggtgaatca   1680
ctggtccgtc ctcctgaaag acaccatctg gcttctgttt ctccagaatc agccatttga   1740
cagccccaca caggacctga gagtcgatgg cgatgaggtt ggcagccaga gagaagacct   1800
tgaccacata ggctgtcagc caggtgctgg gaggccggtt gttgaaggca gcataggcag   1860
agctgggctg tttgaaagcc agctgctggg tgtacccttt cttgatgagc tccagagctt   1920
cttgcctctt ctctaggccg aatttctccc actgttcggt ctgatccaga tagtgtactg   1980
caatgaccgt gggtgtcatg ccaatcatgt tctgctcccc acagccagag gggggtcacga   2040
tcaggtgttt cagccgctcc ccgtccacag cgtcctcggc catctgagcc accggggtcc   2100
cttgcaggag aattctggtc tcagaatctg tgtctggcac ttggtcactg aggtctgctg   2160
caggtacatc ctccctctgc actccccctt gaccgaggtg ttctggatcc agtgtacgga   2220
cagccacagt tttgttgact ctcattcctt ctggcacgac cttcagtatc ttcttgacac   2280
catcactgat gaagtggttg aagacggcgg ccttgacctc cacctcctgg aggccgatct   2340
tcaaggggac aatgacataa ggcacagcca cagaggactt gggagggatt tcgatggtct   2400
ggtagtaccg cttcttggca gtggccatgc tgcagaaggc tgggttatgc aacagttcca   2460
cccttacctt aagtttctcc tgttcacggt aattgaagag cacagctctg atctccacct   2520
gttcattgcg caccacagag tagggcagtc gcaggtcaat gaagaagtcc tgcatcactg   2580
tgatctcata ggggtctgcc acacagatcc ctttcttgtc ggacaagctc actgccagaa   2640
tctcccaggt ggtgatggaa tctttgagaa agatgttcat gaccttcgta gagattccat   2700
ttttctctgg ttctttcaac tcttctatgg tccacaacca gctctctggg aagtggcttc   2760
tagagataat atcttcttct gggattatgt cttcatccac atcactcctg gccaggccca   2820
gcacatggtc tcttctgtgc tgctcacgaa gcttggtgat atagttgcag cagtccatga   2880
aggccttcag gcagctctcg ccctgggtga tgaggcgagc ccggcgctgg cagctgtact   2940
tcatagggat atcacgcatg ccatcctcac aacacttccg cagacccttg tcggtgtact   3000
gaccagcttt gtccatcctc ctttccatca actgcactga gcgacggcgg cgggcagctg   3060
```

-continued

```
gcttggcgca ctcaggatct tctctctgat cagtctgcag gccttggttt gtcttgaagg   3120
tcaggccagc atccatgaag acacccgcat agttcttccc actgcctggg gtgcagccaa   3180
tgtctgcctt ctctactaca tcccagatct tgctctgtgt gagtttgttc ttcttgttca   3240
gcacaaacac cccttgtcc acagccacta gccccactcg ggccccctgg ttcccctcga   3300
tccttagtgt cgtttgatgc ccaggcgcgg gctgtcggtt atctcttggg tcacctttca   3360
ccaccagcgt gcctacacag gagtccttca catccaccca cactgagtcg gccaccacct   3420
ccctttggcc attagctcca atcagggtgt agtaagccac caggcggaag gaaggtataa   3480
attctggagt gatgggcagt gacaagacca ccaggtcctg gccaggctcc cgaacctgac   3540
ggcctgcctt cagtaacttc cccttgttca taaccagata ggtgtagtat cggatcttgg   3600
cctcttggcc agcgtccgtg cgcaggtgga agttgacatt gaggttgtcc ccaggcttga   3660
gctccacccg agacactgac aagtgcaggt agttgttgga attgtgcata gtgctgtagg   3720
gctgggcctg catcgtcctg gtggcctgcc gcgcgtccgg gataccctcc ttcttggtgc   3780
ggaccgtgat agtcaggggt tggcggttgt tgggtgtgtt gacgctcagc ttggccacac   3840
catcatcctg ggtgagagcc tgcgcgtcgg atccctgagt gactactggc actctgcggg   3900
ctggagagcc atcagggttg gtcacaaaca ccatgaggtc gaaaggcatg gctggcttga   3960
agaatttggg tgtcttggtg aagtggatct ggtacgggga agtgacaatt gggatcccac   4020
tgcgctctgc ctctaccatg tcgctacctg agtgcaggat aacagtgaca gagacgtaca   4080
gggacttccc cactagggct tctgggctgg agggccgtac cccgtccatc agcacttttc   4140
ggctgagcac tgcctcccct gaaccatcct cgatcagcac gcgggtgagg gactgggcca   4200
gagaaatctt cttatcctca tcctggaccc caaagatcac gaaagctgtc ccgtccacgt   4260
tcttcccata caggaatctg gctgtgatgg aaacttccag gccctttggg tcatcgatgt   4320
aataaaattt ctctgtaggc tccaccagga cttcgaaact gggcagcacg tattccttca   4380
cctcaaactc tgcagagaag gtctgctttg gtgcatgttc atagaaggct cggatcttcc   4440
actgccccat gttgaccagt tctggaatgt tccaagacaa aggcaagatg ccatattggt   4500
tgtgggaaga tagaatgtct ctcttgatgg gaacgccgtc cggggtctca atgacgatga   4560
cgactgtctt gcccacaggc aataggttgt tgtccacagt gaagatccga tagaaaacag   4620
tggagcctgg ggtgtagatg gtcttgtctg tctggatgaa gaggtaacca ctctgaaagc   4680
ttactagcac cgctttctcc accactgttg ccccgaagtt tgccaccact gtcacgtact   4740
tgtgcccctt atctgcattg aattccttac tggctggaat cttgatggag accctgttca   4800
gatgtccagt ggctcctgtc aacactgtct tctcactggt cagcacttgc ttctttagga   4860
agtcttgcac agtgacagtg actgggacat caccctgagc atcatgggcc tctagtatga   4920
aagtctcttc actctccagc cgcaggacat tgggagtaat gatggagtac atggggctcc   4980
ccagagctag cagggagctg gccaacagca gcagtagcac tagtagctgg gaccctgacg   5040
tgggtcccat ggtaaaggac aaaggtggaa ggagtgaggg gtaaggggta g            5091
```

<210> SEQ ID NO 20
<211> LENGTH: 2693
<212> TYPE: DNA
<213> ORGANISM: Homo sapiens

<400> SEQUENCE: 20

```
tttccttttt ttaaagagtt ctcagacctt tcaaaaggtc tcagacccta agcaccatgt     60
```

-continued

```
tctctaatga ataagattgt acaaccaatg ttaatcagct tctcaggtag gtaaccttac    120
cttatacaac tcataaggct aggtattaag ttggactata taaaattgat gtttttcttt    180
gtaaaatatg atcaaataga aggaatttca cataatttaa actaatagtt tatgttcatt    240
ctattctgct actgaacact atctatatta ttcctttcat ctaactggat tttgtaccc    300
attaaccaac tcctctttat ctcccttcag tcctctggta aactagtagt tttggttac    360
aaatataata tgttttcccc cttggacaca tggatttaaa tcgtagagct aagactagta    420
aaagcaactg ctgtgcacgt ggctggtgct cagcatttgc tgaatgaatg tatgcacacc    480
taagcaaata accaaactaa acataacaat gtaaataaga gttaaattgc atggtacaga    540
cgtgtggtca tggacctggc agaatatgtt aaccatacaa agccgtttga aaattacttt    600
gaagtttttt aaaccaacat tctgttttta atttaatttt gttttttttt agaagagatt    660
ggcattttcc gtgggataaa gcagttctgg cgtatttcac tgttgacttc tcattaggga    720
acaaaaaatg gaaacatcac aggagtttaa ggaagaaaaa tttaaaaaaa aattatagac    780
ctaagagaga agagacttca gaggttggta ggattttcat gaagcatgtt gctatttact    840
tggcagctaa gattatcttc aggggtagga tctgaaggta ctagtgtttt cttcttccac    900
tggagctcag agaagccaac agctctattt ttcattgggg aactctaggg ctggcaatcc    960
ttcagaaatt ttttgtttac tgatttcaca ggcaattccc tcaaatttga atgggcaggc   1020
acacaaacac tttccatcca ttagaatcac tgtacctcca ttttggcatg tgtggcattt   1080
tcttacacta aattcattga tatagtcttc aatggctctt tccaagtttt gtttctttag   1140
gtgtgcattt ttcattttca ctggaaccag attatatata ggagacagtt tttgactaat   1200
gagaacagga gcatcattta tggaagaggc ccagttgaca aagtcagtca catcaatcac   1260
ggttcctcgg agaagctttt ctttcagttc aaatgcatat tttctggttc cacctcttat   1320
gagtgaaaca acatcatcta tgaggttttc actggtgatg tttacagctc taccctctcc   1380
cctctttaca caatcatctt tattaaattc agctccaaca gagatttcag agaaagccag   1440
agatacatcc agatgatacc caaggcatct ctttatgtct tttagttcaa cacctttccg   1500
cttcatggaa gctttatcca aaacatatat tagttcatag agtcctccta gagacccaga   1560
gctactgtag tgagttccat aggtttccaa aaaggcaaaa tattctccct tttcataggt   1620
agttggcaaa gcttttatat catccacaaa agttgttgtg agcacaacat cgcgatttct   1680
cattacaaat cttcccagat gaatttctcc tttcacatgc agaaacattt tttccttctt   1740
tgaagaatat gacaaaaata gttggtaagt ttcatttttg gaatatgaaa accgaaaact   1800
acccttgcca tgtaaagaaa ttgaggaggc tgtttcctca caacattgtt cagctttatt   1860
tgtttcagtg ggtgtaaatt ttagagatat agctgcatta aaatttgatg tcttctcttg   1920
gatgatactt ttaaatgctt caatttgttc ttcgtaatgt tcggttctga aatttttctc   1980
gcctttggtt tcatagatca aagaagccac gttccaaggt cttcggtagt atgtcagagt   2040
gtttccatcc cgatcccggt tacagagtcc attgtagaac tcattgtcaa aaggtgtgct   2100
taggggatcc atccctaaaa tgttgatccc atagcctgct gttcgtgcca gctcagactc   2160
ttctaccact ctgtctctgc aggggggacg gggctcactt tcacaatcat cctcatctga   2220
aaagtctccg cagtcattgt caccattaca ccgaagtcgc atctttatgc atctgcctgt   2280
actgcattga aagtcatttc cgcagtcatc ctcagcatcc tcacagggct ctgtgggcac   2340
acactgtcgt ctgtctccca cagcgtcggt gcatcttttc ccattaaatt gtccaaagac   2400
ctcaatgctt cttgaacgaa acatttgtct gagacaagga tcgcattgtg accattcact   2460
```

ccaggggctc attctgcagt ctatgtgtga tgcagagcca ctgctttctg ttagctctgg 2520
gtcataactg gtcgtgtact gtgctgtgag gatgcttatt tctaaaatgc agattgcaac 2580
tgcaaagctc cggcaggctg acatgctgct cttgctgggt ggctgcgagt ggggtggcag 2640
ggcaggtctg gtaaggcatt tatttgcaaa gggccagagg acagggaaca agc 2693

<210> SEQ ID NO 21
<211> LENGTH: 1767
<212> TYPE: DNA
<213> ORGANISM: Mus musculus

<400> SEQUENCE: 21
cttttttttt ccccccttcca tgtgaaccag ggtttgcttt gtttcctgaa ggctatattt 60
tttgatggat ttcgcaggcc attcccctaa acatcattgg gcaggagcac aggcactgcc 120
catccagaag aattatagta cctccattta gacatgggta gcacctttta gtactgaatt 180
catctatata gtcttcaaca gccttttcca aattttgctt ctttatgtat gcatctttta 240
ttttcaaagg aatgagatta tatatagggg acattctttg actgatgaga gctggagcgt 300
ttgccaggga cgaggcccag ttggcgaagt cagtcttatc aaatgtcttg tctcctctga 360
gaatcttctc tttcaggaga attgcttgct ccctagtccc tcctcttatg aatgaaatga 420
catcatctat gatgttatcg cgggtgatgt ttacagtttt cccattatct gtctttatgc 480
aaccatccgc attaacactt gctgtgactg atgcatcctt taagtcgtct tgtagaggaa 540
tacgtaaatc catattaaat ccaagacaat gttttacatc attcaggtca acacctttct 600
ctttcatgga agctttatcc aagacataga caatttcata ttgtcctccc agggacccag 660
aggtactgta gtgagtccca taggtttcca aaaatccaaa atattctccc ttttcatagg 720
aagttggtag agcttttaca tcatccagga aagttgacct cagcacaaca tcccgattcc 780
tcattacaaa tctccccagt tggaccactc ctctcaagtg cacaaacatc tttttcgact 840
gcgaaaaata agatgatagt cttcgaaaat tttttcccat gaaatatgaa aatttaaatt 900
tagctgaaat gtttgtaggt tttgaagagt gttctgctgg ggagacttcc ccagctccct 960
tttcaggtac ttcggtggct gaaaatttta gggcaaaatc tgcattaaaa ttcgaggtct 1020
tctctcggtt gatggctttg aatacttcca agtgttcgtc atagttctca gttctgaaac 1080
ttttatcagc cttggtttca tagatcagag aaactacatt ccaaggtttg cgatagtatg 1140
tcttttcgtc tcgtacccgg tcacagagtc cgttgtagaa ctcattgtca aaaggtgttc 1200
tcaggggctc catccctaag atgttgatcc catagcctgc tgttagtccc agctctgatt 1260
cttccgctac tcggtcacgg catggggtgc gtgggtcatc gtcacagtca ttctcatcag 1320
aataatctcc acagtcgttg tcaccattac acagaagtct cctctttatg cacctgcctg 1380
tctcacactg aaagtcattt ccacagtttt cctgtatctc ttcacactcc tgggtgggtt 1440
cacagccttg tctgtctccc aaaacatcaa cacagctttt cccattaaac tgtccgaagg 1500
ctaaaatgct tcttgagcga aacctttgtt tgaggcaagg atcacactct gaccaattgc 1560
tccatgggct cattctgcag tctatcggta tgggatagtg ttgttcttgt tcttctctgg 1620
aaacgggtat tggcatctgt gcattgacac ccaaggcaaa gatggcaagg gctaaggtga 1680
tggccatgcc tgaggccatg ctgctcctcc tggggagccc tggaggcttg caaagcattc 1740
ctttgcagcc ggaggacaag gggcagt 1767

<210> SEQ ID NO 22

<211> LENGTH: 2083
<212> TYPE: DNA
<213> ORGANISM: Rattus norvegicus

<400> SEQUENCE: 22

```
tgtttttaat ttaactctgt tttattagcg agagattggc attgcctgtg ggaaaaggca     60
gtcctggcat atctcactgc cgattcttca ttagggataa aaaaaaaaat ggaagcatta    120
taggcattaa agaggggaga aaggcactgt agacctgaaa cagagacgac atcagaggtt    180
ggtaggattt ccatgaagca agctgctttc tacttggcag tgaggattcg ctctagggta    240
ggatgctaag ttggaaagtc ctggggtttt ttcttttctc tctctcttct ctctcctctc    300
tcttcttctt tttttgtcct tttttccacc ttccatgtga accaggtttt gctttgtttc    360
ctgaaggcta tctttgttta ctgatttcgc aggcaatccc cttaaacttg attgtgcagg    420
agcacatgca ctgtccatcc agaagaattg ctgtgcctcc gttttgacat gggtagcact    480
ttctagcact gaattcatta acatagtctt caatagcctt ttccatattc tgtttctttg    540
cgtatgcatc tttcattgtc aaaggaatga gattatagat aggggacagt ttttgactaa    600
tgagagctgg agcgtcatcc aaggatgagg cccagttgat gaagtcgttc acatcaatcg    660
tcttggctcc tctgagaagc ttctctttca ggagaactgc ttgcttcctg gtccctcctc    720
ttatgaatga aataacatca tctatgatgt gatcgcggct gatgtttact actttaccat    780
cccctgtctt taagcaatca ctgtgattaa cattggctgt caatgatggt ccttctaagg    840
cagtttgtag aggcgtatat agagaaacat ccaggttaaa cccaagacac cgctttacgt    900
cgctgagttc aacacctttc tctttcatgg aagctttatc caagacatag atcagttcgt    960
agagccctcc cagggaccca gagctactgt agtgagtccc ataagtctcc aaaaacccaa   1020
aatattcgcc cttttcatag gaaactggta aagcctttac atcatccagg aaagttgtcg   1080
tcagcataac gccccgattc ctcatgacaa atctccccag ttgaatcatt cctctcacgt   1140
gcagaaacat ctttttcgtc tgtgacaagt aggatgacaa tcgttgaaaa ttttctttct   1200
tgaaatatga aaattgaaaa tcaacagaag agtctttagg ctttgaagag tttttttctg   1260
ggctgacttc atcaactcca acttttttta taggtgcttc agtgattgtg aattttagag   1320
ctaaattagc attaaaactc gtggtcctgt ctcggacgat ggttttgaac atttcaaact   1380
gttcttcata attctcagtt ctgaaatttt tgtcagcctt ggtttcatag gccagaaatg   1440
ctacgttcca aggtttgcga tagtatgtca aagtgtttcc gtcccgtacc cggtcacaga   1500
gtccattgta gaactcattg tcaaaaggcg tgcccagggg atccatccct aagatgttga   1560
tcccatatcc tgctgttcgt cccagttccg attcttctac cacccggtca cggcacggga   1620
ggcgcgggtc actttcacag tcactctcat cagaaaaatc tccacagtcg ttgtcaccat   1680
tacacagaag tttcctcttt atgcacctgc ctgtttcaca ctgaaagtca ttcccacagt   1740
tttcctgtac ctcttcacac tcctgagtgg gttcacaatg ttgtctgtct cccaaagcat   1800
cagcacagct ttttccctga aactgtccaa agacttccat gcttcttgag cgaaaccttt   1860
gtttgaggca aggatcacac tgtgaccact gactccatgt gctcattctg cagtctattg   1920
gtaggagggc gtctgctgat ggctcttccc ggggagtggg ctctggggcc tgtgcattga   1980
tctccaaggc aaagattgca atggctaggg tgatggtcac gcctgaggcc atgccgctcc   2040
tcctaggcag ccctggagtc ctgagaagca tttctttgca acc                     2083
```

<210> SEQ ID NO 23
<211> LENGTH: 16

<212> TYPE: PRT
<213> ORGANISM: Unknown
<220> FEATURE:
<221> NAME/KEY: source
<223> OTHER INFORMATION: /note="Description of Unknown: RFGF
hydrophobic membrane translocation peptide"

<400> SEQUENCE: 23

Ala Ala Val Ala Leu Leu Pro Ala Val Leu Leu Ala Leu Leu Ala Pro
1 5 10 15

<210> SEQ ID NO 24
<211> LENGTH: 11
<212> TYPE: PRT
<213> ORGANISM: Unknown
<220> FEATURE:
<221> NAME/KEY: source
<223> OTHER INFORMATION: /note="Description of Unknown: RFGF
analogue peptide"

<400> SEQUENCE: 24

Ala Ala Leu Leu Pro Val Leu Leu Ala Ala Pro
1 5 10

<210> SEQ ID NO 25
<211> LENGTH: 13
<212> TYPE: PRT
<213> ORGANISM: Human immunodeficiency virus

<400> SEQUENCE: 25

Gly Arg Lys Lys Arg Arg Gln Arg Arg Arg Pro Pro Gln
1 5 10

<210> SEQ ID NO 26
<211> LENGTH: 16
<212> TYPE: PRT
<213> ORGANISM: Drosophila sp.

<400> SEQUENCE: 26

Arg Gln Ile Lys Ile Trp Phe Gln Asn Arg Arg Met Lys Trp Lys Lys
1 5 10 15

<210> SEQ ID NO 27
<211> LENGTH: 2289
<212> TYPE: DNA
<213> ORGANISM: Macaca fascicularis

<400> SEQUENCE: 27
atggggagca gtctcagccc ccagctctac ctgatgccct tcatcttggg cctcttatct 60
gcaggtgtga ccaccactcc attgtcttcg gcccagcctc aaggatcctg ctctctggag 120
ggggtagaga tcaaaggtgg ctccttccga cttctccaag agggccaggc actggaatac 180
gtgtgtcctt ctggcttcta cccgtaccct gtgcagacac gtacctgcag atccacgggg 240
tcctggagca ccctgcagac tcaagatcga aaaactgtca agaaggcaga gtgcagagca 300
atccgctgtc cacgaccaca ggacttcgag aacggggaat accggccccg gtctccctac 360
tacaatgtga gtgatgagat ctctttccac tgctatgacg gttacactct ccggggctct 420
gccaatcgca cctgccaagt gaatggccgg tggagtgggc agacagcgat ctgtgacaac 480
ggagcggggt actgctccaa cccaggcatc cccattggca caaggaaggt gggcagccgg 540
taccgccttg aagacagcgt cacctaccac tgcagccggg ggcttaccct gcgtggctcc 600
cagcggcgaa catgtcagga aggtggctct tggagcggga cggagccttc ctgccaagac 660

-continued

```
tccttcatgt acgacacccc tcaagaggtg gccgaagctt tcctgtcttc cctgacggag    720

accatagaag gagtcgatgc cgaggatggg cacagcccag gggaacaaca gaagcggagg    780

atcatcctag acccttcagg ctccatgaac atctacctgg tgctagatgg atcagacagc    840

attggggccg gcaacttcac aggagccaaa aagtgtctag tcaacttaat tgagaaggtg    900

gcaagttatg gtgtgaagcc aagatatgct ctagtgacat atgccacata ccccagaatt    960

tgggtcaaag tgtctgacca agagagcagc aatgcagact gggtcacgaa gaagctcagt   1020

gaaatcaatt atgaagacca caagttgaag tcagggacta acaccaagag ggccctccag   1080

gcagtgtaca gcatgatgag ttggccagag gacatccctc ctgaaggctg gaaccgcacc   1140

cgccatgtca tcatcctcat gaccgatgga ttgcacaaca tgggcgggga cccaattact   1200

gtcattgatg agatccggga cttgttatac atcggcaagg atcgtaaaaa cccgagggag   1260

gattatctgg atgtctatgt gtttggggtt ggacctttgg tggaccaagt gaacatcaat   1320

gctttggctt ccaagaaaga caatgagcaa catgtgttca aagtcaagga tatggaaaac   1380

ctggaagacg ttttcttcca aatgattgat gaaagccagt ctctgagtct ctgtggcatg   1440

gtttgggaac acacgacggg taccgattac cacaagcaac catggcaggc caagatctca   1500

gtcactcgcc cttcgaaggg acatgagagc tgtatggggg ctgtggtgtc tgagtacttt   1560

gtgctgacag cagcacattg ttttactgtg gacgacaagg aacactcgat caaggtcagc   1620

gtggggaaga agcgggacct ggagatagaa aaagtcctat ttcaccccga ctacaacatt   1680

agcgggaaaa aagaagcagg aattcctgaa ttttatgact atgacgttgc cctgatcaag   1740

ctcaagaata agttgaatta tgacccgact atcaggccca tttgtctccc ctgcaccgag   1800

ggaacaactc gagctttgag gcttcctcca actaccactt gccagcaaca gaaggaagag   1860

ctgctccctg cacaggatat caaagctctg tttgtgtctg aggaggagaa gaagctgact   1920

cggaaggagg tctacatcaa gaatggggat aagaaaggca gctgtgagag agatgctcaa   1980

tatgccccag gctatgacaa agtcaaggac atctccgagg tggtcacccc tcggttcctt   2040

tgtactggag gagtgagtcc ctatgctgac cccaatactt gcagaggtga ttctggcggc   2100

cccttgatag ttcacaagag aagtcgtttt attcaagttg gtgtcatcag ctggggagta   2160

gtggatgtct gcaaaaacca gaagcggcaa aagcaggtac ctgctcacgc ccgagacttt   2220

cacgtcaacc tcttccaagt gctgccctgg ctgaaggaga aactccaaga tgaggatttg   2280

ggttttctc                                                           2289
```

<210> SEQ ID NO 28
<211> LENGTH: 4989
<212> TYPE: DNA
<213> ORGANISM: Macaca fascicularis

<400> SEQUENCE: 28

```
atgggactca cctcaggtcc cagcctgctg ctcctgctac taatccacct ccccctggct     60

ctggggactc ccatgtactc tatgatcacc cccaacgtct tgcggctgga gagtgaggag    120

accgtggtgc tggaggccca cgacgcgaat ggggatgttc cggtcactgt cactgtccac    180

gacttcccag gcaaaaaact ggtgctgtcc agtgagaaga ccgtactgac ccctgccacc    240

agccacatgg gcagcgtcac catcaggatc ccagccaaca aggagttcaa gtcagaaaag    300

gggcacaaca agttcgtgac tgtgcaggcc accttcgggg cccaagtggt ggagaaggtg    360

gtactggtca gccttcagag cgggtacctc ttcatccaga cagacaagac catctacacc    420

cctggctcca cagttctctg tcggatcttc accgtcaacc acaagctgct acccgtgggc    480
```

```
cggacggtcg tggtcaacat tgagaacccg gacggcatcc cggtcaagca ggactccttg    540
tcttctcaga accaatttgg catcttgccc ttgtcttggg acattccgga actcgtcaac    600
atgggccagt ggaagatccg agcctactat gaaaattcgc cgcaacaggt cttctccact    660
gagtttgagg tgaaggagta cgtgctgccc agtttcgagg tcatagtgga gcctacagag    720
aaattctact acatctataa ccagaagggc ctggaggtca ccatcaccgc caggttcctc    780
tatggaaaga aagtggaggg aactgccttt gtcatcttcg ggatccagga tggcgagcag    840
aggatttccc tgcctgaatc cctcaagcgc atccagattg aggatggctc aggagacgcc    900
gtgctgagcc ggaaggtact gctggacggg gtgcagaatc cccgaccgga agacctggtg    960
gggaagtcct tgtacgtgtc tgtcaccgtt atcctgcact caggcagtga catggtgcag   1020
gcggagcgca gcgggatccc catcgtgacc tctccctacc agatccactt caccaagacg   1080
cccaagtact tcaaaccagg aatgcccttt gacctcatgg tgttcgtgac gaaccccgat   1140
ggctctccag cctaccgagt ccccgtggca gtccagggcg aggacgctgt gcagtctcta   1200
acccagggag acggcgtggc caaactcagc atcaacacac accccagcca gaagcccttg   1260
agcatcacgg tgcgcacgaa gaagcgggag ctctcggagg cggagcaggc taccaggacc   1320
atggaggctc agccctacag caccgtgggc aactccaaca attacctgca tctctcagtg   1380
ccacgtgcag agctcagacc tggggagacc ctcaacgtca acttcctcct gcgaatggac   1440
cgcacccagg aggccaagat ccgctactac acctacctga ttatgaacaa aggcaagctg   1500
ttgaaggtgg gacgccaggt gcgagagcct ggccaggacc tggtggtgct gcccctgtcc   1560
atcaccaccg acttcatccc ttccttccgc ctggtggcct actacacgct gatcggcgcc   1620
aacggccaga gggaagtggt ggccgactcc gtgtgggtgg acgtcaagga ctcttgcgtg   1680
ggctcgctgg tggtaaaaag cggccagtca gaagacaggc agcctttacc cgggcagcag   1740
atgaccctga agatagaggg tgaccacggg gcccgggtgg gactggtggc tgtggacaag   1800
ggcgtgtttg tgctgaataa gaagaacaag ctgacgcaga gtaagatctg ggacgtggtg   1860
gagaaggcag acatcggctg caccccaggc agtgggaagg attacgctgg tgtcttctcg   1920
gatgcaggcc tgacctttgc gagcagcagt ggccagcaga cggcccagag ggcagaactt   1980
cagtgcccac agccagccgc ccgccgacgc cgttccgtgc agctcgcgga gaagagaatg   2040
gacaaagttg gtcagtaccc caaggagctg cgcaagtgct gcgagcacgg tatgcgggag   2100
aaccccatga ggttctcatg ccagcgccgg acccgttaca tcaccctgga cgaggcgtgc   2160
aagaaggcct tcctggactg ctgcaactac atcactgagc tgcggcggca gcacgcgcgg   2220
gccagtcacc tgggcctggc caggagtaac ctggatgagg acatcatcgc agaagagaac   2280
atcgtttccc gaagtgagtt cccagagagt tggctgtgga agattgaaga gttgaaagag   2340
gcaccgaaaa acggaatctc cacgaagctc atgaatatat ttttgaaaga ctccatcacc   2400
acgtgggaga ttctggccgt gagcttgtca gacaagaaag ggatctgtgt ggcagacccc   2460
ttcgaggtca cagtaatgca ggacttcttc atcgacctgc ggctacccta ctctgttgtt   2520
cgaaacgagc aggtggaaat ccgagctgtt ctctacaatt accggcagaa ccaagagctc   2580
aaggtgaggg tggaactact ccacaatcca gccttctgca gcctggccac cgccaagagg   2640
cgtcaccagc agaccgtaac catccccccc aagtcctcgc tgtccgttcc ttatgtcatc   2700
gtgcccctaa agaccggcca gcaggaagtg gaagtcaagg ctgccgtcta ccattttttc   2760
atcagtgacg gtgtcaggaa gtccctgaag gtcgtgccgg aaggaatcag aatgaacaaa   2820
```

-continued actgtggctg ttcgcacgct ggatccagaa cgcctgggcc aggaaggagt gcagagagag 2880
gacgtcccac ctgcagacct cagtgaccaa gtcccggaca ccgagtctga gaccagaatt 2940
ctcctgcaag ggaccccggt ggcccagatg acagaggatg ccatcgatgc ggaacggctg 3000
aagcacctca tcgtgacccc ctcgggctgc ggagaacaga acatgatcac catgacgccc 3060
acagtcatcg ctgtgcatta cctggatgaa acggaacagt gggagaagtt cggcccggag 3120
aagcggcagg gggccttgga gctcatcaag aaggggtaca cccagcagct ggccttcaga 3180
caacccagct ctgcctttgc ggccttcctg aaccgggcac ccagcacctg gctgaccgcc 3240
tacgtggtca aggtcttctc tctggctgtc aacctcattg ccatcgactc ccaggtcctc 3300
tgcggggctg ttaaatggct gatcctggag aagcagaagc ccgacggggt cttccaggag 3360
gatgcgcccg tgatacatca agaaatgact ggtggattcc ggaacaccaa cgagaaagac 3420
atggccctca cggcctttgt tctcatctcg ctgcaagagg ctaaagagat ttgcgaggag 3480
caggtcaaca gcctgccagg cagcatcact aaagcaggag acttccttga agccaactac 3540
atgaacctac agagatccta cactgtggcc atcgctgcct atgccctggc ccagatgggc 3600
aggctgaagg gacctcttct caacaaattt ctgaccacag ccaaagataa gaaccgctgg 3660
gaggagcctg gtcagcagct ctacaatgtg gaggccacat cctatgccct cttggcccta 3720
ctgcagctaa aagactttga ctttgtgcct cccgtcgtgc gttggctcaa tgaacagaga 3780
tactacggtg gtggctatgg ctctacccag gccaccttca tggtgttcca agccttggct 3840
caataccaaa aggatgtccc tgatcacaag gaactgaacc tggatgtgtc cctccaactg 3900
cccagtcgca gctccaagat catccaccgt atccactggg aatctgccag cctcctgcga 3960
tcagaagaga ccaaggaaaa tgagggtttc acagtcacag ctgaaggaaa aggccaaggc 4020
accttgtcgg tagtgacaat gtaccatgct aaggccaaag gtcaactcac ctgtaataaa 4080
ttcgacctca aggtcaccat aaaaccagca ccggaaacag aaaagaggcc tcaggatgcc 4140
aagaacacta tgatccttga gatctgtacc aggtaccggg gagaccagga tgccactatg 4200
tctatactgg acatatccat gatgactggc ttcgttccag acacagatga cctcaagcag 4260
ctggcaaacg gcgttgacag atacatctcc aagtatgagc tggacaaagc cttctccgat 4320
aggaacaccc tcatcatcta cctggacaag gtctcacact ctgaggatga ctgtatagct 4380
ttcaaagttc accaatattt taatgtagag cttatccagc ctggtgcagt caaggtctac 4440
gcctattaca acctggcgga aagctgtacc cggttctacc acccggaaaa ggaggatgga 4500
aagctgaaca agctctgtcg tgatgagctg tgccgctgtg ctgaggagaa ttgcttcata 4560
caaaagttgg atgacaaagt caccctggaa gaacggctgg acaaggcctg tgagccagga 4620
gtggactatg tgtacaagac ccgactggtc aaggcccagc tgtccaatga ctttgacgag 4680
tacatcatgg ccattgagca gatcatcaag tcaggctcgg atgaggtgca ggttggacaa 4740
cagcgcacgt tcatcagccc catcaagtgc agggaagccc tgaagctgga ggagaggaaa 4800
cactacctca tgtggggtct ctcctccgat ttctggggag agaaacccaa tctcagctac 4860
atcatcggga aggacacctg ggtggagcac tggcccgagg aggacgaatg ccaagatgaa 4920
gagaaccaga aacaatgcca ggacctcggc accttcactg agaacatggt tgtctttggg 4980
tgccccaac 4989

<210> SEQ ID NO 29
<211> LENGTH: 2955
<212> TYPE: DNA
<213> ORGANISM: Macaca fascicularis

<400> SEQUENCE: 29
cccaaattga caaaaaccct gaatgcagac aaacaatact tgttccctgt cctctggccc 60
tttgcaaata aatgccttac ccgacctgct ctgccacccc actcgcagcc acccagcaag 120
agcagcatgt cagcctgctg gagctttgca gctgcaatct gcattttaga aataagcgtc 180
ctcacagcag agtacacgcc cagttatgac ccacagccaa cagaaagccg tggttccgca 240
tcgcacatag actgcagaat gagcccctgg agtgaatggt cacaatgcga tccttgcctc 300
agacaaatgt ttcgttcaag aagcattgag gtcttcggac aatttaatgg gaaaagttgc 360
accgatgctg tgggagacag acgacagtgt gtgcccacag agccctgtga ggatgctgag 420
gatgactgcg gaaatgactt tcaatgcggt acaggcagat gcataaagag gcgactcctg 480
tgtaatggtg acaatgactg tggagacttt tcagatgagg atgattgtga aagtgatccc 540
cgtccccccct gcagagacag agtggtagaa gagtctgagc tggcacgaac agcaggctac 600
gggatcaaca ttttagggat ggatcccccta agcacacctt ttgacaatga gttctacaat 660
ggactctgta accgggatcg ggatggaaac actttgacat actaccgaag accctggaac 720
gtggcttctt tgatctatga aaccaaaggc gagaaaaatt taagaaccga acattatgaa 780
gaacaaattg aagcatttaa aagtatcgtc caagagaaga catcaaattt taatgcagat 840
atatctctaa aatttacacc cactgaagca aataaagtta aaactgaaaa gtcttctgag 900
aaacaagcct cctcaaattc tttacgtggc cagggtagtt ttcggttttc atattccaaa 960
aatgaaactt accaactatt tttgtcatat tcttcaaaga aggaaaaaat gttcctgcat 1020
gtgaaaggag aaattcatct gggaagattt atgatgagaa atcgtgatgt tgtgctcaca 1080
acaacttttg tggatgatat aaaagctttg ccaactacct atgaaaaggg agaatatttt 1140
gcctttttgg aaacctatgg aacccactac agtagctctg ggtctctggg aggactctat 1200
gaactaatat atgttttgga taaagcttcc atgaaccgga aaggtgttga actaaaagat 1260
gtaaagagat gcctcgggta tcatctggat gtatctctgg atttctctaa aatctctgct 1320
ggagctaaag ctgataaaga tgattgtgta aagagggggag agggtagagc tgtaaacatc 1380
accagtgatc acctcataga tgatgttatt tcactcataa gaggtggaac cagacaatat 1440
gcatttgaac tgaaagaaaa gcttctccga ggaaccatga ttgatgtgac tgattttgtc 1500
aactgggcct cttccataaa tgatgctcct gttctcatta gtcaaaaact gtctcctata 1560
tataatctgg ttccagtgaa aatgaaaaat gcacacctaa agaaacaaaa cttggaaaga 1620
gccattgaag actatatcaa tgaatttagt gtaagaaaat gccactcatg ccaaaatgga 1680
ggtacagcaa ttctaatgga tggaaagtgt ttgtgtacct gcccattcaa atttgaggga 1740
attgcctgtg aaatcagtaa acaaaaagtt tctgaaggat tgccagccct agacttcccc 1800
cgtgaaaaat agaactgttg gcttctctga gctccagtgg aagaaaagaa cactaggacc 1860
ttcagatcct atccctgaag ataatcttag ctgccaaaga aatagcaaca tgcttcatga 1920
aaatcctacc aacttctgaa gtctcctctc ttaggtctat aattattttt taatttttct 1980
ttcttaaact cctatgatgt ttccattttt tattccctaa tgaggagtca agagtgaaat 2040
atgccagaac tgctttctcc cacagacaat gccaatctct tcttaaaaaa acaaaattaa 2100
attaaaacag aatgttggtt taaaaacttc aaagtaattg tcaaactgct ttgtacggtt 2160
aacatattct gccaagtcta tgaccacacg tctgtaccat gcaatttaac tcttatttac 2220
attgttatgt ttggtttggt tatttgctta ggtgtgcata cattcattca gcaaatactg 2280

```
aacaccagcc acctgcacag cagttgcttt tattagtctt aactctacca tttaaatcta   2340

tgtgtccaag ggggaaaatg tgttatattt gtaaccaaaa actactagtt taccaaaggc   2400

tggaagggta gtggggaagg gagataaaga ggagatgatt aatacaaaac tccagttaga   2460

tgaaaggaat aatatataca gtgttcagca acacaataga gtgactataa actattagct   2520

taaattatgt gaaattgcct ctatttgatc ttattttaca agagaaaaac atcaatttta   2580

tatagtctaa cttaatacct aggcttatga gttgtataag gtaacgttac ctacctgaga   2640

agctgattaa cattggctgt acaatcttat ccattagaga acatgatact tagggtctga   2700

gaccttttga aaaggtctga aaactcttta aaaaaaagga aagaaagaaa gaaatgagga   2760

aaaacatatc aaaataaaaa aatgcaaaat caaatttaat aaatgcttag acatcagcat   2820

gtgtcatgtt aactttattg ttactattaa tacacatttc acacatttat aaataaatta   2880

tgttactttt tctcacttgg gagaaattct caagaatgca tttgattgct gggagataac   2940

agtaactaaa ttacc                                                   2955
```

<210> SEQ ID NO 30
<211> LENGTH: 2727
<212> TYPE: DNA
<213> ORGANISM: Macaca fascicularis

<400> SEQUENCE: 30

```
atttctggtc cctaagtggg tggtctgggc ttgttgggga ggagctgagg ccagaaggag     60

gtactgaagg ggagagtcct ggaccttggg cagcaaaggg tgggacttct gcagtttctg    120

cttccttgac tggcagctca gcggggccct cccgcttgga tgttccggga aagtgatgag    180

ggtaggacag gcggggcaag ctgcaggtgc cagaacacag attgcataaa aggccgggag    240

ctggtggggg gcaggggaag ggaatgtgac caggtctagg tctggagttt cagcttggac    300

actgagctaa gtagacaagc aaaacaagcc aggacacgcc atcctgcccc aggcccagct    360

tctctcctgc cttctaacgc catggggagc agtctcagcc cccagctcta cctgatgccc    420

ttcatcttgg gcctcttatc tgcaggtgtg accaccactc cattgtcttc ggcccagcct    480

caaggatcct gctctctgga gggggtagag atcaaaggtg gctccttccg acttctccaa    540

gagggccagg cactggaata cgtgtgtcct tctggcttct acccgtaccc tgtgcagaca    600

cgtacctgca gatccacggg gtcctggagc accctgcaga ctcaagatcg aaaaactgtc    660

aagaaggcag agtgcagagc aatccgctgt ccacgaccac aggacttcga gaacggggaa    720

taccggcccc ggtctcccta ctacaatgtg agtgatgaga tctctttcca ctgctatgac    780

ggttacactc tccggggctc tgccaatcgc acctgccaag tgaatggccg gtggagtggg    840

cagacagcga tctgtgacaa cggagcgggg tactgctcca acccaggcat ccccattggc    900

acaaggaagg tgggcagccg gtaccgcctt gaagacagcg tcacctacca ctgcagccgg    960

gggcttaccc tgcgtggctc ccagcggcga acgtgtcagg aaggtggctc ttggagcggg   1020

acggagcctt cctgccaaga ctccttcatg tacgacaccc ctcaagaggt ggccgaagct   1080

ttcctgtctt ccctgacgga gaccatagaa ggagtcgatg ccgaggatgg gcacagccca   1140

ggggaacaac agaagcggag gatcatccta gacccttcag gctccatgaa catctacctg   1200

gtgctagatg gatcagacag cattggggcc ggcaacttca caggagccaa aaagtgtcta   1260

gtcaacttaa ttgagaaggt ggcaagttat ggtgtgaagc caagatatgc tctagtgaca   1320

tatgccacat accccagaat ttgggtcaaa gtgtctgacc aagagagcag caatgcagac   1380

tgggtcacga agaagctcag tgaaatcaat tatgaagacc acaagttgaa gtcagggact   1440
```

```
aacaccaaga gggccctcca ggcagtgtac agcatgatga gttggccaga ggacatccct   1500
cctgaaggct ggaaccgcac ccgccatgtc atcatcctca tgaccgatgg attgcacaac   1560
atgggcgggg acccaattac tgtcattgat gagatccggg acttgttata catcggcaag   1620
gatcgcaaaa acccgaggga ggattatctg gatgtctatg tgtttggggt tggacctttg   1680
gtggaccaag tgaacatcaa tgctttggct tccaagaaag acaatgagca acatgtgttc   1740
aaagtcaagg atatggaaaa cctggaagac gttttcttcc aaatgattga tgaaagccag   1800
tctctgagtc tctgtggcat ggtttgggaa cacacgacgg gtaccgatta ccacaagcaa   1860
ccatggcagg ccaagatctc agtcactcgc ccttcgaagg gacatgagag ctgtatgggg   1920
gctgtggtgt ctgagtactt tgtgctgaca gcagcacatt gttttactgt ggacgacaag   1980
gaacactcga tcaaggtcag cgtggggaag aagcgggacc tggagataga aaaagtccta   2040
tttcaccccg actacaacat tagcgggaaa aaagaagcag gaattcctga attttatgac   2100
tatgacgttg ccctgatcaa gctcaagaaa aagttgaatt atgacccgac tatcaggccc   2160
atttgtctcc cctgtaccga gggaacaact cgagctttga ggcttcctcc aactaccact   2220
tgccagcaac agaaggaaga gctgctccct gcacaggata tcaaagctct gtttgtgtct   2280
gaggaggaga agaagctgac tcggaaggag gtctacatca agaatgggga taagaaaggc   2340
agctgtgaga gagatgctca atatgcccca ggctatgaca aagtcaagga catctcggag   2400
gtggtcaccc ctcggttcct ttgtactgga ggagtgagtc cctatgctga ccccaatact   2460
tgcagaggtg attctggcgg ccccttgata gttcacaaga gaagtcgttt cattcaagtt   2520
ggtgtcatca gctggggagt agtggatgtc tgcaaaaacc agaagcggca aaagcaggta   2580
cctgctcacg cccgagactt tcacgtcaac ctcttccaag tgctgccctg gctgaaggag   2640
aaactccaag atgaggattt gggttttctc taaggggttt cctgctggac aggggcgcgg   2700
gattgaatta aaacagctgc gacaaca                                       2727
```

<210> SEQ ID NO 31
<211> LENGTH: 5106
<212> TYPE: DNA
<213> ORGANISM: Macaca fascicularis

<400> SEQUENCE: 31

```
ctgctcactc ctccccatcc tctccctctg tccctctgtc cctctgaccc tgcactgtcc     60
cagcaccatg ggactcacct caggtcccag cctgctgctc ctgctactaa tccacctccc    120
cctggctctg gggactccca tgtactctat gatcacccca aacgtcttgc ggctggagag    180
tgaggagacc gtggtgctgg aggcccatga cgcgaatggg gatgttccgg tcactgtcac    240
tgtccacgac ttcccaggca aaaaactggt gctgtccagt gagaagaccg tgctgacccc    300
tgccaccagc cacatgggca gcgtcaccat caggatccca gccaacaagg agttcaagtc    360
agaaaagggg cacaacaagt tcgtgactgt gcaggccacc ttcggggccc aagtggtgga    420
gaaggtggta ctggtcagcc ttcagagcgg gtacctcttc atccagacag acaagaccat    480
ctacacccct ggctccacag ttctctgtcg gatcttcacc gtcaaccaca agctgctacc    540
cgtgggccgg acggtcgtgg tcaacattga gaacccggac ggcatcccgg tcaagcagga    600
ctccttgtct tctcagaacc aatttggcat cttgcccttg tcttgggaca ttccggaact    660
cgtcaacatg ggccagtgga agatccgagc ctactatgaa aattcgccgc aacaggtctt    720
ctccactgag tttgaggtga aggagtacgt gctgcccagt ttcgaggtca tagtggagcc    780
```

```
tacagagaaa ttctactaca tctataacca gaagggcctg gaggtcacca tcaccgccag    840
gttcctctat ggaaagaaag tggagggaac tgcctttgtc atcttcggga tccaggatgg    900
cgagcagagg atttccctgc ctgaatccct caagcgcatc cagattgagg atggctcagg    960
agacgccgtg ctgagccgga aggtactgct ggacggggtg cagaatcccc gaccggaaga   1020
cctagtgggg aagtccttgt atgtgtctgt caccgttatc ctgcactcag gcagtgacat   1080
ggtgcaggcg gagcgcagcg ggatccccat cgtgacctct ccctaccaga tccacttcac   1140
caagacgccc aagtacttca aaccaggaat gccctttgac ctcatggtgt tcgtgacgaa   1200
ccccgatggc tctccagcct accgagtccc cgtggcagtc cagggcgagg acgctgtgca   1260
gtctctaacc cagggagacg gcgtggccaa actcagcatc aacacacacc ccagccagaa   1320
gcccttgagc atcacggtgc gcacgaagaa gcgggagctc tcggaggcgg agcaggctac   1380
caggaccatg gaggctcagc cctacagcac cgtgggcaac tccaacaatt acctgcatct   1440
ctcagtgcca cgtgcagagc tcagacctgg ggagaccctc aacgtcaact tcctcctgcg   1500
aatggaccgc acccaggagg ccaagatccg ctactacacc tacctgatta tgaacaaagg   1560
caagctgttg aaggtgggac gccaggtgcg agagcctggc caggacctgg tggtgctgcc   1620
cctgtccatc accaccgact tcatcccttc cttccgcctg gtggcctact acacgctgat   1680
cggcgccaac ggccagaggg aagtggtggc cgactccgtg tgggtggacg tcaaggactc   1740
ttgcgtgggc tcgctggtgg taaaaagcgg ccagtcagaa gacaggcagc ctttacccgg   1800
gcagcagatg accctgaaga tagagggtga ccacggggcc cgggtgggac tggtggctgt   1860
ggacaagggc gtgtttgtgc tgaataagaa gaacaagctg acgcagagta agatctggga   1920
cgtggtggag aaggcagaca tcggctgcac cccaggcagt gggaaggatt acgctggtgt   1980
cttctcggat gcaggcctga cctttgcgag cagcagtggc cagcagacgg cccagagggc   2040
agaacttcag tgcccacagc cagccgcccg ccgacgccgt tccgtgcagc tcgcggagaa   2100
gagaatggac aaagttggtc agtaccccaa ggagctgcgc aagtgctgcg agcacggtat   2160
gcgggagaac cccatgaggt tctcatgcca gcgccggacc cgttacatca ccctggacga   2220
ggcgtgcaag aaggccttcc tggactgctg caactacatc accgagctgc ggcggcagca   2280
cgcgcgggcc agtcacctgg gcctggccag gagtaacctg gatgaggaca tcatcgcaga   2340
agagaacatc gtttcccgaa gtgagttccc agagagttgg ctgtggaaga ttgaagagtt   2400
gaaagaggca ccgaaaaacg gaatctccac gaagctcatg aatatatttt tgaaagactc   2460
catcaccacg tgggagattc tggccgtgag cttgtcagac aagaaaggga tctgtgtggc   2520
agacccctte gaggtcacag taatgcagga cttcttcatc gacctgcggc taccctactc   2580
tgttgttcga aacgagcagg tggaaatccg agctgttctc tacaattacc ggcagaacca   2640
agagctcaag gtgagggtgg aactactcca caatccagcc ttctgcagcc tggccaccgc   2700
caagaggcgt caccagcaga ccgtaaccat ccccccaag tcctcgctgt ccgttcctta   2760
tgtcatcgtg cccctaaaga ccggccagca ggaagtggaa gtcaaggctg ccgtctacca   2820
ttttttcatc agtgacggtg tcaggaagtc cctgaaggtc gtgccggaag gaatcagaat   2880
gaacaaaact gtggctgttc gcacgctgga tccagaacgc ctgggccagg aaggagtgca   2940
gagagaggac gtcccacctg cagacctcag tgaccaagtc ccggacaccg agtctgagac   3000
cagaattctc ctgcaaggga ccccggtggc ccagatgaca gaggatgcca tcgatgcgga   3060
acggctgaag cacctcatcg tgaccccctc gggctgcgga gaacagaaca tgatcaccat   3120
gacgcccaca gtcatcgctg tgcattacct ggatgaaacg gaacagtggg agaagttcgg   3180
```

```
cccggagaag cggcaggggg ccttggagct catcaagaag ggtacaccc agcagctggc   3240
cttcagacaa cccagctctg cctttgcggc cttcctgaac cgggcaccca gcacctggct   3300
gaccgcctac gtggtcaagg tcttctctct ggctgtcaac ctcattgcca tcgactccca   3360
ggtcctctgc ggggctgtta aatggctgat cctggagaag cagaagcccg acggggtctt   3420
ccaggaggat gcgcccgtga tacatcaaga aatgactggt ggattccgga acaccaacga   3480
gaaagacatg gccctcacgg cctttgttct catctcgctg caagaggcta aagagatttg   3540
cgaggagcag gtcaacagcc tgcccggcag catcactaaa gcaggagact tccttgaagc   3600
caactacatg aacctacaga gatcctacac tgtggccatc gctgcctatg ccctggccca   3660
gatgggcagg ctgaagggac ctcttctcaa caaatttctg accacagcca aagataagaa   3720
ccgctgggag gagcctggtc agcagctcta caatgtggag gccacatcct atgccctctt   3780
ggccctactg cagctaaaag actttgactt tgtgcctccc gtcgtgcgtt ggctcaatga   3840
acagagatac tacggtggtg gctatggctc tacccaggcc accttcatgg tgttccaagc   3900
cttggctcaa taccaaaagg atgtccctga tcacaaggaa ctgaacctgg atgtgtccct   3960
ccaactgccc agtcgcagct ccaagatcat ccaccgtatc cactgggaat ctgccagcct   4020
cctgcgatca gaagagacca aggaaaatga gggtttcaca gtcacagctg aaggaaaagg   4080
ccaaggcacc ttgtcggtag tgacaatgta ccatgctaag gccaaaggtc aactcacctg   4140
taataaattc gacctcaagg tcaccataaa accagcaccg gaaacagaaa agaggcctca   4200
ggatgccaag aacactatga tccttgagat ctgtaccagg taccggggag accaggatgc   4260
cactatgtct atactggaca tatccatgat gactggcttc gttccagaca cagatgacct   4320
caagcagctg gcaaacggcg ttgacagata catctccaag tatgagctgg acaaagcctt   4380
ctccgatagg aacaccctca tcatctacct ggacaaggtc tcacactctg aggatgactg   4440
tatagctttc aaagttcacc aatattttaa tgtagagctt atccagcctg gtgcagtcaa   4500
ggtctacgcc tattacaacc tggcggaaag ctgtacccgg ttctaccacc cagaaaagga   4560
ggatggaaag ctgaacaagc tctgtcgtga tgagctgtgc cgctgtgctg aggagaattg   4620
cttcatacaa aagttggatg acaaagtcac cctggaagaa cggctggaca aggcctgtga   4680
gccaggagtg gactatgtgt acaagacccg actggtcaag gcccagctgt ccaatgactt   4740
tgacgagtac atcatggcca ttgagcagat catcaagtca ggctcggatg aggtgcaggt   4800
tggacaacag cgcacgttca tcagccccat caagtgcagg gaagccctga agctggagga   4860
gaggaaacac tacctcatgt ggggtctctc ctccgatttc tggggagaga aacccaatct   4920
cagctacatc atcgggaagg acacctgggt ggagcactgg cccgaggagg acgaatgcca   4980
agatgaagag aaccagaaac aatgccagga cctcggcacc ttcactgaga acatggttgt   5040
ctttgggtgc cccaactgac cacaccccca ttcccccact cccaataaag cttcagttat   5100
atttca                                                             5106
```

<210> SEQ ID NO 32
<211> LENGTH: 2091
<212> TYPE: DNA
<213> ORGANISM: Macaca fascicularis

<400> SEQUENCE: 32

```
ttccctgtcc tctggccctt tgcaaataaa tgccttaccc gacctgctct gccaccccac     60
tcgcagccac ccagcaagag cagcatgtca gcctgctgga gctttgcagc tgcaatctgc    120
```

```
attttagaaa taagcatcct cacagcagag tacacgccca gttatgaccc acagccaaca    180

gaaagccgtg gttccgcatc gcacatagac tgcagaatga gcccctggag tgaatggtca    240

caatgcgatc cttgcctcag acaaatgttt cgttcaagaa gcattgaggt cttcggacaa    300

tttaatggga aaagttgcac cgatgctgtg ggagacagac gacagtgtgt gcccacagag    360

ccctgtgagg atgctgagga tgactgcgga aatgactttc aatgcggtac aggcagatgc    420

ataaagaggc gactcctgtg taatggtgac aatgactgtg gagacttttc agatgaggat    480

gattgtgaag gtgatccccg tccccccctgc agagacagag tggtagaaga gtctgagctg    540

gcacgaacag caggctacgg gatcaacatt ttagggatgg atcccctaag cacacctttt    600

gacaatgagt tctacaatgg actctgtaac cgggatcggg atggaaacac tttgacatac    660

taccgaagac cctggaacgt ggcttctttg atctatgaaa ccaaaggcga gaaaaattta    720

agaaccgaac attatgaaga acaaattgaa gcatttaaaa gtatcgtcca agagaagaca    780

tcaaatttta atgcagatat atctctaaaa tttacaccca ctgaagcaaa taaagttaaa    840

actgaaaagt cttctgagaa acaagcctct tcaaattctt tacgtggcca gggtagtttt    900

cggttttcat attccaaaaa tgaaacttac caactatttt tgtcatattc ttcaaagaag    960

gaaaaaaatgt tcctgcatgt gaaaggagaa attcatctgg gaagatttat gatgagaaat   1020

cgtgatgttg tgctcacaac aacttttgtg gatgatataa aagctttgcc aactacctat   1080

gaaaagggag aatattttgc ctttttggaa acctatggaa cccactacag tagctctggg   1140

tctctgggag gactctatga actaatatat gttttggata aagcttccat gaaccggaaa   1200

ggtgttgaac taaaagatgt aaagagatgc ctcgggtatc atctggatgt atctctggat   1260

ttctctaaaa tctctgctgg agctaaagct gataaagatg attgtgtaaa gaggggagag   1320

ggtagagctg taaacatcac cagtgatcac ctcatagatg atgttatttc actcataaga   1380

ggtggaacca gacaatatgc atttgaactg aaagaaaagc ttctccgagg aaccatgatt   1440

gatgtgactg attttgtcaa ctgggcctct tccataaatg atgctcctgt tctcattagt   1500

caaaaactgt ctcctatata taatctggtt ccagtgaaaa tgaaaaatgc acacctaaag   1560

aaacaaaact tggaaagagc cattgaagac tatatcaatg aatttagtgt aagaaaatgc   1620

cactcatgcc aaaatggagg tacagcaatt ctaatggatg gaaagtgttt gtgtacctgc   1680

ccattcaaat ttgagggaat tgcctgtgaa atcagtaaac aaaaagtttc tgaaggattg   1740

ccagccctag acttcccccg tgaaaaatag aactgttggc ttctctgagc tccagtggaa   1800

gaaaagaaca ctaggacctt cagatcctat ccctgaagat aatcttagct gccaaagaaa   1860

tagcaacatg cttcatgaaa atcctaccaa cttctgaagt ctcctctctt aggtctataa   1920

ttatttttta attttcttt cttaaactcc tatgatgttt ccattttttta ttccctaatg   1980

aggagtcaag agtgaaatat gccagaactg ctttctccca cagacaatgc caatctcttc   2040

taaaaaaaac aaaattaaat taaaacagaa tgttggttta aaaacttcaa a             2091


<210> SEQ ID NO 33
<211> LENGTH: 2289
<212> TYPE: DNA
<213> ORGANISM: Macaca fascicularis

<400> SEQUENCE: 33

gagaaaaccc aaatcctcat cttggagttt ctccttcagc cagggcagca cttggaagag     60

gttgacgtga aagtctcggg cgtgagcagg tacctgcttt tgccgcttct ggtttttgca    120

gacatccact actccccagc tgatgacacc aacttgaata aaacgacttc tcttgtgaac    180
```

```
tatcaagggg ccgccagaat cacctctgca agtattgggg tcagcatagg gactcactcc    240

tccagtacaa aggaaccgag gggtgaccac ctcggagatg tccttgactt tgtcatagcc    300

tggggcatat tgagcatctc tctcacagct gcctttctta tccccattct tgatgtagac    360

ctccttccga gtcagcttct tctcctcctc agacacaaac agagctttga tatcctgtgc    420

agggagcagc tcttccttct gttgctggca agtggtagtt ggaggaagcc tcaaagctcg    480

agttgttccc tcggtgcagg ggagacaaat gggcctgata gtcgggtcat aattcaactt    540

attcttgagc ttgatcaggg caacgtcata gtcataaaat tcaggaattc ctgcttcttt    600

tttcccgcta atgttgtagt cggggtgaaa taggactttt tctatctcca ggtcccgctt    660

cttccccacg ctgaccttga tcgagtgttc cttgtcgtcc acagtaaaac aatgtgctgc    720

tgtcagcaca aagtactcag acaccacagc ccccatacag ctctcatgtc ccttcgaagg    780

gcgagtgact gagatcttgg cctgccatgg ttgcttgtgg taatcggtac ccgtcgtgtg    840

ttcccaaacc atgccacaga gactcagaga ctggctttca tcaatcattt ggaagaaaac    900

gtcttccagg ttttccatat ccttgacttt gaacacatgt tgctcattgt ctttcttgga    960

agccaaagca ttgatgttca cttggtccac caaaggtcca accccaaaca catagacatc   1020

cagataatcc tccctcgggt ttttacgatc cttgccgatg tataacaagt cccggatctc   1080

atcaatgaca gtaattgggt ccccgcccat gttgtgcaat ccatcggtca tgaggatgat   1140

gacatggcgg gtgcggttcc agccttcagg agggatgtcc tctggccaac tcatcatgct   1200

gtacactgcc tggagggccc tcttggtgtt agtccctgac ttcaacttgt ggtcttcata   1260

attgatttca ctgagcttct tcgtgaccca gtctgcattg ctgctctctt ggtcagacac   1320

tttgacccaa attctggggt atgtggcata tgtcactaga gcatatcttg gcttcacacc   1380

ataacttgcc accttctcaa ttaagttgac tagacacttt ttggctcctg tgaagttgcc   1440

ggccccaatg ctgtctgatc catctagcac caggtagatg ttcatggagc ctgaagggtc   1500

taggatgatc ctccgcttct gttgttcccc tgggctgtgc ccatcctcgg catcgactcc   1560

ttctatggtc tccgtcaggg aagacaggaa agcttcggcc acctcttgag gggtgtcgta   1620

catgaaggag tcttggcagg aaggctccgt cccgctccaa gagccacctt cctgacatgt   1680

tcgccgctgg gagccacgca gggtaagccc ccggctgcag tggtaggtga cgctgtcttc   1740

aaggcggtac cggctgccca ccttccttgt gccaatgggg atgcctgggt tggagcagta   1800

ccccgctccg ttgtcacaga tcgctgtctg cccactccac cggccattca cttggcaggt   1860

gcgattggca gagccccgga gagtgtaacc gtcatagcag tggaaagaga tctcatcact   1920

cacattgtag tagggagacc ggggccggta ttccccgttc tcgaagtcct gtggtcgtgg   1980

acagcggatt gctctgcact ctgccttctt gacagttttt cgatcttgag tctgcagggt   2040

gctccaggac cccgtggatc tgcaggtacg tgtctgcaca gggtacgggt agaagccaga   2100

aggacacacg tattccagtg cctggccctc ttggagaagt cggaaggagc cacctttgat   2160

ctctaccccc tccagagagc aggatccttg aggctgggcc gaagacaatg gagtggtggt   2220

cacacctgca gataagaggc ccaagatgaa gggcatcagg tagagctggg ggctgagact   2280

gctccccat                                                          2289
```

<210> SEQ ID NO 34
<211> LENGTH: 4989
<212> TYPE: DNA
<213> ORGANISM: Macaca fascicularis -continued

<400> SEQUENCE: 34

```
gttggggcac ccaaagacaa ccatgttctc agtgaaggtg ccgaggtcct ggcattgttt     60
ctggttctct tcatcttggc attcgtcctc ctcgggccag tgctccaccc aggtgtcctt    120
cccgatgatg tagctgagat tgggtttctc tccccagaaa tcggaggaga gaccccacat    180
gaggtagtgt ttcctctcct ccagcttcag ggcttccctg cacttgatgg ggctgatgaa    240
cgtgcgctgt tgtccaacct gcacctcatc cgagcctgac ttgatgatct gctcaatggc    300
catgatgtac tcgtcaaagt cattggacag ctgggccttg accagtcggg tcttgtacac    360
atagtccact cctggctcac aggccttgtc cagccgttct tccagggtga ctttgtcatc    420
caacttttgt atgaagcaat tctcctcagc acagcggcac agctcatcac gacagagctt    480
gttcagcttt ccatcctcct tttccgggtg gtagaaccgg gtacagcttt ccgccaggtt    540
gtaataggcg tagaccttga ctgcaccagg ctggataagc tctacattaa aatattggtg    600
aactttgaaa gctatacagt catcctcaga gtgtgagacc ttgtccaggt agatgatgag    660
ggtgttccta tcggagaagg ctttgtccag ctcatacttg gagatgtatc tgtcaacgcc    720
gtttgccagc tgcttgaggt catctgtgtc tggaacgaag ccagtcatca tggatatgtc    780
cagtatagac atagtggcat cctggtctcc ccggtacctg gtacagatct caaggatcat    840
agtgttcttg gcatcctgag gcctcttttc tgtttccggt gctggtttta tggtgacctt    900
gaggtcgaat ttattacagg tgagttgacc tttggcctta gcatggtaca ttgtcactac    960
cgacaaggtg ccttggcctt ttccttcagc tgtgactgtg aaaccctcat tttccttggt   1020
ctcttctgat cgcaggaggc tggcagattc ccagtggata cggtggatga tcttggagct   1080
gcgactgggc agttggaggg acacatccag gttcagttcc ttgtgatcag ggacatcctt   1140
ttggtattga gccaaggctt ggaacaccat gaaggtggcc tgggtagagc catagccacc   1200
accgtagtat ctctgttcat tgagccaacg cacgacggga ggcacaaagt caaagtcttt   1260
tagctgcagt agggccaaga gggcatagga tgtggcctcc acattgtaga gctgctgacc   1320
aggctcctcc cagcggttct tatctttggc tgtggtcaga aatttgttga gaagaggtcc   1380
cttcagcctg cccatctggg ccagggcata ggcagcgatg gccacagtgt aggatctctg   1440
taggttcatg tagttggctt caaggaagtc tcctgcttta gtgatgctgc ctggcaggct   1500
gttgacctgc tcctcgcaaa tctctttagc ctcttgcagc gagatgagaa caaaggccgt   1560
gagggccatg tctttctcgt tggtgttccg gaatccacca gtcatttctt gatgtatcac   1620
gggcgcatcc tcctggaaga ccccgtcggg cttctgcttc tccaggatca gccatttaac   1680
agccccgcag aggacctggg agtcgatggc aatgaggttg acagccagag agaagacctt   1740
gaccacgtag gcggtcagcc aggtgctggg tgcccggttc aggaaggccg caaaggcaga   1800
gctgggttgt ctgaaggcca gctgctgggt gtaccccttc ttgatgagct ccaaggcccc   1860
ctgccgcttc tccgggccga acttctccca ctgttccgtt tcatccaggt aatgcacagc   1920
gatgactgtg ggcgtcatgg tgatcatgtt ctgttctccg cagcccgagg gggtcacgat   1980
gaggtgcttc agccgttccg catcgatggc atcctctgtc atctgggcca ccggggtccc   2040
ttgcaggaga attctggtct cagactcggt gtccgggact tggtcactga ggtctgcagg   2100
tgggacgtcc tctctctgca ctccttcctg gcccaggcgt tctggatcca gcgtgcgaac   2160
agccacagtt ttgttcattc tgattccttc cggcacgacc ttcagggact tcctgacacc   2220
gtcactgatg aaaaaatggt agacggcagc cttgacttcc acttcctgct ggccggtctt   2280
taggggcacg atgacataag gaacggacag cgaggacttg ggggggatgg ttacggtctg   2340
```

ctggtgacgc ctcttggcgg tggccaggct gcagaaggct ggattgtgga gtagttccac 2400
cctcaccttg agctcttggt tctgccggta attgtagaga acagctcgga tttccacctg 2460
ctcgtttcga acaacagagt agggtagccg caggtcgatg aagaagtcct gcattactgt 2520
gacctcgaag ggtctgccca cacagatccc tttcttgtct gacaagctca cggccagaat 2580
ctcccacgtg gtgatggagt ctttcaaaaa tatattcatg agcttcgtgg agattccgtt 2640
tttcggtgcc tctttcaact cttcaatctt ccacagccaa ctctctggga actcacttcg 2700
ggaaacgatg ttctcttctg cgatgatgtc ctcatccagg ttactcctgg ccaggcccag 2760
gtgactggcc cgcgcgtgct gccgccgcag ctcagtgatg tagttgcagc agtccaggaa 2820
ggccttcttg cacgcctcgt ccagggtgat gtaacgggtc cggcgctggc atgagaacct 2880
catggggttc tcccgcatac cgtgctcgca gcacttgcgc agctccttgg ggtactgacc 2940
aactttgtcc attctcttct ccgcgagctg cacggaacgg cgtcggcggg cggctggctg 3000
tgggcactga agttctgccc tctgggccgt ctgctggcca ctgctgctcg caaaggtcag 3060
gcctgcatcc gagaagacac cagcgtaatc cttcccactg cctggggtgc agccgatgtc 3120
tgccttctcc accacgtccc agatcttact ctgcgtcagc ttgttcttct tattcagcac 3180
aaacacgccc ttgtccacag ccaccagtcc cacccgggcc ccgtggtcac cctctatctt 3240
cagggtcatc tgctgcccgg gtaaaggctg cctgtcttct gactggccgc tttttaccac 3300
cagcgagccc acgcaagagt ccttgacgtc cacccacacg gagtcggcca ccacttccct 3360
ctggccgttg gcgccgatca gcgtgtagta ggccaccagg cggaaggaag ggatgaagtc 3420
ggtggtgatg gacaggggca gcaccaccag gtcctggcca ggctctcgca cctggcgtcc 3480
caccttcaac agcttgcctt tgttcataat caggtaggtg tagtagcgga tcttggcctc 3540
ctgggtgcgg tccattcgca ggaggaagtt gacgttgagg gtctccccag gtctgagctc 3600
tgcacgtggc actgagagat gcaggtaatt gttggagttg cccacggtgc tgtagggctg 3660
agcctccatg gtcctggtag cctgctccgc ctccgagagc tcccgcttct tcgtgcgcac 3720
cgtgatgctc aagggcttct ggctggggtg tgtgttgatg ctgagtttgg ccacgccgtc 3780
tccctgggtt agagactgca cagcgtcctc gccctggact gccacgggga ctcggtaggc 3840
tggagagcca tcggggttcg tcacgaacac catgaggtca aagggcattc ctggtttgaa 3900
gtacttgggc gtcttggtga agtggatctg gtagggagag gtcacgatgg ggatcccgct 3960
gcgctccgcc tgcaccatgt cactgcctga gtgcaggata acggtgacag acacgtacaa 4020
ggacttcccc accaggtctt ccggtcgggg attctgcacc ccgtccagca gtaccttccg 4080
gctcagcacg gcgtctcctg agccatcctc aatctggatg cgcttgaggg attcaggcag 4140
ggaaatcctc tgctcgccat cctggatccc gaagatgaca aaggcagttc cctccacttt 4200
ctttccatag aggaacctgg cggtgatggt gacctccagg cccttctggt tatagatgta 4260
gtagaatttc tctgtaggct ccactatgac ctcgaaactg ggcagcacgt actccttcac 4320
ctcaaactca gtggagaaga cctgttgcgg cgaattttca tagtaggctc ggatcttcca 4380
ctggcccatg ttgacgagtt ccggaatgtc ccaagacaag ggcaagatgc caaattggtt 4440
ctgagaagac aaggagtcct gcttgaccgg gatgccgtcc gggttctcaa tgttgaccac 4500
gaccgtccgg cccacgggta gcagcttgtg gttgacggtg aagatccgac agagaactgt 4560
ggagccaggg gtgtagatgg tcttgtctgt ctggatgaag aggtacccgc tctgaaggct 4620
gaccagtacc accttctcca ccacttgggc cccgaaggtg gcctgcacag tcacgaactt 4680
gttgtgcccc ttttctgact tgaactcctt gttggctggg atcctgatgg tgacgctgcc 4740
catgtggctg gtggcagggg tcagtacggt cttctcactg gacagcacca gtttttttgcc 4800 tgggaagtcg tggacagtga cagtgaccgg aacatcccca ttcgcgtcgt gggcctccag 4860
caccacggtc tcctcactct ccagccgcaa gacgttgggg gtgatcatag agtacatggg 4920
agtccccaga gccaggggga ggtggattag tagcaggagc agcaggctgg gacctgaggt 4980
gagtcccat 4989

<210> SEQ ID NO 35
<211> LENGTH: 2955
<212> TYPE: DNA
<213> ORGANISM: Macaca fascicularis

<400> SEQUENCE: 35
ggtaatttag ttactgttat ctcccagcaa tcaaatgcat tcttgagaat ttctcccaag 60
tgagaaaaag taacataatt tatttataaa tgtgtgaaat gtgtattaat agtaacaata 120
aagttaacat gacacatgct gatgtctaag catttattaa atttgatttt gcattttttt 180
attttgatat gtttttcctc atttctttct ttctttcctt ttttttaaag agttttcaga 240
ccttttcaaa aggtctcaga ccctaagtat catgttctct aatggataag attgtacagc 300
caatgttaat cagcttctca ggtaggtaac gttaccttat acaactcata agcctaggta 360
ttaagttaga ctatataaaa ttgatgtttt tctcttgtaa aataagatca aatagaggca 420
atttcacata atttaagcta atagtttata gtcactctat tgtgttgctg aacactgtat 480
atattattcc tttcatctaa ctggagtttt gtattaatca tctcctcttt atctcccttc 540
cccactaccc ttccagcctt tggtaaacta gtagtttttg gttacaaata taacacattt 600 tccccccttgg acacatagat ttaaatggta gagttaagac taataaaagc aactgctgtg 660
caggtggctg gtgttcagta tttgctgaat gaatgtatgc acacctaagc aaataaccaa 720
accaaacata acaatgtaaa taagagttaa attgcatggt acagacgtgt ggtcatagac 780
ttggcagaat atgttaaccg tacaaagcag tttgacaatt actttgaagt tttaaaacca 840
acattctgtt ttaatttaat tttgtttttt taagaagaga ttggcattgt ctgtgggaga 900
aagcagttct ggcatatttc actcttgact cctcattagg gaataaaaaa tggaaacatc 960
ataggagttt aagaaagaaa aattaaaaaa taattataga cctaagagag gagacttcag 1020
aagttggtag gattttcatg aagcatgttg ctatttcttt ggcagctaag attatcttca 1080
gggataggat ctgaaggtcc tagtgttctt ttcttccact ggagctcaga gaagccaaca 1140
gttctatttt tcacggggga agtctagggc tggcaatcct tcagaaactt tttgtttact 1200
gatttcacag gcaattccct caaatttgaa tgggcaggta cacaaacact ttccatccat 1260
tagaattgct gtacctccat tttggcatga gtggcatttt cttacactaa attcattgat 1320
atagtcttca atggctcttt ccaagttttg tttctttagg tgtgcatttt tcattttcac 1380
tggaaccaga ttatatatag gagacagttt ttgactaatg agaacaggag catcatttat 1440
ggaagaggcc cagttgacaa aatcagtcac atcaatcatg gttcctcgga gaagcttttc 1500
tttcagttca aatgcatatt gtctggttcc acctcttatg agtgaaataa catcatctat 1560
gaggtgatca ctggtgatgt ttacagctct accctctccc ctctttacac aatcatcttt 1620
atcagcttta gctccagcag agattttaga gaaatccaga gatacatcca gatgataccc 1680
gaggcatctc tttacatctt ttagttcaac acctttccgg ttcatggaag ctttatccaa 1740
aacatatatt agttcataga gtcctcccag agacccagag ctactgtagt gggttccata 1800

```
ggtttccaaa aaggcaaaat attctccctt ttcataggta gttggcaaag cttttatatc   1860
atccacaaaa gttgttgtga gcacaacatc acgatttctc atcataaatc ttcccagatg   1920
aatttctcct ttcacatgca ggaacatttt ttccttcttt gaagaatatg acaaaaatag   1980
ttggtaagtt tcatttttgg aatatgaaaa ccgaaaacta ccctggccac gtaaagaatt   2040
tgaggaggct tgtttctcag aagacttttc agttttaact ttatttgctt cagtgggtgt   2100
aaattttaga gatatatctg cattaaaatt tgatgtcttc tcttggacga tacttttaaa   2160
tgcttcaatt tgttcttcat aatgttcggt tcttaaattt ttctcgcctt tggtttcata   2220
gatcaaagaa gccacgttcc agggtcttcg gtagtatgtc aaagtgtttc catcccgatc   2280
ccggttacag agtccattgt agaactcatt gtcaaaaggt gtgcttaggg gatccatccc   2340
taaaatgttg atcccgtagc ctgctgttcg tgccagctca gactcttcta ccactctgtc   2400
tctgcagggg ggacggggat cactttcaca atcatcctca tctgaaaagt ctccacagtc   2460
attgtcacca ttacacagga gtcgcctctt tatgcatctg cctgtaccgc attgaaagtc   2520
atttccgcag tcatcctcag catcctcaca gggctctgtg ggcacacact gtcgtctgtc   2580
tcccacagca tcggtgcaac ttttcccatt aaattgtccg aagacctcaa tgcttcttga   2640
acgaaacatt tgtctgaggc aaggatcgca ttgtgaccat tcactccagg ggctcattct   2700
gcagtctatg tgcgatgcgg aaccacggct ttctgttggc tgtgggtcat aactgggcgt   2760
gtactctgct gtgaggacgc ttatttctaa aatgcagatt gcagctgcaa agctccagca   2820
ggctgacatg ctgctcttgc tgggtggctg cgagtggggt ggcagagcag gtcgggtaag   2880
gcatttattt gcaaagggcc agaggacagg gaacaagtat tgtttgtctg cattcagggt   2940
ttttgtcaat ttggg                                                    2955
```

<210> SEQ ID NO 36
<211> LENGTH: 2727
<212> TYPE: DNA
<213> ORGANISM: Macaca fascicularis

<400> SEQUENCE: 36

```
tgttgtcgca gctgttttaa ttcaatcccg cgcccctgtc cagcaggaaa ccccttagag     60
aaaacccaaa tcctcatctt ggagtttctc cttcagccag ggcagcactt ggaagaggtt    120
gacgtgaaag tctcgggcgt gagcaggtac ctgcttttgc cgcttctggt ttttgcagac    180
atccactact ccccagctga tgacaccaac ttgaatgaaa cgacttctct tgtgaactat    240
caaggggccg ccagaatcac ctctgcaagt attggggtca gcatagggac tcactcctcc    300
agtacaaagg aaccgagggg tgaccacctc cgagatgtcc ttgactttgt catagcctgg    360
ggcatattga gcatctctct cacagctgcc tttcttatcc ccattcttga tgtagacctc    420
cttccgagtc agcttcttct cctcctcaga cacaaacaga gctttgatat cctgtgcagg    480
gagcagctct tccttctgtt gctggcaagt ggtagttgga ggaagcctca aagctcgagt    540
tgttccctcg gtacagggga gacaaatggg cctgatagtc gggtcataat tcaacttttt    600
cttgagcttg atcagggcaa cgtcatagtc ataaaattca ggaattcctg cttctttttt    660
cccgctaatg ttgtagtcgg ggtgaaatag gactttttct atctccaggt cccgcttctt    720
ccccacgctg accttgatcg agtgttcctt gtcgtccaca gtaaaacaat gtgctgctgt    780
cagcacaaag tactcagaca ccacagcccc catacagctc tcatgtccct tcgaagggcg    840
agtgactgag atcttggcct gccatggttg cttgtggtaa tcggtacccg tcgtgtgttc    900
```

```
ccaaaccatg ccacagagac tcagagactg gctttcatca atcatttgga agaaaacgtc    960
ttccaggttt tccatatcct tgactttgaa cacatgttgc tcattgtctt tcttggaagc   1020
caaagcattg atgttcactt ggtccaccaa aggtccaacc ccaaacacat agacatccag   1080
ataatcctcc ctcgggtttt tgcgatcctt gccgatgtat aacaagtccc ggatctcatc   1140
aatgacagta attgggtccc cgcccatgtt gtgcaatcca tcggtcatga ggatgatgac   1200
atggcgggtg cggttccagc cttcaggagg gatgtcctct ggccaactca tcatgctgta   1260
cactgcctgg agggccctct tggtgttagt ccctgacttc aacttgtggt cttcataatt   1320
gatttcactg agcttcttcg tgacccagtc tgcattgctg ctctcttggt cagacacttt   1380
gacccaaatt ctggggtatg tggcatatgt cactagagca tatcttggct tcacaccata   1440
acttgccacc ttctcaatta agttgactag acactttttg gctcctgtga agttgccggc   1500
cccaatgctg tctgatccat ctagcaccag gtagatgttc atggagcctg aagggtctag   1560
gatgatcctc cgcttctgtt gttcccctgg gctgtgccca tcctcggcat cgactccttc   1620
tatggtctcc gtcagggaag acaggaaagc ttcggccacc tcttgagggg tgtcgtacat   1680
gaaggagtct tggcaggaag gctccgtccc gctccaagag ccaccttcct gacacgttcg   1740
ccgctgggag ccacgcaggg taagcccccg gctgcagtgg taggtgacgc tgtcttcaag   1800
gcggtaccgg ctgcccacct tccttgtgcc aatggggatg cctgggttgg agcagtaccc   1860
cgctccgttg tcacagatcg ctgtctgccc actccaccgg ccattcactt ggcaggtgcg   1920
attggcagag ccccggagag tgtaaccgtc atagcagtgg aaagagatct catcactcac   1980
attgtagtag ggagaccggg gccggtattc cccgttctcg aagtcctgtg gtcgtggaca   2040
gcggattgct ctgcactctg ccttcttgac agtttttcga tcttgagtct gcagggtgct   2100
ccaggacccc gtggatctgc aggtacgtgt ctgcacaggg tacgggtaga agccagaagg   2160
acacacgtat tccagtgcct ggccctcttg gagaagtcgg aaggagccac ctttgatctc   2220
taccccctcc agagagcagg atccttgagg ctgggccgaa gacaatggag tggtggtcac   2280
acctgcagat aagaggccca agatgaaggg catcaggtag agctgggggc tgagactgct   2340
ccccatggcg ttagaaggca ggagagaagc tgggcctggg gcaggatggc gtgtcctggc   2400
ttgttttgct tgtctactta gctcagtgtc caagctgaaa ctccagacct agacctggtc   2460
acattccctt cccctgcccc ccaccagctc ccggcctttt atgcaatctg tgttctggca   2520
cctgcagctt gccccgcctg tcctaccctc atcactttcc cggaacatcc aagcgggagg   2580
gccccgctga gctgccagtc aaggaagcag aaactgcaga agtcccaccc tttgctgccc   2640
aaggtccagg actctcccct tcagtacctc cttctggcct cagctcctcc ccaacaagcc   2700
cagaccaccc acttagggac cagaaat                                       2727
```

<210> SEQ ID NO 37
<211> LENGTH: 5106
<212> TYPE: DNA
<213> ORGANISM: Macaca fascicularis

<400> SEQUENCE: 37

```
tgaaatataa ctgaagcttt attgggagtg ggggaatggg ggtgtggtca gttggggcac     60
ccaaagacaa ccatgttctc agtgaaggtg ccgaggtcct ggcattgttt ctggttctct    120
tcatcttggc attcgtcctc ctcgggccag tgctccaccc aggtgtcctt cccgatgatg    180
tagctgagat tgggtttctc tccccagaaa tcggaggaga gaccccacat gaggtagtgt    240
ttcctctcct ccagcttcag ggcttccctg cacttgatgg ggctgatgaa cgtgcgctgt    300
```

```
tgtccaacct gcacctcatc cgagcctgac ttgatgatct gctcaatggc catgatgtac    360
tcgtcaaagt cattggacag ctgggccttg accagtcggg tcttgtacac atagtccact    420
cctggctcac aggccttgtc cagccgttct tccagggtga ctttgtcatc caacttttgt    480
atgaagcaat tctcctcagc acagcggcac agctcatcac gacagagctt gttcagcttt    540
ccatcctcct tttctgggtg gtagaaccgg gtacagcttt ccgccaggtt gtaataggcg    600
tagaccttga ctgcaccagg ctggataagc tctacattaa aatattggtg aactttgaaa    660
gctatacagt catcctcaga gtgtgagacc ttgtccaggt agatgatgag ggtgttccta    720
tcggagaagg ctttgtccag ctcatacttg gagatgtatc tgtcaacgcc gtttgccagc    780
tgcttgaggt catctgtgtc tggaacgaag ccagtcatca tggatatgtc cagtatagac    840
atagtggcat cctggtctcc ccggtacctg gtacagatct caaggatcat agtgttcttg    900
gcatcctgag gcctcttttc tgtttccggt gctggtttta tggtgacctt gaggtcgaat    960
ttattacagg tgagttgacc tttggcctta gcatggtaca ttgtcactac cgacaaggtg   1020
ccttggcctt ttccttcagc tgtgactgtg aaaccctcat tttccttggt ctcttctgat   1080
cgcaggaggc tggcagattc ccagtggata cggtggatga tcttggagct gcgactgggc   1140
agttggaggg acacatccag gttcagttcc ttgtgatcag ggacatcctt ttggtattga   1200
gccaaggctt ggaacaccat gaaggtggcc tgggtagagc catagccacc accgtagtat   1260
ctctgttcat tgagccaacg cacgacggga ggcacaaagt caaagtcttt tagctgcagt   1320
agggccaaga gggcatagga tgtggcctcc acattgtaga gctgctgacc aggctcctcc   1380
cagcggttct tatctttggc tgtggtcaga aatttgttga gaagaggtcc cttcagcctg   1440
cccatctggg ccagggcata ggcagcgatg gccacagtgt aggatctctg taggttcatg   1500
tagttggctt caaggaagtc tcctgcttta gtgatgctgc cgggcaggct gttgacctgc   1560
tcctcgcaaa tctctttagc ctcttgcagc gagatgagaa caaaggccgt gagggccatg   1620
tctttctcgt tggtgttccg gaatccacca gtcatttctt gatgtatcac gggcgcatcc   1680
tcctggaaga ccccgtcggg cttctgcttc tccaggatca gccatttaac agccccgcag   1740
aggacctggg agtcgatggc aatgaggttg acagccagag agaagacctt gaccacgtag   1800
gcggtcagcc aggtgctggg tgcccggttc aggaaggccg caaaggcaga gctgggttgt   1860
ctgaaggcca gctgctgggt gtaccccttc ttgatgagct ccaaggcccc ctgccgcttc   1920
tccgggccga acttctccca ctgttccgtt tcatccaggt aatgcacagc gatgactgtg   1980
ggcgtcatgg tgatcatgtt ctgttctccg cagcccgagg gggtcacgat gaggtgcttc   2040
agccgttccg catcgatggc atcctctgtc atctgggcca ccggggtccc ttgcaggaga   2100
attctggtct cagactcggt gtccgggact tggtcactga ggtctgcagg tgggacgtcc   2160
tctctctgca ctccttcctg gcccaggcgt tctggatcca gcgtgcgaac agccacagtt   2220
ttgttcattc tgattccttc cggcacgacc ttcagggact tcctgacacc gtcactgatg   2280
aaaaaatggt agacggcagc cttgacttcc acttcctgct ggccggtctt taggggcacg   2340
atgacataag gaacggacag cgaggacttg ggggggatgg ttacggtctg ctggtgacgc   2400
ctcttggcgg tggccaggct gcagaaggct ggattgtgga gtagttccac cctcaccttg   2460
agctcttggt tctgccggta attgtagaga acagctcgga tttccacctg ctcgtttcga   2520
acaacagagt agggtagccg caggtcgatg aagaagtcct gcattactgt gacctcgaag   2580
gggtctgcca cacagatccc tttcttgtct gacaagctca cggccagaat ctcccacgtg   2640
```

-continued gtgatggagt ctttcaaaaa tatattcatg agcttcgtgg agattccgtt tttcggtgcc 2700
tctttcaact cttcaatctt ccacagccaa ctctctggga actcacttcg ggaaacgatg 2760
ttctcttctg cgatgatgtc ctcatccagg ttactcctgg ccaggcccag gtgactggcc 2820
cgcgcgtgct gccgccgcag ctcggtgatg tagttgcagc agtccaggaa ggccttcttg 2880
cacgcctcgt ccagggtgat gtaacgggtc cggcgctggc atgagaacct catggggttc 2940
tcccgcatac cgtgctcgca gcacttgcgc agctccttgg ggtactgacc aactttgtcc 3000
attctcttct ccgcgagctg cacggaacgg cgtcggcggg cggctggctg tgggcactga 3060
agttctgccc tctgggccgt ctgctggcca ctgctgctcg caaaggtcag gcctgcatcc 3120
gagaagacac cagcgtaatc cttcccactg cctggggtgc agccgatgtc tgccttctcc 3180
accacgtccc agatcttact ctgcgtcagc ttgttcttct tattcagcac aaacacgccc 3240
ttgtccacag ccaccagtcc cacccgggcc ccgtggtcac cctctatctt cagggtcatc 3300
tgctgcccgg gtaaaggctg cctgtcttct gactggccgc tttttaccac cagcgagccc 3360
acgcaagagt ccttgacgtc cacccacacg gagtcggcca ccacttccct ctggccgttg 3420
gcgccgatca gcgtgtagta ggccaccagg cggaaggaag ggatgaagtc ggtggtgatg 3480
gacaggggca gcaccaccag gtcctggcca ggctctcgca cctggcgtcc caccttcaac 3540
agcttgcctt tgttcataat caggtaggtg tagtagcgga tcttggcctc ctgggtgcgg 3600
tccattcgca ggaggaagtt gacgttgagg gtctccccag gtctgagctc tgcacgtggc 3660
actgagagat gcaggtaatt gttggagttg cccacggtgc tgtagggctg agcctccatg 3720
gtcctggtag cctgctccgc ctccgagagc tcccgcttct tcgtgcgcac cgtgatgctc 3780
aagggcttct ggctggggtg tgtgttgatg ctgagtttgg ccacgccgtc tccctgggtt 3840
agagactgca cagcgtcctc gccctggact gccacgggga ctcggtaggc tggagagcca 3900
tcggggttcg tcacgaacac catgaggtca aagggcattc ctggtttgaa gtacttgggc 3960
gtcttggtga agtggatctg gtagggagag gtcacgatgg ggatcccgct gcgctccgcc 4020
tgcaccatgt cactgcctga gtgcaggata acggtgacag acacatacaa ggacttcccc 4080
actaggtctt ccggtcgggg attctgcacc ccgtccagca gtaccttccg gctcagcacg 4140
gcgtctcctg agccatcctc aatctggatg cgcttgaggg attcaggcag ggaaatcctc 4200
tgctcgccat cctggatccc gaagatgaca aaggcagttc cctccacttt ctttccatag 4260
aggaacctgg cggtgatggt gacctccagg cccttctggt tatagatgta gtagaatttc 4320
tctgtaggct ccactatgac ctcgaaactg ggcagcacgt actccttcac ctcaaactca 4380
gtggagaaga cctgttgcgg cgaattttca tagtaggctc ggatcttcca ctggcccatg 4440
ttgacgagtt ccggaatgtc ccaagacaag ggcaagatgc caaattggtt ctgagaagac 4500
aaggagtcct gcttgaccgg gatgccgtcc gggttctcaa tgttgaccac gaccgtccgg 4560
cccacgggta gcagcttgtg gttgacggtg aagatccgac agagaactgt ggagccaggg 4620
gtgtagatgg tcttgtctgt ctggatgaag aggtacccgc tctgaaggct gaccagtacc 4680
accttctcca ccacttgggc cccgaaggtg gcctgcacag tcacgaactt gttgtgcccc 4740
ttttctgact tgaactcctt gttggctggg atcctgatgg tgacgctgcc catgtggctg 4800
gtggcagggg tcagcacggt cttctcactg gacagcacca gttttttgcc tgggaagtcg 4860
tggacagtga cagtgaccgg aacatcccca ttcgcgtcat gggcctccag caccacggtc 4920
tcctcactct ccagccgcaa gacgtttggg gtgatcatag agtacatggg agtccccaga 4980
gccaggggga ggtggattag tagcaggagc agcaggctgg gacctgaggt gagtcccatg 5040
gtgctgggac agtgcagggt cagagggaca gagggacaga gggagaggat ggggaggagt 5100
gagcag 5106

<210> SEQ ID NO 38
<211> LENGTH: 2091
<212> TYPE: DNA
<213> ORGANISM: Macaca fascicularis

<400> SEQUENCE: 38
tttgaagttt ttaaaccaac attctgtttt aatttaattt tgttttttttt agaagagatt 60 ggcattgtct gtgggagaaa gcagttctgg catatttcac tcttgactcc tcattaggga 120
ataaaaaatg gaaacatcat aggagtttaa gaaagaaaaa ttaaaaaata attatagacc 180
taagagagga gacttcagaa gttggtagga ttttcatgaa gcatgttgct atttctttgg 240
cagctaagat tatcttcagg gataggatct gaaggtccta gtgttctttt cttccactgg 300
agctcagaga agccaacagt tctatttttc acgggggaag tctagggctg gcaatccttc 360
agaaactttt tgtttactga tttcacaggc aattccctca aatttgaatg ggcaggtaca 420
caaacacttt ccatccatta gaattgctgt acctccattt tggcatgagt ggcattttct 480
tacactaaat tcattgatat agtcttcaat ggctctttcc aagttttgtt tctttaggtg 540
tgcatttttc attttcactg gaaccagatt atatatagga gacagttttt gactaatgag 600
aacaggagca tcatttatgg aagaggccca gttgacaaaa tcagtcacat caatcatggt 660
tcctcggaga agcttttctt tcagttcaaa tgcatattgt ctggttccac ctcttatgag 720
tgaaataaca tcatctatga ggtgatcact ggtgatgttt acagctctac cctctcccct 780
ctttacacaa tcatctttat cagctttagc tccagcagag attttagaga aatccagaga 840
tacatccaga tgatacccga ggcatctctt tacatctttt agttcaacac ctttccggtt 900
catggaagct ttatccaaaa catatattag ttcatagagt cctcccagag acccagagct 960
actgtagtgg gttccatagg tttccaaaaa ggcaaaatat tctccctttt cataggtagt 1020
tggcaaagct tttatatcat ccacaaaagt tgttgtgagc acaacatcac gatttctcat 1080
cataaatctt cccagatgaa tttctccttt cacatgcagg aacatttttt ccttctttga 1140
agaatatgac aaaaatagtt ggtaagtttc atttttggaa tatgaaaacc gaaaactacc 1200
ctggccacgt aaagaatttg aagaggcttg tttctcagaa gacttttcag ttttaacttt 1260
atttgcttca gtgggtgtaa attttagaga tatatctgca ttaaaatttg atgtcttctc 1320
ttggacgata cttttaaatg cttcaatttg ttcttcataa tgttcggttc ttaaattttt 1380
ctcgcctttg gtttcataga tcaaagaagc cacgttccag ggtcttcggt agtatgtcaa 1440
agtgtttcca tcccgatccc ggttacagag tccattgtag aactcattgt caaaaggtgt 1500
gcttagggga tccatcccta aaatgttgat cccgtagcct gctgttcgtg ccagctcaga 1560
ctcttctacc actctgtctc tgcagggggg acggggatca ccttcacaat catcctcatc 1620
tgaaaagtct ccacagtcat tgtcaccatt acacaggagt cgcctcttta tgcatctgcc 1680
tgtaccgcat tgaaagtcat ttccgcagtc atcctcagca tcctcacagg gctctgtggg 1740
cacacactgt cgtctgtctc ccacagcatc ggtgcaactt ttcccattaa attgtccgaa 1800
gacctcaatg cttcttgaac gaaacatttg tctgaggcaa ggatcgcatt gtgaccattc 1860
actccagggg ctcattctgc agtctatgtg cgatgcggaa ccacggcttt ctgttggctg 1920
tgggtcataa ctgggcgtgt actctgctgt gaggatgctt atttctaaaa tgcagattgc 1980
agctgcaaag ctccagcagg ctgacatgct gctcttgctg ggtggctgcg agtggggtgg 2040
cagagcaggt cgggtaaggc atttatttgc aaagggccag aggacaggga a 2091

<210> SEQ ID NO 39
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 39
cuuacgcuga guacuucgat t 21

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 40
ucgaaguacu cagcguaagt t 21

<210> SEQ ID NO 41
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 41
auuccugaau uuuaugacua u 21

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 42
ccugaucaag cucaagaaua a 21

<210> SEQ ID NO 43
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 43
gaagcaggaa uuccugaauu u 21

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 44
agcaacaugu guucaaaguc a 21

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 45
gcuguggugu cugaguacuu u 21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 46
aagugucuag ucaacuuaau u 21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 47
agcugugaga gagaugcuca a 21

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 48
agccaaaaag ugucuaguca a 21

<210> SEQ ID NO 49
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 49
ugugagugau gagaucucuu u 21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
aauugagaag guggcaaguu a 21

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51
caacaugugu ucaaagucaa g 21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
ugugagagag augcucaaua u 21

<210> SEQ ID NO 53
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 53
gucuagucaa cuuaauugag a 21

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 54
uccaagaaag acaaugagca a 21

<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 55
uguguucaaa gucaaggaua u 21

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 56
auugaugaga uccgggacuu g 21

<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 57
cugugagaga gaugcucaau a 21

<210> SEQ ID NO 58
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 58
gagccaaaaa gugucuaguc a 21

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 59
uccaagauga ggauuugggu u 21

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 60
cccuugauag uucacaagag a 21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 61
caaagucaag gauauggaaa a 21

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 62
uaguucacaa gagaagucgu u 21

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 63
ggccccuuga uaguucacaa g 21

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 64
uggugcuaga uggaucagac a 21

<210> SEQ ID NO 65
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 65
gcuagaugga ucagacagca u 21

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 66
uaccuggugc uagauggauc a 21

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 67
ggugcuagau ggaucagaca a 21

<210> SEQ ID NO 68
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 68
ucugagucuc uguggcaugg u 21

<210> SEQ ID NO 69
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 69
gugcuagaug gaucagacag a 21

<210> SEQ ID NO 70
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 70
cuaccuggug cuagauggau a 21

<210> SEQ ID NO 71
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 71
accuggugcu agauggauca a 21

```
<210> SEQ ID NO 72
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72

auagucauaa aauucaggaa uuc                                              23


<210> SEQ ID NO 73
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73

uuauucuuga gcuugaucag ggc                                              23


<210> SEQ ID NO 74
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74

aaauucagga auuccugcuu cuu                                              23


<210> SEQ ID NO 75
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75

ugacuuugaa cacauguugc uca                                              23


<210> SEQ ID NO 76
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76

aaaguacuca gacaccacag ccc                                              23


<210> SEQ ID NO 77
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 77
aauuaaguug acuagacacu uuu 23

<210> SEQ ID NO 78
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 78
uugagcaucu cucucacagc ugc 23

<210> SEQ ID NO 79
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 79
uugacuagac acuuuuuggc ucc 23

<210> SEQ ID NO 80
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 80
aaagagaucu caucacucac auu 23

<210> SEQ ID NO 81
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 81
uaacuugcca ccuucucaau uaa 23

<210> SEQ ID NO 82
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 82
cuugacuuug aacacauguu gcu 23

<210> SEQ ID NO 83
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
auauugagca ucucucucac agc 23

<210> SEQ ID NO 84
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 84
ucucaauuaa guugacuaga cac 23

<210> SEQ ID NO 85
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
uugcucauug ucuuucuugg aag 23

<210> SEQ ID NO 86
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 86
auauccuuga cuuugaacac aug 23

<210> SEQ ID NO 87
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 87
caagucccgg aucucaucaa uga 23

<210> SEQ ID NO 88
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 88
uauugagcau cucucucaca gcu 23

<210> SEQ ID NO 89
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 89
ugacuagaca cuuuuuggcu ccu 23

<210> SEQ ID NO 90
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 90
aacccaaauc cucaucuugg agu 23

<210> SEQ ID NO 91
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 91
ucucuuguga acuaucaagg ggc 23

<210> SEQ ID NO 92
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 92
uuuuccauau ccuugacuuu gaa 23

<210> SEQ ID NO 93
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 93
aacgacuucu cuugugaacu auc 23

<210> SEQ ID NO 94
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 94
cuugugaacu aucaaggggc cgc 23

<210> SEQ ID NO 95
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 95
ugucugaucc aucuagcacc agg 23

<210> SEQ ID NO 96
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 96
augcugucug auccaucuag cac 23

<210> SEQ ID NO 97
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 97
ugauccaucu agcaccaggu aga 23

<210> SEQ ID NO 98
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 98
uugucugauc caucuagcac cag 23

<210> SEQ ID NO 99
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 99
accaugccac agagacucag aga 23

<210> SEQ ID NO 100
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100
ucugucugau ccaucuagca cca 23

<210> SEQ ID NO 101
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
uauccaucua gcaccaggua gau 23

<210> SEQ ID NO 102
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
uugauccauc uagcaccagg uag 23

<210> SEQ ID NO 103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
gcaagccaag aucucaguca c 21

<210> SEQ ID NO 104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
gauugagaag guggcgaguu a 21

<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
cacaagagaa gccgcuucau u 21

<210> SEQ ID NO 106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 106
uugugagaga gaugcuacaa a 21

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 107
uccuucauga auguuccggg a 21

<210> SEQ ID NO 108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 108
ucacagagaa gcucaaccaa a 21

<210> SEQ ID NO 109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 109
cucaaccaaa ucaguuauga a 21

<210> SEQ ID NO 110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 110
cccugacaga gaccaucgaa g 21

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 111
gagcagauug cauaaaaggu u 21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 112
cuucaugaau guuccgggaa g 21

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 113
cuucauucaa guugguguga u 21

<210> SEQ ID NO 114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 114
gauugaagag guccuguucc a 21

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 115
auuucuuuuc aaugcuauga u 21

<210> SEQ ID NO 116
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 116
ccagagcaga uugcauaaaa g 21

<210> SEQ ID NO 117

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117

cacagagaag cucaaccaaa u                                              21


<210> SEQ ID NO 118
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118

gugacugaga ucuuggcuug cca                                            23


<210> SEQ ID NO 119
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119

uaacucgcca ccuucucaau caa                                            23


<210> SEQ ID NO 120
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120

aaugaagcgg cuucucuugu gaa                                            23


<210> SEQ ID NO 121
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121

uuuguagcau cucucucaca acu                                            23


<210> SEQ ID NO 122
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
```

ucccggaaca uucaugaagg agg 23

<210> SEQ ID NO 123
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 123
uuugguugag cuucucugug acc 23

<210> SEQ ID NO 124
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 124
uucauaacug auuugguuga gcu 23

<210> SEQ ID NO 125
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 125
cuucgauggu cucugucagg gag 23

<210> SEQ ID NO 126
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 126
aaccuuuuau gcaaucugcu cug 23

<210> SEQ ID NO 127
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 127
cuucccggaa cauucaugaa gga 23

<210> SEQ ID NO 128
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 128
aucacaccaa cuugaaugaa gcg 23

<210> SEQ ID NO 129
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
uggaacagga ccucuucaau cuc 23

<210> SEQ ID NO 130
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
aucauagcau ugaaaagaaa ucu 23

<210> SEQ ID NO 131
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
cuuuuaugca aucugcucug gca 23

<210> SEQ ID NO 132
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
auuugguuga gcuucucugu gac 23

<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
auuccugaau uuuaugacua u 21

<210> SEQ ID NO 134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 134
ccugaucaag cucaagaaua a 21

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 135
gaagcaggaa uuccugaauu u 21

<210> SEQ ID NO 136
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
agcaacaugu guucaaaguc a 21

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 137
gcuguggugu cugaguacuu u 21

<210> SEQ ID NO 138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 138
aagugucuag ucaacuuaau u 21

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 139
agcugugaga gagaugcuca a 21

<210> SEQ ID NO 140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
agccaaaaag ugucuaguca a 21

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 141
ugugagugau gagaucucuu u 21

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 142
aauugagaag guggcaaguu a 21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 143
caacaugugu ucaaagucaa g 21

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 144
ugugagagag augcucaaua u 21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 145
gucuagucaa cuuaauugag a 21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 146
uccaagaaag acaaugagca a 21

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 147
uguguucaaa gucaaggaua u 21

<210> SEQ ID NO 148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 148
auugaugaga uccgggacuu g 21

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 149
cugugagaga gaugcucaau a 21

<210> SEQ ID NO 150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 150
gagccaaaaa gugucuaguc a 21

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 151
uccaagauga ggauuugggu u 21

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
cccuugauag uucacaagag a 21

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
caaagucaag gauauggaaa a 21

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
uaguucacaa gagaagucgu u 21

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
ggccccuuga uaguucacaa g 21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
uggugcuaga uggaucagac a 21

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
gcuagaugga ucagacagca u 21

<210> SEQ ID NO 158
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
uaccuggugc uagauggauc a 21

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 159
ggugcuagau ggaucagaca a 21

<210> SEQ ID NO 160
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
ucugagucuc uguggcaugg u 21

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 161
gugcuagaug gaucagacag a 21

<210> SEQ ID NO 162
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 162
cuaccuggug cuagauggau a 21

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
accuggugcu agauggauca a 21

<210> SEQ ID NO 164
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
auagucauaa aauucaggaa uuc 23

<210> SEQ ID NO 165
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 165
uuauucuuga gcuugaucag ggc 23

<210> SEQ ID NO 166
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 166
aaauucagga auuccugcuu cuu 23

<210> SEQ ID NO 167
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 167
ugacuuugaa cacauguugc uca 23

<210> SEQ ID NO 168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 168
aaaguacuca gacaccacag ccc 23

<210> SEQ ID NO 169
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 169
aauuaaguug acuagacacu uuu 23

<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 170
uugagcaucu cucucacagc ugc 23

<210> SEQ ID NO 171
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 171
uugacuagac acuuuuuggc ucc 23

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
aaagagaucu caucacucac auu 23

<210> SEQ ID NO 173
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 173
uaacuugcca ccuucucaau uaa 23

<210> SEQ ID NO 174
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 174
cuugacuuug aacacauguu gcu 23

<210> SEQ ID NO 175
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 175
auauugagca ucucucucac agc 23

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
ucucaauuaa guugacuaga cac 23

<210> SEQ ID NO 177
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
uugcucauug ucuuucuugg aag 23

<210> SEQ ID NO 178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
auauccuuga cuuugaacac aug 23

<210> SEQ ID NO 179
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
caagucccgg aucucaucaa uga 23

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
uauugagcau cucucucaca gcu 23

<210> SEQ ID NO 181
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
ugacuagaca cuuuuuggcu ccu 23

<210> SEQ ID NO 182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
aacccaaauc cucaucuugg agu 23

<210> SEQ ID NO 183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
ucucuuguga acuaucaagg ggc 23

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 184
uuuuccauau ccuugacuuu gaa 23

<210> SEQ ID NO 185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 185
aacgacuucu cuugugaacu auc 23

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 186
cuugugaacu aucaaggggc cgc 23

<210> SEQ ID NO 187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 187
ugucugaucc aucuagcacc agg 23

<210> SEQ ID NO 188
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 188
augcugucug auccaucuag cac 23

<210> SEQ ID NO 189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 189
ugauccaucu agcaccaggu aga 23

<210> SEQ ID NO 190
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 190
uugucugauc caucuagcac cag 23

<210> SEQ ID NO 191
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 191
accaugccac agagacucag aga 23

<210> SEQ ID NO 192
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 192
ucugucugau ccaucuagca cca 23

<210> SEQ ID NO 193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 193
uauccaucua gcaccaggua gau 23

<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 194
uugauccauc uagcaccagg uag 23

<210> SEQ ID NO 195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 195
gcaagccaag aucucaguca c 21

<210> SEQ ID NO 196

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196
gauugagaag guggcgaguu a 21

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
cacaagagaa gccgcuucau u 21

<210> SEQ ID NO 198
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
uugugagaga gaugcuacaa a 21

<210> SEQ ID NO 199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 199
uccuucauga auguuccggg a 21

<210> SEQ ID NO 200
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 200
ucacagagaa gcucaaccaa a 21

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 201
cucaaccaaa ucaguuauga a 21

<210> SEQ ID NO 202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 202
cccugacaga gaccaucgaa g 21

<210> SEQ ID NO 203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 203
gagcagauug cauaaaaggu u 21

<210> SEQ ID NO 204
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 204
cuucaugaau guuccgggaa g 21

<210> SEQ ID NO 205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 205
cuucauucaa guugguguga u 21

<210> SEQ ID NO 206
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 206
gauugaagag guccuguucc a 21

<210> SEQ ID NO 207
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 207
auuucuuuuc aaugcuauga u 21

<210> SEQ ID NO 208
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 208
ccagagcaga uugcauaaaa g 21

<210> SEQ ID NO 209
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 209
cacagagaag cucaaccaaa u 21

<210> SEQ ID NO 210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 210
gugacugaga ucuuggcuug cca 23

<210> SEQ ID NO 211
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 211
uaacucgcca ccuucucaau caa 23

<210> SEQ ID NO 212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 212
aaugaagcgg cuucucuugu gaa 23

```
<210> SEQ ID NO 213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213

uuuguagcau cucucucaca acu                                              23


<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214

ucccggaaca uucaugaagg agg                                              23


<210> SEQ ID NO 215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215

uuugguugag cuucucugug acc                                              23


<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216

uucauaacug auuugguuga gcu                                              23


<210> SEQ ID NO 217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217

cuucgauggu cucugucagg gag                                              23


<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 218
aaccuuuuau gcaaucugcu cug 23

<210> SEQ ID NO 219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 219
cuucccggaa cauucaugaa gga 23

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 220
aucacaccaa cuugaaugaa gcg 23

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
uggaacagga ccucuucaau cuc 23

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
aucauagcau ugaaaagaaa ucu 23

<210> SEQ ID NO 223
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
cuuuuaugca aucugcucug gca 23

<210> SEQ ID NO 224
<211> LENGTH: 23
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 224

auuugguuga gcuucucugu gac                                         23

<210> SEQ ID NO 225
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225

cguggucaag gucuucucuc u                                           21

<210> SEQ ID NO 226
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226

acguggucaa ggucuucucu a                                           21

<210> SEQ ID NO 227
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227

uuugaccuca ugguguucgu g                                           21

<210> SEQ ID NO 228
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228

ggagaauugc uucauacaaa a                                           21

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229

uguuaaaugg cugauccugg a                                           21
```

<210> SEQ ID NO 230
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 230
gacagacaag accaucuaca c 21

<210> SEQ ID NO 231
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 231
ccagacagac aagaccaucu a 21

<210> SEQ ID NO 232
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 232
ccagauccac uucaccaaga a 21

<210> SEQ ID NO 233
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 233
uugaccucau gguguucgug a 21

<210> SEQ ID NO 234
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 234
ccccuucgag gucacaguaa u 21

<210> SEQ ID NO 235
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 235
augaacaaaa cuguggcugu u 21

<210> SEQ ID NO 236
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 236
agacagacaa gaccaucuac a 21

<210> SEQ ID NO 237
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 237
ccagauccac uucaccaaga c 21

<210> SEQ ID NO 238
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 238
agggaucugu guggcagacc a 21

<210> SEQ ID NO 239
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 239
gacaagacca ucuacacccc u 21

<210> SEQ ID NO 240
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 240
gcugaggaga auugcuucau a 21

<210> SEQ ID NO 241
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: S
ynthetic oligonucleotide"

<400> SEQUENCE: 241
acguggucaa ggucuucucu c 21

<210> SEQ ID NO 242
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 242
ggaucugugu ggcagacccc u 21

<210> SEQ ID NO 243
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 243
acagacaaga ccaucuacac a 21

<210> SEQ ID NO 244
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 244
auccagacag acaagaccau u 21

<210> SEQ ID NO 245
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 245
cuccgugugg guggacguca a 21

<210> SEQ ID NO 246
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 246
uccagacaga caagaccauc u 21

<210> SEQ ID NO 247
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 247
agggaucugu guggcagacc c 21

<210> SEQ ID NO 248
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 248
caagaaaggg aucugugugg a 21

<210> SEQ ID NO 249
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
ugaccucaug guguucguga u 21

<210> SEQ ID NO 250
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
gcagcuaaaa gacuuugacu u 21

<210> SEQ ID NO 251
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
cauccagaca gacaagacca u 21

<210> SEQ ID NO 252
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 252
acagacaaga ccaucuacac c 21

<210> SEQ ID NO 253
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
auccagacag acaagaccau c 21

<210> SEQ ID NO 254
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
uuugaccuca ugguguucgu u 21

<210> SEQ ID NO 255
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
ggaugccaag aacacuauga u 21

<210> SEQ ID NO 256
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
aagaaaggga ucuguguggc a 21

<210> SEQ ID NO 257
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
caagaaaggg aucuguguggc c 21

<210> SEQ ID NO 258
<211> LENGTH: 21

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
uacgugguca aggucuucuc u 21

<210> SEQ ID NO 259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
caguuucgag gucauagugg a 21

<210> SEQ ID NO 260
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 260
cgugccggaa ggaaucagaa u 21

<210> SEQ ID NO 261
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 261
gaaagggauc uguguggcag a 21

<210> SEQ ID NO 262
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
gacagacaag accaucuaca a 21

<210> SEQ ID NO 263
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 263
ugaccucaug guguucguga c 21

<210> SEQ ID NO 264
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 264
uguaauaaau ucgaccucaa g 21

<210> SEQ ID NO 265
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 265
aacuacauga accuacagag a 21

<210> SEQ ID NO 266
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 266
agagagaaga ccuugaccac gua 23

<210> SEQ ID NO 267
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 267
uagagaagac cuugaccacg uag 23

<210> SEQ ID NO 268
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 268
cacgaacacc augaggucaa agg 23

<210> SEQ ID NO 269
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
uuuuguauga agcaauucuc cuc 23

<210> SEQ ID NO 270
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
uccaggauca gccauuuaac agc 23

<210> SEQ ID NO 271
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
guguagaugg ucuugucugu cug 23

<210> SEQ ID NO 272
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
uagauggucu ugucugucug gau 23

<210> SEQ ID NO 273
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
uucuugguga aguggaucug gua 23

<210> SEQ ID NO 274
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
ucacgaacac caugagguca aag 23

<210> SEQ ID NO 275

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 275
auuacuguga ccucgaaggg guc 23

<210> SEQ ID NO 276
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 276
aacagccaca guuuuguuca uuc 23

<210> SEQ ID NO 277
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 277
uguagauggu cuugucuguc ugg 23

<210> SEQ ID NO 278
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 278
gucuugguga aguggaucug gua 23

<210> SEQ ID NO 279
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 279
uggucugcca cacagauccc uuu 23

<210> SEQ ID NO 280
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 280 aggggguguag auggucuugu cug 23

<210> SEQ ID NO 281
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 281
uaugaagcaa uucuccucag cac 23

<210> SEQ ID NO 282
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 282
gagagaagac cuugaccacg uag 23

<210> SEQ ID NO 283
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 283
aggggucugc cacacagauc ccu 23

<210> SEQ ID NO 284
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 284
uguguagaug gucuugucug ucu 23

<210> SEQ ID NO 285
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 285
aauggucuug ucugucugga uga 23

<210> SEQ ID NO 286
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 286
uugacgucca cccacacgga guc 23

<210> SEQ ID NO 287
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
agauggucuu gucugucugg aug 23

<210> SEQ ID NO 288
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
gggucugcca cacagauccc uuu 23

<210> SEQ ID NO 289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
uccacacaga ucccuuucuu guc 23

<210> SEQ ID NO 290
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
aucacgaaca ccaugagguc aaa 23

<210> SEQ ID NO 291
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
aagucaaagu cuuuuagcug cag 23

<210> SEQ ID NO 292
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 292
auggucuugu cugucuggau gaa 23

<210> SEQ ID NO 293
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 293
gguguagaug gucuugucug ucu 23

<210> SEQ ID NO 294
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 294
gauggucuug ucugucugga uga 23

<210> SEQ ID NO 295
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 295
aacgaacacc augaggucaa agg 23

<210> SEQ ID NO 296
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 296
aucauagugu ucuuggcauc cug 23

<210> SEQ ID NO 297
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 297
ugccacacag aucccuuucu ugu 23

<210> SEQ ID NO 298
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
gccacacaga ucccuuucuu guc 23

<210> SEQ ID NO 299
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 299
agagaagacc uugaccacgu agg 23

<210> SEQ ID NO 300
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
uccacuauga ccucgaaacu ggg 23

<210> SEQ ID NO 301
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
auucugauuc cuuccggcac gac 23

<210> SEQ ID NO 302
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
ucugccacac agaucccuuu cuu 23

<210> SEQ ID NO 303
<211> LENGTH: 23
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 303

uuguagaugg ucuugucugu cug                                              23


<210> SEQ ID NO 304
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304

gucacgaaca ccaugagguc aaa                                              23


<210> SEQ ID NO 305
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305

cuugaggucg aauuuauuac agg                                              23


<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306

ucucuguagg uucauguagu ugg                                              23


<210> SEQ ID NO 307
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307

cguggucaag gucuucucuc u                                                21


<210> SEQ ID NO 308
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308

acguggucaa ggucuucucu a                                                21
```

<210> SEQ ID NO 309
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 309
uuugaccuca ugguguucgu g 21

<210> SEQ ID NO 310
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 310
ggagaauugc uucauacaaa a 21

<210> SEQ ID NO 311
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 311
uguuaaaugg cugauccugg a 21

<210> SEQ ID NO 312
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 312
gacagacaag accaucuaca c 21

<210> SEQ ID NO 313
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 313
ccagacagac aagaccaucu a 21

<210> SEQ ID NO 314
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 314
ccagauccac uucaccaaga a 21

<210> SEQ ID NO 315
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 315
uugaccucau gguguucgug a 21

<210> SEQ ID NO 316
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 316
ccccuucgag gucacaguaa u 21

<210> SEQ ID NO 317
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 317
augaacaaaa cuguggcugu u 21

<210> SEQ ID NO 318
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 318
agacagacaa gaccaucuac a 21

<210> SEQ ID NO 319
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 319
ccagauccac uucaccaaga c 21

<210> SEQ ID NO 320
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 320
agggaucugu guggcagacc a 21

<210> SEQ ID NO 321
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 321
gacaagacca ucuacacccc u 21

<210> SEQ ID NO 322
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 322
gcugaggaga auugcuucau a 21

<210> SEQ ID NO 323
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 323
acguggucaa ggucuucucu c 21

<210> SEQ ID NO 324
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 324
ggaucugugu ggcagacccc u 21

<210> SEQ ID NO 325
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 325
acagacaaga ccaucuacac a 21

<210> SEQ ID NO 326
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 326
auccagacag acaagaccau u 21

<210> SEQ ID NO 327
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 327
cuccgugugg guggacguca a 21

<210> SEQ ID NO 328
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 328
uccagacaga caagaccauc u 21

<210> SEQ ID NO 329
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 329
agggaucugu guggcagacc c 21

<210> SEQ ID NO 330
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 330
caagaaaggg aucugugugg a 21

<210> SEQ ID NO 331
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 331
ugaccucaug guguucguga u 21

<210> SEQ ID NO 332
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 332
gcagcuaaaa gacuuugacu u 21

<210> SEQ ID NO 333
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 333
cauccagaca gacaagacca u 21

<210> SEQ ID NO 334
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 334
acagacaaga ccaucuacac c 21

<210> SEQ ID NO 335
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 335
auccagacag acaagaccau c 21

<210> SEQ ID NO 336
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 336
uuugaccuca ugguguucgu u 21

<210> SEQ ID NO 337
<211> LENGTH: 21

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 337
ggaugccaag aacacuauga u 21

<210> SEQ ID NO 338
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 338
aagaaaggga ucuguguggc a 21

<210> SEQ ID NO 339
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 339
caagaaaggg aucugugugg c 21

<210> SEQ ID NO 340
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 340
uacgugguca aggucuucuc u 21

<210> SEQ ID NO 341
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 341
caguuucgag gucauagugg a 21

<210> SEQ ID NO 342
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 342
cgugccggaa ggaaucagaa u 21

<210> SEQ ID NO 343
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 343
gaaagggauc uguguggcag a 21

<210> SEQ ID NO 344
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 344
gacagacaag accaucuaca a 21

<210> SEQ ID NO 345
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 345
ugaccucaug guguucguga c 21

<210> SEQ ID NO 346
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 346
uguaauaaau ucgaccucaa g 21

<210> SEQ ID NO 347
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 347
aacuacauga accuacagag a 21

<210> SEQ ID NO 348
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 348

agagagaaga ccuugaccac gua                                              23


<210> SEQ ID NO 349
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349

uagagaagac cuugaccacg uag                                              23


<210> SEQ ID NO 350
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350

cacgaacacc augaggucaa agg                                              23


<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351

uuuuguauga agcaauucuc cuc                                              23


<210> SEQ ID NO 352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352

uccaggauca gccauuuaac agc                                              23


<210> SEQ ID NO 353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353

guguagaugg ucuugucugu cug                                              23


<210> SEQ ID NO 354
```

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 354
uagauggucu ugucugucug gau 23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 355
uucuugguga aguggaucug gua 23

<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 356
ucacgaacac caugagguca aag 23

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 357
auuacuguga ccucgaaggg guc 23

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 358
aacagccaca guuuuguuca uuc 23

<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 359
uguagauggu cuugucuguc ugg 23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 360
gucuugguga aguggaucug gua 23

<210> SEQ ID NO 361
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 361
uggucugcca cacagauccc uuu 23

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 362
agggguguag auggucuugu cug 23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 363
uaugaagcaa uucuccucag cac 23

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 364
gagagaagac cuugaccacg uag 23

<210> SEQ ID NO 365
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 365
aggggucugc cacacagauc ccu 23

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 366
uguguagaug gucuugucug ucu 23

<210> SEQ ID NO 367
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 367
aauggucuug ucugucugga uga 23

<210> SEQ ID NO 368
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 368
uugacgucca cccacacgga guc 23

<210> SEQ ID NO 369
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 369
agauggucuu gucugucugg aug 23

<210> SEQ ID NO 370
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 370
gggucugcca cacagauccc uuu 23

<210> SEQ ID NO 371
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 371
uccacacaga ucccuuucuu guc 23

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372
aucacgaaca ccaugagguc aaa 23

<210> SEQ ID NO 373
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373
aagucaaagu cuuuuagcug cag 23

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 374
auggucuugu cugucuggau gaa 23

<210> SEQ ID NO 375
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 375
gguguagaug gucuugucug ucu 23

<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 376
gauggucuug ucugucugga uga 23

<210> SEQ ID NO 377
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 377
aacgaacacc augaggucaa agg 23

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 378
aucauagugu ucuuggcauc cug 23

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 379
ugccacacag aucccuuucu ugu 23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 380
gccacacaga ucccuuucuu guc 23

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 381
agagaagacc uugaccacgu agg 23

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 382
uccacuauga ccucgaaacu ggg 23

<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 383
auucugauuc cuuccggcac gac 23

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 384
ucugccacac agaucccuuu cuu 23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 385
uuguagaugg ucuugucugu cug 23

<210> SEQ ID NO 386
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 386
gucacgaaca ccaugagguc aaa 23

<210> SEQ ID NO 387
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 387
cuugaggucg aauuuauuac agg 23

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 388
ucucuguagg uucauguagu ugg 23

<210> SEQ ID NO 389
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 389
uuuugacaau gaguucuaca a 21

<210> SEQ ID NO 390
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 390
aucaaugaau uuaguguaag a 21

<210> SEQ ID NO 391
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 391
agacaaaugu uucguucaag a 21

<210> SEQ ID NO 392
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 392
cuuuugacaa ugaguucuac a 21

<210> SEQ ID NO 393
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 393
aacuuggaaa gagccauuga a 21

<210> SEQ ID NO 394
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
uaccugagaa gcugauuaac a 21

<210> SEQ ID NO 395
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
accuuuugac aaugaguucu a 21

<210> SEQ ID NO 396
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
gacugcggaa augacuuuca a 21

<210> SEQ ID NO 397
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 397
gcccauucaa auuugaggga a 21

<210> SEQ ID NO 398
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 398
uuuuggauaa agcuuccaug a 21

<210> SEQ ID NO 399
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 399
aaccaaaggc gagaaaaauu u 21

<210> SEQ ID NO 400
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 400
cuuugccaac uaccuaugaa a 21

<210> SEQ ID NO 401
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 401
caccuuuuga caaugaguuc u 21

<210> SEQ ID NO 402
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 402
gagaagacau caaauuuuaa u 21

<210> SEQ ID NO 403
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 403
gacaaugagu ucuacaaugg a 21

<210> SEQ ID NO 404
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 404
uuuggauaaa gcuuccauga a 21

<210> SEQ ID NO 405
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 405
aucuaugaaa ccaaaggcga g 21

<210> SEQ ID NO 406
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 406
auaucaauga auuuagugua a 21

<210> SEQ ID NO 407
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 407
cacaccuuuu gacaaugagu u 21

<210> SEQ ID NO 408
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 408
uagggucuga gaccuuuuga a 21

<210> SEQ ID NO 409
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 409
caaaacuugg aaagagccau u 21

<210> SEQ ID NO 410
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 410
gcacaccuuu ugacaaugag u 21

<210> SEQ ID NO 411
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 411
ugaaaccaaa ggcgagaaaa a 21

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 412
uuguagaacu cauugucaaa agg 23

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 413
ucuuacacua aauucauuga uau 23

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 414
ucuugaacga aacauuuguc uga 23

<210> SEQ ID NO 415
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 415
uguagaacuc auugucaaaa ggu 23

<210> SEQ ID NO 416
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 416
uucaauggcu cuuuccaagu uuu 23

<210> SEQ ID NO 417
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 417
uguuaaucag cuucucaggu agg 23

<210> SEQ ID NO 418
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 418
uagaacucau ugucaaaagg ugu 23

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 419
uugaaaguca uuuccgcagu cau 23

<210> SEQ ID NO 420
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 420
uucccucaaa uuugaauggg cag 23

<210> SEQ ID NO 421
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 421
ucauggaagc uuuauccaaa aca 23

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 422
aaauuuuucu cgccuuuggu uuc 23

<210> SEQ ID NO 423
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 423
uuucauaggu aguuggcaaa gcu 23

<210> SEQ ID NO 424
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 424
agaacucauu gucaaaaggu gug 23

<210> SEQ ID NO 425
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 425
auuaaaauuu gaugucuucu cuu 23

<210> SEQ ID NO 426
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 426
uccauuguag aacucauugu caa 23

<210> SEQ ID NO 427
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 427
uucauggaag cuuuauccaa aac 23

<210> SEQ ID NO 428
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 428
cucgccuuug guuucauaga uca 23

<210> SEQ ID NO 429
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 429
uuacacuaaa uucauugaua uag 23

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 430
aacucauugu caaaaggugu gcu 23

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 431
uucaaaaggu cucagacccu aag 23

<210> SEQ ID NO 432
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 432
aauggcucuu uccaaguuuu guu 23

<210> SEQ ID NO 433

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 433
acucauuguc aaaaggugug cuu 23

<210> SEQ ID NO 434
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434
uuuuucucgc cuuugguuuc aua 23

<210> SEQ ID NO 435
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 435
uuuugacaau gaguucuaca a 21

<210> SEQ ID NO 436
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 436
aucaaugaau uuaguguaag a 21

<210> SEQ ID NO 437
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 437
agacaaaugu uucguucaag a 21

<210> SEQ ID NO 438
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438
cuuuugacaa ugaguucuac a 21

<210> SEQ ID NO 439
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
aacuuggaaa gagccauuga a 21

<210> SEQ ID NO 440
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
uaccugagaa gcugauuaac a 21

<210> SEQ ID NO 441
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
accuuuugac aaugaguucu a 21

<210> SEQ ID NO 442
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
gacugcggaa augacuuuca a 21

<210> SEQ ID NO 443
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
gcccauucaa auuugaggga a 21

<210> SEQ ID NO 444
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 444
uuuuggauaa agcuuccaug a 21

<210> SEQ ID NO 445
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 445
aaccaaaggc gagaaaaauu u 21

<210> SEQ ID NO 446
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 446
cuuugccaac uaccuaugaa a 21

<210> SEQ ID NO 447
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 447
caccuuuuga caaugaguuc u 21

<210> SEQ ID NO 448
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 448
gagaagacau caaauuuuaa u 21

<210> SEQ ID NO 449
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 449
gacaaugagu ucuacaaugg a 21

<210> SEQ ID NO 450
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 450
uuuggauaaa gcuuccauga a 21

<210> SEQ ID NO 451
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 451
aucuaugaaa ccaaaggcga g 21

<210> SEQ ID NO 452
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 452
auaucaauga auuuagugua a 21

<210> SEQ ID NO 453
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 453
cacaccuuuu gacaaugagu u 21

<210> SEQ ID NO 454
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 454
uagggucuga gaccuuuuga a 21

<210> SEQ ID NO 455
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 455
caaaacuugg aaagagccau u 21

<210> SEQ ID NO 456
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 456
gcacaccuuu ugacaaugag u 21

<210> SEQ ID NO 457
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 457
ugaaaccaaa ggcgagaaaa a 21

<210> SEQ ID NO 458
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 458
uuguagaacu cauugucaaa agg 23

<210> SEQ ID NO 459
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 459
ucuuacacua aauucauuga uau 23

<210> SEQ ID NO 460
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 460
ucuugaacga aacauuuguc uga 23

<210> SEQ ID NO 461
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 461
uguagaacuc auugucaaaa ggu 23

<210> SEQ ID NO 462
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 462
uucaauggcu cuuuccaagu uuu 23

<210> SEQ ID NO 463
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 463
uguuaaucag cuucucaggu agg 23

<210> SEQ ID NO 464
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 464
uagaacucau ugucaaaagg ugu 23

<210> SEQ ID NO 465
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 465
uugaaaguca uuuccgcagu cau 23

<210> SEQ ID NO 466
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 466
uucccucaaa uuugaauggg cag 23

<210> SEQ ID NO 467
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 467
ucauggaagc uuuauccaaa aca 23

<210> SEQ ID NO 468
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 468
aaauuuuucu cgccuuuggu uuc 23

<210> SEQ ID NO 469
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 469
uuucauaggu aguuggcaaa gcu 23

<210> SEQ ID NO 470
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 470
agaacucauu gucaaaaggu gug 23

<210> SEQ ID NO 471
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 471
auuaaaauuu gaugucuucu cuu 23

<210> SEQ ID NO 472
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 472
uccauuguag aacucauugu caa 23

<210> SEQ ID NO 473
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 473
uucauggaag cuuuauccaa aac 23

<210> SEQ ID NO 474
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 474
cucgccuuug guuucauaga uca 23

<210> SEQ ID NO 475
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 475
uuacacuaaa uucauugaua uag 23

<210> SEQ ID NO 476
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 476
aacucauugu caaaaggugu gcu 23

<210> SEQ ID NO 477
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 477
uucaaaaggu cucagacccu aag 23

<210> SEQ ID NO 478
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 478
aauggcucuu uccaaguuuu guu 23

<210> SEQ ID NO 479
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 479
acucauuguc aaaaggugug cuu 23

<210> SEQ ID NO 480
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 480
uuuuucucgc cuuugguuuc aua 23

<210> SEQ ID NO 481
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 481
gauugagaag guggcgaguu a 21

<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 482
agcaacaugu guucaaaguc a 21

<210> SEQ ID NO 483
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 483
gcuguggugu cugaguacuu u 21

<210> SEQ ID NO 484
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 484
uaacucgcca ccuucucaau caa 23

<210> SEQ ID NO 485
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 485
ugacuuugaa cacauguugc uca 23

<210> SEQ ID NO 486
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 486
aaaguacuca gacaccacag ccc 23

<210> SEQ ID NO 487
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 487
uaacucgcca ccuucucaau caa 23

<210> SEQ ID NO 488
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 488
ugacuuugaa cacauguugc uca 23

<210> SEQ ID NO 489
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

```
      Synthetic oligonucleotide"

<400> SEQUENCE: 489

aaaguacuca gacaccacag ccc                                          23


<210> SEQ ID NO 490
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490

uaacucgcca ccuucucaau caa                                          23


<210> SEQ ID NO 491
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491

ugacuuugaa cacauguugc uca                                          23


<210> SEQ ID NO 492
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492

aaaguacuca gacaccacag ccc                                          23
```

COMPLEMENT COMPONENT IRNA COMPOSITIONS AND METHODS OF USE THEREOF

RELATED APPLICATIONS

This application is a divisional of U.S. patent application Ser. No. 15/176,231, filed on Jun. 8, 2016, which is a 35 § U.S.C. 111(a) continuation application which claims the benefit of priority to PCT/US2014/069951, filed on Dec. 12, 2014, and U.S. Provisional Patent Application No. 61/915, 210, filed on Dec. 12, 2013. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Sep. 10, 2019, is named 121301_01103_SL.txt and is 266,163 bytes in size.

BACKGROUND OF THE INVENTION

Complement was first discovered in the 1890s when it was found to aid or "complement" the killing of bacteria by heat-stable antibodies present in normal serum (Walport, M. J. (2001) *N Engl J Med.* 344:1058). The complement system consists of more than 30 proteins that are either present as soluble proteins in the blood or are present as membrane-associated proteins. Activation of complement leads to a sequential cascade of enzymatic reactions, known as complement activation pathways resulting in the formation of the potent anaphylatoxins C3a and C5a that elicit a plethora of physiological responses that range from chemoattraction to apoptosis. Initially, complement was thought to play a major role in innate immunity where a robust and rapid response is mounted against invading pathogens. However, recently it is becoming increasingly evident that complement also plays an important role in adaptive immunity involving T and B cells that help in elimination of pathogens (Dunkelberger J R and Song W C. (2010) *Cell Res.* 20:34; Molina H, et al. (1996) *Proc Natl Acad Sci USA.* 93:3357), in maintaining immunologic memory preventing pathogenic re-invasion, and is involved in numerous human pathological states (Qu, H, et al. (2009) *Mol Immunol.* 47:185; Wagner, E. and Frank M M. (2010) *Nat Rev Drug Discov.* 9:43).

Complement activation is known to occur through three different pathways: alternate, classical and lectin (FIG. 1) involving proteins that mostly exist as inactive zymogens that are then sequentially cleaved and activated.

The classical pathway is often activated by antibody-antigen complexes or by the C-reactive protein (CRP), both of which interact with complement component C1q. In addition, the classical pathway can be activated by phosphatidyl serine present in apoptotic bodies in the absence of immune complexes.

The lectin pathway is initiated by the mannose-binding lectins (MBL) that bind to complex carbohydrate residues on the surface of pathogens. The activation of the classical pathway or the lectin pathway leads to activation of the (C4b2b) C3 convertase.

The alternate pathway is activated by the binding of C3b, which is spontaneously generated by the hydrolysis of C3, on targeted surfaces. This surface-bound C3b is then recognized by factor B, forming the complex C3bB. The C3bB complex, in turn, is cleaved by factor D to yield the active form of the C3 convertase of the AP (C3bBb). Both types of C3 convertases will cleave C3, forming C3b. C3b then either binds to more factor B, enhancing the complement activation through the AP (the so-called alternative or amplification loop), or leads to the formation of the active C5 convertase (C3bBbC3b or C4bC2bC3b), which cleaves C5 and triggers the late events that result in the formation of the membrane attack complex (MAC) (C5b-9).

Inappropriate activation of the complement system is responsible for propagating and/or initiating pathology in many different diseases, including, for example, paroxysmal nocturnal hemoglobinuria, atypical hemolytic uremic syndrome, rheumatoid arthritis, ischemia-reperfusion injuries and neurodegenerative diseases.

To date, only one therapeutic that targets the C5-C5a axis is available for the treatment of complement component-associated diseases, the anti-C5 antibody, eculizumab (Soliris®). Although eculizumab has been shown to be effective for the treatment of paroxysmal nocturnal hemoglobinuria (PNH) and atypical hemolytic uremic syndrome (aHUS) and is currently being evaluated in clinical trials for additional complement component-associated diseases, eculizumab therapy requires weekly high dose infusions followed by biweekly maintenance infusions at a high cost. Furthermore, approximately 50% of eculizumab-treated PNH subjects have low level of hemolysis and require residual transfusions (Hill A, et al. (2010) *Haematologica* 95(4):567-73). Accordingly, there is a need in the art for alternative therapies and combination therapies for subjects having a complement component-associated disease.

SUMMARY OF THE INVENTION

The present invention provides iRNA compositions which effect the RNA-induced silencing complex (RISC)-mediated cleavage of RNA transcripts of a CFB gene. The CFB gene may be within a cell, e.g., a cell within a subject, such as a human.

The present invention also provides iRNA compositions which effect the RNA-induced silencing complex (RISC)-mediated cleavage of RNA transcripts of a C3 gene. The C3 gene may be within a cell, e.g., a cell within a subject, such as a human.

In addition, the present invention provides iRNA compositions which effect the RNA-induced silencing complex (RISC)-mediated cleavage of RNA transcripts of a C9 gene. The C9 gene may be within a cell, e.g., a cell within a subject, such as a human.

The present invention also provides methods and combination therapies for treating a subject having a disorder that would benefit from inhibiting or reducing the expression of a CFB, C3, and/or C9 gene, e.g., a complement component-associated disease, such as paroxysmal nocturnal hemoglobinuria (PNH) and atypical hemolytic uremic syndrome (aHUS) using iRNA compositions which effect the RNA-induced silencing complex (RISC)-mediated cleavage of RNA transcripts of a CFB, C3, and/or C9 gene for inhibiting the expression of a CFB, C3, and/or C9 gene.

Accordingly, in one aspect the present invention provides double-stranded ribonucleic acids (dsRNA) for inhibiting expression of complement factor B (CFB) in a cell, wherein the dsRNA comprises a sense strand and an antisense strand, wherein the sense strand comprises at least 15 contiguous nucleotides differing by no more than 3 nucleotides from any one of the nucleotide sequence of SEQ ID NOs: 1-5, 27, and 30, and the antisense strand comprises at least 15 contiguous nucleotides differing by no more than 3 nucleotides from any one of the nucleotide sequence of SEQ ID NOs:12-16, 33, and 36.

In another aspect the present invention provides double-stranded ribonucleic acids (dsRNA) for inhibiting expression of complement factor B (CFB) in a cell, wherein the dsRNA comprises a sense strand and an antisense strand, the antisense strand comprising a region of complementarity which comprises at least 15 contiguous nucleotides differing by no more than 3 nucleotides from any one of the antisense sequences listed in Table 3 and 4.

In one embodiment, the sense and antisense strands comprise sequences selected from the group consisting of AD-60304, AD-60331, and AD-60344 and any one of the agents listed in Tables 3 and 4.

In one embodiment the region of complementarity consists of the nucleotide sequence of one of the antisense sequences of any one of Tables 3 and 4.

In one embodiment, the dsRNA comprises a sense strand consisting of the nucleotide sequence of a sense strand sequence selected from the sequence of any one of Tables 3 and 4, and an antisense strand consisting of the nucleotide sequence of an antisense sequence selected from the sequences of any one of Tables 3 and 4.

In another aspect the present invention provides double-stranded ribonucleic acids (dsRNA) for inhibiting expression of complement component C3 in a cell, wherein the dsRNA comprises a sense strand and an antisense strand, wherein the sense strand comprises at least 15 contiguous nucleotides differing by no more than 3 nucleotides from any one of the nucleotide sequence of SEQ ID NOs:6-8, 28, and 31, and the antisense strand comprises at least 15 contiguous nucleotides differing by no more than 3 nucleotides from any one of the nucleotide sequence of SEQ ID NOs:17-19, 34, and 37.

In another aspect the present invention provides double-stranded ribonucleic acids (dsRNA) for inhibiting expression of complement component C3 in a cell, wherein the dsRNA comprises a sense strand and an antisense strand, the antisense strand comprising a region of complementarity which comprises at least 15 contiguous nucleotides differing by no more than 3 nucleotides from any one of the antisense sequences listed in Table 5 and 6.

In one embodiment, the sense and antisense strands comprise sequences selected from the group consisting of AD-60169 and any one of the agents listed in Tables 5 and 6.

In one embodiment the region of complementarity consists of the nucleotide sequence of one of the antisense sequences of any one of Tables 5 and 6.

In one embodiment, the dsRNA comprises a sense strand consisting of the nucleotide sequence of a sense strand sequence selected from the sequence of any one of Tables 5 and 6, and an antisense strand consisting of the nucleotide sequence of an antisense sequence selected from the sequences of any one of Tables 5 and 6.

In another aspect the present invention provides double-stranded ribonucleic acids (dsRNA) for inhibiting expression of complement component C9 in a cell, wherein the dsRNA comprises a sense strand and an antisense strand, wherein the sense strand comprises at least 15 contiguous nucleotides differing by no more than 3 nucleotides from any one of the nucleotide sequence of SEQ ID NOs:9-11, 29, and 32, and the antisense strand comprises at least 15 contiguous nucleotides differing by no more than 3 nucleotides from any one of the nucleotide sequence of SEQ ID NOs:20-22, 35, and 38.

In another aspect the present invention provides double-stranded ribonucleic acids (dsRNA) for inhibiting expression of complement component C9 in a cell, wherein the dsRNA comprises a sense strand and an antisense strand, the antisense strand comprising a region of complementarity which comprises at least 15 contiguous nucleotides differing by no more than 3 nucleotides from any one of the antisense sequences listed in Table 7 and 8.

In one embodiment, the sense and antisense strands comprise sequences selected from the group consisting of any one of the agents listed in Tables 7 and 8.

In one embodiment the region of complementarity consists of the nucleotide sequence of one of the antisense sequences of any one of Tables 7 and 8.

In one embodiment, the dsRNA comprises a sense strand consisting of the nucleotide sequence of a sense strand sequence selected from the sequence of any one of Tables 7 and 8, and an antisense strand consisting of the nucleotide sequence of an antisense sequence selected from the sequences of any one of Tables 7 and 8.

The dsRNA may include at least one modified nucleotide, e.g., a 2'-O-methyl modified nucleotide, a nucleotide comprising a 5'-phosphorothioate group, a deoxynucleotide, a 3'-terminal deoxy-thymine (dT) nucleotide, a 2'-O-methyl modified nucleotide, a 2'-fluoro modified nucleotide, a 2'-deoxy-modified nucleotide, a terminal nucleotide linked to a cholesteryl derivative or a dodecanoic acid bisdecylamide group, a 2'-deoxy-2'-fluoro modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In one embodiment, substantially all the nucleotides of the sense strand and the antisense strand are modified nucleotides. In another embodiment, all the nucleotides of the sense strand and the antisense strand are modified nucleotides.

The region of complementarity may be at least 17 nucleotides in length, such as 19 nucleotides in length, or no more than 30 nucleotides in length.

The region of complementarity may be between 19 and 21 nucleotides in length.

At least one strand of the dsRNA may include a 3' overhang of at least 1 nucleotide, or at least 2 nucleotides.

The dsRNA may further include a ligand. In one embodiment, the ligand is conjugated to the 3' end of the sense strand of the dsRNA. In one embodiment, the ligand is an N-acetylgalactosamine (GalNAc) derivative. In one embodiment, the ligand is

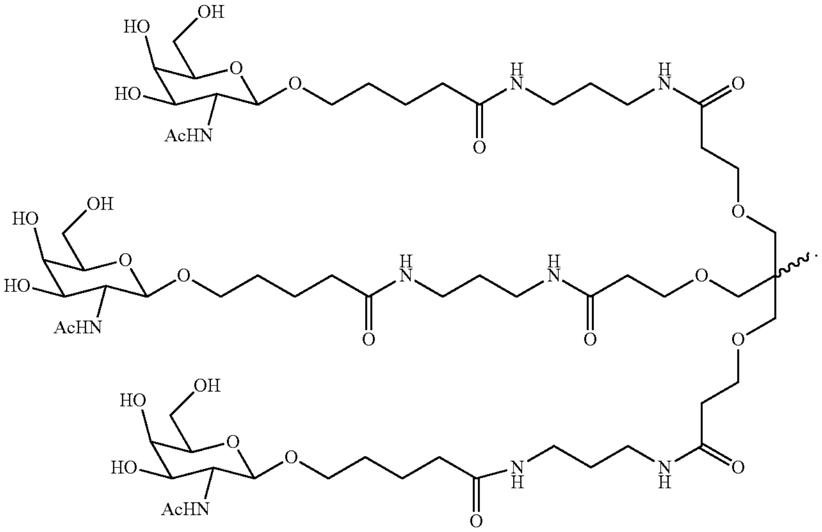 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA is conjugated to the ligand as shown in the following schematic

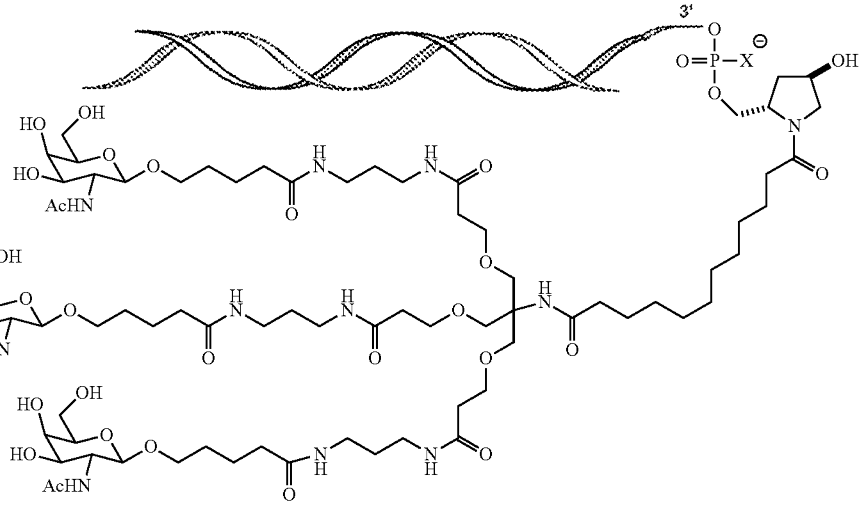

and, wherein X is O or S.

In one embodiment, the X is O.

In another aspect, the present invention provides double stranded RNAi agents capable of inhibiting the expression of complement factor B (CFB) in a cell. The agents include a sense strand complementary to an antisense strand, wherein the antisense strand comprises a region complementary to part of an mRNA encoding CFB, wherein each strand is about 14 to about 30 nucleotides in length, wherein the double stranded RNAi agent is represented by formula (III):

(III)

sense:
5' $n_p$-$N_a$-(X X X)$_i$-$N_b$-Y Y Y-$N_b$-(Z Z Z)$_j$-$N_a$-$n_q$ 3' antisense:
3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and l are each independently 0 or 1;

p, p', q, and q' are each independently 0-6;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

each $n_p$, $n_p$', $n_q$, and $n_q$', each of which may or may not be present, independently represents an overhang nucleotide;

XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b$' differ from the modification on Y'; and wherein the sense strand is conjugated to at least one ligand.

In another aspect, the present invention provides double stranded RNAi agents capable of inhibiting the expression of complement component 3 (C3) in a cell. The agents include a sense strand complementary to an antisense strand, wherein the antisense strand comprises a region complementary to part of an mRNA encoding C3, wherein each strand is about 14 to about 30 nucleotides in length, wherein the double stranded RNAi agent is represented by formula (III):

(III)

sense: 5' $n_p$-$N_a$-(X X X)$_i$-$N_b$-Y Y Y-$N_b$-(Z Z Z)$_j$-$N_a$-$n_q$ 3' antisense: 3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and l are each independently 0 or 1;

p, p', q, and q' are each independently 0-6;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

each $n_p$, $n_p$', $n_q$, and $n_q$', each of which may or may not be present, independently represents an overhang nucleotide;

XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b$' differ from the modification on Y'; and wherein the sense strand is conjugated to at least one ligand.

In a further aspect, the present invention provides double stranded RNAi agents capable of inhibiting the expression of complement component 9 (C9) in a cell. The agents include a sense strand complementary to an antisense strand, wherein the antisense strand comprises a region complementary to part of an mRNA encoding C9, wherein each strand is about 14 to about 30 nucleotides in length, wherein the double stranded RNAi agent is represented by formula (III):

(III)

sense: 5' $n_p$-$N_a$-(X X X)$_i$-$N_b$-Y Y Y-$N_b$-(Z Z Z)$_j$-$N_a$-$n_q$ 3' antisense: 3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and l are each independently 0 or 1;

p, p', q, and q' are each independently 0-6;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

each $n_p$, $n_p$', $n_q$, and $n_q$', each of which may or may not be present, independently represents an overhang nucleotide;

XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b$' differ from the modification on Y'; and wherein the sense strand is conjugated to at least one ligand.

In one embodiment, i is 0; j is 0; i is 1; j is 1; both i and j are 0; or both i and j are 1.

In one embodiment, k is 0; l is 0; k is 1; l is 1; both k and l are 0; or both k and l are 1.

In one embodiment, XXX is complementary to X'X'X', YYY is complementary to Y'Y'Y', and ZZZ is complementary to Z'Z'Z'.

In one embodiment, the YYY motif occurs at or near the cleavage site of the sense strand.

In one embodiment, the Y'Y'Y' motif occurs at the 11, 12 and 13 positions of the antisense strand from the 5'-end.

In one embodiment, the Y' is 2'-O-methyl.

In one embodiment, formula (III) is represented by formula (IIIa):

(IIIa)

sense: 5' $n_p$-$N_a$-Y Y Y-$N_a$-$n_q$ 3' antisense: 3' $n_{p'}$-$N_{a'}$-Y'Y'Y'-$N_{a'}$-$n_{q'}$ 5'.

In one embodiment, formula (III) is represented by formula (IIIb):

(IIIb)

sense: 5' $n_p$-$N_a$-Y Y Y-$N_b$-Z Z Z-$N_a$-$n_q$ 3' antisense: 3' $n_{p'}$-$N_{a'}$-Y'Y'Y'-$N_{b'}$-Z'Z'Z'-$N_{a'}$-$n_{q'}$ 5' wherein each $N_b$ and $N_b$' independently represents an oligonucleotide sequence comprising 1-5 modified nucleotides.

In one embodiment, formula (III) is represented by formula (IIIc):

(IIIc)

sense: 5' $n_p$-$N_a$-X X X-$N_b$-Y Y Y-$N_a$-$n_q$ 3' antisense: 3' $n_{p'}$-$N_{a'}$-X'X'X'-$N_{b'}$-Y'Y'Y'-$N_{a'}$-$n_{q'}$ 5' wherein each $N_b$ and $N_b$' independently represents an oligonucleotide sequence comprising 1-5 modified nucleotides.

In one embodiment, formula (III) is represented by formula (IIId):

(IIId)

sense:
$5'\ n_p\text{-}N_a\text{-}X\ X\ X\text{-}N_b\text{-}Y\ Y\ Y\text{-}N_b\text{-}Z\ Z\ Z\text{-}N_a\text{-}n_q\ 3'$ antisense:
$3'\ n_{p'}\text{-}N_{a'}\text{-}X'X'X'\text{-}N_{b'}\text{-}Y'Y'Y'\text{-}N_{b'}\text{-}Z'Z'Z'\text{-}N_{a'}\text{-}n_{q'}\ 5'$ wherein each $N_b$ and $N_b'$ independently represents an oligonucleotide sequence comprising 1-5 modified nucleotides and each $N_a$ and $N_a'$ independently represents an oligonucleotide sequence comprising 2-10 modified nucleotides.

The double-stranded region may 15-30 nucleotide pairs in length, 17-23 nucleotide pairs in length, 17-25 nucleotide pairs in length, 23-27 nucleotide pairs in length, 19-21 nucleotide pairs in length, or 21-23 nucleotide pairs in length.

In one embodiment, each strand has 15-30 nucleotides.

In one embodiment, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof.

In one embodiment, the modifications on the nucleotides are 2'-O-methyl or 2'-fluoro modifications.

In one embodiment, the ligand is one or more GalNAc derivatives attached through a bivalent or trivalent branched linker.

In one embodiment, the ligand is

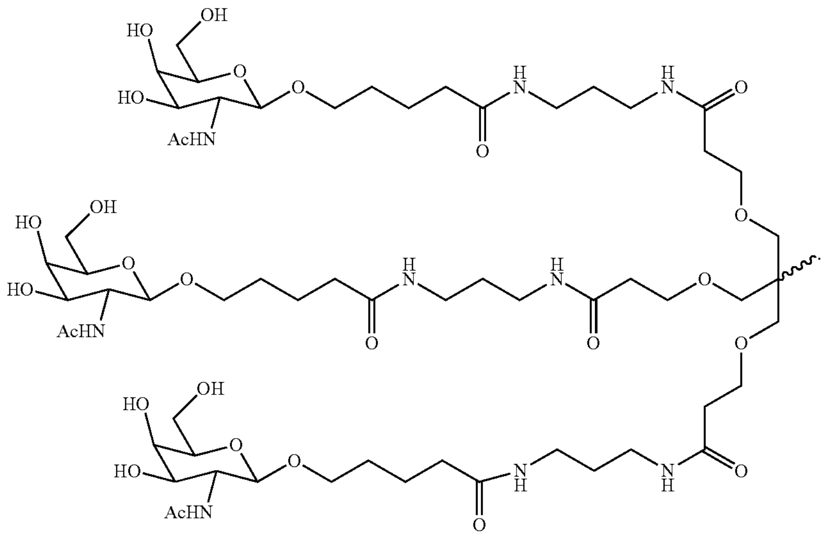 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the ligand is attached to the 3' end of the sense strand.

In one embodiment, the RNAi agent is conjugated to the ligand as shown in the following schematic

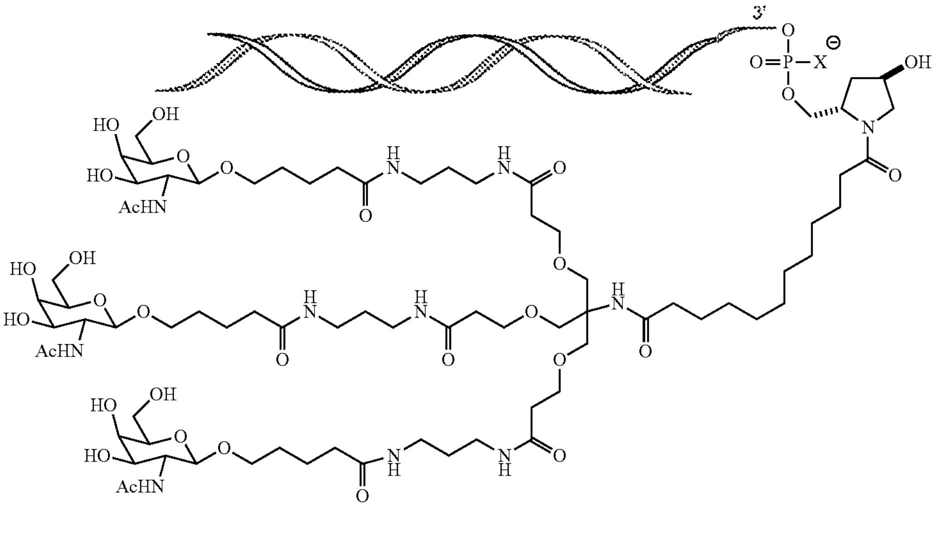

and, wherein X is O or S.

In one embodiment, the X is O.

In one embodiment, the agent further comprises at least one phosphorothioate or methylphosphonate internucleotide linkage.

In one embodiment, the phosphorothioate or methylphosphonate internucleotide linkage is at the 3'-terminus of one strand. In one embodiment, the strand is the antisense strand. In another embodiment, the strand is the sense strand.

In another embodiment, the phosphorothioate or methylphosphonate internucleotide linkage is at the 5'-terminus of one strand. In one embodiment, the strand is the antisense strand. In another embodiment, the strand is the sense strand.

In one embodiment, the phosphorothioate or methylphosphonate internucleotide linkage is at the both the 5'- and 3'-terminus of one strand. In one embodiment, the strand is the antisense strand.

In one embodiment, the base pair at the 1 position of the 5'-end of the antisense strand of the duplex is an AU base pair.

In one embodiment, the Y nucleotides contain a 2'-fluoro modification.

In one embodiment, the Y' nucleotides contain a 2'-O-methyl modification.

In one embodiment, p'>0. In another embodiment, p'=2.

In one embodiment, q'=0, p=0, q=0, and p' overhang nucleotides are complementary to the target mRNA.

In another embodiment, q'=0, p=0, q=0, and p' overhang nucleotides are non-complementary to the target mRNA.

In one embodiment, the sense strand has a total of 21 nucleotides and the antisense strand has a total of 23 nucleotides.

In one embodiment, at least one $n_p'$ is linked to a neighboring nucleotide via a phosphorothioate linkage. In another embodiment, all $n_p'$ are linked to neighboring nucleotides via phosphorothioate linkages.

In one embodiment, the RNAi agent is selected from the group of RNAi agents listed in Tables 3 and 4. In one embodiment, the RNAi agent is selected from the group of RNAi agents AD-60304, AD-60331, and AD-60344.

In another embodiment, the RNAi agent is selected from the group of RNAi agents listed in Tables 5 and 6.

In yet another embodiment, the RNAi agent is selected from the group of RNAi agents listed in Tables 7 and 8.

In one aspect, the present invention provides double stranded RNAi agents comprising the RNAi agents listed in any one of Tables 3, 5, and 7.

In one aspect, the present invention provides compositions comprising a modified antisense polynucleotide agent. The agents are capable of inhibiting the expression of Complement Factor B (CFB) in a cell, and include a sequence complementary to a sense sequence selected from the group of the sequences listed in Table 3, wherein the polynucleotide is about 14 to about 30 nucleotides in length.

In another aspect, the present invention provides compositions comprising a modified antisense polynucleotide agent. The agents are capable of inhibiting the expression of Complement Component 3 (C3) in a cell, and include a sequence complementary to a sense sequence selected from the group of the sequences listed in Table 5, wherein the polynucleotide is about 14 to about 30 nucleotides in length.

In yet another aspect, the present invention provides compositions comprising a modified antisense polynucleotide agent. The agents are capable of inhibiting the expression of Complement Component 9 (C9) in a cell, and include a sequence complementary to a sense sequence selected from the group of the sequences listed in Table 7, wherein the polynucleotide is about 14 to about 30 nucleotides in length.

In one aspect, the present invention provides double stranded RNAi agents capable of inhibiting the expression of Complement Factor B (CFB) in a cell. The agent include a sense strand complementary to an antisense strand, wherein the antisense strand comprises a region complementary to part of an mRNA encoding CFB, wherein each strand is about 14 to about 30 nucleotides in length, wherein the double stranded RNAi agent is represented by formula (III):

(III)

sense:
$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$ antisense:
$3'\ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$ wherein:

i, j, k, and 1 are each independently 0 or 1;

p, p', q, and q' are each independently 0-6;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

each $n_p$, $n_p'$, $n_q$, and $n_q'$, each of which may or may not be present independently represents an overhang nucleotide;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In another aspect, the invention provides double stranded RNAi agents capable of inhibiting the expression of Complement Factor B (CFB) in a cell. The agents include a sense strand complementary to an antisense strand, wherein the antisense strand comprises a region complementary to part of an mRNA encoding CFB, wherein each strand is about 14 to about 30 nucleotides in length, wherein the double stranded RNAi agent is represented by formula (III):

(III)

sense:
$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$ antisense:
$3'\ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$ wherein:

i, j, k, and 1 are each independently 0 or 1;

each $n_p$, $n_q$, and $n_q'$, each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y'; and wherein the sense strand is conjugated to at least one ligand.

In another aspect, the present invention provides double stranded RNAi agents capable of inhibiting the expression of Complement Factor B (CFB) in a cell. The agents include a sense strand complementary to an antisense strand, wherein the antisense strand comprises a region complementary to part of an mRNA encoding CFB, wherein each strand is about 14 to about 30 nucleotides in length, wherein the double stranded RNAi agent is represented by formula (III):

(III)

sense:
$5'\ n_p\text{-}N_a\text{-}(XXX)_i\text{-}N_b\text{-}YYY\text{-}N_b\text{-}(ZZZ)_j\text{-}N_a\text{-}n_q\ 3'$ antisense:
$3'\ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$ wherein:

i, j, k, and 1 are each independently 0 or 1;

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y'; and wherein the sense strand is conjugated to at least one ligand, wherein the ligand is one or more GalNAc derivatives attached through a bivalent or trivalent branched linker.

In yet a further aspect, the present invention provides double stranded RNAi agents capable of inhibiting the expression of Complement Factor B (CFB) in a cell. The agents include a sense strand complementary to an antisense strand, wherein the antisense strand comprises a region complementary to part of an mRNA encoding CFB, wherein each strand is about 14 to about 30 nucleotides in length, wherein the double stranded RNAi agent is represented by formula (III):

(III)

sense:
$5'\ n_p\text{-}N_a\text{-}(XXX)_i\text{-}N_b\text{-}YYY\text{-}N_b\text{-}(ZZZ)_j\text{-}N_a\text{-}n_q\ 3'$ antisense:
$3'\ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$ wherein:

i, j, k, and 1 are each independently 0 or 1;

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

In another aspect, the invention provides double stranded RNAi agents capable of inhibiting the expression of Complement Factor B (CFB) in a cell. The agents include a sense strand complementary to an antisense strand, wherein the antisense strand comprises a region complementary to part of an mRNA encoding CFB, wherein each strand is about 14 to about 30 nucleotides in length, wherein the double stranded RNAi agent is represented by formula (III):

(IIIa)

sense:
$5'\ n_p\text{-}N_a\text{-}YYY\text{-}N_a\text{-}n_q\ 3'$ antisense:
$3'\ n_p'\text{-}N_a'\text{-}Y'Y'Y'\text{-}N_a'\text{-}n_q'\ 5'$ wherein:

each $n_p$, $n_q$, and $n_q$', each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand comprises at least one phosphorothioate linkage; and wherein the sense strand is conjugated to at least one ligand, wherein the ligand is one or more GalNAc derivatives attached through a bivalent or trivalent branched linker.

In one aspect, the present invention provides double stranded RNAi agents capable of inhibiting the expression of Complement Component 3 (C3) in a cell. The agents include a sense strand complementary to an antisense strand, wherein the antisense strand comprises a region complementary to part of an mRNA encoding C3, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:

i, j, k, and 1 are each independently 0 or 1;

p, p', q, and q' are each independently 0-6;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

each $n_p$, $n_p'$, $n_q$, and $n_q'$, each of which may or may not be present independently represents an overhang nucleotide;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In another aspect, the present invention provides double stranded RNAi agents capable of inhibiting the expression of Complement Component 3 (C3) in a cell. The agents include a sense strand complementary to an antisense strand, wherein the antisense strand comprises a region complementary to part of an mRNA encoding C3, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:

i, j, k, and 1 are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In another aspect, the invention provides double stranded RNAi agents capable of inhibiting the expression of Complement Component 3 (C3) in a cell. The agents include a sense strand complementary to an antisense strand, wherein the antisense strand comprises a region complementary to part of an mRNA encoding C3, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:

i, j, k, and 1 are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y'; and wherein the sense strand is conjugated to at least one ligand, wherein the ligand is one or more GalNAc derivatives attached through a bivalent or trivalent branched linker.

In yet another aspect, the present invention provides double stranded RNAi agents capable of inhibiting the expression of Complement Component 3 (C3) in a cell. The agents include a sense strand complementary to an antisense strand, wherein the antisense strand comprises a region complementary to part of an mRNA encoding C3, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and 1 are each independently 0 or 1;

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

In one aspect, the present invention provides double stranded RNAi agents capable of inhibiting the expression of Complement Component 3 (C3) in a cell. The agents include a sense strand complementary to an antisense strand, wherein the antisense strand comprises a region complementary to part of an mRNA encoding C3, wherein each strand is about 14 to about 30 nucleotides in length, wherein the double stranded RNAi agent is represented by formula (III):

(IIIa)

sense:
5' $n_p$-$N_a$-YYY-$N_a$-$n_q$ 3' antisense:
3' $n_p$'-$N_a$'-Y'Y'Y'-$N_a$'-$n_q$' 5' wherein:

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand comprises at least one phosphorothioate linkage; and wherein the sense strand is conjugated to at least one ligand, wherein the ligand is one or more GalNAc derivatives attached through a bivalent or trivalent branched linker.

In another aspect, the present invention provides double stranded RNAi agents capable of inhibiting the expression of Complement Component 9 (C9) in a cell. The agents include a sense strand complementary to an antisense strand, wherein the antisense strand comprises a region complementary to part of an mRNA encoding C9, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and 1 are each independently 0 or 1;

p, p', q, and q' are each independently 0-6;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

each $n_p$, $n_p$', $n_q$, and $n_q$', each of which may or may not be present independently represents an overhang nucleotide;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y'; and wherein the sense strand is conjugated to at least one ligand.

In one aspect, the invention provides double stranded RNAi agents capable of inhibiting the expression of Complement Component 9 (C9) in a cell. The agents include a sense strand complementary to an antisense strand, wherein the antisense strand comprises a region complementary to part of an mRNA encoding C9, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and 1 are each independently 0 or 1;

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y'; and wherein the sense strand is conjugated to at least one ligand.

In another aspect, the invention provides double stranded RNAi agents capable of inhibiting the expression of Complement Component 9 (C9) in a cell. The agents include a sense strand complementary to an antisense strand, wherein the antisense strand comprises a region complementary to part of an mRNA encoding C9, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and 1 are each independently 0 or 1;

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y'; and wherein the sense strand is conjugated to at least one ligand, wherein the ligand is one or more GalNAc derivatives attached through a bivalent or trivalent branched linker.

In another aspect, the invention provides double stranded RNAi agents capable of inhibiting the expression of Complement Component 9 (C9) in a cell. The agents include a sense strand complementary to an antisense strand, wherein the antisense strand comprises a region complementary to part of an mRNA encoding C9, wherein each strand is about 14 to about 30 nucleotides in length, wherein the double stranded RNAi agent is represented by formula (III):

(III)

sense:
5' $n_p$-$N_a$-(XXX)$_i$-$N_b$-YYY-$N_b$-(ZZZ)$_j$-$N_a$-$n_q$ 3' antisense:
3' $n_p$'-$N_a$'-(X'X'X')$_k$-$N_b$'-Y'Y'Y'-$N_b$'-(Z'Z'Z')$_l$-$N_a$'-$n_q$' 5' wherein:

i, j, k, and 1 are each independently 0 or 1;

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b$' differ from the modification on Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

In a further aspect, the present invention provises double stranded RNAi agents capable of inhibiting the expression of Complement Component 9 (C9) in a cell. The agent include a sense strand complementary to an antisense strand, wherein the antisense strand comprises a region complementary to part of an mRNA encoding C9, wherein each strand is about 14 to about 30 nucleotides in length, wherein the double stranded RNAi agent is represented by formula (III):

(IIIa)

sense:
5' $n_p$-$N_a$-YYY-$N_a$-$n_q$ 3' antisense:
3' $n_p$'-$N_a$'-Y'Y'Y'-$N_a$'-$n_q$' 5' wherein:

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand comprises at least one phosphorothioate linkage; and wherein the sense strand is conjugated to at least one ligand, wherein the ligand is one or more GalNAc derivatives attached through a bivalent or trivalent branched linker.

In another aspect, the invention provides double stranded RNAi agents for inhibiting expression of complement factor B (CFB) in a cell, wherein the double stranded RNAi agent comprises a sense strand and an antisense strand forming a double stranded region, wherein the sense strand comprises at least 15 contiguous nucleotides differing by no more than 3 nucleotides from the nucleotide sequence of any one of SEQ ID NOs:1-5, 27, and 30, and the antisense strand comprises at least 15 contiguous nucleotides differing by no more than 3 nucleotides from any one of the nucleotide sequence of SEQ ID NOs:12-16, 33, and 36, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, and wherein the sense strand is conjugated to one or more GalNAc derivatives attached through a branched bivalent or trivalent linker at the 3'-terminus.

In another aspect, the present invention provides double stranded RNAi agents for inhibiting expression of complement component C3 in a cell, wherein the double stranded RNAi agent comprises a sense strand and an antisense strand forming a double stranded region, wherein the sense strand comprises at least 15 contiguous nucleotides differing by no more than 3 nucleotides from the nucleotide sequence of any one of SEQ ID NOs:6-8, 28, and 31, and the antisense strand comprises at least 15 contiguous nucleotides differing by no more than 3 nucleotides from any one of the nucleotide sequence of SEQ ID NOs:17-19, 34, and 37, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, and wherein the sense strand is conjugated to one or more GalNAc derivatives attached through a branched bivalent or trivalent linker at the 3'-terminus.

In yet another aspect, the present invention provides double stranded RNAi agents for inhibiting expression of complement component C9 in a cell, wherein the double stranded RNAi agent comprises a sense strand and an antisense strand forming a double stranded region, wherein the sense strand comprises at least 15 contiguous nucleotides differing by no more than 3 nucleotides from the nucleotide sequence of any one of SEQ ID NOs:9-11, 29, and 32, and the antisense strand comprises at least 15 contiguous nucleotides differing by no more than 3 nucleotides from any one of the nucleotide sequence of SEQ ID NOs:20-22, 35, and 38, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, and wherein the sense strand is conjugated to one or more GalNAc derivatives attached through a branched bivalent or trivalent linker at the 3'-terminus.

In one embodiment, all of the nucleotides of the sense strand and all of the nucleotides of the antisense strand comprise a modification.

In another aspect, the present invention provides cells containing the agents of the invention.

In one aspect, the invention provides vectors encoding at least one strand of the agents of the invention.

In another aspect, the invention provides cells comprising the vectors of the invention.

In one aspect, the present invention provides pharmaceutical compositions for inhibiting expression of a complement component factor B gene comprising the agents the invention.

In another aspect, the present invention provides pharmaceutical compositions for inhibiting expression of a complement component C3 gene comprising the agents of the invention.

In yet another aspect, the present invention provides pharmaceutical compositions for inhibiting expression of a complement component C9 gene comprising the agents of the invention.

In one embodiment, the RNAi agent is administered in an unbuffered solution.

In one embodiment, the unbuffered solution is saline or water.

In one embodiment, the RNAi agent is administered with a buffer solution.

In one embodiment, the buffer solution comprises acetate, citrate, prolamine, carbonate, or phosphate or any combination thereof.

In one embodiment, the buffer solution is phosphate buffered saline (PBS).

In one aspect, the present invention provides methods of inhibiting complement factor B (CFB) expression in a cell. The methods include contacting the cell with the agent of a the invention or a pharmaceutical composition of the invention, and maintaining the cell produced for a time sufficient to obtain degradation of the mRNA transcript of a CFB gene, thereby inhibiting expression of the CFB gene in the cell.

In another aspect, the present invention provides methods of inhibiting complement component 3 (C3) expression in a cell. The methods include contacting the cell with the agent of a the invention or a pharmaceutical composition of the invention, and maintaining the cell produced for a time sufficient to obtain degradation of the mRNA transcript of a C3 gene, thereby inhibiting expression of the C3 gene in the cell.

In yet another aspect, the present invention provides methods of inhibiting complement component 9 (C9) expression in a cell. The methods include contacting the cell with the agent of a the invention or a pharmaceutical composition of the invention, and maintaining the cell produced for a time sufficient to obtain degradation of the mRNA transcript of a C9 gene, thereby inhibiting expression of the C9 gene in the cell.

In one embodiment, the cell is within a subject.

In one embodiment, the subject is a human.

In one embodiment, the human subject suffers from a complement component-associated disease.

In one embodiment, the complement component-associated disease is selected from the group consisting of paroxysmal nocturnal hemoglobinuria (PNH), asthma, rheumatoid arthritis, systemic lupus erythmatosis, glomerulonephritis, psoriasis, dermatomyositis bullous pemphigoid, atypical hemolytic uremic syndrome, Shiga toxin *E. coli*-related hemolytic uremic syndrome, myasthenia gravis, neuromyelistis optica, dense deposit disease, C3 neuropathy, age-related macular degeneration, cold agglutinin disease, anti-neutrophil cytoplasmic antibody-associated vasculitis, humoral and vascular transplant rejection, graft dysfunction, myocardial infarction, a sensitized recipient of a transplant, and sepsis.

In one embodiment, the complement component-associated disease is paroxysmal nocturnal hemoglobinuria (PNH).

In another embodiment, the complement component-associated disease is atypical hemolytic uremic syndrome (aHUS).

In one embodiment, the CFB expression is inhibited by at least about 30%.

In one embodiment, the C3 expression is inhibited by at least about 30%.

In one embodiment, the C9 expression is inhibited by at least about 30%.

In one embodiment, the agent is administered at a dose of about 0.01 mg/kg to about 10 mg/kg or about 0.5 mg/kg to about 50 mg/kg.

In another embodiment, the agent is administered at a dose of about 10 mg/kg to about 30 mg/kg.

In one embodiment, the agent is administered subcutaneously.

In another embodiment, the agent is administered intravenously.

In one aspect, the present invention provides methods of treating a subject having a disorder that would benefit from reduction in complement factor B (CFB) expression. The methods include administering to the subject a therapeutically effective amount of the agent of the invention, thereby treating the subject.

In another aspect, the present invention provides methods of preventing at least one symptom in a subject having a disease or disorder that would benefit from reduction in complement factor B (CFB) expression. The methods include administering to the subject a therapeutically effective amount of the agent of the invention, thereby preventing at least one symptom in the subject having a disorder that would benefit from reduction in CFB expression.

In yet another aspect, the present invention provides methods of treating a subject having a disorder that would benefit from reduction in complement component C3 (C3) expression. The methods include administering to the subject a therapeutically effective amount of the agent of the invention, thereby treating the subject.

In one aspect, the present invention provides methods of preventing at least one symptom in a subject having a disease or disorder that would benefit from reduction in complement component C3 (C3) expression. The methods include administering to the subject a therapeutically effective amount of the agent of the invention, thereby preventing at least one symptom in the subject having a disorder that would benefit from reduction in C3 expression.

In another aspect, the present invention provides methods of treating a subject having a disorder that would benefit from reduction in complement component C9 (C9) expression. The methods include administering to the subject a therapeutically effective amount of the agent of the invention, thereby treating the subject.

In one aspect, the present invention provides methods of preventing at least one symptom in a subject having a disease or disorder that would benefit from reduction in complement component C9 (C9) expression. The methods include administering to the subject a therapeutically effective amount of the agent of the invention, thereby preventing at least one symptom in the subject having a disorder that would benefit from reduction in C9 expression.

In one embodiment, the disorder is a complement component-associated disease.

In one embodiment, the complement component-associated disease is selected from the group consisting of paroxysmal nocturnal hemoglobinuria (PNH), asthma, rheumatoid arthritis, systemic lupus erythmatosis, glomerulonephritis, psoriasis, dermatomyositis bullous pemphigoid, atypical hemolytic uremic syndrome, Shiga toxin *E. coli*-related hemolytic uremic syndrome, myasthenia gravis, neuromyelistis optica, dense deposit disease, C3 neuropathy, age-related macular degeneration, cold agglutinin disease, anti-neutrophil cytoplasmic antibody-associated vasculitis, humoral and vascular transplant rejection, graft dysfunction, myocardial infarction, a sensitized recipient of a transplant, and sepsis.

In one embodiment, the complement component-associated disease is paroxysmal nocturnal hemoglobinuria (PNH).

In another embodiment, the complement component-associated disease is atypical hemolytic uremic syndrome (aHUS).

In one embodiment, the administration of the agent to the subject causes a decrease in hemolysis and/or a decrease in CFB protein accumulation.

In one embodiment, the administration of the agent to the subject causes a decrease in hemolysis and/or a decrease in C3 protein accumulation.

In one embodiment, the administration of the agent to the subject causes a decrease in hemolysis and/or a decrease in C9 protein accumulation.

In one embodiment, the methods further include administration of eculizumab to the subject.

In another embodiment, the methods further include administration of compstatin to the subject.

In one embodiment, the agent is administered at a dose of about 0.01 mg/kg to about 10 mg/kg or about 0.5 mg/kg to about 50 mg/kg.

In another embodiment, the agent is administered at a dose of about 10 mg/kg to about 30 mg/kg.

In yet another embodiment, the agent is administered at a dose selected from the group consisting of 0.5 mg/kg 1 mg/kg, 1.5 mg/kg, 3 mg/kg, 10 mg/kg, and 30 mg/kg.

In one embodiment, the agent is administered to the subject once a week.

In another embodiment, the agent is administered to the subject twice a month.

In one embodiment, the methods further include measuring LDH levels in the subject.

In one aspect, the present invention provides methods of inhibiting the expression of complement factor B (CFB) in a subject. The methods include administering to the subject a therapeutically effective amount of the agent of the invention, thereby inhibiting the expression of CFB in the subject.

In another aspect, the present invention provides methods of inhibiting the expression of complement component C3 (C3) in a subject. The methods include administering to the subject a therapeutically effective amount of the agent of the invention, thereby inhibiting the expression of C3 in the subject.

In yet another aspect, the present invention provides methods of inhibiting the expression of complement component C9 (C9) in a subject. The methods include administering to the subject a therapeutically effective amount of the agent of any one of the invention, thereby inhibiting the expression of C9 in the subject.

In one embodiment, the methods further include administering eculizumab to the subject.

In another embodiment, the methods further include administering compstatin to the subject.

In one embodiment, the agent is administered at a dose of about 0.01 mg/kg to about 10 mg/kg or about 0.5 mg/kg to about 50 mg/kg.

In another embodiment, the agent is administered at a dose of about 10 mg/kg to about 30 mg/kg.

In yet another embodiment, the agent is administered at a dose selected from the group consisting of 1 mg/kg, 3 mg/kg, 10 mg/kg, and 30 mg/kg.

In one embodiment, the agent is administered to the subject once a week.

In another embodiment, the dsRNA agent is administered to the subject twice a month.

DETAILED DESCRIPTION OF THE INVENTION

Figure 1:
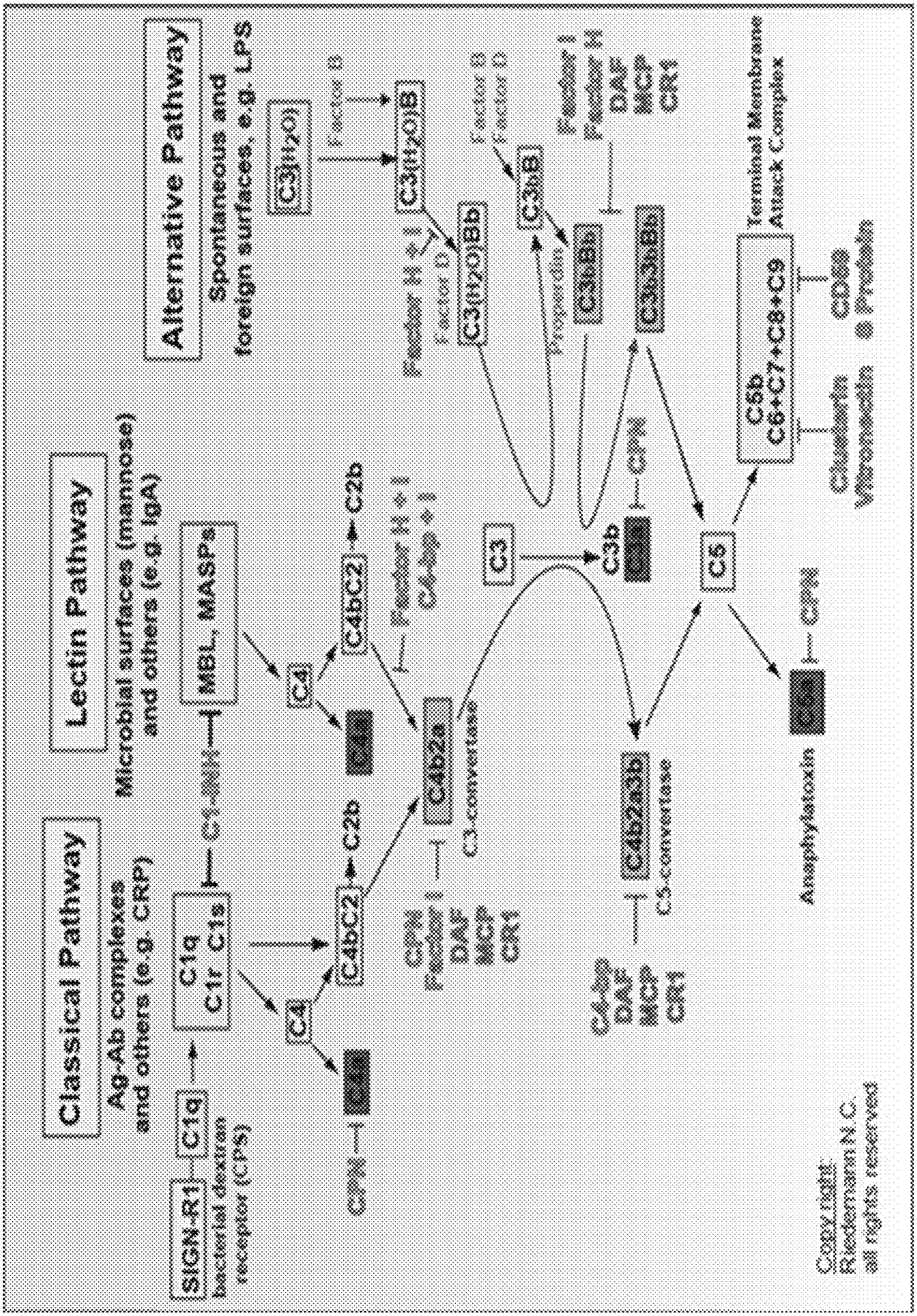
FIG. 1 is a schematic of the three complement pathways: alternative, classical and lectin.

The present invention provides iRNA compositions, which effect the RNA-induced silencing complex (RISC)-mediated cleavage of RNA transcripts of a complement component gene, i.e., a CFB, C3, or C9 gene. The gene may be within a cell, e.g., a cell within a subject, such as a human.

The present invention also provides methods and combination therapies for treating a subject having a disorder that would benefit from inhibiting or reducing the expression of a CFB, C9, and/or C3 gene, e.g., a complement component-associated disease, such as paroxysmal nocturnal hemoglobinuria (PNH) and atypical hemolytic uremic syndrome (aHUS) using iRNA compositions which effect the RNA-induced silencing complex (RISC)-mediated cleavage of RNA transcripts of a CFB, C3, and/or C9 gene.

The present invention also provides methods for preventing at least one symptom, e.g., hemolysis, in a subject having a disorder that would benefit from inhibiting or reducing the expression of a CFB, C3, and/or C9 gene, e.g., a complement component-associated disease, such as paroxysmal nocturnal hemoglobinuria (PNH) and atypical hemolytic uremic syndrome (aHUS).

The iRNAs of the invention include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of a CFB, C3, or C9 gene. The use of these iRNAs enables the targeted degradation of mRNAs of the corresponding gene (CFB, C3, or C9 gene) in mammals. Very low dosages of the iRNAs of the invention, in particular, can specifically and efficiently mediate RNA interference (RNAi), resulting in significant inhibition of expression of the correponding gene (CFB, C3, or C9 gene). Using cell-based assays, the present inventors have demonstrated that iRNAs targeting these complement component genes can mediate RNAi, resulting in significant inhibition of expression of a complement gene (i.e., CFB, C3, or C9). Thus, methods and compositions including these iRNAs are useful for treating a subject having a complement component-associated disease, such as paroxysmal nocturnal hemoglobinuria (PNH) and atypical hemolytic uremic syndrome (aHUS).

The following detailed description discloses how to make and use compositions containing iRNAs to inhibit the expression of a complement gene (i.e., CFB, $C_3$ or C9) as well as compositions, uses, and methods for treating subjects having diseases and disorders that would benefit from inhibition and/or reduction of the expression of these genes.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, the term "Complement Factor B," used interchangeably with the term "CFB," refers to the well-known gene and polypeptide, also known in the art as AHUS, BF, CFAB, BFD, FB, GBG, FBI12, B-Factor, Properdin, H2-Bf, Glycine-Rich Beta Glycoprotein, C3 Proaccelerator, Properdin Factor 2B, C3 Proactivator, PBF2, Glycine-Rich Beta-Glycoprotein, C3/C5 Convertase, EC 3.4.21, and EC 3.4.21.473. The term "CFB" includes human CFB, the amino acid and nucleotide sequence of which may be found in, for example, GenBank Accession No. GI:189181756; mouse CFB, the amino acid and nucleotide sequence of which may be found in, for example, GenBank Accession Nos. GI:218156288 and GI:218156290; rat CFB, the amino acid and nucleotide sequence of which may be found in, for example, GenBank Accession No. GI:218156284; and chimpanzee CFB, the amino acid and nucleotide sequence of which may be found in, for example, GenBank Accession No. GI:57114201. The term "CFB" also includes *Macaca fascicularis* CFB, the amino acid and nucleotide sequence of which may be found in, for example, GenBank Accession No. GI:544428919 and in the entry for the gene, ENSMMUP00000000985 (locus=scaffold3881:47830:53620), in the *Macaca* genome project web site (http://macaqcue.genomics.orgcngpage/specles/index.jsp). Additional examples of CFB mRNA sequences are readily available using, e.g., GenBank, UniProt, OMIM, and the *Macaca* genome project web site.

Exemplary CFB nucleotide sequences may also be found in SEQ ID NOs:1-5, 27, and 30. SEQ ID NOs:12-16, 33, and 36 are the antisense sequences of SEQ ID NOs: 1-5, 27, and 30, respectively.

The term "CFB," as used herein, also refers to naturally occurring DNA sequence variations of the CFB gene. Non-limiting examples of sequence variations within the CFB gene include 1598A>G in exon 12, which results in a lysine being changed to an arginine at amino acid residue 533; 858C>G in exon 6, which results in a phenylalanine being changed to a leucine at amino acid residue 286; and 967A>G in exon 7, which results in a lysine being changed to an alanine at amino acid residue 323 (Tawadrous H. et al. (2010) *Pediatr Nephrol.* 25:947; Goicoechea de Jorge E et al. (2007) *Proc Natl Acad Sci. USA* 104:240). The term "CFB," as used herein, also refers to single nucleotide polymorphisms in the CFB gene. Numerous sequence variations within the CFB gene have been identified and may be found at, for example, NCBI dbSNP and UniProt (see, e.g., ncbi.nlm.nih.gov/snp).

As used herein, the term "Complement Component 3," used interchangeably with the term "C3," refers to the well-known gene and polypeptide, also known in the art as ARMD9, C3a Anaphylatoxin, ASP, Complement Component C3a, C3a, Complement Component C3b, C3b, prepro-C3, Acylation-Stimulating Protein Cleavage Product, CPAMD1, Complement C3, C3 And PZP-Like Alpha-2-Macroglobulin Domain-Containing Protein 1, Complement Component C3, and AHUS5. The term "C3" includes human C3, the amino acid and nucleotide sequence of which may be found in, for example, GenBank Accession No. GI:115298677; mouse C3, the amino acid and nucleotide sequence of which may be found in, for example, GenBank Accession No. GI: 126518316; and rat C3, the amino acid and nucleotide sequence of which may be found in, for example, GenBank Accession No. GI: 158138560. The term "C3" also includes Macacafascicularis CFB, the amino acid and nucleotide sequence of which may be found in, for example, GenBank Accession No. GI:544508182 and in the entry for the gene, ENSP00000245907 (locus=chr19:6921416:6963034), in the *Macaca* genome project web site (http://macaque.genonmics.org.cn/page/species/index.jsp). Additional examples of C3 mRNA sequences are readily available using, e.g., GenBank, UniProt, OMIM, and the *Macaca* genome project web site.

Exemplary C3 nucleotide sequences may also be found in SEQ ID NOs:6-8, 28, and 31. SEQ ID NOs:17-19, 34, and 37 are the antisense sequences of SEQ ID NOs: 6-8, 28, and 31, respectively.

The term "C3," as used herein, also refers to naturally occurring DNA sequence variations of the C3 gene. Numerous sequence variations within the C3 gene have been identified and may be found at, for example, NCBI dbSNP and UniProt (see, e.g., ncbi.nlm.nih.gov/snp).

As used herein, the term "Complement Component 9," used interchangeably with the term "C9," refers to the well-known gene and polypeptide. The term "C9" includes human C9, the amino acid and nucleotide sequence of which may be found in, for example, GenBank Accession No. GI:187608340; mouse C9, the amino acid and nucleotide sequence of which may be found in, for example, GenBank Accession No. GI:15375311; and rat C9, the amino acid and nucleotide sequence of which may be found in, for example, GenBank Accession No. GI:16924005. The term "C9" also includes Macacafascicularis CFB, the amino acid and nucleotide sequence of which may be found in, for example, GenBank Accession No. GI:544436867 and in the entry for the gene, isotig05361 (isogroup03350 length=2955 numContigs=1), in the *Macaca* genome project web site (http://macaque.genomics.org.cn/page/species/index.jsp). Additional examples of C3 mRNA sequences are readily available using, e.g., GenBank, UniProt, OMIM, and the *Macaca* genome project web site.

Exemplary C9 nucleotide sequences may also be found in SEQ ID NOs:9-11, 29, and 32. SEQ ID NOs:20-22, 35, and 38 are the antisense sequences of SEQ ID NOs: 9-11, 29, and 32, respectively.

The term "C9," as used herein, also refers to naturally occurring DNA sequence variations of the C9 gene. Numerous sequence variations within the C9 gene have been identified and may be found at, for example, NCBI dbSNP and UniProt (see, e.g., ncbi.nlm.nih.gov/snp).

As used herein, "target sequence" refers to a contiguous portion of the nucleotide sequence of an mRNA molecule formed during the transcription of a CFB, C3, or C9 gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of a CFB, C3, or C9 gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of the target gene in a cell, e.g., a cell within a subject, such as a mammalian subject.

In one embodiment, an RNAi agent of the invention includes a single stranded RNA that interacts with a target RNA sequence, e.g., a CFB, C3, or C9 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a CFB, C3, or C9 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150; 883-894.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a CFB, C3, or C9 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi. In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides.

As used herein, the term "modified nucleotide" refers to a nucleotide having, independently, a modified sugar moiety, a modified internucleotide linkage, and/or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised of separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

"Blunt" or "blunt end" means that there are no unpaired nucleotides at that end of the double stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" or "guide strand" refers to the strand of an iRNA, e.g., a dsRNA, which includes a region that is substantially complementary to a target sequence, e.g., a CFB, C3, or C9 mRNA. As used herein, the term "region of complementarity" refers to the region on the antisense strand that is substantially complementary to a sequence, for example a target sequence, e.g., a CFB, C3, or C9 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand," or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding CFB, C3, or C9). For example, a polynucleotide is complementary to at least a part of a CFB mRNA if the sequence is substantially complementary to a non-interrupted portion of an mRNA encoding CFB.

In general, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

In one aspect of the invention, an agent for use in the methods and compositions of the invention is a single-stranded antisense RNA molecule that inhibits a target mRNA via an antisense inhibition mechanism. The single-stranded antisense RNA molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences described herein.

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in CFB, C3, and/or C9 expression; a human at risk for a disease, disorder or condition that would benefit from reduction in CFB, C3, and/or C9 expression; a human having a disease, disorder or condition that would benefit from reduction in CFB, C3, and/or C9 expression; and/or human being treated for a disease, disorder or condition that would benefit from reduction in CFB, C3, and/or C9 expression as described herein.

As used herein, the term "complement component-associated disease" is a disease or disorder that is caused by, or associated with complement activation. The term "complement component-associated disease" includes a disease, disorder or condition that would benefit from reduction in CFB (i.e., a "CFB-associated disease"), C3 (i.e., a "C3-associated disease"), and/or C9 (i.e., a "C9-associated disease") expression. Such diseases are typically associated with inflammation and/or immune system activation, e.g., membrane attack complex-mediated lysis, anaphylaxis, and/or hemolysis. Non-limiting examples of complement component-associated diseases include paroxysmal nocturnal hemoglobinuria (PNH), atypical hemolytic uremic syndrome (aHUS), asthma, rheumatoid arthritis (RA); antiphospholipid antibody syndrome; lupus nephritis; ischemia-reperfusion injury; typical or infectious hemolytic uremic syndrome (tHUS); dense deposit disease (DDD); neuromyelitis optica (NMO); multifocal motor neuropathy (MMN); multiple sclerosis (MS); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; pre-eclampsia, traumatic brain injury, myasthenia gravis, cold agglutinin disease, dermatomyositis bullous pemphigoid, Shiga toxin *E. coli*-related hemolytic uremic syndrome, C3 neuropathy, anti-neutrophil cytoplasmic antibody-associated vasculitis (e.g., granulomatosis with polyangiitis (previously known as Wegener granulomatosis), Churg-Strauss syndrome, and microscopic polyangiitis), humoral and vascular transplant rejection, graft dysfunction, myocardial infarction (e.g., tissue damage and ischemia in myocardial infarction), an allogenic transplant, sepsis (e.g., poor outcome in sepsis), Coronary artery disease, dermatomyositis, Graves' disease, atherosclerosis, Alzheimer's disease, systemic inflammatory response sepsis, septic shock, spinal cord injury, glomerulonephritis, Hashimoto's thyroiditis, type I diabetes, psoriasis, pemphigus, autoimmune hemolytic anemia (AIHA), ITP, Goodpasture syndrome, Degos disease, antiphospholipid syndrome (APS), catastrophic APS (CAPS), a cardiovascular disorder, myocarditis, a cerebrovascular disorder, a peripheral (e.g., musculoskeletal) vascular disorder, a renovascular disorder, a mesenteric/enteric vascular disorder, vasculitis, Henoch-Schnlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease (arteritis), venous gas embolus (VGE), and restenosis following stent placement, rotational atherectomy, and percutaneous transluminal coronary angioplasty (PTCA) (see, e.g., Holers (2008) Immunological Reviews 223:300-316; Holers and Thurman (2004) Molecular Immunology 41:147-152; U.S. Patent Publication No. 20070172483).

In one embodiment, a complement component-associated disease is paroxysmal nocturnal hemoglobinuria (PNH). The PNH may be classical PNH or PNH in the setting of another bone marrow failure syndrome and/or myelodysplastic syndromes (MDS), e.g., cytopenias. In another embodiment, a complement component-associated disease is atypical hemolytic uremic syndrome (aHUS). In yet another embodiment, a complement component-associated disease is rheumatoid arthritis.

"Therapeutically effective amount," as used herein, is intended to include the amount of an RNAi agent that, when administered to a subject having a complement component-associated disease, is sufficient to effect treatment of the disease (e.g., by diminishing, ameliorating or maintaining the existing disease or one or more symptoms of disease). The "therapeutically effective amount" may vary depending on the RNAi agent or antibody, or antigen-binding fragment thereof, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA agent that, when administered to a subject having a complement component-associate disease but not yet (or currently) experiencing or displaying symptoms of the disease, and/or a subject at risk of developing a complement component-associated disease, e.g., a subject having a graft and/or transplant, e.g., a sensitized or allogenic recipient, a subject having sepsis, and/or a subject having a myocardial infarction, is sufficient to prevent or ameliorate the disease or one or more symptoms of the disease. Ameliorating the disease includes slowing the course of the disease or reducing the severity of later-developing disease. The "prophylactically effective amount" may vary depending on the iRNA agent, how the agent is administered, the degree of risk of disease, and the history, age, weight, family history, genetic makeup, the types of preceding or concomitant treatments, if any, and other individual characteristics of the patient to be treated.

A "therapeutically effective amount" or "prophylactically effective amount" also includes an amount of an RNAi agent that produces some desired local or systemic effect at a reasonable benefit/risk ratio applicable to any treatment. iRNA agents employed in the methods of the present invention may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum and serosal fluids, plasma, urine, lymph, cerebrospinal fluid, ocular fluids, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue (or subcomponents thereof) derived from the subject.

II. iRNAs of the Invention

The present invention provides iRNAs which inhibit the expression of a complement component gene. In one embodiment, the iRNA agent includes double-stranded ribonucleic acid (dsRNA) molecules for inhibiting the expression of a CFB gene in a cell, such as a cell within a subject, e.g., a mammal, such as a human having a complement component-associated disease as described herein, e.g., PNH. In another embodiment, the iRNA agent includes double-stranded ribonucleic acid (dsRNA) molecules for inhibiting the expression of a C3 gene in a cell, such as a cell within a subject, e.g., a mammal, such as a human having a complement component-associated disease as described herein, e.g., PNH. In a further embodiment, the iRNA agent includes double-stranded ribonucleic acid (dsRNA) molecules for inhibiting the expression of a C9 gene in a cell, such as a cell within a subject, e.g., a mammal, such as a human having a complement component-associated disease as described herein, e.g., PNH. The dsRNA includes an antisense strand having a region of complementarity which is complementary to at least a part of an mRNA formed in the expression of a target gene, i.e., CFB, C3, or C9 gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the target gene, the iRNA inhibits the expression of the target gene (e.g., a human, a primate, a non-primate, or a bird CFB, C3, or C9 gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence.

The target sequence can be derived from the sequence of an mRNA formed during the expression of a CFB, C3, or C9 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is between about 15 and about 20 nucleotides in length, or between about 25 and about 30 nucleotides in length. In one embodiment, an RNAi agent of the invention is a dsRNA of 24-30 nucleotides that interacts with a target RNA sequence, i.e., a CFB, C3, or C9 target mRNA sequence, to direct the cleavage of the target RNA. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target CFB, C3, or C9 expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art as further discussed below, e.g., by use of an automated DNA synthesizer, such as are commercially available from, for example, Biosearch, Applied Biosystems, Inc. iRNA compounds of the invention may be prepared using a two-step procedure.

First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an anti-sense sequence.

In one embodiment, a dsRNA of the invention targeting CFB includes a sense strand selected from the group of sequences provided in any one of Tables 3 and 4, and the corresponding antisense strand of the sense strand is selected from the group of sequences of any one of Tables 3 and 4. In this aspect, one of the two sequences is complementary to the other of the two sequences, with one of the sequences being substantially complementary to a sequence of an mRNA generated in the expression of a CFB gene. As such, in this aspect, a dsRNA will include two oligonucleotides, where one oligonucleotide is described as the sense strand in any one of Tables 3 and 4, and the second oligonucleotide is described as the corresponding antisense strand of the sense strand in any one of Tables 3 and 4. In one embodiment, the substantially complementary sequences of the dsRNA are contained on separate oligonucleotides. In another embodiment, the substantially complementary sequences of the dsRNA are contained on a single oligonucleotide.

In one embodiment, a dsRNA of the invention targeting C3 includes a sense strand selected from the group of sequences provided in any one of Tables 5 and 6, and the corresponding antisense strand of the sense strand is selected from the group of sequences of any one of Tables 5 and 6. In this aspect, one of the two sequences is complementary to the other of the two sequences, with one of the sequences being substantially complementary to a sequence of an mRNA generated in the expression of a C3 gene. As such, in this aspect, a dsRNA will include two oligonucleotides, where one oligonucleotide is described as the sense strand in any one of Tables 5 and 6, and the second oligonucleotide is described as the corresponding antisense strand of the sense strand in any one of Tables 5 and 6. In one embodiment, the substantially complementary sequences of the dsRNA are contained on separate oligonucleotides. In another embodiment, the substantially complementary sequences of the dsRNA are contained on a single oligonucleotide.

In one embodiment, a dsRNA of the invention targeting C9 includes a sense strand selected from the group of sequences provided in any one of Tables 7 and 8, and the corresponding antisense strand of the sense strand is selected from the group of sequences of any one of Tables 7 and 8. In this aspect, one of the two sequences is complementary to the other of the two sequences, with one of the sequences being substantially complementary to a sequence of an mRNA generated in the expression of a C9 gene. As such, in this aspect, a dsRNA will include two oligonucleotides, where one oligonucleotide is described as the sense strand in any one of Tables 7 and 8, and the second oligonucleotide is described as the corresponding antisense strand of the sense strand in any one of Tables 7 and 8. In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Tables 3-8 are described as modified and/or conjugated sequences, the RNA of the iRNA of the invention e.g., a dsRNA of the invention, may comprise any one of the sequences set forth in Tables 3-8 that is un-modified, un-conjugated, and/or modified and/or conjugated differently than described therein.

The skilled person is well aware that dsRNAs having a duplex structure of between about 20 and 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 3-8 dsRNAs described herein can include at least one strand of a length of minimally 21 nucleotides. It can be reasonably expected that shorter duplexes having one of the sequences of any one of Tables 3-8 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of Tables 3-8, and differing in their ability to inhibit the expression of the taret gene by not more than about 5, 10, 15, 20, 25, or 30% inhibition from a dsRNA comprising the full sequence, are contemplated to be within the scope of the present invention.

In addition, the RNAs provided in any one of Tables 3 and 4 identify a site(s) in a CFB transcript that is susceptible to RISC-mediated cleavage. Similarly, the RNAs provided in any one of Tables 5 and 6 identify a site(s) in a C3 transcript that is susceptible to RISC-mediated cleavage, and the RNAs provided in any one of Tables 7 and 8 identify a site(s) in a C9 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in any one of Tables 3-8 coupled to additional nucleotide sequences taken from the region contiguous to the selected sequence in the target gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in any one of Tables 3-8 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in any one of Tables 3-8, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of, e.g., a CFB gene, generally does not contain any mismatch within the central 13 nucleotides. The methods described herein or methods known in the art can be used to determine whether an iRNA containing a mismatch to a target sequence is effective in inhibiting the expression of a target gene, e.g., a CFB, C3, or C9 gene. Consideration of the efficacy of iRNAs with mismatches in inhibiting expression of a target gene is important, especially if the particular region of complementarity in a target gene is known to have polymorphic sequence variation within the population.

III. Modified iRNAs of the Invention

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA of the invention are modified iRNAs of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages.

Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylpho sphotriesters, methyl and other alkyl phosphonates including 3'-alkylene phosphonates and chiral phosphonates, phosphinates, phosphoramidates including 3'-amino phosphoramidate and aminoalkylpho sphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular $—CH_2—NH—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2—$ [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O—, S—, or N-alkyl; O—, S—, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)._nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more bicyclic sugar moities. A "bicyclic sugar" is a furanosyl ring modified by the bridging of two atoms. A"bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., J. Org. Chem., 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and P3-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and -C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference. Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

A. Modified iRNAs Comprising Motifs of the Invention

In certain aspects of the invention, the double-stranded RNAi agents of the invention include agents with chemical modifications as disclosed, for example, in U.S. Provisional Application No. 61/561,710, filed on Nov. 18, 2011, or in PCT/US2012/065691, the entire contents of each of which are incorporated herein by reference.

As shown herein and in Provisional Application No. 61/561,710 or in PCT/US2012/065691, a superior result may be obtained by introducing one or more motifs of three identical modifications on three consecutive nucleotides into a sense strand and/or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double-stranded RNAi agent are completely modified to have one or more motifs of three identical modifications on three consecutive nucleotides at or near the cleavage site of at least one strand of an RNAi agent, the gene silencing acitivity of the RNAi agent was superiorly enhanced.

Accordingly, the invention provides double-stranded RNAi agents capable of inhibiting the expression of a target gene (i.e., a CFB, C3, or C9 gene) in vivo. The RNAi agent comprises a sense strand and an antisense strand. Each strand of the RNAi agent may range from 12-30 nucleotides in length. For example, each strand may be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5'-end. The antisense strand contains at least one motif of three 2'-O-methyl modifications on three consecutive nucleotides at positions 11, 12, 13 from the 5'-end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'-end. The antisense strand contains at least one motif of three 2'-O-methyl modifications on three consecutive nucleotides at positions 11, 12, 13 from the 5'-end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'-end. The antisense strand contains at least one motif of three 2'-O-methyl modifications on three consecutive nucleotides at positions 11, 12, 13 from the 5'-end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'-end; the antisense strand contains at least one motif of three 2'-O-methyl modifications on three consecutive nucleotides at positions 11, 12, 13 from the 5'-end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably $GalNAC_3$).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand.

For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adajacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified.

Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The κ' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisenese strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing acitivty to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_aYYYN_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In one embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5'-end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. The mistmatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense and/or antisense strand.

In one embodiment, the sense strand sequence may be represented by formula (I):

$$5'\ n_p\text{-}N_a\text{-}(XXX)_i\text{-}N_b\text{-}YYY\text{-}N_b\text{-}(ZZZ)_j\text{-}N_a\text{-}n_q\ 3' \quad (I)$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each n, and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the $1^{st}$ nucleotide, from the 5'-end; or optionally, the count starting at the $1^{st}$ paired nucleotide within the duplex region, from the 5'-end.

In one embodiment, i is 1 and j is 0, or i is 0 and j is 1, or both i and j are 1. The sense strand can therefore be represented by the following formulas:

$$5'\ n_p\text{-}N_a\text{-}YYY\text{-}N_b\text{-}ZZZ\text{-}N_a\text{-}n_q\ 3'; \quad (Ib)$$

$$5'\ n_p\text{-}N_a\text{-}XXX\text{-}N_b\text{-}YYY\text{-}N_a\text{-}n_q\ 3'; \quad (Ic)$$

or $$5'\ n_p\text{-}N_a\text{-}XXX\text{-}N_b\text{-}YYY\text{-}N_b\text{-}ZZZ\text{-}N_a\text{-}n_q\ 3'. \quad (Id)$$

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

$$5'\ n_p\text{-}N_a\text{-}YYY\text{-}N_a\text{-}n_q\ 3'. \quad (Ia)$$

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

$$5'\ n_{q'}\text{-}N_a'\text{-}(ZZZ)_k\text{-}N_b'\text{-}Y'Y'Y'\text{-}N_b'(X'X'X')_l\text{-}N'_a\text{-}n_p'\ 3' \quad (II)$$

wherein:

k and 1 are each independently 0 or 1;

p' and q' are each independently 0-6;

each $N_a$' independently represents an oligonucleotide sequence comprising 0-25 modified nucleotides, each sequence comprising at least two differently modified nucleotides;

each $N_b$' independently represents an oligonucleotide sequence comprising 0-10 modified nucleotides;

each $n_p$' and $n_q$' independently represent an overhang nucleotide;

wherein $N_b$' and Y' do not have the same modification; and

X'X'X', Y'Y'Y' and Z'Z'Z' each independently represent one motif of three identical modifications on three consecutive nucleotides.

In one embodiment, the $N_a$' and/or $N_b$' comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the $1^{st}$ nucleotide, from the 5'-end; or optionally, the count starting at the $1^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and 1 is 0, or k is 0 and 1 is 1, or both k and 1 are 1.

The antisense strand can therefore be represented by the following formulas:

$$5'\ n_{q'}\text{-}N_a'\text{-}Z'Z'Z'\text{-}N_b'\text{-}Y'Y'Y'\text{-}N_a'\text{-}n_{p'}\ 3'; \quad \text{(IIb)}$$

$$5'\ n_{q'}\text{-}N_a'\text{-}Y'Y'Y'\text{-}N_b'\text{-}X'X'X'\text{-}n_{p'}\ 3'; \quad \text{(IIc)}$$

or $$5'\ n_{q'}\text{-}N_a'\text{-}Z'Z'Z'\text{-}N_b'\text{-}Y'Y'Y'\text{-}N_b'\text{-}X'X'X'\text{-}N_a'\text{-}n_{p'}\ 3'. \quad \text{(IId)}$$

When the antisense strand is represented by formula (IIb), $N_b$ represents an oligonucleotide sequence comprising 0-10, 0-7, 0-10, 0-7, 0-5, 0-4, 0-2 or 0 modified nucleotides. Each $N_a$' independently represents an oligonucleotide sequence comprising 2-20, 2-15, or 2-10 modified nucleotides.

When the antisense strand is represented as formula (IIc), $N_b$' represents an oligonucleotide sequence comprising 0-10, 0-7, 0-10, 0-7, 0-5, 0-4, 0-2 or 0 modified nucleotides. Each $N_a$' independently represents an oligonucleotide sequence comprising 2-20, 2-15, or 2-10 modified nucleotides.

When the antisense strand is represented as formula (IId), each $N_b$' independently represents an oligonucleotide sequence comprising 0-10, 0-7, 0-10, 0-7, 0-5, 0-4, 0-2 or 0 modified nucleotides. Each $N_a$' independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and 1 is 0 and the antisense strand may be represented by the formula:

$$5'\ n_{p'}\text{-}N_{a'}\text{-}Y'Y'Y'\text{-}N_{a'}\text{-}n_{q'}\ 3'. \quad \text{(Ia)}$$

When the antisense strand is represented as formula (IIa), each $N_a$' independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the $1^{st}$ nucleotide from the 5'-end, or optionally, the count starting at the $1^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the $1^{st}$ nucleotide from the 5'-end, or optionally, the count starting at the $1^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

(III)

sense:

$$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$$

antisense:

$$3'\ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$$

wherein:

i, j, k, and 1 are each independently 0 or 1;

p, p', q, and q' are each independently 0-6;

each $N_a$ and $N_a$' independently represents an oligonucleotide sequence comprising 0-25 modified nucleotides, each sequence comprising at least two differently modified nucleotides;

each $N_b$ and $N_b$ independently represents an oligonucleotide sequence comprising 0-10 modified nucleotides; wherein each $n_p$', $n_p$, $n_q$', and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and 1 is 0; or k is 1 and 1 is 0; k is 0 and 1 is 1; or both k and 1 are 0; or both k and 1 are 1.

Exemplary combinations of the sense strand and antisense strand forming a RNAi duplex include the formulas below:

(IIIa)

5' $n_p$-$N_a$-Y Y Y-$N_a$-$n_q$ 3'

3' $n_p$'-$N_a$'-Y'Y'Y'-$N_a$'-$n_q$' 5'

(IIIb)

5' $n_p$-$N_a$-Y Y Y-$N_b$-Z Z Z-$N_a$-$n_q$ 3'

3' $n_p$'-$N_a$'-Y'Y'Y'-$N_b$'-Z'Z'Z'-$N_a$' $n_q$' 5'

(IIIc)

5' $n_p$-$N_a$-X X X-$N_b$-Y Y Y-$N_a$-$n_q$ 3'

3' $n_p$'-$N_a$'-X'X'X'-$N_b$'-Y'Y'Y'-$N_a$'-$n_q$' 5'

(IIId)

5' $n_p$-$N_a$-X X X-$N_b$-Y Y Y-$N_b$-Z Z Z-$N_a$-$n_q$ 3'

3' $n_p$'-$N_a$'-X'X'X'-$N_b$'-Y'Y'Y'-$N_b$'-Z'Z'Z'-$N_a$-$n_q$' 5'

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b$' independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b$' independently represents an oligonucleotide sequence comprising 0-10, 0-7, 0-10, 0-7, 0-5, 0-4, 0-2 or 0 modified nucleotides. Each $N_a$, $N_a$' independently represents an oligonucleotide sequence comprising 2-20, 2-15, or 2-10 modified nucleotides. Each of $N_a$, $N_a$', $N_b$ and $N_b$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p$'>0 and at least one $n_p$' is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p$'>0 and at least one $n_p$' is linked to a neighboring nucleotide via phosphorothioate linkage, and the sense strand is conjugated to one or more GalNAc derivatives attached through a bivalent or trivalent branched linker (described below). In another embodiment, when the RNAi agent is represented by formula (IIId), the $N_a$ modifications are 2'-O-methyl or 2'-fluoro modifications, $n_p$'>0 and at least one $n_p$' is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p$'>0 and at least one $n_p$' is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

As described in more detail below, the RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In certain specific embodiments, the RNAi agent for use in the methods of the invention is an agent selected from the group of agents listed in any one of Tables 3-8. These agents may further comprise a ligand.

IV. iRNAs Conjugated to Ligands

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N. Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 23). An RFGF analogue (e.g., amino acid sequence AALLPVLLAAP (SEQ ID NO: 24) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 25) and the *Drosophila* Antennapedia protein (RQIKIWFQNRRMKWKK (SEQ ID NO: 26) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine, such as Formula II

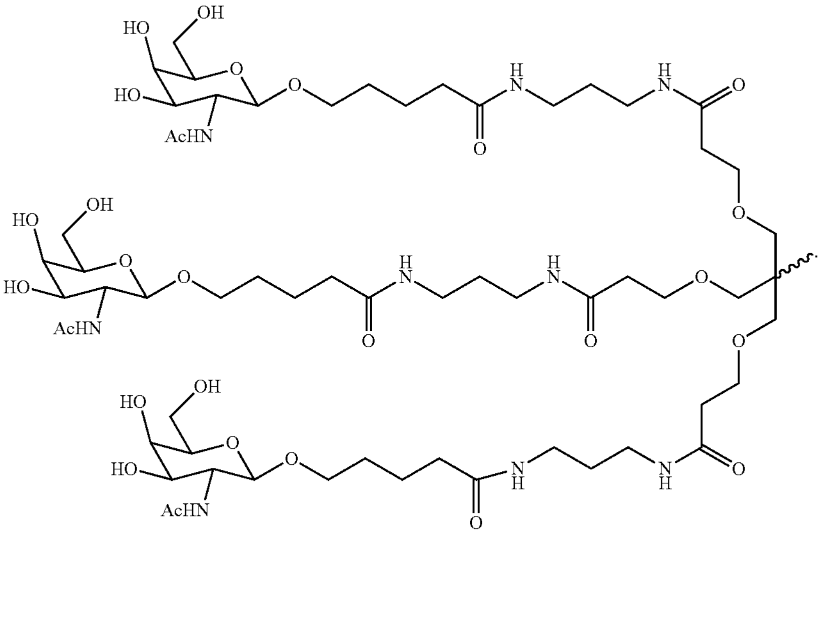

In another embodiment, a carbohydrate conjugate for use in the compositions and methods of the invention is selected from the group consisting of:
Formula II
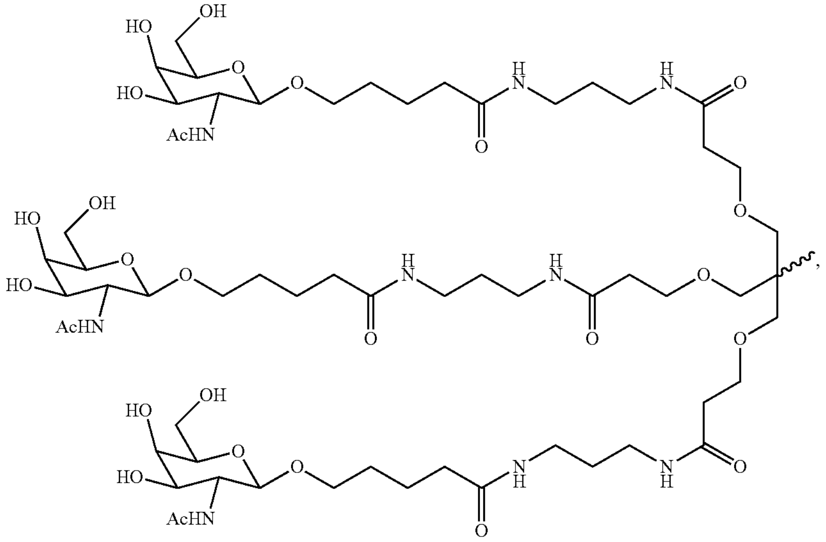
Formula III
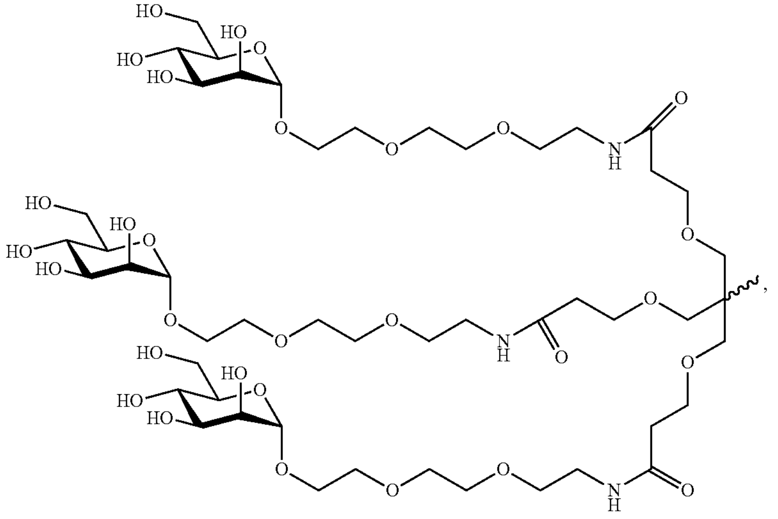
Formula IV
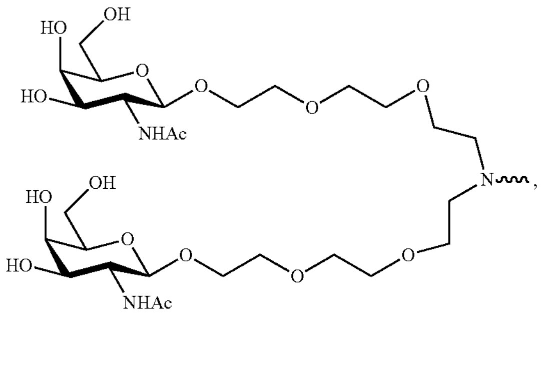
Formula V
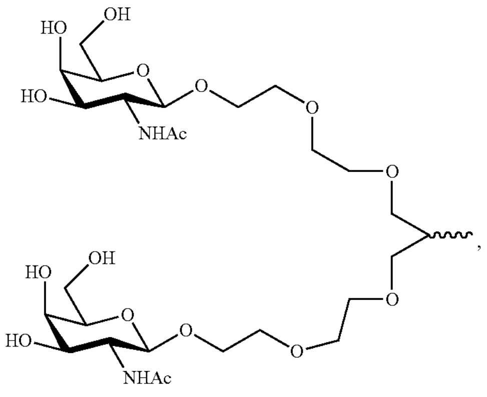

-continued
Formula VI
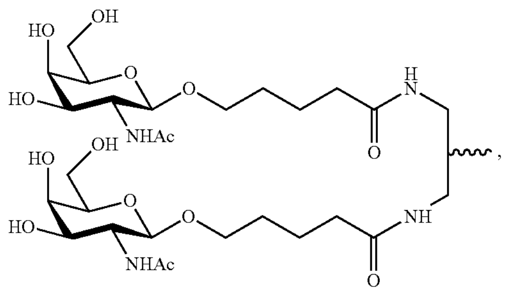
Formula VII
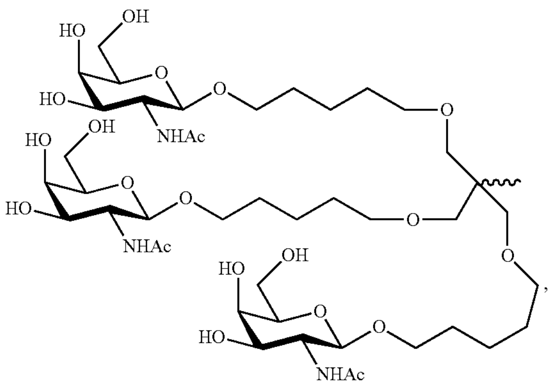
Formula VIII
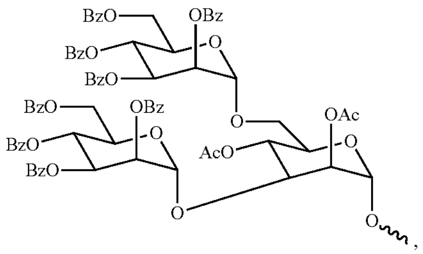
Formula IX
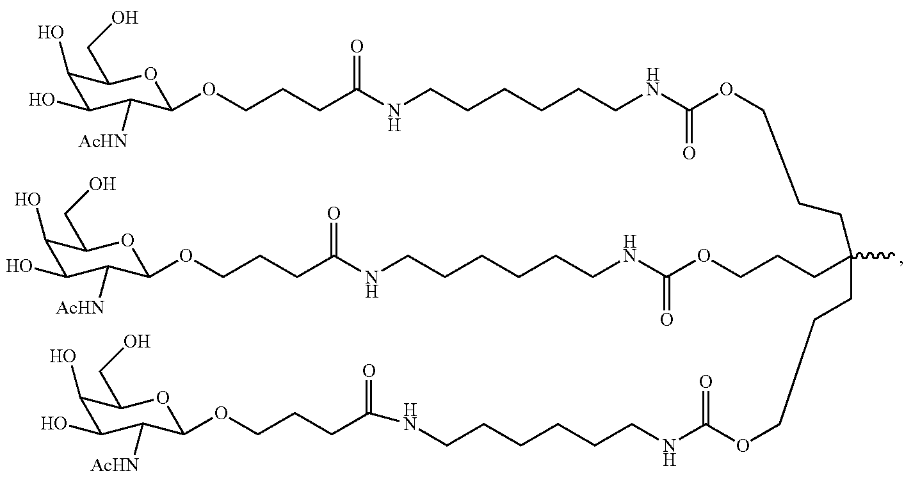

-continued
Formula X
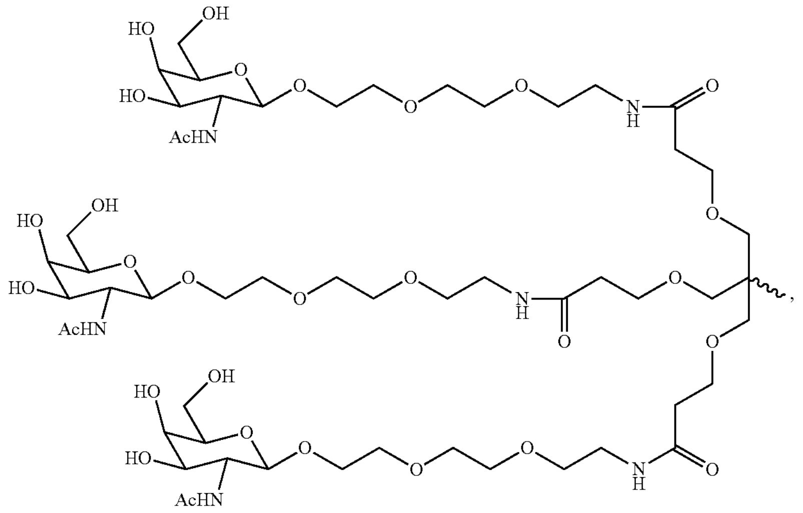
Formula XI
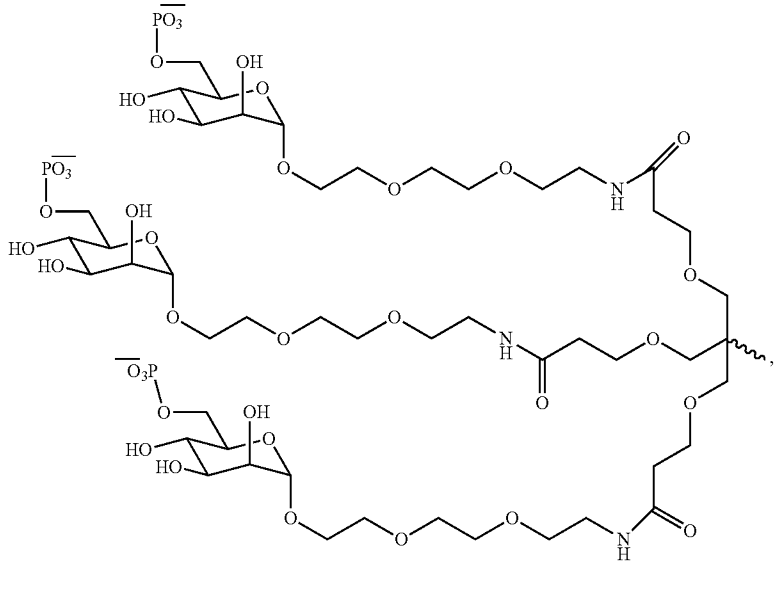

-continued
Formula XII
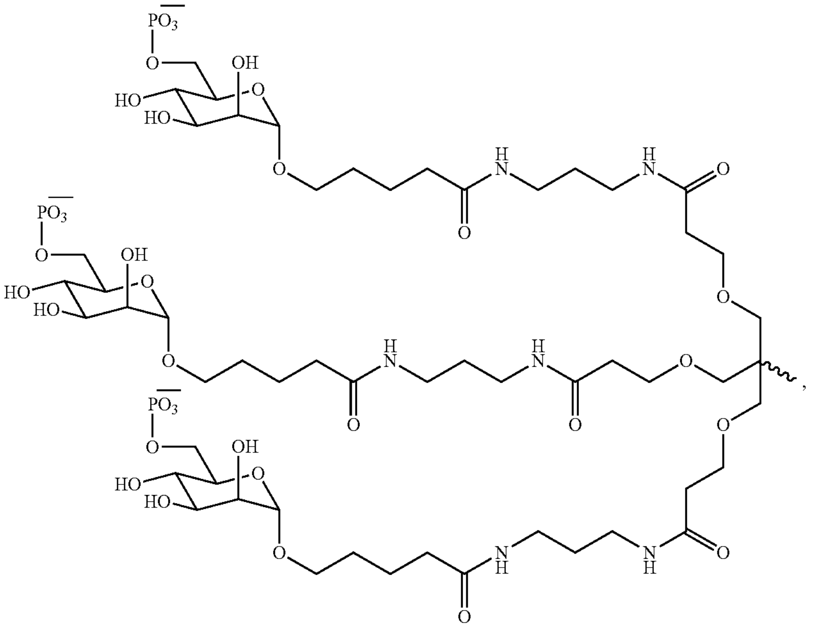
Formula XIII
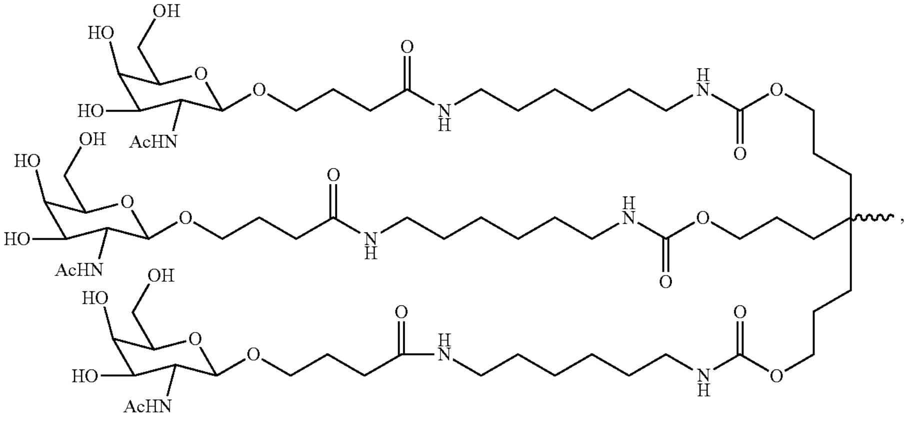
Formula XIV
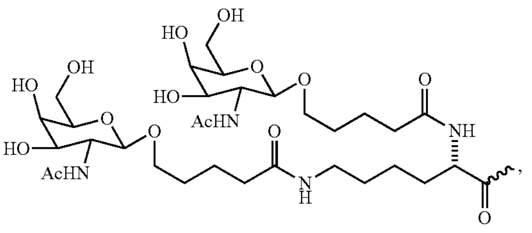
Formula XV
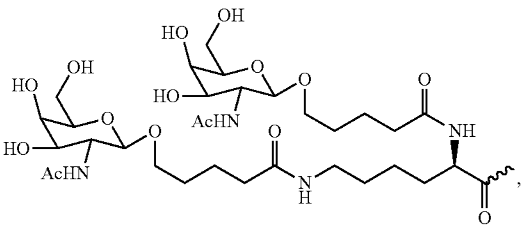
Formula XVI
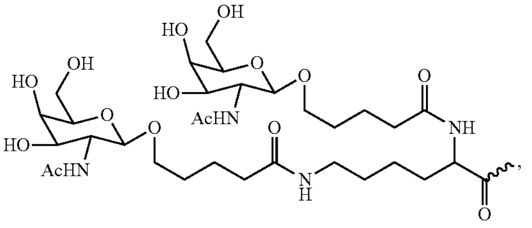
Formula XVII
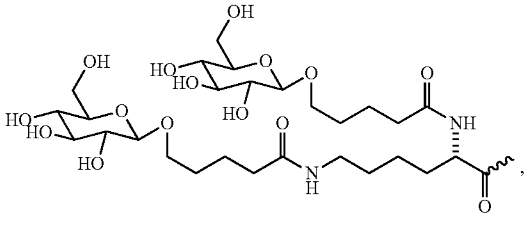

-continued
Formula XVIII
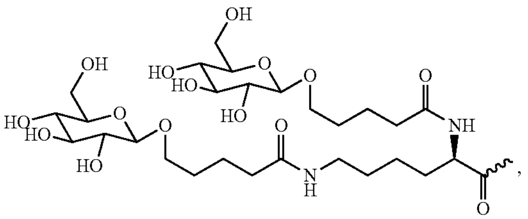
Formula XIX
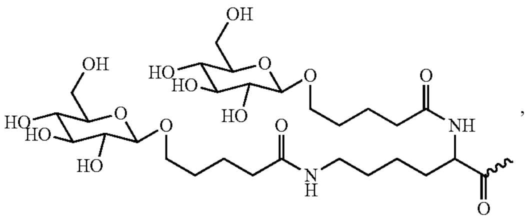
Formula XX
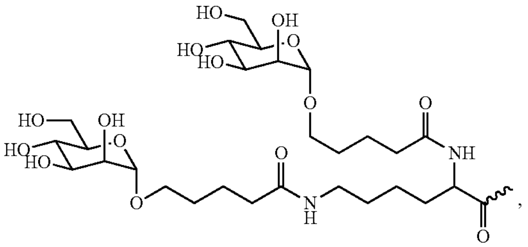
Formula XXI
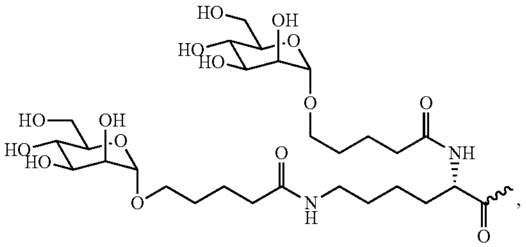
Formula XXII
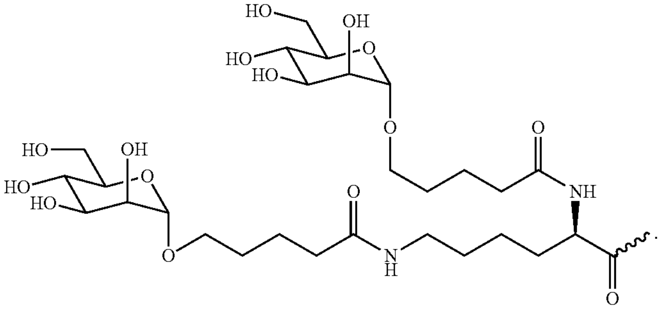
Another representative carbohydrate conjugate for use in the embodiments described herein includes, but is not limited to,
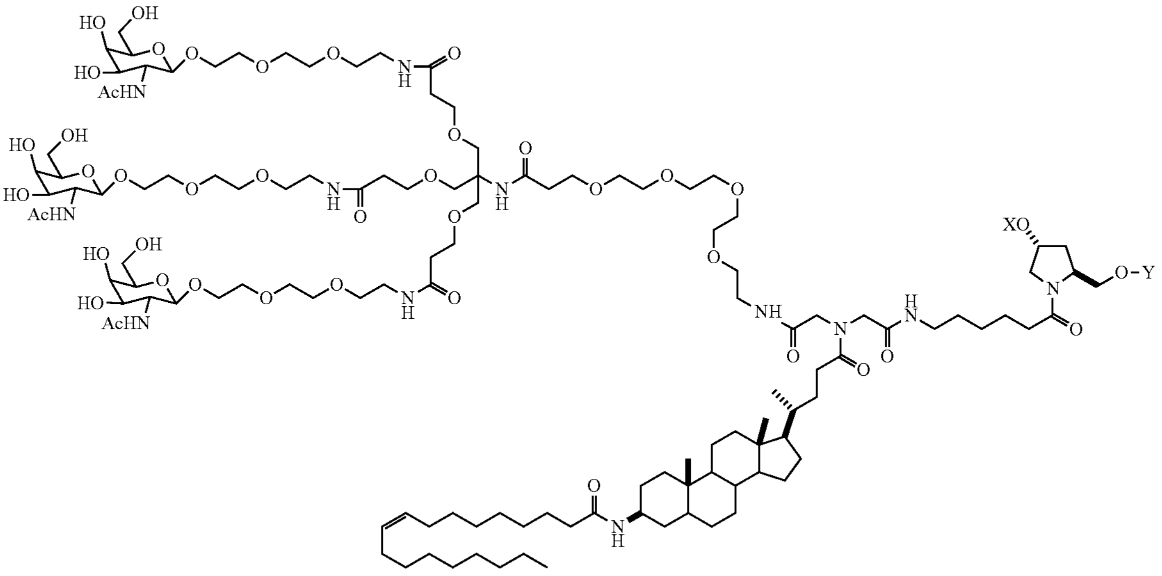

(Formula XXIII), when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—.

These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)

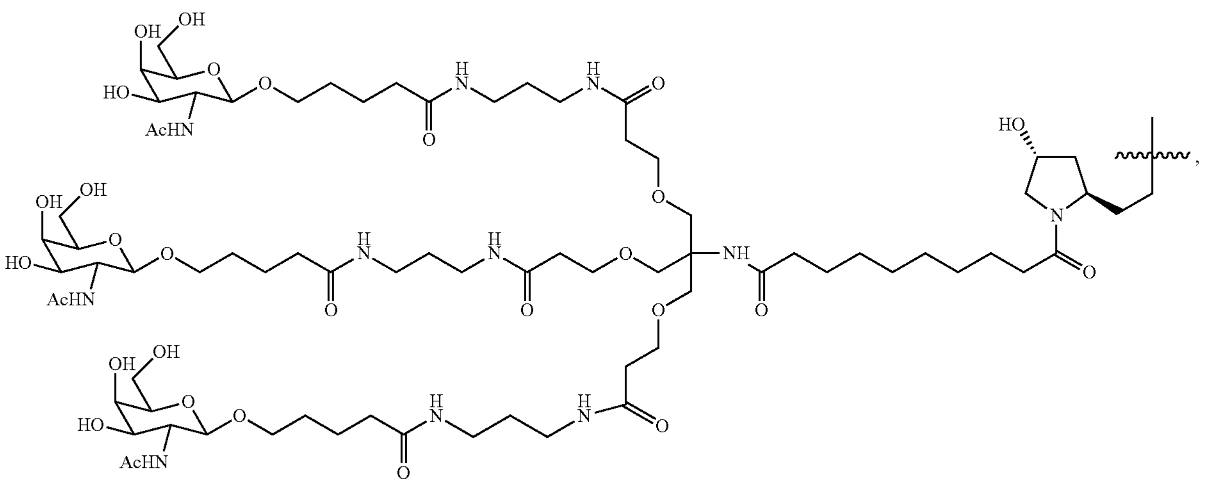

-continued
(Formula XXV)
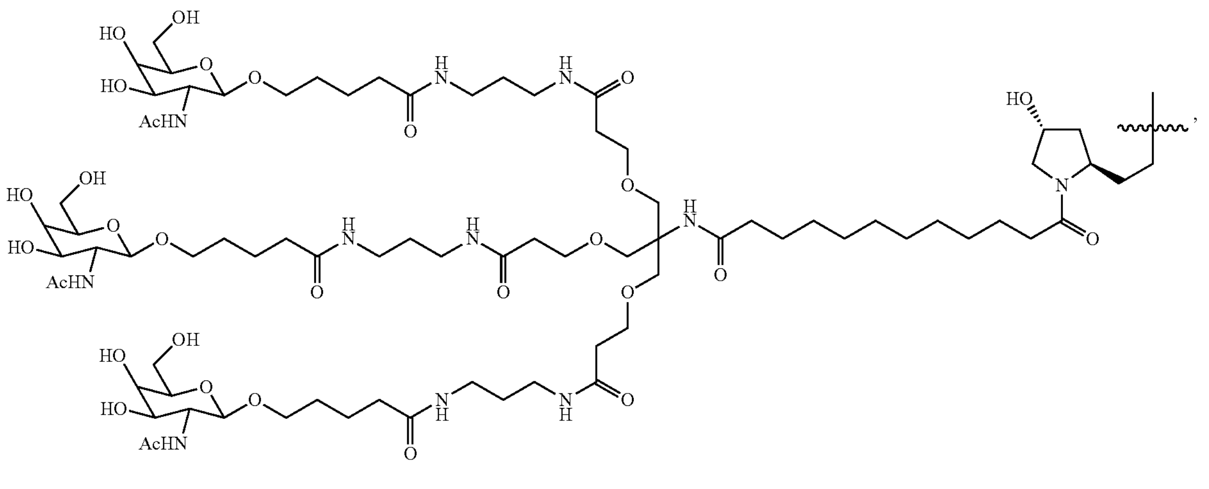
(Formula XXVI)
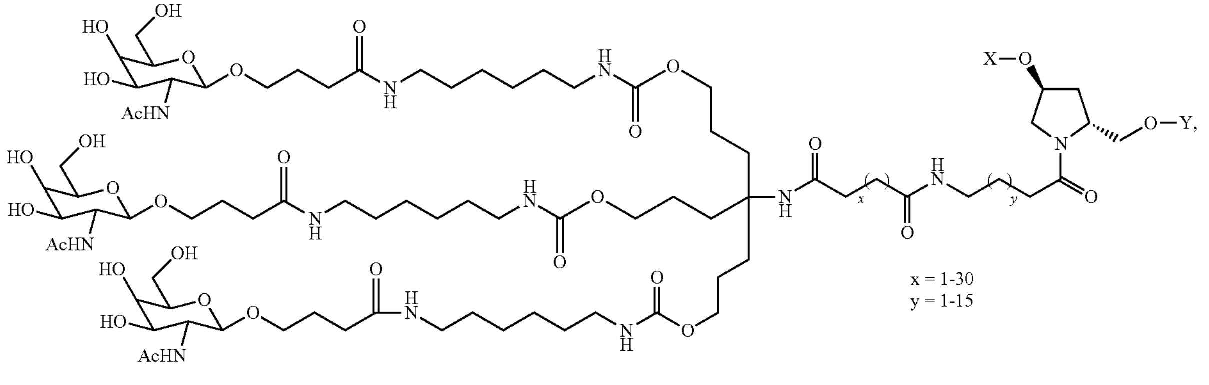
(Formula XXVII)
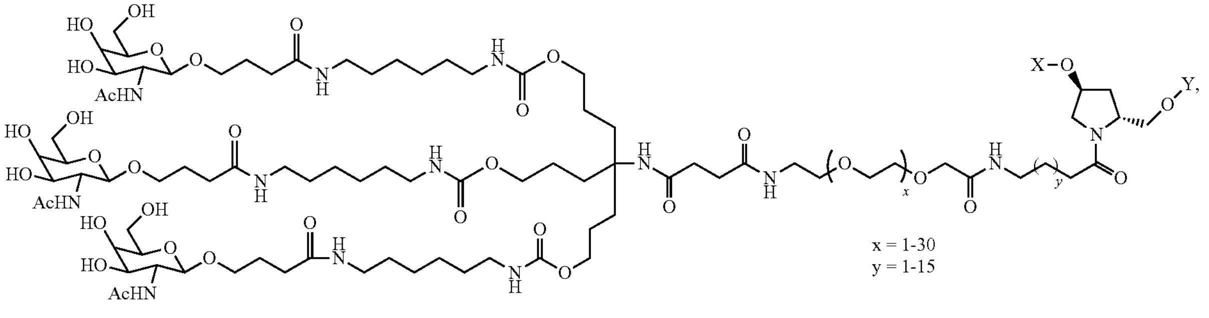
(Formula XXVIII)
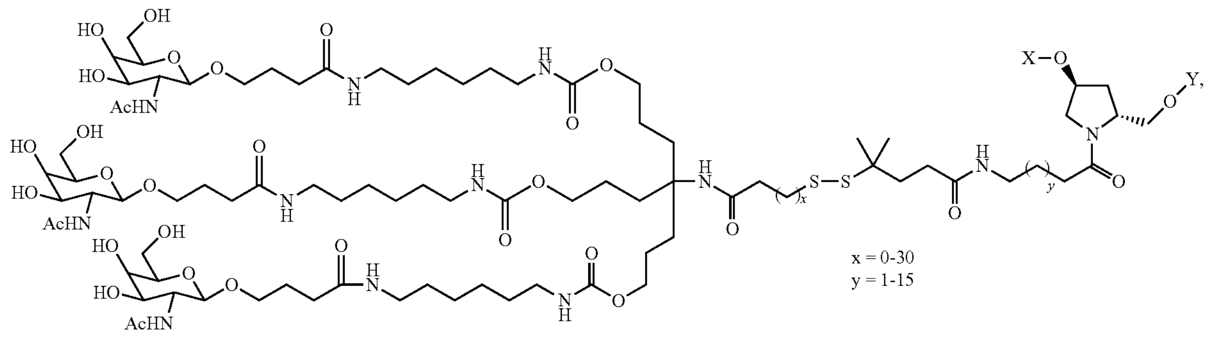

-continued (Formula XXIX)

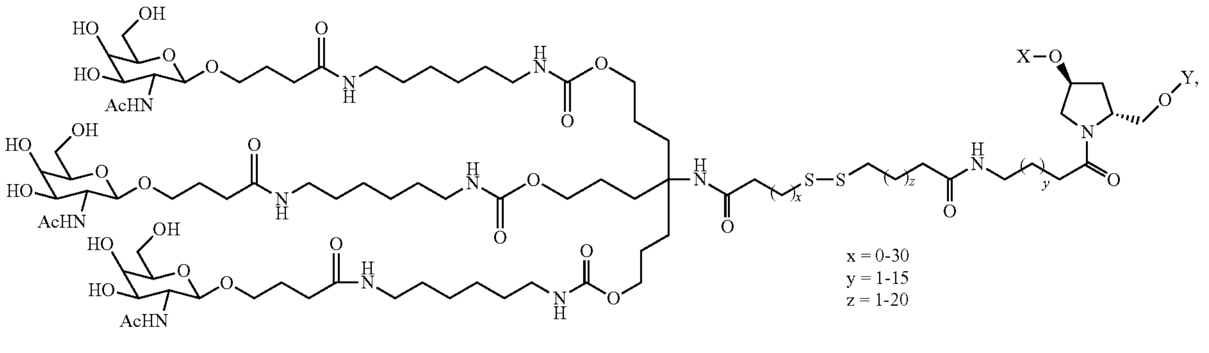

x = 0-30
y = 1-15
z = 1-20

(Formula XXX)

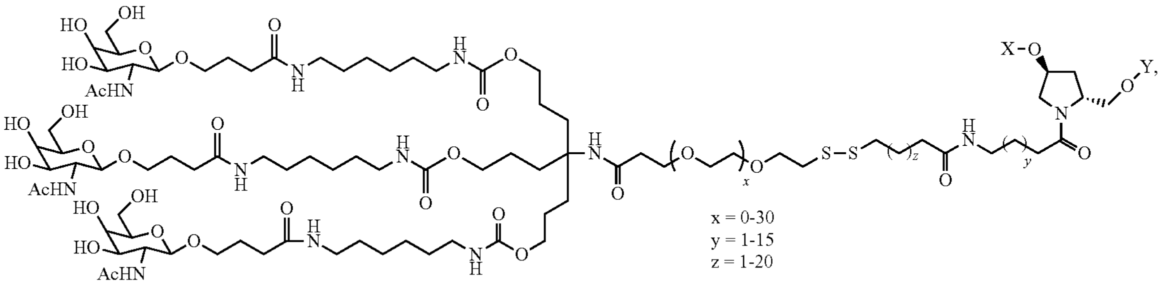

and x = 0-30
y = 1-15
z = 1-20

(Formula XXXI)

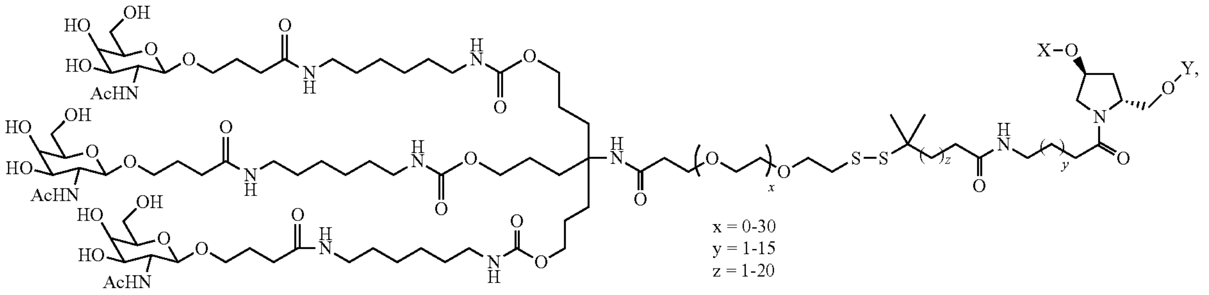

x = 0-30
y = 1-15
z = 1-20 when one of X or Y is an oligonucleotide, the other is a hydrogen.

In certain embodiments of the compositions and methods of the invention, a ligand is one or more "GalNAc" (N-acetyl-galactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

Formula XXXII

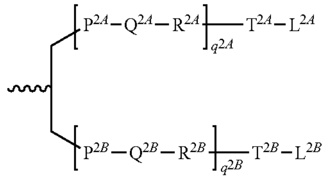

-continued

Formula XXXIII

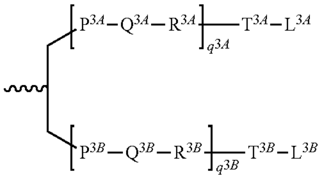

Formula XXXIV

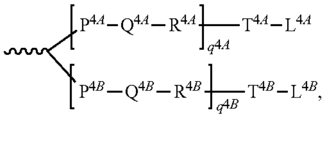

or

Formula XXXV

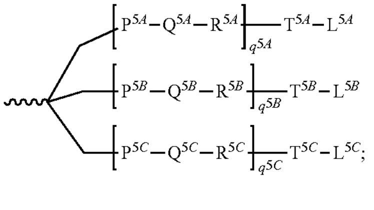

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, $—C(O)—CH(R^a)—NH—$, CO,

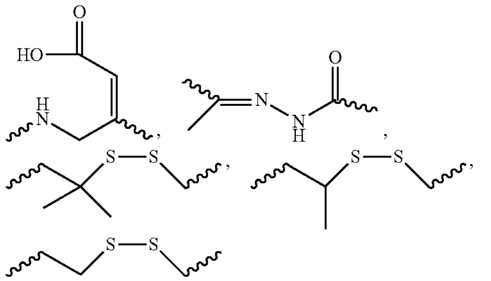

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXV):

Formula XXXV

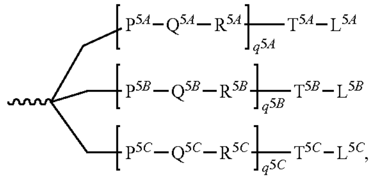

(VII)

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyloxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an iRNA of the Invention

The delivery of an iRNA of the invention to a cell e.g., a cell within a subject, such as a human subject (e.g., a subject in need thereof, such as a subject having a complement component-associated disease as described herein) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) Clin. *Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting a CFB, C3, or C9 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., *Proc. Soc. Exp. Biol. Med.* 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J.*

*Virol,* 70: 520-532; Samulski R et al. (1989), *J. Virol.* 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another viral vector suitable for delivery of an iRNA of the inevtion is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VI. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a CFB, C3, and/or C9 gene, e.g. a complement component-associated disease as descried herein. Such pharmaceutical compositions are formulated based on the mode of delivery. One example is compositions that are formulated for systemic administration via parenteral delivery, e.g., by subcutaneous (SC) or intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of the taregt gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered, e.g., subcutaneously or intravenously, a single therapeutic amount of iRNA, such as about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In some embodiments, subjects are administered, e.g., subcutaneously or intravenously, multiple doses of a therapeutic amount of iRNA, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A multi-dose regimine may include administration of a therapeutic amount of iRNA daily, such as for two days, three days, four days, five days, six days, seven days, or longer.

In other embodiments, subjects are administered, e.g., subcutaneously or intravenously, a repeat dose of a therapeutic amount of iRNA, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A repeat-dose regimine may include administration of a therapeutic amount of iRNA on a regular basis, such as every other day, every third day, every fourth day, twice a week, once a week, every other week, or once a month.

The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a disorder that would benefit from reduction in the expression of CFB, C3, or C9. Such models can be used for in vivo testing of iRNA, as well as for determining a therapeutically effective dose. Suitable mouse models are known in the art and include, for example, collagen-induced arthritis mouse model (Courtenay, J. S., et al. (1980) *Nature* 283, 666-668), myocardial ischemia (Homeister J W and Lucchesi B R (1994) *Annu Rev Pharmacol Toxicol* 34:17-40), ovalbumin induced asthma mouse models (e.g., Tomkinson A., et al. (2001). *J. Immunol.* 166, 5792-5800), (NZB×NZW)F1, MRL/Fas$^{lpr}$ (MRL/lpr) and BXSB mouse models (Theofilopoulos, A. N. and Kono, D. H. 1999. Murine lupus models: gene-specific and genome-wide studies. In Lahita R. G., ed., *Systemic Lupus Erythematosus,* 3rd edn, p. 145. Academic Press, San Diego, Calif.), mouse aHUS model (Goicoechea de Jorge et al. (2011) *The development of atypical hemolytic uremic syndrome depeds on complement C5, JAm Soc Nephrol* 22:137-145.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ allkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers.

Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release,* 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P.Pharma. Sci.,* 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L.

et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., *Journal of Drug Targeting,* 1992, vol. 2,405-410 and du Plessis et al., *Antiviral Research,* 18, 1992, 259-265; Mannino, R. J. and Fould-Fogerite, S., *Biotechniques* 6:682-690, 1988; Itani, T. et al. *Gene* 56:267-276. 1987; Nicolau, C. et al. *Meth. Enz.* 149:157-176, 1987; Straubinger, *R. M. and Papahadjopoulos, D. Meth. Enz.* 101:512-527, 1983; Wang, C. Y. and Huang, L., *Proc. Natl. Acad. Sci. USA* 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ allkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N- dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech GI), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylpho sphatidylcholine (DOPC), dipalmitoylpho sphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylpho sphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HC1 (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

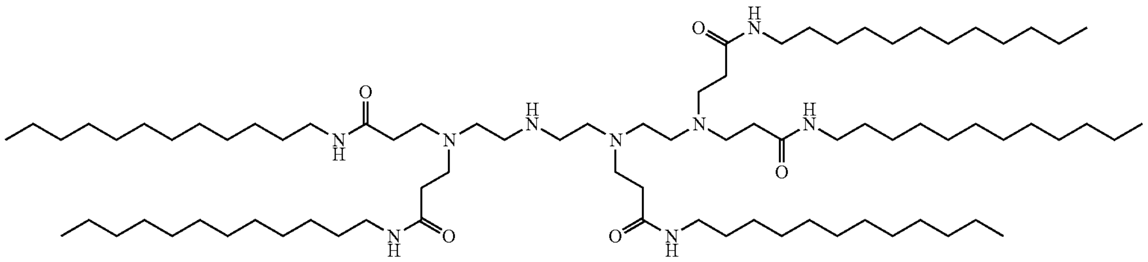

ND98 Isomer I

LNP01 formulations are described, e.g., in International Application Publication No. WO 2008/042973, which is hereby incorporated by reference.

Additional exemplary lipid-dsRNA formulations are described in Table 1.

TABLE 1

| | Ionizable/Cationic Lipid | cationic lipid/non-cationic lipid/cholesterol/ PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/ Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/ Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/ Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/ Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/ Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/ Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/ Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/ Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/ Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyedidodecan-2-ol (Tech G1) | Tech G1/DSPC/ Cholesterol/PEG-DMG 50/10/38.5/1.5 Lipid:siRNA 10:1 |
| LNP13 | XTC | XTC/DSPC/ Chol/PEG-DMG 50/10/38.5/1.5 Lipid:siRNA: 33:1 |
| LNP14 | MC3 | MC3/DSPC/ Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/ Chol/PEG-DMG 50/10/38.5/1.5 Lipid:siRNA: 7:1 |
| LNP17 | MC3 | MC3/DSPC/ Chol/PEG-DSG 50/10/38.5/1.5 Lipid:siRNA: 10:1 |
| LNP18 | MC3 | MC3/DSPC/ Chol/PEG-DMG 50/10/38.5/1.5 Lipid:siRNA: 12:1 |
| LNP19 | MC3 | MC3/DSPC/ Chol/PEG-DMG 50/10/35/5 Lipid:siRNA: 8:1 |
| LNP20 | MC3 | MC3/DSPC/ Chol/PEG-DPG 50/10/38.5/1.5 Lipid:siRNA: 10:1 |
| LNP21 | C12-200 | C12-200/DSPC/ Chol/PEG-DSG 50/10/38.5/1.5 Lipid:siRNA: 7:1 |
| LNP22 | XTC | XTC/DSPC/ Chol/PEG-DSG 50/10/38.5/1.5 Lipid:siRNA: 10:1 |

DSPC: distearoylpho sphatidylcholine
DPPC: dipalmitoylpho sphatidylcho line
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US 10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(═O)alkyl, —C(═O)alkenyl, and —C(═O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (═O) two hydrogen atoms are replaced. In this regard, substituents include oxo, halogen, heterocycle, —CN, —ORx, —NRxRy, —NRxC(═O)Ry, —NRxSO2Ry, —C(═O)Rx, —C(═O)ORx, —C(═O)NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(═O)Ry, —NRxSO2Ry, —C(═O)Rx, —C(═O)ORx, —C(═O)NRx Ry, —SOnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

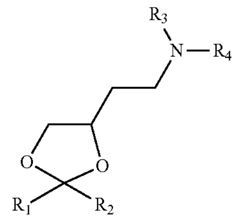

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

Scheme 1

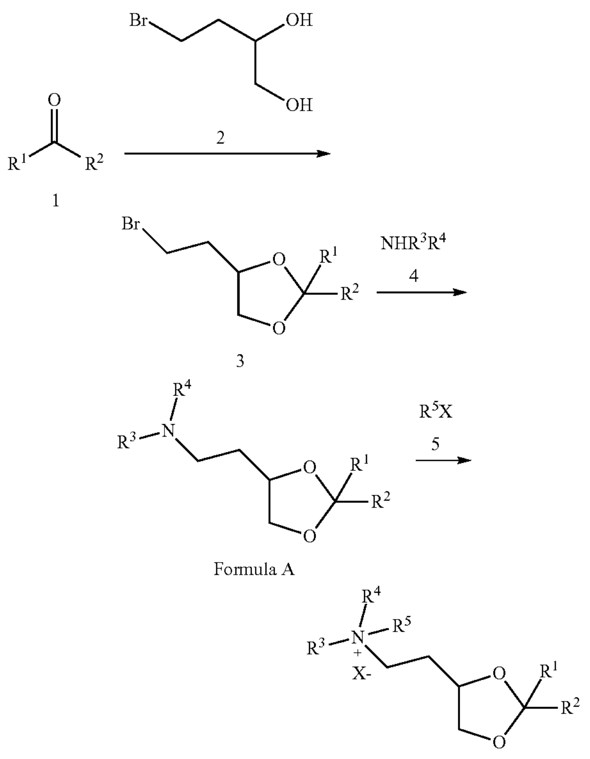

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

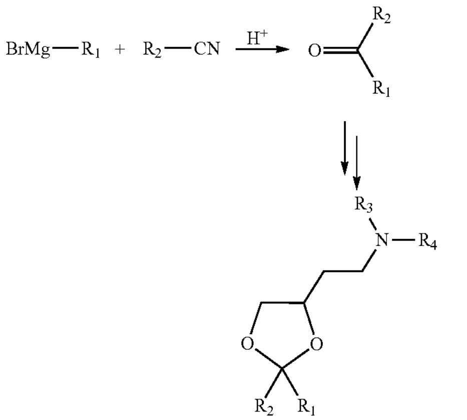

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino) butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g). Synthesis of ALNY-100

Synthesis of ketal 519 [ALNY-100] was performed using the following scheme 3:

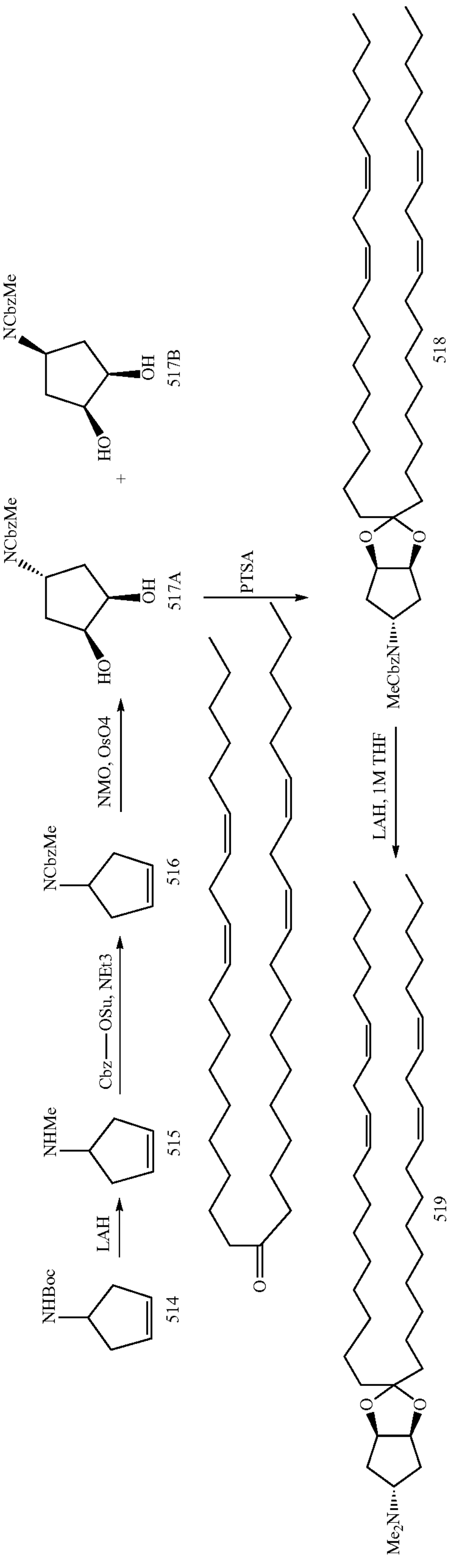
514 515 516 517A + 517B 518 519

Synthesis of 515

To a stirred suspension of LiAlH4 (3.74 g, 0.09852 mol) in 200 ml anhydrous THF in a two neck RBF (IL), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated $NaHCO_3$ solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated $NaHCO_3$ (1×50 mL) solution, water (1×30 mL) and finally with brine (1×50 mL). Organic phase was dried over an Na2SO4 and solvent was removed in vacuum. Silica gel column chromatographic purification of the crude material was afforded a mixture of diastereomers, which were separated by prep HPLC. Yield:—6 g crude 517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]-266.3, [M+NH4+]-283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 400° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H8ONO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include polyamino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyamino styrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s).

In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, LV., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, LV., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, LV., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, LV., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

iii. Microparticles an RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.,* 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ allkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J.* Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term “bile salts” includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.,* 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass[a] D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers Certain compositions of the present invention also incorporate carrier compounds in the formulation. As used herein, “carrier compound” or “carrier” can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a “pharmaceutical carrier” or “excipient” is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a hemolytic disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by CFB, C3, and/or C9 expression. In any event, the administering physician can adjust the amount and timing of iRNA administration on the basis of results observed using standard measures of efficacy known in the art or described herein.

VII. Methods for Inhibiting Complement Component Expression

The present invention provides methods of inhibiting expression of a complement component as described herein. In one aspect, the present invention provides methods of inhibiting expression of CFB in a cell. The methods include contacting a cell with an RNAi agent, e.g., a double stranded RNAi agent, in an amount effective to inhibit expression of the CFB in the cell, thereby inhibiting expression of the CFB in the cell.

The present invention also provides methods of inhibiting expression of C3 in a cell. The methods include contacting a cell with an RNAi agent, e.g., a double stranded RNAi agent, in an amount effective to inhibit expression of the C3 in the cell, thereby inhibiting expression of the C3 in the cell.

In addition, the present invention provides methods of inhibiting expression of C9 in a cell. The methods include contacting a cell with an RNAi agent, e.g., a double stranded RNAi agent, in an amount effective to inhibit expression of the C9 in the cell, thereby inhibiting expression of the C9 in the cell.

Contacting of a cell with a double stranded RNAi agent may be done in vitro or in vivo. Contacting a cell in vivo with the RNAi agent includes contacting a cell or group of cells within a subject, e.g., a human subject, with the RNAi agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a $GalNAc_3$ ligand, or any other ligand that directs the RNAi agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a CFB" is intended to refer to inhibition of expression of any CFB gene (such as, e.g., a mouse CFB gene, a rat CFB gene, a monkey CFB gene, or a human CFB gene) as well as variants or mutants of a CFB gene. Thus, the CFB gene may be a wild-type CFB gene, a mutant CFB gene, or a transgenic CFB gene in the context of a genetically manipulated cell, group of cells, or organism.

"Inhibiting expression of a CFB gene" includes any level of inhibition of a CFB gene, e.g., at least partial suppression of the expression of a CFB gene. The expression of the CFB gene may be assessed based on the level, or the change in the level, of any variable associated with CFB gene expression, e.g., CFB mRNA level, CFB protein level, or, for example, $CH_{50}$ activity as a measure of total hemolytic complement, $AH_{50}$ to measure the hemolytic activity of the alternate pathway of complement, and/or lactate dehydrogenase (LDH) levels as a measure of intravascular hemolysis, and/or hemoglobin levels. Levels of C3, C9, C5, C5a, C5b, and soluble C5b-9 complex may also be measured to assess CFB expression. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

The phrase "inhibiting expression of a C3" is intended to refer to inhibition of expression of any C3 gene (such as, e.g., a mouse C3 gene, a rat C3 gene, a monkey C3 gene, or a human C3 gene) as well as variants or mutants of a C3 gene. Thus, the C3 gene may be a wild-type C3 gene, a mutant C3 gene, or a transgenic C3 gene in the context of a genetically manipulated cell, group of cells, or organism.

"Inhibiting expression of a C3 gene" includes any level of inhibition of a C3 gene, e.g., at least partial suppression of the expression of a C3 gene. The expression of the C3 gene may be assessed based on the level, or the change in the level, of any variable associated with C3 gene expression, e.g., C3 mRNA level, C3 protein level, or, for example, $CH_{50}$ activity as a measure of total hemolytic complement, $AH_{50}$ to measure the hemolytic activity of the alternate pathway of complement, and/or lactate dehydrogenase (LDH) levels as a measure of intravascular hemolysis, and/or hemoglobin levels. Levels of CFB, C9, C5, C5a, C5b, and soluble C5b-9 complex may also be measured to assess C3 expression. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

The phrase "inhibiting expression of a C9" is intended to refer to inhibition of expression of any C9 gene (such as, e.g., a mouse C9 gene, a rat C9 gene, a monkey C9 gene, or a human C9 gene) as well as variants or mutants of a C9 gene. Thus, the C9 gene may be a wild-type C9 gene, a mutant C9 gene, or a transgenic C9 gene in the context of a genetically manipulated cell, group of cells, or organism.

"Inhibiting expression of a C9 gene" includes any level of inhibition of a C9 gene, e.g., at least partial suppression of the expression of a C9 gene. The expression of the C9 gene may be assessed based on the level, or the change in the level, of any variable associated with C9 gene expression, e.g., C9 mRNA level, C9 protein level, or, for example, $CH_{50}$ activity as a measure of total hemolytic complement, $AH_{50}$ to measure the hemolytic activity of the alternate pathway of complement, and/or lactate dehydrogenase (LDH) levels as a measure of intravascular hemolysis, and/or hemoglobin levels. Levels of CFB, C3, C5, C5a, C5b, and soluble C5b-9 complex may also be measured to assess C9 expression. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a target gene, e.g., CFB, C3, or C9 gene, is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

Inhibition of the expression of the target gene, e.g., a CFB, C3, or C9, gene may be manifested by a reduction of the amount of mRNA expressed by a first cell or group of cells (such cells may be present, for example, in a sample derived from a subject) in which a target gene is transcribed and which has or have been treated (e.g., by contacting the cell or cells with an RNAi agent of the invention, or by administering an RNAi agent of the invention to a subject in which the cells are or were present) such that the expression of a target gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Inhibition of the expression of a complement component protein may be manifested by a reduction in the level of the protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a target gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of CFB, C3, or C9 mRNA that is expressed by a cell or group of cells may be determined using any method known in the art for assessing mRNA expression. In one embodiment, the level of expression of CFB, C3, and/or C9 in a sample is determined by detecting a transcribed polynucleotide, or portion thereof, e.g., mRNA of the CFB, C3, and/or C9 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of expression of CFB, C3, and/or C9 is determined using a nucleic acid probe. The term "probe", as used herein, refers to any molecule that is capable of selectively binding to a specific CFB, C3, or C9. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize, e.g., specifically hybridize, to CFB, C3, or C9 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of CFB, C3, and/or C9 mRNA.

An alternative method for determining the level of expression of CFB, C3, and/or C9 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of CFB, C3, and/or C9 is determined by quantitative fluorogenic RT-PCR (i.e., the TaqMan™ System).

The expression levels of CFB, C3, and/or C9 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of PCSK9 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of CFB, C3, and/or C9 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the RNAi agent is administered to a subject such that the RNAi agent is delivered to a specific site within the subject. The inhibition of expression of CFB, C3, and/or C9 may be assessed using measurements of the level or change in the level of CFB, C3, and/or C9 mRNA and/or CFB, C3, and/or C9 protein in a sample derived from fluid or tissue from the specific site within the subject. In preferred embodiments, the site is sthe liver. The site may also be a subsection or subgroup of cells from any one of the aforementioned sites. The site may also include cells that express a particular type of receptor.

VIII. Methods for Treating or Preventing a Complement Component-Associated Disease The present invention provides therapeutic and prophylactic methods which include administering to a subject having a complement component-associated disease, as described herein, e.g., PNH or aHUS, an iRNA agent, pharmaceutical compositions comprising an iRNA agent, or vector comprising an iRNA of the invention.

It is to be understood, that any of the methods of the invention may be practiced with a single iRNA agent of the invention or a combination of iRNA agents of the invention. For example, in some aspects, the methods (and uses) of the invention include using an iRNA agent targeting a CFB gene and an iRNA agent targeting a C3 gene. In some aspects, the methods (and uses) of the invention include using an iRNA agent targeting a CFB gene and an iRNA agent targeting a C9 gene. In some aspects, the methods (and uses) of the invention include using an iRNA agent targeting a C3 gene and an iRNA agent targeting a C9 gene. In other aspects, the methods (and uses) of the invention include using an iRNA agent targeting a CFB gene, an iRNA agent targeting a C3 gene, and an iRNA agent targeting a C9 gene. In some aspects of the invention, the methods which include either a single iRNA agent of the invention or a combination of iRNA agents, further include administering to the subject one or more additional therapeutic agents such as, for example, Soliris® (as further described below).

In one aspect, the present invention provides methods of treating a subject having a disorder that would benefit from reduction in CFB expression, e.g., "a complement component-associated disease," e.g., PNH, aHUS, or rheumatoid arthritis. The treatment methods (and uses) of the invention include administering to the subject, e.g., a human, a therapeutically effective amount of an iRNA agent targeting a CFB gene or a pharmaceutical composition comprising an iRNA agent targeting a CFB gene, thereby treating the subject having a disorder that would benefit from reduction in CFB expression.

In another aspect, the present invention provides methods of treating a subject having a disorder that would benefit from reduction in C3 expression, e.g., "a complement component-associated disease," e.g., PNH, aHUS, or rheumatoid arthritis. The treatment methods (and uses) of the invention include administering to the subject, e.g., a human, a therapeutically effective amount of an iRNA agent targeting a C3 gene or a pharmaceutical composition comprising an iRNA agent targeting a C3 gene, thereby treating the subject having a disorder that would benefit from reduction in C3 expression.

In a further aspect, the present invention provides methods of treating a subject having a disorder that would benefit from reduction in C9 expression, e.g., "a complement component-associated disease," e.g., PNH, aHUS, or rheumatoid arthritis. The treatment methods (and uses) of the invention include administering to the subject, e.g., a human, a therapeutically effective amount of an iRNA agent targeting a C9 gene or a pharmaceutical composition comprising an iRNA agent targeting a C9 gene, thereby treating the subject having a disorder that would benefit from reduction in C9 expression.

In one aspect, the invention provides methods of preventing at least one symptom in a subject having a disorder that would benefit from reduction in CFB expression, e.g., a complement component-associated disease, e.g., PNH, aHUS, or rheumatoid arthritis. The methods include administering to the subject a therapeutically effective amount of the iRNA agent, e.g., dsRNA, or vector of the invention, thereby preventing at least one symptom in the subject having a disorder that would benefit from reduction in CFB expression. For example, the invention provides methods for preventing hemolysis in a subject suffering from a disorder that would benefit from reduction in CFB expression, e.g., a complement component-associated disease, e.g., PNH, aHUS, or rheumatoid arthritis.

In one aspect, the invention provides methods of preventing at least one symptom in a subject having a disorder that would benefit from reduction in C3 expression, e.g., a complement component-associated disease, e.g., PNH, aHUS, or rheumatoid arthritis. The methods include administering to the subject a therapeutically effective amount of the iRNA agent, e.g., dsRNA, or vector of the invention, thereby preventing at least one symptom in the subject having a disorder that would benefit from reduction in C3 expression. For example, the invention provides methods for preventing hemolysis in a subject suffering from a disorder that would benefit from reduction in C3 expression, e.g., a complement component-associated disease, e.g., PNH, aHUS, or rheumatoid arthritis.

In one aspect, the invention provides methods of preventing at least one symptom in a subject having a disorder that would benefit from reduction in C9 expression, e.g., a complement component-associated disease, e.g., PNH, aHUS, or rheumatoid arthritis. The methods include administering to the subject a therapeutically effective amount of the iRNA agent, e.g., dsRNA, or vector of the invention, thereby preventing at least one symptom in the subject having a disorder that would benefit from reduction in C9 expression. For example, the invention provides methods for preventing hemolysis in a subject suffering from a disorder that would benefit from reduction in C9 expression, e.g., a complement component-associated disease, e.g., PNH, aHUS, or rheumatoid arthritis.

In another aspect, the present invention provides uses of a therapeutically effective amount of an iRNA agent of the invention for treating a subject, e.g., a subject that would benefit from a reduction and/or inhibition of CFB expression.

In a further aspect, the present invention provides uses of a therapeutically effective amount of an iRNA agent of the invention for treating a subject, e.g., a subject that would benefit from a reduction and/or inhibition of C3 expression.

In yet another aspect, the present invention provides uses of a therapeutically effective amount of an iRNA agent of the invention for treating a subject, e.g., a subject that would benefit from a reduction and/or inhibition of C9 expression.

In yet another aspect, the present invention provides use of an iRNA agent, e.g., a dsRNA, of the invention targeting a CFB gene or a pharmaceutical composition comprising an iRNA agent targeting a CFB gene in the manufacture of a medicament for treating a subject, e.g., a subject that would benefit from a reduction and/or inhibition of CFB expression, such as a subject having a disorder that would benefit from reduction in CFB expression, e.g., a complement component-associated disease, e.g., PNH, aHUS, or rheumatoid arthritis.

In a further aspect, the present invention provides use of an iRNA agent, e.g., a dsRNA, of the invention targeting a C3 gene or a pharmaceutical composition comprising an iRNA agent targeting a C3 gene in the manufacture of a medicament for treating a subject, e.g., a subject that would benefit from a reduction and/or inhibition of C3 expression, such as a subject having a disorder that would benefit from reduction in C3 expression, e.g., a complement component-associated disease, e.g., PNH, aHUS, or rheumatoid arthritis.

In yet a further aspect, the present invention provides use of an iRNA agent, e.g., a dsRNA, of the invention targeting a C9 gene or a pharmaceutical composition comprising an iRNA agent targeting a C9 gene in the manufacture of a medicament for treating a subject, e.g., a subject that would benefit from a reduction and/or inhibition of C9 expression, such as a subject having a disorder that would benefit from reduction in C9 expression, e.g., a complement component-associated disease, e.g., PNH, aHUS, or rheumatoid arthritis.

In another aspect, the invention provides uses of an iRNA, e.g., a dsRNA, of the invention for preventing at least one symptom in a subject suffering from a disorder that would benefit from a reduction and/or inhibition of CFB expression, such as a complement component-associated disease, e.g., PNH, aHUS, or rheumatoid arthritis.

In another aspect, the invention provides uses of an iRNA, e.g., a dsRNA, of the invention for preventing at least one symptom in a subject suffering from a disorder that would benefit from a reduction and/or inhibition of C3 expression, such as a complement component-associated disease, e.g., PNH, aHUS, or rheumatoid arthritis.

In another aspect, the invention provides uses of an iRNA, e.g., a dsRNA, of the invention for preventing at least one symptom in a subject suffering from a disorder that would benefit from a reduction and/or inhibition of C9 expression, such as a complement component-associated disease, e.g., PNH, aHUS, or rheumatoid arthritis.

In a further aspect, the present invention provides uses of an iRNA agent of the invention in the manufacture of a medicament for preventing at least one symptom in a subject suffering from a disorder that would benefit from a reduction and/or inhibition of CFB expression, such as a a complement component-associated disease, e.g., PNH, aHUS, or rheumatoid arthritis.

In a further aspect, the present invention provides uses of an iRNA agent of the invention in the manufacture of a medicament for preventing at least one symptom in a subject suffering from a disorder that would benefit from a reduction and/or inhibition of C3 expression, such as a a complement component-associated disease, e.g., PNH, aHUS, or rheumatoid arthritis.

In a further aspect, the present invention provides uses of an iRNA agent of the invention in the manufacture of a medicament for preventing at least one symptom in a subject suffering from a disorder that would benefit from a reduction and/or inhibition of C9 expression, such as a a complement component-associated disease, e.g., PNH, aHUS, or rheumatoid arthritis.

In some aspects of the invention, the methods which include either a single iRNA agent of the invention or a combination of iRNA agents, further include administering to the subject one or more additional therapeutic agents.

In some aspects, the additional therapeutic agent is an iRNA agent targeting a C5 gene, such as described in U.S. Provisional Patent Application No. 61/782,531, filed on Mar. 14, 2013, U.S. Provisional Patent Application No. 61/837,3991, filed on Jun. 20, 2013, and U.S. Provisional Patent Application No. 61/904,579, filed on Nov. 15, 2013, the entire contents of each of which are hereby incorporated herein by reference.

In other aspects, the additional therapeutic agent is an anti-complement component C5 antibody, or antigen-binding fragment thereof (e.g., eculizumab). Eculizumab is a humanized monoclonal IgG2/4, kappa light chain antibody that specifically binds complement component C5 with high affinity and inhibits cleavage of C5 to C5a and C5b, thereby inhibiting the generation of the terminal complement complex C5b-9. Eculizumab is described in U.S. Pat. No. 6,355,245, the entire contents of which are incorporated herein by reference.

In yet other aspects, the additional therapeutic is a C3 peptide inhibitor, or analog thereof. In one embodiment, the C3 peptide inhibitor is compstatin. Compstatin is a cyclic tridecapeptide with potent and selective C3 inhibitory activity. Compstatin, and its analogs, are described in U.S. Pat. Nos. 7,888,323, 7,989,589, and 8,442,776, in U.S. Patent Publication No. 2012/0178694 and 2013/0053302, and in PCT Publication Nos. WO 2012/174055, WO 2012/2178083, WO 2013/036778, the entire contents of each of which are incorporated herein by reference.

Accordingly, in one aspect, the present invention provides methods of treating a subject having a disorder that would benefit from reduction in CFB expression, e.g., a complement component-associated disease, e.g., PNH, aHUS, or rheumatoid arthritis, which include administering to the subject, e.g., a human, a therapeutically effective amount of an iRNA agent targeting a CFB gene or a pharmaceutical composition comprising an iRNA agent targeting a CFB gene, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), thereby treating the subject having a disorder that would benefit from reduction in CFB expression.

In another aspect, the present invention provides methods of treating a subject having a disorder that would benefit from reduction in C3 expression, e.g., a complement component-associated disease, e.g., PNH, aHUS, or rheumatoid arthritis, which include administering to the subject, e.g., a human, a therapeutically effective amount of an iRNA agent targeting a C3 gene or a pharmaceutical composition comprising an iRNA agent targeting a C3 gene, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), thereby treating the subject having a disorder that would benefit from reduction in C3 expression.

In another aspect, the present invention provides methods of treating a subject having a disorder that would benefit from reduction in C9 expression, e.g., a complement component-associated disease, e.g., PNH, aHUS, or rheumatoid arthritis, which include administering to the subject, e.g., a human, a therapeutically effective amount of an iRNA agent targeting a C9 gene or a pharmaceutical composition comprising an iRNA agent targeting a C9 gene, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), thereby treating the subject having a disorder that would benefit from reduction in C9 expression.

In another aspect, the invention provides methods of preventing at least one symptom in a subject having a disorder that would benefit from reduction in CFB expression, e.g., a complement component-associated disease, e.g., PNH, aHUS, or rheumatoid arthritis. The methods include administering to the subject a therapeutically effective amount of the iRNA agent, e.g., dsRNA, or vector of the invention, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), thereby preventing at least one symptom in the subject having a disorder that would benefit from reduction in CFB expression.

In another aspect, the invention provides methods of preventing at least one symptom in a subject having a disorder that would benefit from reduction in C3 expression, e.g., a complement component-associated disease, e.g., PNH, aHUS, or rheumatoid arthritis. The methods include administering to the subject a therapeutically effective amount of the iRNA agent, e.g., dsRNA, or vector of the invention, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), thereby preventing at least one symptom in the subject having a disorder that would benefit from reduction in C3 expression.

In another aspect, the invention provides methods of preventing at least one symptom in a subject having a disorder that would benefit from reduction in C9 expression, e.g., a complement component-associated disease, e.g., PNH, aHUS, or rheumatoid arthritis. The methods include administering to the subject a therapeutically effective amount of the iRNA agent, e.g., dsRNA, or vector of the invention, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), thereby preventing at least one symptom in the subject having a disorder that would benefit from reduction in C9 expression.

In another aspect, the present invention provides uses of a therapeutically effective amount of an iRNA agent of the invention and an additional therapeutic agent, such as an anti-complement component C5 antibody, or antigen-binding fragment thereof (e.g., eculizumab), an iRNA agent targeting complement component C5, and/or a C3 peptide inhibitor (e.g., comstatin), for treating a subject, e.g., a subject that would benefit from a reduction and/or inhibition of CFB expression.

In another aspect, the present invention provides uses of a therapeutically effective amount of an iRNA agent of the invention and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for treating a subject, e.g., a subject that would benefit from a reduction and/or inhibition of C3 expression.

In another aspect, the present invention provides uses of a therapeutically effective amount of an iRNA agent of the invention and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for treating a subject, e.g., a subject that would benefit from a reduction and/or inhibition of C9 expression.

In another aspect, the present invention provides uses of an iRNA agent, e.g., a dsRNA, of the invention targeting a CFB gene or a pharmaceutical composition comprising an iRNA agent targeting a CFB gene in the manufacture of a medicament for use in combination with an additional therapeutic agent, such as an anti-complement component CFB antibody, or antigen-binding fragment thereof (e.g., eculizumab), an iRNA agent targeting complement component C5, and/or a C3 peptide inhibitor (e.g., compstatin), for treating a subject, e.g., a subject that would benefit from a reduction and/or inhibition of CFB expression, e.g., a complement component-associated disease, e.g., PNH, aHUS, or rheumatoid arthritis.

In another aspect, the present invention provides uses of an iRNA agent, e.g., a dsRNA, of the invention targeting a C3 gene or a pharmaceutical composition comprising an iRNA agent targeting a C3 gene in the manufacture of a medicament for use in combination with an additional therapeutic agent, such as an anti-complement component C3 antibody, or antigen-binding fragment thereof (e.g., eculizumab), an iRNA agent targeting complement component C5, and/or a C3 peptide inhibitor (e.g., compstatin), for treating a subject, e.g., a subject that would benefit from a reduction and/or inhibition of C3 expression, e.g., a complement component-associated disease, e.g., PNH, aHUS, or rheumatoid arthritis.

In another aspect, the present invention provides uses of an iRNA agent, e.g., a dsRNA, of the invention targeting a C9 gene or a pharmaceutical composition comprising an iRNA agent targeting a C9 gene in the manufacture of a medicament for use in combination with an additional therapeutic agent, such as an anti-complement component C9 antibody, or antigen-binding fragment thereof (e.g., eculizumab), an iRNA agent targeting complement component C5, and/or a C3 peptide inhibitor (e.g., compstatin), for treating a subject, e.g., a subject that would benefit from a reduction and/or inhibition of C9 expression, e.g., a complement component-associated disease, e.g., PNH, aHUS, or rheumatoid arthritis.

In yet another aspect, the invention provides uses of an iRNA agent, e.g., a dsRNA, of the invention, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for preventing at least one symptom in a subject suffering from a disorder that would benefit from a reduction and/or inhibition of CFB expression, such as a complement component-associated disease, e.g., PNH, aHUS, or rheumatoid arthritis.

In yet another aspect, the invention provides uses of an iRNA agent, e.g., a dsRNA, of the invention, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for preventing at least one symptom in a subject suffering from a disorder that would benefit from a reduction and/or inhibition of C3 expression, such as a complement component-associated disease, e.g., PNH, aHUS, or rheumatoid arthritis.

In yet another aspect, the invention provides uses of an iRNA agent, e.g., a dsRNA, of the invention, and an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for preventing at least one symptom in a subject suffering from a disorder that would benefit from a reduction and/or inhibition of C9 expression, such as a complement component-associated disease, e.g., PNH, aHUS, or rheumatoid arthritis.

In a further aspect, the present invention provides uses of an iRNA agent of the invention in the manufacture of a medicament for use in combination with an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for preventing at least one symptom in a subject suffering from a disorder that would benefit from a reduction and/or inhibition of CFB expression, such as a a complement component-associated disease, e.g., PNH, aHUS, or rheumatoid arthritis.

In a further aspect, the present invention provides uses of an iRNA agent of the invention in the manufacture of a medicament for use in combination with an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for preventing at least one symptom in a subject suffering from a disorder that would benefit from a reduction and/or inhibition of C3 expression, such as a a complement component-associated disease, e.g., PNH, aHUS, or rheumatoid arthritis.

In a further aspect, the present invention provides uses of an iRNA agent of the invention in the manufacture of a medicament for use in combination with an additional therapeutic agent, such as an anti-complement component C5 antibody, or antigen-binding fragment thereof (e.g., eculizumab), an iRNA agent targeting complement component C5, and/or a C3 peptide inhibitor (e.g., compstatin), for preventing at least one symptom in a subject suffering from a disorder that would benefit from a reduction and/or inhibition of C9 expression, such as a a complement component-associated disease, e.g., PNH, aHUS, or rheumatoid arthritis.

In one embodiment, an iRNA agent targeting CFB, C3, or C9 is administered to a subject having a complement component-associated disease as described herein such that CFB, C3, and/or C9 levels, e.g., in a cell, tissue, blood, urine or other tissue or fluid of the subject are reduced by at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 712%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more and, subsequently, an additional therapeutic is administered to the subject.

The additional therapeutic may be an anti-complement component C5 antibody, or antigen-binding fragment or derivative thereof. In one embodiment, the anti-complement component C5 antibody is eculizumab (SOLIRIS®), or antigen-binding fragment or derivative thereof.

The methods of the invention comprising administration of an iRNA agent of the invention and eculizumab to a subject may further comprise administration of a meningococcal vaccine to the subject.

The additional therapeutic, e.g., eculizumab and/or a meningococcal vaccine, may be administered to the subject at the same time as the iRNA agent targeting CFB, C3, and/or C9 (and/or C5) or at a different time.

Moreover, the additional therapeutic, e.g., eculizumab, may be administered to the subject in the same formulation as the iRNA agent targeting CFB, C3, and/or C9 (and/or C5) or in a different formulation as the iRNA agent targeting CFB, C3, and/or C9 (and/or C5).

Eculizumab dosage regimens are described in, for example, the product insert for eculizumab (SOLIRIS®) and in U.S. Patent Application No. 2012/0225056, the entire contents of each of which are incorporated herein by reference. In exemplary methods of the invention for treating a complement component-associated disease, e.g., PNH, aHUS, or rheumatoid arthritis, an iRNA agent targeting, e.g., CFB, C3, or C9, is administered (e.g., subcutaneously) to the subject first, such that the C5 levels in the subject are reduced (e.g., by at least about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%,84%, 85%, 86%, 87%, 88%, 89%, 90%, 91%, 92%, 93%, 94%, 95%, 96%, 97%, 98%, or at least about 99% or more) and subsequently eculizumab is administered at doses lower than the ones described in the product insert for SOLIRIS®. For example, eculizumab may be adminsitered to the subject weekly at a dose less than about 600 mg for 4 weeks followed by a fifth dose at about one week later of less than about 900 mg, followed by a dose less than about 900 mg about every two weeks thereafter. Eculizumab may also be administered to the subject weekly at a dose less than about 900 mg for 4 weeks followed by a fifth dose at about one week later of less than about 1200 mg, followed by a dose less than about 1200 mg about every two weeks thereafter. If the subject is less than 18 years of age, eculizumab may be administered to the subject weekly at a dose less than about 900 mg for 4 weeks followed by a fifth dose at about one week later of less than about 1200 mg, followed by a dose less than about 1200 mg about every two weeks thereafter; or if the subject is less than 18 years of age, eculizumab may be administered to the subject weekly at a dose less than about 600 mg for 2 weeks followed by a third dose at about one week later of less than about 900 mg, followed by a dose less than about 900 mg about every two weeks thereafter; or if the subject is less than 18 years of age, eculizumab may be administered to the subject weekly at a dose less than about 600 mg for 2 weeks followed by a third dose at about one week later of less than about 600 mg, followed by a dose less than about 600 mg about every two weeks thereafter; or if the subject is less than 18 years of age, eculizumab may be administered to the subject weekly at a dose less than about 600 mg for 1 week followed by a second dose at about one week later of less than about 300 mg, followed by a dose less than about 300 mg about every two weeks thereafter; or if the subject is less than 18 years of age, eculizumab may be administered to the subject weekly at a dose less than about 300 mg for 1 week followed by a second dose at about one week later of less than about 300 mg, followed by a dose less than about 300 mg about every two weeks thereafter. If the subject is receiving plamapheresis or plasma exchange, eculizumab may be administered to the subject at a dose less than about 300 mg (e.g., if the most recent does of eculizumab was about 300 mg) or less than about 600 mg (e.g., if the most recent does of eculizumab was about 600 mg or more). If the subject is receiving plasma infusion, eculizumab may be administered to the subject at a dose less than about 300 mg (e.g., if the most recent does of eculizumab was about 300 mg or more). The lower doses of eculizumab allow for either subcutaneous or intravenous administration of eculizumab.

In the combination therapies of the present invention comprising eculizumab, eculizumab may be adminisitered to the subject, e.g., subcutaneously, at a dose of about 0.01 mg/kg to about 10 mg/kg, or about 5 mg/kg to about 10 mg/kg, or about 0.5 mg/kg to about 15 mg/kg. For example, eculizumab may be administered to the subject, e.g., subcutaneously, at a dose of 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, or15 mg/kg.

The methods and uses of the invention include administering a composition described herein such that expression of the target CFB, C3, and/or C9 (and/or C5) gene is decreased, such as for about 1, 2, 3, 4, 5, 6, 7, 8, 12, 16, 18, 24, 28, 32, 36, 40, 44, 48, 52, 56, 60, 64, 68, 72, 76, or about 80 hours. In one embodiment, expression of the target gene is decreased for an extended duration, e.g., at least about two, three, four, five, six, seven days or more, e.g., about one week, two weeks, three weeks, or about four weeks or longer.

Administration of the dsRNA according to the methods and uses of the invention may result in a reduction of the severity, signs, symptoms, and/or markers of such diseases or disorders in a patient with a complement component-associated disease. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a hemolytic disorder may be assessed, for example, by periodic monitoring of LDH and $CH_{50}$ levels.

Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting CFB, C3, and/or C9, or pharmaceutical composition thereof, "effective against" a complement component-associated disease indicates that administration in a clinically appropriate manner results in a beneficial effect for at least a statistically significant fraction of patients, such as improvement of symptoms, a cure, a reduction in disease, extension of life, improvement in quality of life, or other effect generally recognized as positive by medical doctors familiar with treating a complement component-associated disease and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale, as but one example the Rheumatoid Arthritis Severity Scale (RASS). Any positive change resulting in e.g., lessening of severity of disease measured using the appropriate scale, represents adequate treatment using an iRNA or iRNA formulation as described herein.

Subjects can be administered a therapeutic amount of iRNA, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg dsRNA, 2.6 mg/kg dsRNA, 2.7 mg/kg dsRNA, 2.8 mg/kg dsRNA, 2.9 mg/kg dsRNA, 3.0 mg/kg dsRNA, 3.1 mg/kg dsRNA, 3.2 mg/kg dsRNA, 3.3 mg/kg dsRNA, 3.4 mg/kg dsRNA, 3.5 mg/kg dsRNA, 3.6 mg/kg dsRNA, 3.7 mg/kg dsRNA, 3.8 mg/kg dsRNA, 3.9 mg/kg dsRNA, 4.0 mg/kg dsRNA, 4.1 mg/kg dsRNA, 4.2 mg/kg dsRNA, 4.3 mg/kg dsRNA, 4.4 mg/kg dsRNA, 4.5 mg/kg dsRNA, 4.6 mg/kg dsRNA, 4.7 mg/kg dsRNA, 4.8 mg/kg dsRNA, 4.9 mg/kg dsRNA, 5.0 mg/kg dsRNA, 5.1 mg/kg dsRNA, 5.2 mg/kg dsRNA, 5.3 mg/kg dsRNA, 5.4 mg/kg dsRNA, 5.5 mg/kg dsRNA, 5.6 mg/kg dsRNA, 5.7 mg/kg dsRNA, 5.8 mg/kg dsRNA, 5.9 mg/kg dsRNA, 6.0 mg/kg dsRNA, 6.1 mg/kg dsRNA, 6.2 mg/kg dsRNA, 6.3 mg/kg dsRNA, 6.4 mg/kg dsRNA, 6.5 mg/kg dsRNA, 6.6 mg/kg dsRNA, 6.7 mg/kg dsRNA, 6.8 mg/kg dsRNA, 6.9 mg/kg dsRNA, 7.0 mg/kg dsRNA, 7.1 mg/kg dsRNA, 7.2 mg/kg dsRNA, 7.3 mg/kg dsRNA, 7.4 mg/kg dsRNA, 7.5 mg/kg dsRNA, 7.6 mg/kg dsRNA, 7.7 mg/kg dsRNA, 7.8 mg/kg dsRNA, 7.9 mg/kg dsRNA, 8.0 mg/kg dsRNA, 8.1 mg/kg dsRNA, 8.2 mg/kg dsRNA, 8.3 mg/kg dsRNA, 8.4 mg/kg dsRNA, 8.5 mg/kg dsRNA, 8.6 mg/kg dsRNA, 8.7 mg/kg dsRNA, 8.8 mg/kg dsRNA, 8.9 mg/kg dsRNA, 9.0 mg/kg dsRNA, 9.1 mg/kg dsRNA, 9.2 mg/kg dsRNA, 9.3 mg/kg dsRNA, 9.4 mg/kg dsRNA, 9.5 mg/kg dsRNA, 9.6 mg/kg dsRNA, 9.7 mg/kg dsRNA, 9.8 mg/kg dsRNA, 9.9 mg/kg dsRNA, 9.0 mg/kg dsRNA, 10 mg/kg dsRNA, 15 mg/kg dsRNA, 20 mg/kg dsRNA, 25 mg/kg dsRNA, 30 mg/kg dsRNA, 35 mg/kg dsRNA, 40 mg/kg dsRNA, 45 mg/kg dsRNA, or about 50 mg/kg dsRNA. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a dsRNA as described herein and an N-acetylgalactosamine, subjects can be administered a therapeutic amount of iRNA, such as a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a dsRNA as described herein and an N-acetylgalactosamine, subjects can be administered a therapeutic amount of about 10 to about 30 mg/kg of dsRNA. Values and ranges intermediate to the recited values are also intended to be part of this invention.

For example, subjects can be administered a therapeutic amount of iRNA, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In certain embodiments of the invention, for example, when a double-stranded RNAi agent includes a modification (e.g., one or more motifs of three identical modifications on three consecutive nucleotides), including one such motif at or near the cleavage site of the agent, six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

The iRNA can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

Administration of the iRNA can reduce CFB, C3, and/or C9 (and/or C5) levels, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more.

Before administration of a full dose of the iRNA, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on CFB, C3, and/or C9 expression, a composition according to the invention or a pharmaceutical composition prepared therefrom can enhance the quality of life.

An iRNA of the invention may be administered in “naked” form, or as a “free iRNA.” A naked iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of CFB, C3, and/or C9 gene expression are those having a complement component-associated disease or disorder as described herein. In one embodiment, a subject having a complement component-associated disease has paroxysmal nocturnal hemoglobinuria (PNH). In another embodiment, a subject having a complement component-associated disease has asthma. In another embodiment, a subject having a complement component-associated disease has rheumatoid arthritis. In yet another embodiment, a subject having a complement component-associated disease has systemic lupus erythmatosis. In one embodiment, a subject having a complement component-associated disease has glomerulonephritis. In another embodiment, a subject having a complement component-associated disease has psoriasis. In yet another embodiment, a subject having a complement component-associated disease has dermatomyositis bullous pemphigoid. In one embodiment, a subject having a complement component-associated disease has atypical hemolytic uremic syndrome. In another embodiment, a subject having a complement component-associated disease has Shiga toxin *E. coli*-related hemolytic uremic syndrome. In another embodiment, a subject having a complement component-associated disease has myasthenia gravis. In yet another embodiment, a subject having a complement component-associated disease has neuromyelistis optica. In one embodiment, a subject having a complement component-associated disease has dense deposit disease. In one embodiment, a subject having a complement component-associated disease has C3 neuropathy. In another embodiment, a subject having a complement component-associated disease has age-related macular degeneration. In another embodiment, a subject having a complement component-associated disease has cold agglutinin disease. In one embodiment, a subject having a complement component-associated disease has anti-neutrophil cytoplasmic antibody-associated vasculitis. In another embodiment, a subject having a complement component-associated disease has humoral and vascular transplant rejection. In one embodiment, a subject having a complement component-associated disease has graft dysfunction. In one embodiment, a subject having a complement component-associated disease has had a myocardial infarction. In another embodiment, a subject having a complement component-associated disease is a sensitized recipient of a transplant. In yet another embodiment, a subject having a complement component-associated disease has sepsis.

Treatment of a subject that would benefit from a reduction and/or inhibition of CFB, C3, and/or C9 gene expression includes therapeutic and prophylactic (e.g., the subject is to undergo sensitized (or allogenic) transplant surgery treatment.

The invention further provides methods and uses of an iRNA agent or a pharmaceutical composition thereof (including methods and uses of an iRNA agent or a pharmaceutical composition comprising an iRNA agent and an additional therapeutic agent, e.g. an anti-complement component C5 antibody, or antigen-binding fragment thereof) for treating a subject that would benefit from reduction and/or inhibition of a target gene of the invention, e.g., CFB, C3, and C9, expression, e.g., a subject having a complement component-associated disease, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting CFB is administered in combination with, e.g., an agent useful in treating a complement component-associated disease as described elsewhere herein.

For example, additional therapeutics and therapeutic methods suitable for treating a subject that would benefit from reducton in CFB, C3, and/or C9 expression, e.g., a subject having a complement component-associated disease, include plasmaphoresis, thrombolytic therapy (e.g., streptokinase), antiplatelet agents, folic acid, corticosteroids; immunosuppressive agents; estrogens, methotrexate, 6-MP, azathioprine sulphasalazine, mesalazine, olsalazine, chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines, such as TNF-α or IL-1 (e.g., IRAK, NIK, IKK, p38 or MAP kinase inhibitors), IL-1β converting enzyme inhibitors, TNFαconverting enzyme (TACE) inhibitors, T-cell signalling inhibitors, such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, and sIL-6R), antiinflammatory cytokines (e.g., IL-4, IL-10, IL-11, IL-13 and TGF3), celecoxib, folic acid, hydroxychloroquine sulfate, rofecoxib, etanercept, infliximonoclonal antibody, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hydrochloride, hydrocodone bitartrate/apap, diclofenac sodium/misoprostol, fentanyl, anakinra, human recombinant, tramadol hydrochloride, salsalate, sulindac, cyanocobalamin/folic acid/pyridoxine, acetaminophen, alendronate sodium, prednisolone, morphine sulfate, lidocaine hydrochloride, indomethacin, glucosamine sulf/chondroitin, amitriptyline hydrochloride, sulfadiazine, oxycodone hydrochloride/acetaminophen, olopatadine hydrochloride, misoprostol, naproxen sodium, omeprazole, cyclophosphamide, rituximonoclonal antibody, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, Mesopram, cyclosporine, cytokine suppressive anti-inflammatory drug(s) (CSAIDs); CDP-571/BAY-10-3356 (humanized anti-TNF(antibody; Celltech/Bayer); cA2/infliximonoclonal antibody (chimeric anti-TNF(antibody; Centocor); 75 kdTNFR-IgG/etanercept (75 kD TNF receptor-IgG fusion protein; Immunex; see e.g., (1994) Arthr. Rheum. 37: S295; (1996) J. Invest. Med. 44: 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., (1995) Arthr. Rheum. 38: S185); DAB 486-IL-2 and/or DAB 389-IL-2 (IL-2 fusion proteins; Seragen; see e.g., (1993) Arthrit. Rheum. 36: 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., (1996) Arthr. Rheum. 39(9 (supplement)): S284; (1995) Amer. J. Physiol.—Heart and Circ. Physiol. 268: 37-42); R973401 (phosphodiesterase Type IV inhibitor; see e.g., (1996) Arthr. Rheum. 39(9 (supplement): S282); MK-966 (COX-2 Inhibitor; see e.g., (1996) Arthr. Rheum. 39(9 (supplement): S81); Iloprost (see e.g., (1996) Arthr. Rheum. 39(9 (supplement): S82); methotrexate; thalidomide (see e.g., (1996) Arthr. Rheum. 39(9 (supplement): S282) and thalidomide-related drugs (e.g., Celgen); leflunomide (anti-inflammatory and cytokine inhibitor; see e.g., (1996) Arthr. Rheum. 39(9 (supplement): S131; (1996) Inflamm. Res. 45: 103-107); tranexamic acid (inhibitor of plasminogen activation; see e.g., (1996) Arthr. Rheum. 39(9 (supplement): S284); T-614 (cytokine inhibitor; see e.g., (1996) Arthr. Rheum. 39(9 (supplement): S282); prostaglandin E1 (see e.g., (1996) Arthr. Rheum. 39(9 (supplement): S282); Tenidap (non-steroidal anti-inflammatory drug; see e.g., (1996) Arthr. Rheum. 39(9 (supplement): S280); Naproxen (non-steroidal anti-inflammatory drug; see e.g., (1996) Neuro. Report 7: 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., (1996) Arthr. Rheum. 39(9 (supplement): S281); Azathioprine (see e.g., (1996) Arthr. Rheum. 39(9 (supplement): S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., (1996) Arthr. Rheum. 39(9 (supplement): S296); interleukin-13 (see e.g., (1996) Arthr. Rheum. 39(9 (supplement): S308); interleukin-17 inhibitors (see e.g., (1996) Arthr. Rheum. 39(9 (supplement): S 120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) Rheum. Dis. Clin. North Am. 21: 759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; bcl-2 inhibitors (see Bruncko, M. et al. (2007) J. Med. Chem. 50(4): 641-662); antivirals and immune-modulating agents, small molecule inhibitor of KDR, small molecule inhibitor of Tie-2; methotrexate; prednisone; celecoxib; folic acid;

hydroxychloroquine sulfate; rofecoxib; etanercept; infliximonoclonal antibody; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hydrochloride; sulfadiazine; oxycodone hcl/acetaminophen; olopatadine hcl; misoprostol; naproxen sodium; omeprazole; mycophenolate mofetil; cyclophosphamide; rituximonoclonal antibody; IL-1 TRAP; MRA; CTLA4-IG; IL-18 BP; IL-12/23; anti-IL 18; anti-IL 15; BIRB-796; SCIO-469; VX-702; AMG-548; VX-740; Roflumilast; IC-485; CDC-801; mesopram, albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate, aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

The iRNA agent (and/or an anti-complement component C5 antibody) and an additional therapeutic agent and/or treatment may be administered at the same time and/or in the same combination, e.g., parenterally, or the additional therapeutic agent can be administered as part of a separate composition or at separate times and/or by another method known in the art or described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

Transcripts siRNA design was carried out to identify siRNAs targeting human (*Homo sapiens*), cynomolgus monkey (Macacafascicularis; henceforth “cyno”), mouse (*Mus musculus*), and rat (*Rattus norvegicus*) transcripts. In general, the design of duplexes used human, mouse, and rat transcripts from the NCBI RefSeq collection, annotated in the NCBI Gene database (http://www.ncbi.nlm.nih.gov/gene/). For cyno, the design used either transcripts downloaded from the *M. fascicularis* genome project (http://macaque-.genomics.org.cn/page/species/download.jsp) and/or transcripts obtained from a liver-derived cDNA library.

Design of CFB siRNAs used the following transcripts from the NCBI RefSeq collection: Human—NM_001710; Cyno (from the *M. fascicularis* genome project)—ENSMMUP00000000985 (locus=scaffold3881:47830:53620); Mouse—NM_001142706 and NM_008198; and Rat—NM_212466.3.

Design of C3 siRNAs used the following transcripts from the NCBI RefSeq collection: Human—NM_000064; Cyno (from the *M. fascicularis* genome project)—ENSP00000245907 (locus=chr19:6921416:6963034); Mouse—NM_009778; and Rat—NM_016994

Design of C9 siRNAs used the following transcripts from the NCBI RefSeq collection: Human—NM_001737; Cyno (from liver cDNA library)—isotig05361; Mouse—NM_013485; AND Rat—NM_057146.

siRNA duplexes were designed in several separate batches, including but not limited to batches containing duplexes matching human transcripts only; human and cyno transcripts; human, cyno, and mouse transcripts; AND human, cyno, mouse, and rat transcripts. Most siRNA duplexes were designed that shared 100% identity with the listed human transcript and other species transcripts considered in each design batch (above). In some instances, however, when the antisense strand:target mRNA complementary basepair was a GC or CG pair, siRNA duplexes were designed with mismatches between duplex and mRNA target at the first antisense (last sense) position (see, e.g. Table 5, oligos with label G21U, G21A, C21A, G21A). In these cases, duplexes were designed with UA or AU basepairs at the first antisense:last sense pair. Thus the duplexes maintained complementarity but were mismatched with respect to target (U:C, U:G, A:C, or A:G).

siRNA Design, Specificity, and Efficacy Prediction

The predicted specificity of all possible 19mers was predicted from each sequence. Candidate 19mers were then selected that lacked repeats longer than 7 nucleotides.

The following sets of candidate siRNAs were used in comprehensive searches against the appropriate transcriptomes (defined as the set of NM_ and XM_records within the human, mouse, or rat NCBI Refseq sets, and the cyno transcriptome set in NCBI nucleotide) using an exhaustive "brute-force" algorithm implemented in the python script 'BruteForce.py'.

C3: 46 human/cyno/mouse/rat, 80 human/cyno/mouse, 2384 human/cyno.

C9: 7 human/cyno/mouse/rat, 12 human/cyno/mouse, 816 human/cyno.

CFB: 23 human/cyno/mouse, 1232 human/cyno.

The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5'-end of the molecule.

Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start were used to create 2 heptamers and one octamer. 'Heptamerl' was created by adding a 3'-A to the hexamer; heptamer2 was created by adding a 5'-A to the hexamer; the octomer was created by adding an A to both 5'- and 3'-ends of the hexamer. The frequency of octamers and heptamers in the human, rhesus, mouse, or rat 3'-UTRome (defined as the subsequence of the transcriptome from NCBI's Refseq database where the end of the coding region, the 'CDS', is clearly defined) was pre-calculated. The octamer frequency was normalized to the heptamer frequency using the median value from the range of octamer frequencies. A 'mirSeedScore' was then calculated by calculating the sum of ((3× normalized octamer count)+(2× heptamer2 count)+(1× heptamer1 count)).

Both siRNAs strands were assigned to a category of specificity according to the calculated scores: a score above 3 qualifies as highly specific, equal to 3 as specific and between 2.2 and 2.8 as moderately specific. The duplexes were sorted by the specificity of the antisense strand and those duplexes whose antisense oligos lacked GC at the first position, lacked G at both positions 13 and 14, and had 3 or more Us or As in the seed region were selected.

For GalNaC-conjugated duplexes, sense 21mer and antisense 23mer oligos were designed by extending antisense 19mers (described above) to 23 nucleotides of target-complementary sequence. All species transcripts included in the design batch were checked for complementarity. Only 23mers that preserved 100% sequence complementarity in at least 2 species were used. For each duplex, the sense 21mer was specified as the reverse complement of the first 21 nucleotides of the antisense strand.

siRNA Sequence Selection

The following 21/23mer duplex sets for GalNac conjugate design were synthesized and formed into duplexes.

C3: twenty sense and 20 antisense derived human/cyno/mouse/rat oligo pairs, including 6 where the first antisense position was swapped to UA (above); 10 sense and 10 antisense derived human/cyno/mouse oligo pairs, including 3 where the first antisense position was swapped to UA (above); 12 sense and 12 antisense derived human/cyno oligo pairs.

C9: one sense and 1 antisense derived human/cyno/mouse/rat oligo pair; 2 sense and 2 antisense derived human/cyno/mouse oligo pairs; 1 sense and 1 antisense derived human/cyno/rat oligo pairs; 19 sense and 19 antisense derived human/cyno oligo pairs.

CFB: nine sense and 9 antisense derived human/cyno/mouse oligo pairs, including 4 where the first antisense position was swapped to UA (above); 23 sense and 23 antisense derived human/cyno oligo pairs.

A detailed list of CFB sense and antisense strand sequences is shown in Tables 3-4.

A detailed list of C3 sense and antisense strand sequences is shown in Tables 5-6.

A detailed list of C9 sense and antisense strand sequences is shown in Tables 7-8.

siRNA Synthesis

General Small and Medium Scale RNA Synthesis Procedure

RNA oligonucleotides were synthesized at scales between 0.2-500 μmol using commercially available 5'-O-(4,4'-dimethoxytrityl)-2'-O-t-butyldimethylsilyl-3'-O-(2-cyanoethyl-N,N-diisopropyl)phosphoramidite monomers of uridine, 4-N-acetylcytidine, 6-N-benzoyladenosine and 2-N-isobutyrylguanosine and the corresponding 2'-O-methyl and 2'-fluoro phosphoramidites according to standard solid phase oligonucleotide synthesis protocols. The amidite solutions were prepared at 0.1-0.15 M concentration and 5-ethylthio-1H-tetrazole (0.25-0.6 M in acetonitrile) was used as the activator. Phosphorothioate backbone modifications were introduced during synthesis using 0.2 M phenylacetyl disulfide (PADS) in lutidine:acetonitrile (1:1) (v;v) or 0.1 M 3-(dimethylaminomethylene) amino-3H-1,2,4-dithiazole-5-thione (DDTT) in pyridine for the oxidation step. After completion of synthesis, the sequences were cleaved from the solid support and deprotected using methylamine followed by triethylamine.3HF to remove any 2'-O-t-butyldimethylsilyl protecting groups present.

For synthesis scales between 5-500 μmol and fully 2' modified sequences (2'-fluoro and/or 2'-O-methyl or combinations thereof) the oligonucleotides where deprotected using 3:1 (v/v) ethanol and concentrated (28-32%) aqueous ammonia either at 35° C. 16 h or 55° C. for 5.5 h. Prior to ammonia deprotection the oligonucleotides where treated with 0.5 M piperidine in acetonitrile for 20 min on the solid support. The crude oligonucleotides were analyzed by LC-MS and anion-exchange HPLC (IEX-HPLC). Purification of the oligonucleotides was carried out by IEX HPLC using: 20 mM phosphate, 10%-15% ACN, pH=8.5 (buffer A) and 20 mM phosphate, 10%-15% ACN, 1 M NaBr, pH=8.5 (buffer B). Fractions were analyzed for purity by analytical HPLC. The product-containing fractions with suitable purity were pooled and concentrated on a rotary evaporator prior to desalting. The samples were desalted by size exclusion chromatography and lyophilized to dryness. Equal molar amounts of sense and antisense strands were annealed in 1×PBS buffer to prepare the corresponding siRNA duplexes.

For small scales (0.2-1 μmol), synthesis was performed on a MerMade 192 synthesizer in a 96 well format. In case of fully 2'-modified sequences (2'-fluoro and/or 2'-O-methyl or combinations thereof) the oligonucleotides where deprotected using methylamine at room temperature for 30-60 min followed by incubation at 60° C. for 30 min or using 3:1

(v/v) ethanol and concentrated (28-32%) aqueous ammonia at room temperature for 30-60 min followed by incubation at 40° C. for 1.5 hours. The crude oligonucleotides were then precipitated in a solution of acetonitrile:acetone (9:1) and isolated by centrifugation and decanting the supernatant. The crude oligonucleotide pellet was re-suspended in 20 mM NaOAc buffer and analyzed by LC-MS and anion exchange HPLC. The crude oligonucleotide sequences were desalted in 96 deep well plates on a 5 mL HiTrap Sephadex G25 column (GE Healthcare). In each well about 1.5 mL samples corresponding to an individual sequence was collected. These purified desalted oligonucleotides were analyzed by LC-MS and anion exchange chromatography. Duplexes were prepared by annealing equimolar amounts of sense and antisense sequences on a Tecan robot. Concentration of duplexes was adjusted to 10 μM in 1×PBS buffer.

I. Synthesis of GalNAc-Conjugated Oligonucleotides for In Vivo Analysis

Oligonucleotides conjugated with GalNAc ligand at their 3'-terminus were synthesized at scales between 0.2-500 μmol using a solid support pre-loaded with a Y-shaped linker bearing a 4,4'-dimethoxytrityl (DMT)-protected primary hydroxy group for oligonucleotide synthesis and a GalNAc ligand attached through a tether.

For synthesis of GalNAc conjugates in the scales between 5-500 μmol, the above synthesis protocol for RNA was followed with the following adaptions: For polystyrene-based synthesis supports 5% dichloroacetic acid in toluene was used for DMT-cleavage during synthesis. Cleavage from the support and deprotection was performed as described above. Phosphorothioate-rich sequences (usually >5 phorphorothioates) were synthesized without removing the final 5'-DMT group ("DMT-on") and, after cleavage and deprotection as described above, purified by reverse phase HPLC using 50 mM ammonium acetate in water (buffer A) and 50 mM ammoniumacetate in 80% acetonitirile (buffer B). Fractions were analyzed for purity by analytical HPLC and/or LC-MS. The product-containing fractions with suitable purity were pooled and concentrated on a rotary evaporator. The DMT-group was removed using 20%-25% acetic acid in water until completion. The samples were desalted by size exclusion chromatography and lyophilized to dryness. Equal molar amounts of sense and antisense strands were annealed in 1×PBS buffer to prepare the corresponding siRNA duplexes.

For small scale synthesis of GalNAc conjugates (0.2-1 μmol), including sequences with multiple phosphorothioate linkages, the protocols described above for synthesis of RNA or fully 2'-F/2'-OMe-containing sequences on MerMade platform were applied. Synthesis was performed on pre-packed columns containing GalNAc-functionalized controlled pore glass support.

Example 2. In Vitro Screening

Cell Culture and Transfections

Hep3B cells (ATCC, Manassas, Va.) were grown to near confluence at 37° C. in an atmosphere of 5% CO2 in Eagle's Minimum Essential Medium (ATCC) supplemented with 10% FBS, streptomycin, and glutamine (ATCC) before being released from the plate by trypsinization. Cells were washed and re-suspended at $0.25\times10^6$ cells/ml. During transfections, cells were plated onto a 96-well plate with about 20,000 cells per well.

Primary mouse hepatocytes (PMH) were freshly isolated from a C57BL/6 female mouse (Charles River Labortories International, Inc. Willmington, Mass.) less than 1 hour prior to transfections and grown in primary hepatocyte media. Cells were resuspended at $0.11\times10^6$ cells/ml in InVitroGRO CP Rat (plating) medium (Celsis In Vitro Technologies, catalog number S01494). During transfections, cells were plated onto a BD BioCoat 96 well collagen plate (BD, 356407) at 10,000 cells per well and incubated at 37° C. in an atmosphere of 5% $CO_2$.

For Hep3B and PMH, transfection was carried out by adding 14.8 μl of Opti-MEM plus 0.2 μl of Lipofectamine RNAiMax per well (Invitrogen, Carlsbad Calif. catalog number13778-150) to 5 μl of each siRNA duplex to an individual well in a 96-well plate. The mixture was then incubated at room temperature for 20 minutes. Eighty μl of complete growth media without antibiotic containing the appropriate cell number were then added to the siRNA mixture. Cells were incubated for 24 hours prior to RNA purification.

Single dose experiments were performed at InM and 0.01 nM final duplex concentration for GalNAc modified sequences. Dose response experiments were done at 3, 1, 0.3, 0.1, 0.037, 0.0123, 0.00412, and 0.00137 nM final duplex concentration for primary mouse hepatocytes and at 3, 1, 0.3, 0.1, 0.037, 0.0123, 0.00412, 0.00137, 0.00046, 0.00015, 0.00005, and 0.000017 nM final duplex concentration for Hep3B cells.

Total RNA Isolation Using DYNABEADS mRNA Isolation Kit (Invitrogen, Part #: 610-12)

Cells were harvested and lysed in 150 μl of Lysis/Binding Buffer then mixed for 5 minutes at 850 rpm using an Eppendorf Thermomixer (the mixing speed was the same throughout the process). Ten microliters of magnetic beads and 80 μl Lysis/Binding Buffer mixture were added to a round bottom plate and mixed for 1 minute. Magnetic beads were captured using a magnetic stand and the supernatant was removed without disturbing the beads. After removing the supernatant, the lysed cells were added to the remaining beads and mixed for 5 minutes. After removing the supernatant, magnetic beads were washed 2 times with 150 μl Wash Buffer A and mixed for 1 minute. The beads were capturedagain and the supernatant was removed. The beads were then washed with 150 μl Wash Buffer B, captured and the supernatant was removed. The beads were next washed with 150 μl Elution Buffer, captured and the supernatant removed. Finally, the beads were allowed to dry for 2 minutes. After drying, 50 μl of Elution Buffer was added and mixed for 5 minutes at 70° C. The beads were captured on magnet for 5 minutes. Forty-five μl of supernatant was removed and added to another 96 well plate.

cDNA Synthesis Using ABI High Capacity cDNA Reverse Transcription Kit (Applied Biosystems, Foster City, Calif., Cat #4368813)

A master mix of 2 μl 10× Buffer, 0.8 μl 25×dNTPs, 2 μl Random primers, 1 μl Reverse Transcriptase, 1 μl RNase inhibitor and 3.2 μl of $H_2O$ per reaction as prepared. Equal volumes master mix and RNA were mixed for a final volume of 12 μl for in vitro screened or 2011 for in vivo screened samples. cDNA was generated using a Bio-Rad C-1000 or S-1000 thermal cycler (Hercules, Calif.) through the following steps: 25° C. for 10 minutes, 37° C. for 120 minutes, 85° C. for 5 seconds, and 4° C. hold.

Real Time PCR

Two μl of cDNA were added to a master mix containing 2 μl of $H_2O$, 0.5 μl GAPDH TaqMan Probe (Life Technologies catalog number 4326317E for Hep3B cells, catalog number 352339E for primary mouse hepatocytes or custom probe for cynomolgus primary hepatocytes), 0.5 μl of appropriate TaqMan probe (Life Technologies c catalog number Hs00156197_m1 for Hep3B cells or mm00439275_m1 for Primary Mouse Hepatoctyes or custom probe for cynomolgus primary hepatocytes) and 5 μl Lightcycler 480 probe master mix (Roche catalog number 04887301001) per well in a 384 well plates (Roche catalog number 04887301001). Real time PCR was performed in an Roche LC480 Real Time PCR system (Roche) using the ΔΔCt(RQ) assay. For in vitro screening, each duplex was tested with two biological replicates unless otherwise noted and each Real Time PCR was performed in duplicate technical replicates. For in vivo screening, each duplex was tested in one or more experiments (3 mice per group) and each Real Time PCR was run in duplicate technical replicates.

To calculate relative fold change in mRNA levels, real time data were analyzed using the ΔΔCt method and normalized to assays performed with cells transfected with 10 nM AD-1955, or mock transfected cells. $IC_{50}$s were calculated using a 4 parameter fit model using XLFit and normalized to cells transfected with AD-1955 over the same dose range, or to its own lowest dose.

The sense and antisense sequences of AD-1955 are:

```
SENSE:
                                  (SEQ ID NO: 39)
cuuAcGcuGAGuAcuucGAdTsdT

ANTISENSE:
                                  (SEQ ID NO: 40)
UCGAAGuACUcAGCGuAAGdTsdT.
```

Table 9 shows the results of a single dose screen in Hep3B cells transfected with the indicated CFB GalNAC conjugated iRNAs. Data are expressed as percent of message remaining relative to untreated cells.

Table 10 shows the results of a single dose screen in primary mouse hepatocytes ransfected with the indicated CFB GalNAC conjugated iRNAs. Data are expressed as percent of message remaining relative to untreated cells.

Table 11 shows the dose response in Hep3B cells transfected with the indicated CFB GalNAC conjugated iRNAs. The indicated $IC_{50}$ values represent the $IC_{50}$ values relative to untreated cells.

Table 12 shows the dose response in primary mouse hepatocytes transfected with the indicated CFB GalNAC conjugated iRNAs. The indicated $IC_{50}$ values represent the $IC_{50}$ values relative to untreated cells.

Table 13 shows the results of a single dose screen in primary mouse hepatocytes ransfected with the indicated C9 GalNAC conjugated iRNAs. Data are expressed as percent of message remaining relative to untreated cells.

Table 14 shows the results of a single dose screen in primary mouse hepatocytes ransfected with the indicated C3 GalNAC conjugated iRNAs. Data are expressed as percent of message remaining relative to untreated cells.

Table 15 shows the results of a single dose screen in Hep3B cells transfected with the indicated C3 GalNAC conjugated iRNAs. Data are expressed as percent of message remaining relative to untreated cells.

Table 16 shows the dose response in primary mouse hepatocytes transfected with the indicated C3 GalNAC conjugated iRNAs. The indicated $IC_{50}$ values represent the $IC_{50}$ values relative to untreated cells.

Table 17 shows the dose response in Hep3B cells transfected with the indicated C3 GalNAC conjugated iRNAs. The indicated $IC_{50}$ values represent the $IC_{50}$ values relative to untreated cells.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |

TABLE 3

Complement Factor B (CFB) unmodified sequences

Human CFB Sequences

| Duplex ID | Sense ID | Sense Sequence (SEQ ID NOS: 41-71, respectively, in order of appearance) | Position in NM_001710.5 | Antisense ID | Antisense Sequence (SEQ ID NOS: 72-102, respectively, in order of appearance) | Position in NM_001710.5 |
|---|---|---|---|---|---|---|
| AD-60315.1 | A-122021.1 | AUUCCUGAAUUUUAUGACUAU | 1987-2007 | A-122022.1 | AUAGUCAUAAAAUUCAGGAAUUC | 1985-2007 |
| AD-60326.1 | A-122009.1 | CCUGAUCAAGCUCAAGAAUAA | 2016-2036 | A-122010.1 | UUAUUCUUGAGCUUGAUCAGGGC | 2014-2036 |

TABLE 3-continued

| | | | | | | |
|---|---|---|---|---|---|---|
| Complement Factor B (CFB) unmodified sequences | | | | | | |
| AD-60303.1 | A-122017.1 | GAAGCAGGAAUUCCUGAAUUU | 1978-1998 | A-122018.1 | AAAUUCAGGAAUUCCUGCUUCUU | 1976-1998 |
| AD-60331.1 | A-121995.1 | AGCAACAUGUGUUCAAAGUCA | 1628-1648 | A-121996.1 | UGACUUUGAACACAUGUUGCUCA | 1626-1648 |
| AD-60344.1 | A-122015.1 | GCUGUGGUGUCUGAGUACUUU | 1822-1842 | A-122016.1 | AAAGUACUCAGACACCACAGCCC | 1820-1842 |
| AD-60345.1 | A-122031.1 | AAGUGUCUAGUCAACUUAAUU | 1153-1173 | A-122032.1 | AAUUAAGUUGACUAGACACUUUU | 1151-1173 |
| AD-60319.1 | A-121991.1 | AGCUGUGAGAGAGAUGCUCAA | 2245-2265 | A-121992.1 | UUGAGCAUCUCUCUCACAGCUGC | 2243-2265 |
| AD-60308.1 | A-122003.1 | AGCCAAAAAGUGUCUAGUCAA | 1146-1166 | A-122004.1 | UUGACUAGACACUUUUUGGCUCC | 1144-1166 |
| AD-60332.1 | A-122011.1 | UGUGAGUGAUGAGAUCUCUUU | 648-668 | A-122012.1 | AAAGAGAUCUCAUCACUCACAUU | 646-668 |
| AD-60313.1 | A-121989.1 | AAUUGAGAAGGUGGCAAGUUA | 1170-1190 | A-121990.1 | UAACUUGCCACCUUCUCAAUUAA | 1168-1190 |
| AD-60321.1 | A-122023.1 | CAACAUGUGUUCAAAGUCAAG | 1630-1650 | A-122024.1 | CUUGACUUUGAACACAUGUUGCU | 1628-1650 |
| AD-60327.1 | A-122025.1 | UGUGAGAGAGAUGCUCAAUAU | 2248-2268 | A-122026.1 | AUAUUGAGCAUCUCUCUCACAGC | 2246-2268 |
| AD-60302.1 | A-122001.1 | GUCUAGUCAACUUAAUUGAGA | 1157-1177 | A-122002.1 | UCUCAAUUAAGUUGACUAGACAC | 1155-1177 |
| AD-60325.1 | A-121993.1 | UCCAAGAAAGACAAUGAGCAA | 1612-1632 | A-121994.1 | UUGCUCAUUGUCUUUCUUGGAAG | 1610-1632 |
| AD-60337.1 | A-121997.1 | UGUGUUCAAAGUCAAGGAUAU | 1635-1655 | A-121998.1 | AUAUCCUUGACUUUGAACACAUG | 1633-1655 |
| AD-60333.1 | A-122027.1 | AUUGAUGAGAUCCGGGACUUG | 1486-1506 | A-122028.1 | CAAGUCCCGGAUCUCAUCAAUGA | 1484-1506 |
| AD-60314.1 | A-122005.1 | CUGUGAGAGAGAUGCUCAAUA | 2247-2267 | A-122006.1 | UAUUGAGCAUCUCUCUCACAGCU | 2245-2267 |
| AD-60320.1 | A-122007.1 | GAGCCAAAAAGUGUCUAGUCA | 1145-1165 | A-122008.1 | UGACUAGACACUUUUUGGCUCCU | 1143-1165 |
| AD-60339.1 | A-122029.1 | UCCAAGAUGAGGAUUUGGGUU | 2549-2569 | A-122030.1 | AACCCAAAUCCUCAUCUUGGAGU | 2547-2569 |
| AD-60338.1 | A-122013.1 | CCCUUGAUAGUUCACAAGAGA | 2386-2406 | A-122014.1 | UCUCUUGUGAACUAUCAAGGGGC | 2384-2406 |
| AD-60307.1 | A-121987.1 | CAAAGUCAAGGAUAUGGAAAA | 1641-1661 | A-121988.1 | UUUUCCAUAUCCUUGACUUUGAA | 1639-1661 |
| AD-60309.1 | A-122019.1 | UAGUUCACAAGAGAAGUCGUU | 2393-2413 | A-122020.1 | AACGACUUCUCUUGUGAACUAUC | 2391-2413 |
| AD-60343.1 | A-121999.1 | GGCCCCUUGAUAGUUCACAAG | 2383-2403 | A-122000.1 | CUUGUGAACUAUCAAGGGGCCGC | 2381-2403 |
| AD-60324.1 | A-121977.1 | UGGUGCUAGAUGGAUCAGACA | 1100-1120 | A-121978.1 | UGUCUGAUCCAUCUAGCACCAGG | 1098-1120 |
| AD-60318.1 | A-121975.1 | GCUAGAUGGAUCAGACAGCAU | 1104-1124 | A-121976.1 | AUGCUGUCUGAUCCAUCUAGCAC | 1102-1124 |
| AD-60300.1 | A-121969.1 | UACCUGGUGCUAGAUGGAUCA | 1096-1116 | A-121970.1 | UGAUCCAUCUAGCACCAGGUAGA | 1094-1116 |
| AD-60330.1 | A-121979.1 | GGUGCUAGAUGGAUCAGACAA | 1101-1121 (G19A) | A-121980.1 | UUGUCUGAUCCAUCUAGCACCAG | 1099-1121 (G19A) |
| AD-60306.1 | A-121971.1 | UCUGAGUCUCUGUGGCAUGGU | 1704-1724 | A-121972.1 | ACCAUGCCACAGAGACUCAGAGA | 1702-1724 |
| AD-60336.1 | A-121981.1 | GUGCUAGAUGGAUCAGACAGA | 1102-1122 (C19A) | A-121982.1 | UCUGUCUGAUCCAUCUAGCACCA | 1100-1122 (C19A) |
| AD-60301.1 | A-121985.1 | CUACCUGGUGCUAGAUGGAUA | 1095-1115 (C19A) | A-121986.1 | UAUCCAUCUAGCACCAGGUAGAU | 1093-1115 (C19A) |
| AD-60342.1 | A-121983.1 | ACCUGGUGCUAGAUGGAUCAA | 1097-1117 (G19A) | A-121984.1 | UUGAUCCAUCUAGCACCAGGUAG | 1095-1117 |
| Rodent CFB Sequences | | | | | | |
| Duplex ID | Sense ID | Sense Sequence (SEQ ID NOS: 103-117, respectively, in order of appearance) | Position in NM_001142706.1 | Antisense ID | Antisense Sequence (SEQ ID NOS: 118-132, respectively, in order of appearance) | Position in NM_001142706.1 |
| AD-60334.1 | A-122043.1 | GCAAGCCAAGAUCUCAGUCAC | 1888-1908 | A-122044.1 | GUGACUGAGAUCUUGGCUUGCCA | 1886-1908 |
| AD-60304.1 | A-122033.1 | GAUUGAGAAGGUGGCGAGUUA | 1291-1311 | A-122034.1 | UAACUCGCCACCUUCUCAAUCAA | 1289-1311 |
| AD-60310.1 | A-122035.1 | CACAAGAGAAGCCGCUUCAUU | 2515-2535 | A-122036.1 | AAUGAAGCGGCUUCUCUUGUGAA | 2513-2535 |
| AD-60328.1 | A-122041.1 | UUGUGAGAGAGAUGCUACAAA | 2364-2384 | A-122042.1 | UUUGUAGCAUCUCUCUCACAACU | 2362-2384 |
| AD-60322.1 | A-122039.1 | UCCUUCAUGAAUGUUCCGGGA | 193-213 | A-122040.1 | UCCCGGAACAUUCAUGAAGGAGG | 191-213 |

TABLE 3-continued

| Complement Factor B (CFB) unmodified sequences | | | | | |
|---|---|---|---|---|---|
| AD-60316.1 | A-122037.1UCACAGAGAAGCUCA ACCAAA | 1407-1427 | A-122038.1 | UUUGGUUGAGCUUCUCUGUGACC | 1405-1427 |
| AD-60346.1 | A-122047.1CUCAACCAAAUCAGU UAUGAA | 1418-1438 | A-122048.1 | UUCAUAACUGAUUUGGUUGAGCU | 1416-1438 |
| AD-60335.1 | A-122059.1CCCUGACAGAGACCA UCGAAG | 1113-1133 | A-122060.1 | CUUCGAUGGUCUCUGUCAGGGAG | 1111-1133 |
| AD-60323.1 | A-122055.1GAGCAGAUUGCAUAA AAGGUU | 261-281 | A-122056.1 | AACCUUUUAUGCAAUCUGCUCUG | 259-281 |
| AD-60340.1 | A-122045.1CUUCAUGAAUGUUCC GGGAAG | 195-215 | A-122046.1 | CUUCCCGGAACAUUCAUGAAGGA | 193-215 |
| AD-60305.1 | A-122049.1CUUCAUUCAAGUUGG UGUGAU | 2529-2549 | A-122050.1 | AUCACACCAACUUGAAUGAAGCG | 2527-2549 |
| AD-60317.1 | A-122053.1GAUUGAAGAGGUCCU GUUCCA | 2050-2070 | A-122054.1 | UGGAACAGGACCUCUUCAAUCUC | 2048-2070 |
| AD-60329.1 | A-122057.1AUUUCUUUUCAAUGC UAUGAU | 782-802 | A-122058.1 | AUCAUAGCAUUGAAAAGAAAUCU | 780-802 |
| AD-60341.1 | A-122061.1CCAGAGCAGAUUGCA UAAAAG | 258-278 | A-122062.1 | CUUUUAUGCAAUCUGCUCUGGCA | 256-278 |
| AD-60311.1 | A-122051.1CACAGAGAAGCUCAA CCAAAU | 1408-1428 | A-122052.1 | AUUUGGUUGAGCUUCUCUGUGAC | 1406-1428 |

TABLE 4

| Complement Factor B (CFB) modified sequences | | | | |
|---|---|---|---|---|
| Human CFB Sequences | | | | |
| Duplex ID | Sense ID | Sense Sequence (SEQ ID NOS 133-163, respectively, in order of appearance) | Antisense ID | Antisense Sequence (SEQ ID NOS 164-194, respectively, in order of appearance) |
| AD-60315.1 | A-122021.1 | AfsusUfcCfuGfaAfUfUfuUfaUfgAfcUfaUfL96 | A-122022.1 | asUfsaGfuCfaUfaAfaau UfcAfgGfaAfususc |
| AD-60326.1 | A-122009.1 | CfscsUfgAfuCfaAfGfCfuCfaAfgAfaUfaAfL96 | A-122010.1 | usUfsaUfuCfuUfgAfgcu UfgAfuCfaGfgsgsc |
| AD-60303.1 | A-122017.1 | GfsasAfgCfaGfgAfAfUfuCfcUfgAfaUfuUfL96 | A-122018.1 | asAfsaUfuCfaGfgAfauu CfcUfgCfuUfcsusu |
| AD-60331.1 | A-121995.1 | AfsgsCfaAfcAfuGfUfGfuUfcAfaAfgUfcAfL96 | A-121996.1 | usGfsaCfuUfuGfaAfcac AfuGfuUfgCfuscsa |
| AD-60344.1 | A-122015.1 | GfscsUfgUfgGfuGfUfCfuGfaGfuAfcUfuUfL96 | A-122016.1 | asAfsaGfuAfcUfcAfgac AfcCfaCfaGfcscsc |
| AD-60345.1 | A-122031.1 | AfsasGfuGfuCfuAfGfUfcAfaCfuUfaAfuUfL96 | A-122032.1 | asAfsuUfaAfgUfuGfacu AfgAfcAfcUfususu |
| AD-60319.1 | A-121991.1 | AfsgsCfuGfuGfaGfAfGfaGfaUfgCfuCfaAfL96 | A-121992.1 | usUfsgAfgCfaUfcUfcuc UfcAfcAfgCfusgsc |
| AD-60308.1 | A-122003.1 | AfsgsCfcAfaAfaAfGfUfgUfcUfaGfuCfaAfL96 | A-122004.1 | usUfsgAfcUfaGfaCfacu UfuUfuGfgCfuscsc |
| AD-60332.1 | A-122011.1 | UfsgsUfgAfgUfgAfUfGfaGfaUfcUfcUfuUfL96 | A-122012.1 | asAfsaGfaGfaUfcUfcau CfaCfuCfaCfasusu |
| AD-60313.1 | A-121989.1 | AfsasUfuGfaGfaAfGfGfuGfgCfaAfgUfuAfL96 | A-121990.1 | usAfsaCfuUfgCfcAfccu UfcUfcAfaUfusasa |
| AD-60321.1 | A-122023.1 | CfsasAfcAfuGfuGfUfUfcAfaAfgUfcAfaGfL96 | A-122024.1 | csUfsuGfaCfuUfuGfaac AfcAfuGfuUfgscsu |
| AD-60327.1 | A-122025.1 | UfsgsUfgAfgAfgAfGfAfuGfcUfcAfaUfaUfL96 | A-122026.1 | asUfsaUfuGfaGfcAfucu CfuCfuCfaCfasgsc |
| AD-60302.1 | A-122001.1 | GfsusCfuAfgUfcAfAfCfuUfaAfuUfgAfgAfL96 | A-122002.1 | usCfsuCfaAfuUfaAfguu GfaCfuAfgAfcsasc |
| AD-60325.1 | A-121993.1 | UfscsCfaAfgAfaAfGfAfcAfaUfgAfgCfaAfL96 | A-121994.1 | usUfsgCfuCfaUfuGfucu UfuCfuUfgGfasasg |
| AD-60337.1 | A-121997.1 | UfsgsUfgUfuCfaAfAfGfuCfaAfgGfaUfaUfL96 | A-121998.1 | asUfsaUfcCfuUfgAfcuu UfgAfaCfaCfasusg |
| AD-60333.1 | A-122027.1 | AfsusUfgAfuGfaGfAfUfcCfgGfgAfcUfuGfL96 | A-122028.1 | csAfsaGfuCfcCfgGfauc UfcAfuCfaAfusgsa |
| AD-60314.1 | A-122005.1 | CfsusGfuGfaGfaGfAfGfaUfgCfuCfaAfuAfL96 | A-122006.1 | usAfsuUfgAfgCfaUfcuc UfcUfcAfcAfgscsu |
| AD-60320.1 | A-122007.1 | GfsasGfcCfaAfaAfAfGfuGfuCfuAfgUfcAfL96 | A-122008.1 | usGfsaCfuAfgAfcAfcuu UfuUfgGfcUfcscsu |
| AD-60339.1 | A-122029.1 | UfscsCfaAfgAfuGfAfGfgAfuUfuGfgGfuUfL96 | A-122030.1 | asAfscCfcAfaAfuCfcuc AfuCfuUfgGfasgsu |
| AD-60338.1 | A-122013.1 | CfscsCfuUfgAfuAfGfUfuCfaCfaAfgAfgAfL96 | A-122014.1 | usCfsuCfuUfgUfgAfacu AfuCfaAfgGfgsgsc |
| AD-60307.1 | A-121987.1 | CfsasAfaGfuCfaAfGfGfaUfaUfgGfaAfaAfL96 | A-121988.1 | usUfsuUfcCfaUfaUfccu UfgAfcUfuUfgsasa |

TABLE 4-continued

| Complement Factor B (CFB) modified sequences | | | | |
|---|---|---|---|---|
| AD-60309.1 | A-122019.1 | UfsasGfuUfcAfcAfAfGfaGfaAfgUfcGfuUfL96 | A-122020.1 | asAfscGfaCfuUfcUfcuuGfuGfaAfcUfasusc |
| AD-60343.1 | A-121999.1 | GfsgsCfcCfcUfuGfAfUfaGfuUfcAfcAfaGfL96 | A-122000.1 | csUfsuGfuGfaAfcUfaucAfaGfgGfgCfcsgsc |
| AD-60324.1 | A-121977.1 | UfsgsGfuGfcUfaGfAfUfgGfaUfcAfgAfcAfL96 | A-121978.1 | usGfsuCfuGfaUfcCfaucUfaGfcAfcCfasgsg |
| AD-60318.1 | A-121975.1 | GfscsUfaGfaUfgGfAfUfcAfgAfcAfgCfaUfL96 | A-121976.1 | asUfsgCfuGfuCfuGfaucCfaUfcUfaGfcsasc |
| AD-60300.1 | A-121969.1 | UfsasCfcUfgGfuGfCfUfaGfaUfgGfaUfcAfL96 | A-121970.1 | usGfsaUfcCfaUfcUfagcAfcCfaGfgUfasgsa |
| AD-60330.1 | A-121979.1 | GfsgsUfgCfuAfgAfUfGfgAfuCfaGfaCfaAfL96 | A-121980.1 | usUfsgUfcUfgAfuCfcauCfuAfgCfaCfcsasg |
| AD-60306.1 | A-121971.1 | UfscsUfgAfgUfcUfCfUfgUfgGfcAfuGfgUfL96 | A-121972.1 | asCfscAfuGfcCfaCfagaGfaCfuCfaGfasgsa |
| AD-60336.1 | A-121981.1 | GfsusGfcUfaGfaUfGfGfaUfcAfgAfcAfgAfL96 | A-121982.1 | usCfsuGfuCfuGfaUfccaUfcUfaGfcAfcscsa |
| AD-60301.1 | A-121985.1 | CfsusAfcCfuGfgUfGfCfuAfgAfuGfgAfuAfL96 | A-121986.1 | usAfsuCfcAfuCfuAfgcaCfcAfgGfuAfgsasu |
| AD-60342.1 | A-121983.1 | AfscsCfuGfgUfgCfUfAfgAfuGfgAfuCfaAfL96 | A-121984.1 | usUfsgAfuCfcAfuCfuagCfaCfcAfgGfusasg |

Rodent CFB Sequencs

| Duplex ID | Sense ID | Sense Sequence (SEQ ID NOS 195-209, respectively, in order of appearance) | Antisense ID | Antisense Sequence (SEQ ID NOS 210-224, respectively, in order of appearance) |
|---|---|---|---|---|
| AD-60334.1 | A-122043.1 | GfscsAfaGfcCfaAfGfAfuCfuCfaGfuCfaCfL96 | A-122044.1 | gsUfsgAfcUfgAfgAfucuUfgGfcUfuGfcscsa |
| AD-60304.1 | A-122033.1 | GfsasUfuGfaGfaAfGfGfuGfgCfgAfgUfuAfL96 | A-122034.1 | usAfsaCfuCfgCfcAfccuUfcUfcAfaUfcsasa |
| AD-60310.1 | A-122035.1 | CfsasCfaAfgAfgAfAfGfcCfgCfuUfcAfuUfL96 | A-122036.1 | asAfsuGfaAfgCfgGfcuuCfuCfuUfgUfgsasa |
| AD-60328.1 | A-122041.1 | UfsusGfuGfaGfaGfAfGfaUfgCfuAfcAfaAfL96 | A-122042.1 | usUfsuGfuAfgCfaUfcucUfcUfcAfcAfascsu |
| AD-60322.1 | A-122039.1 | UfscsCfuUfcAfuGfAfAfuGfuUfcCfgGfgAfL96 | A-122040.1 | usCfscCfgGfaAfcAfuucAfuGfaAfgGfasgsg |
| AD-60316.1 | A-122037.1 | UfscsAfcAfgAfgAfAfGfcUfcAfaCfcAfaAfL96 | A-122038.1 | usUfsuGfgUfuGfaGfcuuCfuCfuGfuGfascsc |
| AD-60346.1 | A-122047.1 | CfsusCfaAfcCfaAfAfUfcAfgUfuAfuGfaAfL96 | A-122048.1 | usUfscAfuAfaCfuGfauuUfgGfuUfgAfgscsu |
| AD-60335.1 | A-122059.1 | CfscsCfuGfaCfaGfAfGfaCfcAfuCfgAfaGfL96 | A-122060.1 | csUfsuCfgAfuGfgUfcucUfgUfcAfgGfgsasg |
| AD-60323.1 | A-122055.1 | GfsasGfcAfgAfuUfGfCfaUfaAfaAfgGfuUfL96 | A-122056.1 | asAfscCfuUfuUfaUfgcaAfuCfuGfcUfcsusg |
| AD-60340.1 | A-122045.1 | CfsusUfcAfuGfaAfUfGfuUfcCfgGfgAfaGfL96 | A-122046.1 | csUfsuCfcCfgGfaAfcauUfcAfuGfaAfgsgsa |
| AD-60305.1 | A-122049.1 | CfsusUfcAfuUfcAfAfGfuUfgGfuGfuGfaUfL96 | A-122050.1 | asUfscAfcAfcCfaAfcuuGfaAfuGfaAfgscsg |
| AD-60317.1 | A-122053.1 | GfsasUfuGfaAfgAfGfGfuCfcUfgUfuCfcAfL96 | A-122054.1 | usGfsgAfaCfaGfgAfccuCfuUfcAfaUfcsusc |
| AD-60329.1 | A-122057.1 | AfsusUfuCfuUfuUfCfAfaUfgCfuAfuGfaUfL96 | A-122058.1 | asUfscAfuAfgCfaUfugaAfaAfgAfaAfuscsu |
| AD-60341.1 | A-122061.1 | CfscsAfgAfgCfaGfAfUfuGfcAfuAfaAfaGfL96 | A-122062.1 | csUfsuUfuAfuGfcAfaucUfgCfuCfuGfgscsa |
| AD-60311.1 | A-122051.1 | CfsasCfaGfaGfaAfGfCfuCfaAfcCfaAfaUfL96 | A-122052.1 | asUfsuUfgGfuUfgAfgcuUfcUfcUfgUfgsasc |

TABLE 5

C3 unmodified sequences

| Duplex ID | Sense ID | Sense Sequence (SEQ ID NOS 225-265, respectively, in oder of appearance) | Position in NM_ 000064.2 | Antisense ID | Antisense Sequence (SEQ ID NOS 266-306, respectively, in order of appearance) | Position IN NM_ 000064.2 |
|---|---|---|---|---|---|---|
| AD-60149.1 | A-121853.1 | CGUGGUCAAGGUCUUCUCUCU | 3309-3329 | A-121854.1 | AGAGAGAAGACCUUGACCACGUA | 3307-3329 |
| AD-60151.1 | A-121885.1 | ACGUGGUCAAGGUCUUCUCUA | 3308-3324_C21A | A-121886.1 | UAGAGAAGACCUUGACCACGUAG | 3306-3324_C21A |
| AD-60152.1 | A-121901.1 | UUUGACCUCAUGGUGUUCGUG | 1174-1194 | A-121902.1 | CACGAACACCAUGAGGUCAAAGG | 1172-1194 |

TABLE 5-continued

C3 unmodified sequences

| Duplex ID | Sense ID | Sense Sequence (SEQ ID NOS 225-265, respectively, in oder of appearance) | Position in NM_ 000064.2 | Antisense ID | Antisense Sequence (SEQ ID NOS 266-306, respectively, in order of appearance) | Position IN NM_ 000064.2 |
|---|---|---|---|---|---|---|
| AD-60153.1 | A-121917.1 | GGAGAAUUGCUUCAUACAAAA | 4611-4631 | A-121918.1 | UUUUGUAUGAAGCAAUUCUCCUC | 4609-4631 |
| AD-60154.1 | A-121933.1 | UGUUAAAUGGCUGAUCCUGGA | 3375-3395 | A-121934.1 | UCCAGGAUCAGCCAUUUAACAGC | 3373-3395 |
| AD-60155.1 | A-121855.1 | GACAGACAAGACCAUCUACAC | 465-485 | A-121856.1 | GUGUAGAUGGUCUUGUCUGUCUG | 463-485 |
| AD-60156.1 | A-121871.1 | CCAGACAGACAAGACCAUCUA | 462-482 | A-121872.1 | UAGAUGGUCUUGUCUGUCUGGAU | 460-482 |
| AD-60157.1 | A-121887.1 | CCAGAUCCACUUCACCAAGAA | 1125-1141_C21A | A-121888.1 | UUCUUGGUGAAGUGGAUCUGGUA | 1123-1141_C21A |
| AD-60158.1 | A-121903.1 | UUGACCUCAUGGUGUUCGUGA | 1175-1195 | A-121904.1 | UCACGAACACCAUGAGGUCAAAG | 1173-1195 |
| AD-60159.1 | A-121919.1 | CCCCUUCGAGGUCACAGUAAU | 2523-2543 | A-121920.1 | AUUACUGUGACCUCGAAGGGGUC | 2521-2543 |
| AD-60160.1 | A-121935.1 | AUGAACAAAACUGUGGCUGUU | 2878-2898 | A-121936.1 | AACAGCCACAGUUUUGUUCAUUC | 2876-2898 |
| AD-60161.1 | A-121857.1 | AGACAGACAAGACCAUCUACA | 464-484 | A-121858.1 | UGUAGAUGGUCUUGUCUGUCUGG | 462-484 |
| AD-60162.1 | A-121873.1 | CCAGAUCCACUUCACCAAGAC | 1125-1145 | A-121874.1 | GUCUUGGUGAAGUGGAUCUGGUA | 1123-1145 |
| AD-60163.1 | A-121889.1 | AGGGAUCUGUGUGGCAGACCA | 2505-2521_C21A | A-121890.1 | UGGUCUGCCACACAGAUCCCUUU | 2503-2521_C21A |
| AD-60164.1 | A-121905.1 | GACAAGACCAUCUACACCCCU | 469-489 | A-121906.1 | AGGGGUGUAGAUGGUCUUGUCUG | 467-489 |
| AD-60165.1 | A-121921.1 | GCUGAGGAGAAUUGCUUCAUA | 4606-4626 | A-121922.1 | UAUGAAGCAAUUCUCCUCAGCAC | 4604-4626 |
| AD-60166.1 | A-121859.1 | ACGUGGUCAAGGUCUUCUCUC | 3308-3328 | A-121860.1 | GAGAGAAGACCUUGACCACGUAG | 3306-3328 |
| AD-60167.1 | A-121875.1 | GGAUCUGUGUGGCAGACCCCU | 2507-2527 | A-121876.1 | AGGGGUCUGCCACACAGAUCCCU | 2505-2527 |
| AD-60168.1 | A-121891.1 | ACAGACAAGACCAUCUACACA | 466-482_C21A | A-121892.1 | UGUGUAGAUGGUCUUGUCUGUCU | 464-482_C21A |
| AD-60169.1 | A-121907.1 | AUCCAGACAGACAAGACCAUU | 460-476_C21U | A-121908.1 | AAUGGUCUUGUCUGUCUGGAUGA | 458-476_C21U |
| AD-60170.1 | A-121923.1 | CUCCGUGUGGGUGGACGUCAA | 1713-1733 | A-121924.1 | UUGACGUCCACCCACACGGAGUC | 1711-1733 |
| AD-60171.1 | A-121861.1 | UCCAGACAGACAAGACCAUCU | 461-481 | A-121862.1 | AGAUGGUCUUGUCUGUCUGGAUG | 459-481 |
| AD-60172.1 | A-121877.1 | AGGGAUCUGUGUGGCAGACCC | 2505-2525 | A-121878.1 | GGGUCUGCCACACAGAUCCCUUU | 2503-2525 |
| AD-60173.1 | A-121893.1 | CAAGAAAGGGAUCUGUGUGGA | 2499-2515_C21A | A-121894.1 | UCCACACAGAUCCCUUUCUUGUC | 2497-2515_C21A |
| AD-60174.1 | A-121909.1 | UGACCUCAUGGUGUUCGUGAU | 1176-1192_C21U | A-121910.1 | AUCACGAACACCAUGAGGUCAAA | 1174-1192_C21U |
| AD-60175.1 | A-121925.1 | GCAGCUAAAAGACUUUGACUU | 3789-3809 | A-121926.1 | AAGUCAAAGUCUUUUAGCUGCAG | 3787-3809 |
| AD-60176.1 | A-121863.1 | CAUCCAGACAGACAAGACCAU | 459-479 | A-121864.1 | AUGGUCUUGUCUGUCUGGAUGAA | 457-479 |
| AD-60177.1 | A-121879.1 | ACAGACAAGACCAUCUACACC | 466-486 | A-121880.1 | GGUGUAGAUGGUCUUGUCUGUCU | 464-486 |
| AD-60178.1 | A-121895.1 | AUCCAGACAGACAAGACCAUC | 460-480 | A-121896.1 | GAUGGUCUUGUCUGUCUGGAUGA | 458-480 |
| AD-60179.1 | A-121911.1 | UUUGACCUCAUGGUGUUCGUU | 1174-1190_G21U | A-121912.1 | AACGAACACCAUGAGGUCAAAGG | 1172-1190_G21U |
| AD-60180.1 | A-121927.1 | GGAUGCCAAGAACACUAUGAU | 4200-4220 | A-121928.1 | AUCAUAGUGUUCUUGGCAUCCUG | 4198-4220 |
| AD-60181.1 | A-121865.1 | AAGAAAGGGAUCUGUGUGGCA | 2500-2520 | A-121866.1 | UGCCACACAGAUCCCUUUCUUGU | 2498-2520 |
| AD-60182.1 | A-121881.1 | CAAGAAAGGGAUCUGUGUGGC | 2499-2519 | A-121882.1 | GCCACACAGAUCCCUUUCUUGUC | 2497-2519 |
| AD-60183.1 | A-121897.1 | UACGUGGUCAAGGUCUUCUCU | 3307-3327 | A-121898.1 | AGAGAAGACCUUGACCACGUAGG | 3305-3327 |
| AD-60184.1 | A-121913.1 | CAGUUUCGAGGUCAUAGUGGA | 756-776 | A-121914.1 | UCCACUAUGACCUCGAAACUGGG | 754-776 |
| AD-60185.1 | A-121929.1 | CGUGCCGGAAGGAAUCAGAAU | 2859-2879 | A-121930.1 | AUUCUGAUUCCUUCCGGCACGAC | 2857-2879 |
| AD-60186.1 | A-121867.1 | GAAAGGGAUCUGUGUGGCAGA | 2502-2522 | A-121868.1 | UCUGCCACACAGAUCCCUUUCUU | 2500-2522 |

TABLE 5-continued

| C3 unmodified sequences | | | | | | |
|---|---|---|---|---|---|---|
| Duplex ID | Sense ID | Sense Sequence (SEQ ID NOS 225-265, respectively, in oder of appearance) | Position in NM_ 000064.2 | Antisense ID | Antisense Sequence (SEQ ID NOS 266-306, respectively, in order of appearance) | Position IN NM_ 000064.2 |
| AD-60187.1 | A-121883.1 | GACAGACAAGACCAUCUACAA | 465-481_C21A | A-121884.1 | UUGUAGAUGGUCUUGUCUGUCUG | 463-481_C21A |
| AD-60188.1 | A-121899.1 | UGACCUCAUGGUGUUCGUGAC | 1176-1196 | A-121900.1 | GUCACGAACACCAUGAGGUCAAA | 1174-1196 |
| AD-60189.1 | A-121915.1 | UGUAAUAAAUUCGACCUCAAG | 4138-4158 | A-121916.1 | CUUGAGGUCGAAUUUAUUACAGG | 4136-4158 |
| AD-60190.1 | A-121931.1 | AACUACAUGAACCUACAGAGA | 3601-3621 | A-121932.1 | UCUCUGUAGGUUCAUGUAGUUGG | 3599-3621 |

TABLE 6

| C3 modified sequences | | | | |
|---|---|---|---|---|
| Duplex ID | Sense ID | Sense Sequence (SEQ ID NOS 308-347, respectively, in order or appearance | Antisense ID | Antisense Sequence (SEQ ID NOS 348-388, respectively, in order |
| AD-60149.1 | A-121853.1 | CfsgsUfgGfuCfaAfGfGfuCfuUfcUfcUfcUfL96 | A-121854.1 | asGfsaGfaGfaAfgAfccuUfgAfcCfaCfgsusa |
| AD-60151.1 | A-121885.1 | AfscsGfuGfgUfcAfAfGfgUfcUfuCfuCfuAfL96 | A-121886.1 | usAfsgAfgAfaGfaCfcuuGfaCfcAfcGfusasg |
| AD-60152.1 | A-121901.1 | UfsusUfgAfcCfuCfAfUfgGfuGfuUfcGfuGfL96 | A-121902.1 | csAfscGfaAfcAfcCfaugAfgGfuCfaAfasgsg |
| AD-60153.1 | A-121917.1 | GfsgsAfgAfaUfuGfCfUfuCfaUfaCfaAfaAfL96 | A-121918.1 | usUfsuUfgUfaUfgAfagcAfaUfuCfuCfcsusc |
| AD-60154.1 | A-121933.1 | UfsgsUfuAfaAfuGfGfCfuGfaUfcCfuGfgAfL96 | A-121934.1 | usCfscAfgGfaUfcAfgccAfuUfuAfaCfasgsc |
| AD-60155.1 | A-121855.1 | GfsasCfaGfaCfaAfGfAfcCfaUfcUfaCfaCfL96 | A-121856.1 | gsUfsgUfaGfaUfgGfucuUfgUfcUfgUfcsusg |
| AD-60156.1 | A-121871.1 | CfscsAfgAfcAfgAfCfAfaGfaCfcAfuCfuAfL96 | A-121872.1 | usAfsgAfuGfgUfcUfuguCfuGfuCfuGfgsasu |
| AD-60157.1 | A-121887.1 | CfscsAfgAfuCfcAfCfUfuCfaCfcAfaGfaAfL96 | A-121888.1 | usUfscUfuGfgUfgAfaguGfgAfuCfuGfgsusa |
| AD-60158.1 | A-121903.1 | UfsusGfaCfcUfcAfUfGfgUfgUfuCfgUfgAfL96 | A-121904.1 | usCfsaCfgAfaCfaCfcauGfaGfgUfcAfasasg |
| AD-60159.1 | A-121919.1 | CfscsCfcUfuCfgAfGfGfuCfaCfaGfuAfaUfL96 | A-121920.1 | asUfsuAfcUfgUfgAfccuCfgAfaGfgGfgsusc |
| AD-60160.1 | A-121935.1 | AfsusGfaAfcAfaAfAfCfuGfuGfgCfuGfuUfL96 | A-121936.1 | asAfscAfgCfcAfcAfguuUfuGfuUfcAfususc |
| AD-60161.1 | A-121857.1 | AfsgsAfcAfgAfcAfAfGfaCfcAfuCfuAfcAfL96 | A-121858.1 | usGfsuAfgAfuGfgUfcuuGfuCfuGfuCfusgsg |
| AD-60162.1 | A-121873.1 | CfscsAfgAfuCfcAfCfUfuCfaCfcAfaGfaCfL96 | A-121874.1 | gsUfscUfuGfgUfgAfaguGfgAfuCfuGfgsusa |
| AD-60163.1 | A-121889.1 | AfsgsGfgAfuCfuGfUfGfuGfgCfaGfaCfcAfL96 | A-121890.1 | usGfsgUfcUfgCfcAfcacAfgAfuCfcCfususu |
| AD-60164.1 | A-121905.1 | GfsasCfaAfgAfcCfAfUfcUfaCfaCfcCfcUfL96 | A-121906.1 | asGfsgGfgUfgUfaGfaugGfuCfuUfgUfcsusg |
| AD-60165.1 | A-121921.1 | GfscsUfgAfgGfaGfAfAfuUfgCfuUfcAfuAfL96 | A-121922.1 | usAfsuGfaAfgCfaAfuucUfcCfuCfaGfcsasc |
| AD-60166.1 | A-121859.1 | AfscsGfuGfgUfcAfAfGfgUfcUfuCfuCfuCfL96 | A-121860.1 | gsAfsgAfgAfaGfaCfcuuGfaCfcAfcGfusasg |

TABLE 6-continued

C3 modified sequences

| Duplex ID | Sense ID | Sense Sequence (SEQ ID NOS 308-347, respectively, in order or appearance | Antisense ID | Antisense Sequence (SEQ ID NOS 348-388, respectively, in order |
|---|---|---|---|---|
| AD-60167.1 | A-121875.1 | GfsgsAfuCfuGfuGfUfGfgCfaGfaCfcCfcUfL96 | A-121876.1 | asGfsgGfgUfcUfgCfcacAfcAfgAfuCfcscsu |
| AD-60168.1 | A-121891.1 | AfscsAfgAfcAfaGfAfCfcAfuCfuAfcAfcAfL96 | A-121892.1 | usGfsuGfuAfgAfuGfgucUfuGfuCfuGfuscsu |
| AD-60169.1 | A-121907.1 | AfsusCfcAfgAfcAfGfAfcAfaGfaCfcAfuUfL96 | A-121908.1 | asAfsuGfgUfcUfuGfucuGfuCfuGfgAfusgsa |
| AD-60170.1 | A-121923.1 | CfsusCfcGfuGfuGfGfGfuGfgAfcGfuCfaAfL96 | A-121924.1 | usUfsgAfcGfuCfcAfcccAfcAfcGfgAfgsusc |
| AD-60171.1 | A-121861.1 | UfscsCfaGfaCfaGfAfCfaAfgAfcCfaUfcUfL96 | A-121862.1 | asGfsaUfgGfuCfuUfgucUfgUfcUfgGfasusg |
| AD-60172.1 | A-121877.1 | AfsgsGfgAfuCfuGfUfGfuGfgCfaGfaCfcCfL96 | A-121878.1 | gsGfsgUfcUfgCfcAfcacAfgAfuCfcCfususu |
| AD-60173.1 | A-121893.1 | CfsasAfgAfaAfgGfGfAfuCfuGfuGfuGfgAfL96 | A-121894.1 | usCfscAfcAfcAfgAfuccCfuUfuCfuUfgsusc |
| AD-60174.1 | A-121909.1 | UfsgsAfcCfuCfaUfGfGfuGfuUfcGfuGfaUfL96 | A-121910.1 | asUfscAfcGfaAfcAfccaUfgAfgGfuCfasasa |
| AD-60175.1 | A-121925.1 | GfscsAfgCfuAfaAfAfGfaCfuUfuGfaCfuUfL96 | A-121926.1 | asAfsgUfcAfaAfgUfcuuUfuAfgCfuGfcsasg |
| AD-60176.1 | A-121863.1 | CfsasUfcCfaGfaCfAfGfaCfaAfgAfcCfaUfL96 | A-121864.1 | asUfsgGfuCfuUfgUfcugUfcUfgGfaUfgsasa |
| AD-60177.1 | A-121879.1 | AfscsAfgAfcAfaGfAfCfcAfuCfuAfcAfcCfL96 | A-121880.1 | gsGfsuGfuAfgAfuGfgucUfuGfuCfuGfuscsu |
| AD-60178.1 | A-121895.1 | AfsusCfcAfgAfcAfGfAfcAfaGfaCfcAfuCfL96 | A-121896.1 | gsAfsuGfgUfcUfuGfucuGfuCfuGfgAfusgsa |
| AD-60179.1 | A-121911.1 | UfsusUfgAfcCfuCfAfUfgGfuGfuUfcGfuUfL96 | A-121912.1 | asAfscGfaAfcAfcCfaugAfgGfuCfaAfasgsg |
| AD-60180.1 | A-121927.1 | GfsgsAfuGfcCfaAfGfAfaCfaCfuAfuGfaUfL96 | A-121928.1 | asUfscAfuAfgUfgUfucuUfgGfcAfuCfcsusg |
| AD-60181.1 | A-121865.1 | AfsasGfaAfaGfgGfAfUfcUfgUfgUfgGfcAfL96 | A-121866.1 | usGfscCfaCfaCfaGfaucCfcUfuUfcUfusgsu |
| AD-60182.1 | A-121881.1 | CfsasAfgAfaAfgGfGfAfuCfuGfuGfuGfgCfL96 | A-121882.1 | gsCfscAfcAfcAfgAfuccCfuUfuCfuUfgsusc |
| AD-60183.1 | A-121897.1 | UfsasCfgUfgGfuCfAfAfgGfuCfuUfcUfcUfL96 | A-121898.1 | asGfsaGfaAfgAfcCfuugAfcCfaCfgUfasgsg |
| AD-60184.1 | A-121913.1 | CfsasGfuUfuCfgAfGfGfuCfaUfaGfuGfgAfL96 | A-121914.1 | usCfscAfcUfaUfgAfccuCfgAfaAfcUfgsgsg |
| AD-60185.1 | A-121929.1 | CfsgsUfgCfcGfgAfAfGfgAfaUfcAfgAfaUfL96 | A-121930.1 | asUfsuCfuGfaUfuCfcuuCfcGfgCfaCfgsasc |
| AD-60186.1 | A-121867.1 | GfsasAfaGfgGfaUfCfUfgUfgUfgGfcAfgAfL96 | A-121868.1 | usCfsuGfcCfaCfaCfagaUfcCfcUfuUfcsusu |
| AD-60187.1 | A-121883.1 | GfsasCfaGfaCfaAfGfAfcCfaUfcUfaCfaAfL96 | A-121884.1 | usUfsgUfaGfaUfgGfucuUfgUfcUfgUfcsusg |
| AD-60188.1 | A-121899.1 | UfsgsAfcCfuCfaUfGfGfuGfuUfcGfuGfaCfL96 | A-121900.1 | gsUfscAfcGfaAfcAfccaUfgAfgGfuCfasasa |
| AD-60189.1 | A-121915.1 | UfsgsUfaAfuAfaAfUfUfcGfaCfcUfcAfaGfL96 | A-121916.1 | csUfsuGfaGfgUfcGfaauUfuAfuUfaCfasgsg |
| AD-60190.1 | A-121931.1 | AfsasCfuAfcAfuGfAfAfcCfuAfcAfgAfgAfL96 | A-121932.1 | usCfsuCfuGfuAfgGfuucAfuGfuAfgUfusgsg |

TABLE 7

C9 unmodified sequences

| Duplex ID | Sense ID | Sense Sequence (SEQ ID NOS 389-411, respectively, in order of appearance) | Position in NM_ 001737.3 | Antisense ID | Antisense Sequence (SEQ ID NOS 412-434, respectively, in order of appearance) | Position in NM_ 001737.3 |
|---|---|---|---|---|---|---|
| AD-59663.1 | A-121046.1 | UUUUGACAAUGAGUUCUACAA | 606-626 | A-121047.1 | UUGUAGAACUCAUUGUCAAAAGG | 604-626 |
| AD-59664.1 | A-121062.1 | AUCAAUGAAUUUAGUGUAAGA | 1597-1617 | A-121063.1 | UCUUACACUAAAUUCAUUGAUAU | 1595-1617 |
| AD-59665.1 | A-121078.1 | AGACAAAUGUUUCGUUCAAGA | 268-288 | A-121079.1 | UCUUGAACGAAACAUUUGUCUGA | 266-288 |
| AD-59668.1 | A-121048.1 | CUUUUGACAAUGAGUUCUACA | 605-625 | A-121049.1 | UGUAGAACUCAUUGUCAAAAGGU | 603-625 |
| AD-59669.1 | A-121064.1 | AACUUGGAAAGAGCCAUUGAA | 1570-1590 | A-121065.1 | UUCAAUGGCUCUUUCCAAGUUUU | 1568-1590 |
| AD-59670.1 | A-121080.1 | UACCUGAGAAGCUGAUUAACA | 2589-2609 | A-121081.1 | UGUUAAUCAGCUUCUCAGGUAGG | 2587-2609 |
| AD-59673.1 | A-121050.1 | ACCUUUUGACAAUGAGUUCUA | 603-623 | A-121051.1 | UAGAACUCAUUGUCAAAAGGUGU | 601-623 |
| AD-59674.1 | A-121066.1 | GACUGCGGAAAUGACUUUCAA | 391-411 | A-121067.1 | UUGAAAGUCAUUUCCGCAGUCAU | 389-411 |
| AD-59675.1 | A-121082.1 | GCCCAUUCAAAUUUGAGGGAA | 1682-1702 | A-121083.1 | UUCCCUCAAAUUUGAAUGGGCAG | 1680-1702 |
| AD-59678.1 | A-121052.1 | UUUUGGAUAAAGCUUCCAUGA | 1175-1195 | A-121053.1 | UCAUGGAAGCUUUAUCCAAAACA | 1173-1195 |
| AD-59679.1 | A-121068.1 | AACCAAAGGCGAGAAAAAUUU | 708-728 | A-121069.1 | AAAUUUUUCUCGCCUUUGGUUUC | 706-728 |
| AD-59680.1 | A-121084.1 | CUUUGCCAACUACCUAUGAAA | 1067-1087 | A-121085.1 | UUUCAUAGGUAGUUGGCAAAGCU | 1065-1087 |
| AD-59683.1 | A-121054.1 | CACCUUUUGACAAUGAGUUCU | 602-622 | A-121055.1 | AGAACUCAUUGUCAAAAGGUGUG | 600-622 |
| AD-59684.1 | A-121070.1 | GAGAAGACAUCAAAUUUUAAU | 781-801 | A-121071.1 | AUUAAAAUUUGAUGUCUUCUCUU | 779-801 |
| AD-59685.1 | A-121086.1 | GACAAUGAGUUCUACAAUGGA | 610-630 | A-121087.1 | UCCAUUGUAGAACUCAUUGUCAA | 608-630 |
| AD-59688.1 | A-121056.1 | UUUGGAUAAAGCUUCCAUGAA | 1176-1196 | A-121057.1 | UUCAUGGAAGCUUUAUCCAAAAC | 1174-1196 |
| AD-59689.1 | A-121072.1 | AUCUAUGAAACCAAAGGCGAG | 700-720 | A-121073.1 | CUCGCCUUUGGUUUCAUAGAUCA | 698-720 |
| AD-59690.1 | A-121088.1 | AUAUCAAUGAAUUUAGUGUAA | 1595-1615 | A-121089.1 | UUACACUAAAUUCAUUGAUAUAG | 1593-1615 |
| AD-59692.1 | A-121058.1 | CACACCUUUUGACAAUGAGUU | 600-620 | A-121059.1 | AACUCAUUGUCAAAAGGUGUGCU | 598-620 |
| AD-59693.1 | A-121074.1 | UAGGGUCUGAGACCUUUUGAA | 2648-2668 | A-121075.1 | UUCAAAAGGUCUCAGACCCUAAG | 2646-2668 |
| AD-59694.1 | A-121090.1 | CAAAACUUGGAAAGAGCCAUU | 1567-1587 | A-121091.1 | AAUGGCUCUUUCCAAGUUUUGUU | 1565-1587 |
| AD-59696.1 | A-121060.1 | GCACACCUUUUGACAAUGAGU | 599-619 | A-121061.1 | ACUCAUUGUCAAAAGGUGUGCUU | 597-619 |
| AD-59697.1 | A-121076.1 | UGAAACCAAAGGCGAGAAAAA | 705-725 | A-121077.1 | UUUUUCUCGCCUUUGGUUUCAUA | 703-725 |

TABLE 8

C9 modified sequences

| Duplex ID | Sense ID | Sense Sequence (SEQ ID NOS 435-457, respectively, in order of appearance) | Antisense ID | Antisense Sequence (SEQ ID NOS 458-480, respectively, in order of appearance) |
|---|---|---|---|---|
| AD-59663.1 | A-121046.1 | UfsusUfuGfaCfaAfUfGfaGfuUfcUfaCfaAfL96 | A-121047.1 | usUfsgUfaGfaAfcUfcauUfgUfcAfaAfasgsg |
| AD-59664.1 | A-121062.1 | AfsusCfaAfuGfaAfUfUfuAfgUfgUfaAfgAfL96 | A-121063.1 | usCfsuUfaCfaCfuAfaauUfcAfuUfgAfusasu |
| AD-59665.1 | A-121078.1 | AfsgsAfcAfaAfuGfUfUfuCfgUfuCfaAfgAfL96 | A-121079.1 | usCfsuUfgAfaCfgAfaacAfuUfuGfuCfusgsa |
| AD-59668.1 | A-121048.1 | CfsusUfuUfgAfcAfAfUfgAfgUfuCfuAfcAfL96 | A-121049.1 | usGfsuAfgAfaCfuCfauuGfuCfaAfaAfgsgsu |
| AD-59669.1 | A-121064.1 | AfsasCfuUfgGfaAfAfGfaGfcCfaUfuGfaAfL96 | A-121065.1 | usUfscAfaUfgGfcUfcuuUfcCfaAfgUfususu |

TABLE 8-continued

| C9 modified sequences | | | | |
|---|---|---|---|---|
| Duplex ID | Sense ID | Sense Sequence (SEQ ID NOS 435-457, respectively, in order of appearance) | Antisense ID | Antisense Sequence (SEQ ID NOS 458-480, respectively, in order of appearance) |
| AD-59670.1 | A-121080.1 | UfsasCfcUfgAfgAfAfGfcUfgAfuUfaAfcAfL96 | A-121081.1 | usGfsuUfaAfuCfaGfcuuCfuCfaGfgUfasgsg |
| AD-59673.1 | A-121050.1 | AfscsCfuUfuUfgAfCfAfaUfgAfgUfuCfuAfL96 | A-121051.1 | usAfsgAfaCfuCfaUfuguCfaAfaAfgGfusgsu |
| AD-59674.1 | A-121066.1 | GfsasCfuGfcGfgAfAfAfuGfaCfuUfuCfaAfL96 | A-121067.1 | usUfsgAfaAfgUfcAfuuuCfcGfcAfgUfcsasu |
| AD-59675.1 | A-121082.1 | GfscsCfcAfuUfcAfAfAfuUfuGfaGfgGfaAfL96 | A-121083.1 | usUfscCfcUfcAfaAfuuuGfaAfuGfgGfcsasg |
| AD-59678.1 | A-121052.1 | UfsusUfuGfgAfuAfAfAfgCfuUfcCfaUfgAfL96 | A-121053.1 | usCfsaUfgGfaAfgCfuuuAfuCfcAfaAfascsa |
| AD-59679.1 | A-121068.1 | AfsasCfcAfaAfgGfCfGfaGfaAfaAfaUfuUfL96 | A-121069.1 | asAfsaUfuUfuUfcUfcgcCfuUfuGfgUfususc |
| AD-59680.1 | A-121084.1 | CfsusUfuGfcCfaAfCfUfaCfcUfaUfgAfaAfL96 | A-121085.1 | usUfsuCfaUfaGfgUfaguUfgGfcAfaAfgscsu |
| AD-59683.1 | A-121054.1 | CfsasCfcUfuUfuGfAfCfaAfuGfaGfuUfcUfL96 | A-121055.1 | asGfsaAfcUfcAfuUfgucAfaAfaGfgUfgsusg |
| AD-59684.1 | A-121070.1 | GfsasGfaAfgAfcAfUfCfaAfaUfuUfuAfaUfL96 | A-121071.1 | asUfsuAfaAfaUfuUfgauGfuCfuUfcUfcsusu |
| AD-59685.1 | A-121086.1 | GfsasCfaAfuGfaGfUfUfcUfaCfaAfuGfgAfL96 | A-121087.1 | usCfscAfuUfgUfaGfaacUfcAfuUfgUfcsasa |
| AD-59688.1 | A-121056.1 | UfsusUfgGfaUfaAfAfGfcUfuCfcAfuGfaAfL96 | A-121057.1 | usUfscAfuGfgAfaGfcuuUfaUfcCfaAfasasc |
| AD-59689.1 | A-121072.1 | AfsusCfuAfuGfaAfAfCfcAfaAfgGfcGfaGfL96 | A-121073.1 | csUfscGfcCfuUfuGfguuUfcAfuAfgAfuscsa |
| AD-59690.1 | A-121088.1 | AfsusAfuCfaAfuGfAfAfuUfuAfgUfgUfaAfL96 | A-121089.1 | usUfsaCfaCfuAfaAfuucAfuUfgAfuAfusasg |
| AD-59692.1 | A-121058.1 | CfsasCfaCfcUfuUfUfGfaCfaAfuGfaGfuUfL96 | A-121059.1 | asAfscUfcAfuUfgUfcaaAfaGfgUfgUfgscsu |
| AD-59693.1 | A-121074.1 | UfsasGfgGfuCfuGfAfGfaCfcUfuUfuGfaAfL96 | A-121075.1 | usUfscAfaAfaGfgUfcucAfgAfcCfcUfasasg |
| AD-59694.1 | A-121090.1 | CfsasAfaAfcUfuGfGfAfaAfgAfgCfcAfuUfL96 | A-121091.1 | asAfsuGfgCfuCfuUfuccAfaGfuUfuUfgsusu |
| AD-59696.1 | A-121060.1 | GfscsAfcAfcCfuUfUfUfgAfcAfaUfgAfgUfL96 | A-121061.1 | asCfsuCfaUfuGfuCfaaaAfgGfuGfuGfcsusu |
| AD-59697.1 | A-121076.1 | UfsgsAfaAfcCfaAfAfGfgCfgAfgAfaAfaAfL96 | A-121077.1 | usUfsuUfuCfuCfgCfcuuUfgGfuUfuCfasusa |

TABLE 9

| CFB single dose screen in Hep3B Cells | | | | |
|---|---|---|---|---|
| | 10 nM | 0.1 nM | 10 nM SD | 0.1 nM SD |
| AD-60315.1 | 22.82 | 17.15 | 20.03 | 9.73 |
| AD-60326.1 | 9.33 | 17.49 | 0.29 | 4.75 |
| AD-60303.1 | 8.45 | 28.08 | 4.67 | 10.75 |
| AD-60331.1 | 14.47 | 29.99 | 4.36 | 4.99 |
| AD-60344.1 | 17.61 | 30.59 | 6.96 | 1.70 |
| AD-60345.1 | 8.98 | 33.88 | 0.65 | 7.11 |
| AD-60319.1 | 14.36 | 33.98 | 1.17 | 12.16 |
| AD-60308.1 | 12.64 | 34.07 | 0.19 | 11.41 |
| AD-60332.1 | 20.19 | 35.92 | 3.53 | 3.23 |
| AD-60313.1 | 23.94 | 38.26 | 19.92 | 13.16 |

TABLE 9-continued

| CFB single dose screen in Hep3B Cells | | | | |
|---|---|---|---|---|
| | 10 nM | 0.1 nM | 10 nM SD | 0.1 nM SD |
| AD-60321.1 | 13.32 | 46.50 | 4.83 | 1.00 |
| AD-60327.1 | 18.44 | 50.40 | 6.45 | 5.21 |
| AD-60302.1 | 13.82 | 53.31 | 4.21 | 12.46 |
| AD-60325.1 | 11.73 | 54.59 | 0.27 | 15.34 |
| AD-60337.1 | 16.17 | 56.04 | 3.64 | 33.50 |
| AD-60333.1 | 17.72 | 65.14 | 2.22 | 8.79 |
| AD-60314.1 | 27.79 | 67.44 | 2.02 | 9.10 |
| AD-60320.1 | 18.12 | 85.78 | 5.39 | 33.24 |
| AD-60339.1 | 20.86 | 88.73 | 9.59 | 10.47 |
| AD-60338.1 | 18.14 | 91.03 | 4.11 | 10.07 |

TABLE 9-continued

| CFB single dose screen in Hep3B Cells | | | | |
|---|---|---|---|---|
| | 10 nM | 0.1 nM | 10 nM SD | 0.1 nM SD |
| AD-60307.1 | 21.76 | 91.13 | 3.49 | 43.21 |
| AD-60309.1 | 20.64 | 95.13 | 0.34 | 53.77 |
| AD-60343.1 | 61.82 | 112.57 | 5.56 | 17.11 |
| AD-60324.1 | 24.20 | 81.08 | 3.41 | 18.95 |
| AD-60318.1 | 43.11 | 99.07 | 13.83 | 17.69 |
| AD-60300.1 | 35.21 | 111.33 | 5.35 | 12.86 |
| AD-60330.1 | 58.80 | 111.85 | 8.86 | 32.76 |
| AD-60306.1 | 85.87 | 113.97 | 12.01 | 33.11 |
| AD-60336.1 | 35.90 | 119.80 | 3.75 | 4.92 |
| AD-60301.1 | 28.95 | 121.90 | 7.73 | 23.23 |
| AD-60342.1 | 49.16 | 123.56 | 17.53 | 14.88 |
| AD-60334.1 | 26.12 | 55.28 | 22.52 | 7.86 |
| AD-60304.1 | 20.62 | 74.38 | 4.43 | 16.50 |
| AD-60310.1 | 18.93 | 77.08 | 0.87 | 35.20 |
| AD-60328.1 | 63.55 | 86.20 | 1.91 | 4.07 |
| AD-60322.1 | 81.67 | 86.30 | 21.22 | 25.58 |
| AD-60316.1 | 105.01 | 93.22 | 8.55 | 14.39 |
| AD-60346.1 | 109.11 | 99.09 | 2.07 | 25.51 |
| AD-60335.1 | 42.63 | 101.00 | 5.91 | 54.15 |
| AD-60323.1 | 81.31 | 103.20 | 4.03 | 3.86 |
| AD-60340.1 | 50.41 | 109.25 | 20.73 | 1.67 |
| AD-60305.1 | 30.06 | 114.59 | 5.00 | 17.97 |
| AD-60317.1 | 102.87 | 126.87 | 1.95 | 30.25 |
| AD-60329.1 | 106.30 | 131.90 | 0.20 | 53.49 |
| AD-60341.1 | 112.98 | 137.99 | 3.94 | 31.92 |
| AD-60311.1 | 162.39 | 140.07 | 10.04 | 63.65 |

TABLE 10

| CFB single dose screen in Primary Mouse Hepatocytes | | | | |
|---|---|---|---|---|
| | Avg 10 nM | Avg 0.1 nM | 10 nM SD | 0.1 nM SD |
| AD-60302.1 | 112.73 | 109.72 | 15.29 | 1.75 |
| AD-60303.1 | 119.44 | 102.70 | 0.15 | 23.82 |
| AD-60307.1 | 67.92 | 99.67 | 2.91 | 6.47 |
| AD-60308.1 | 116.89 | 111.68 | 12.15 | 4.51 |
| AD-60309.1 | 100.72 | 112.85 | 10.72 | 4.84 |
| AD-60313.1 | 50.21 | 102.05 | 10.08 | 4.13 |
| AD-60314.1 | 74.12 | 113.15 | 4.99 | 12.59 |
| AD-60315.1 | 101.22 | 104.79 | 6.07 | 29.27 |
| AD-60319.1 | 18.56 | 81.28 | 4.22 | 6.27 |
| AD-60320.1 | 103.08 | 123.28 | 8.71 | 18.51 |
| AD-60321.1 | 45.03 | 104.98 | 3.91 | 25.35 |
| AD-60325.1 | 121.99 | 127.67 | 4.63 | 24.72 |
| AD-60326.1 | 55.24 | 102.10 | 4.66 | 13.35 |
| AD-60327.1 | 79.42 | 108.21 | 4.77 | 21.99 |
| AD-60331.1 | 4.51 | 52.03 | 0.35 | 8.06 |
| AD-60332.1 | 115.05 | 120.93 | 6.06 | 4.00 |
| AD-60333.1 | 102.19 | 113.88 | 0.38 | 31.81 |
| AD-60337.1 | 3.93 | 31.08 | 1.12 | 0.49 |
| AD-60338.1 | 120.85 | 115.74 | 9.02 | 8.93 |
| AD-60339.1 | 16.97 | 75.02 | 0.27 | 10.17 |
| AD-60343.1 | 126.10 | 131.79 | 24.11 | 14.66 |
| AD-60344.1 | 8.06 | 35.14 | 0.31 | 11.86 |
| AD-60345.1 | 132.64 | 133.75 | 7.96 | 27.82 |
| AD-60300.1 | 27.05 | 81.40 | 8.63 | 8.86 |
| AD-60301.1 | 10.24 | 72.49 | 0.46 | 5.41 |
| AD-60306.1 | 97.07 | 114.32 | 4.87 | 18.27 |
| AD-60318.1 | 37.73 | 98.00 | 3.09 | 7.56 |
| AD-60324.1 | 42.83 | 99.93 | 1.21 | 12.09 |
| AD-60330.1 | 70.05 | 116.47 | 1.46 | 15.23 |
| AD-60336.1 | 31.97 | 95.19 | 13.63 | 1.75 |
| AD-60342.1 | 38.22 | 108.31 | 4.90 | 6.76 |
| AD-60304.1 | 7.88 | 18.03 | 3.57 | 18.03 |
| AD-60305.1 | 13.09 | 64.61 | 2.19 | 11.26 |
| AD-60310.1 | 1.36 | 21.17 | 0.24 | 1.27 |
| AD-60311.1 | 2.11 | 28.70 | 0.22 | 4.79 |
| AD-60316.1 | 2.23 | 28.29 | 1.11 | 4.66 |
| AD-60317.1 | 60.25 | 84.11 | 5.23 | 5.66 |
| AD-60322.1 | 70.53 | 115.47 | 1.47 | 11.72 |
| AD-60323.1 | 108.71 | 117.31 | 17.38 | 7.90 |
| AD-60328.1 | 4.04 | 38.52 | 0.21 | 10.03 |

TABLE 10-continued

| CFB single dose screen in Primary Mouse Hepatocytes | | | | |
|---|---|---|---|---|
| | Avg 10 nM | Avg 0.1 nM | 10 nM SD | 0.1 nM SD |
| AD-60329.1 | 6.73 | 36.47 | 0.21 | 8.72 |
| AD-60334.1 | 49.74 | 99.41 | 2.74 | 8.64 |
| AD-60335.1 | 34.99 | 99.57 | 3.64 | 1.59 |
| AD-60340.1 | 99.13 | 106.94 | 5.71 | 9.81 |
| AD-60341.1 | 92.74 | 112.17 | 0.34 | 8.10 |
| AD-60346.1 | 5.65 | 53.30 | 0.52 | 5.28 |

TABLE 11

| CFB Dose response screen in Hep 3B cells | |
|---|---|
| Duplex ID | Hep3B IC50(nM) |
| AD-60303.1 | 0.119 |
| AD-60326.1 | 0.062 |
| AD-60319.1 | 0.351 |
| AD-60331.1 | 0.225 |
| AD-60337.1 | 0.418 |
| AD-60344.1 | 0.347 |
| AD-60304.1 | >10 |
| AD-60324.1 | 7.039 |

TABLE 12

| CFB Dose response screen in Primary Mouse Hepatocytes | |
|---|---|
| Duplex ID | PrimaryMouse IC50(nM) |
| AD-60303.1 | Not achieved |
| AD-60326.1 | 4.063 |
| AD-60319.1 | 0.162 |
| AD-60331.1 | 0.031 |
| AD-60337.1 | 0.014 |
| AD-60344.1 | 0.003 |
| AD-60304.1 | 0.028 |
| AD-60324.1 | 0.854 |

TABLE 13

| C9 Single dose screen in Primary Mouse Hepatocytes | | | | |
|---|---|---|---|---|
| Duplex ID | Avg 10 nM | Avg 0.1 nM | SD 10 nM | SD 0.1 nM |
| AD-59663.1 | 5.92 | 27.33 | 2.13 | 16.40 |
| AD-59664.1 | 83.71 | 76.56 | 42.80 | 21.75 |
| AD-59665.1 | 91.76 | 85.56 | 20.62 | 26.31 |
| AD-59668.1 | 30.66 | 49.06 | 4.23 | 13.47 |
| AD-59669.1 | 95.36 | 64.74 | 18.69 | 19.30 |
| AD-59670.1 | 96.91 | 103.65 | 26.38 | 7.23 |
| AD-59673.1 | 22.34 | 31.20 | 7.34 | 20.44 |
| AD-59674.1 | 12.16 | 45.36 | 5.13 | 14.79 |
| AD-59675.1 | 93.18 | 109.59 | 3.77 | 8.45 |
| AD-59678.1 | 47.33 | 47.23 | 14.22 | 6.86 |
| AD-59679.1 | 98.53 | 30.06 | 12.88 | 32.30 |
| AD-59680.1 | 33.75 | 86.68 | 1.20 | 28.07 |
| AD-59683.1 | 25.81 | 44.31 | 9.78 | 23.12 |
| AD-59684.1 | 58.89 | 96.75 | 16.45 | 21.05 |
| AD-59685.1 | 68.90 | 115.36 | 8.17 | 6.36 |
| AD-59688.1 | 32.69 | 41.63 | 6.49 | 21.72 |
| AD-59689.1 | 86.86 | 102.46 | 24.47 | 0.38 |
| AD-59690.1 | 101.98 | 131.95 | 4.87 | 0.16 |
| AD-59692.1 | 33.98 | 36.81 | 9.73 | 3.38 |
| AD-59693.1 | 84.70 | 75.60 | 35.91 | 16.09 |
| AD-59694.1 | 108.88 | 132.73 | 2.53 | 45.43 |
| AD-59696.1 | 32.87 | 45.82 | 9.72 | 15.79 |
| AD-59697.1 | 110.00 | 120.20 | 1.21 | 3.98 |

TABLE 13-continued

| C9 Single dose screen in Primary Mouse Hepatocytes | | | | |
|---|---|---|---|---|
| Duplex ID | Avg 10 nM | Avg 0.1 nM | SD 10 nM | SD 0.1 nM |
| AD-1955 | 109.44 | 92.04 | 24.08 | 32.14 |
| AD-1955 | 105.93 | 104.33 | 4.54 | 6.01 |
| AD-1955 | 87.62 | 93.01 | 6.11 | 3.30 |
| AD-1955 | 90.95 | 117.91 | 3.90 | 29.31 |
| AD-1955 | 91.04 | 93.49 | 6.80 | 8.35 |
| AD-1955 | 106.63 | 107.78 | 1.44 | 9.89 |
| AD-1955 | 95.33 | 82.10 | 9.45 | 2.92 |
| AD-1955 | 123.15 | 121.27 | 44.13 | 11.42 |

TABLE 14

| C3 Single dose screen in Primary Mouse Hepatocytes | | | | |
|---|---|---|---|---|
| Duplex ID | Avg 10 nM | Avg 0.1 nM | 10 nM SD | 0.1 nM SD |
| AD-60149.1 | 0.08 | 33.89 | 0.04 | 44.73 |
| AD-60151.1 | 0.11 | 81.49 | 0.14 | 7.88 |
| AD-60152.1 | 1.72 | 92.02 | 0.89 | 9.34 |
| AD-60153.1 | 93.57 | 97.06 | 17.16 | 4.16 |
| AD-60154.1 | 97.73 | 122.73 | 0.66 | 28.17 |
| AD-60155.1 | 12.94 | 91.38 | 17.39 | 9.28 |
| AD-60156.1 | 8.02 | 41.58 | 9.16 | 56.27 |
| AD-60157.1 | 23.61 | 98.22 | 33.22 | 8.77 |
| AD-60158.1 | 0.75 | 77.42 | 0.76 | 8.61 |
| AD-60159.1 | 100.47 | 93.53 | 11.61 | 7.44 |
| AD-60160.1 | 89.34 | 92.97 | 18.42 | 9.21 |
| AD-60161.1 | 2.33 | 82.37 | 0.32 | 21.06 |
| AD-60162.1 | 60.59 | 46.83 | 1.37 | 65.96 |
| AD-60163.1 | 104.09 | 53.32 | 5.42 | 75.38 |
| AD-60164.1 | 61.13 | 40.41 | 5.57 | 57.13 |
| AD-60165.1 | 61.93 | 86.61 | 4.44 | 11.53 |
| AD-60166.1 | 2.27 | 96.48 | 0.70 | 17.52 |
| AD-60167.1 | 87.51 | 84.41 | 3.70 | 9.19 |
| AD-60168.1 | 35.16 | 98.47 | 0.28 | 20.95 |
| AD-60169.1 | 0.42 | 51.78 | 0.13 | 18.79 |
| AD-60170.1 | 125.00 | 99.12 | 1.46 | 12.72 |
| AD-60171.1 | 0.44 | 59.53 | 0.01 | 1.82 |
| AD-60172.1 | 89.05 | 102.11 | 4.20 | 10.62 |
| AD-60173.1 | 81.29 | 95.39 | 16.08 | 3.86 |
| AD-60174.1 | 0.06 | 25.26 | 0.02 | 31.64 |
| AD-60175.1 | 0.89 | 80.59 | 0.23 | 6.61 |
| AD-60176.1 | 0.88 | 52.71 | 0.02 | 6.12 |
| AD-60177.1 | 63.14 | 85.00 | 16.41 | 9.25 |
| AD-60178.1 | 42.97 | 64.33 | 4.75 | 14.00 |
| AD-60179.1 | 0.12 | 54.36 | 0.01 | 6.05 |
| AD-60180.1 | 94.57 | 98.11 | 13.68 | 5.65 |
| AD-60181.1 | 69.28 | 85.66 | 6.99 | 31.48 |
| AD-60182.1 | 84.22 | 79.05 | 2.63 | 8.99 |
| AD-60183.1 | 0.08 | 44.17 | 0.05 | 7.27 |
| AD-60184.1 | 80.50 | 81.13 | 9.59 | 14.73 |
| AD-60185.1 | 92.21 | 99.75 | 12.00 | 2.32 |
| AD-60186.1 | 60.60 | 93.85 | 18.81 | 29.73 |
| AD-60187.1 | 2.33 | 71.77 | 0.20 | 1.49 |
| AD-60188.1 | 0.33 | 78.13 | 0.37 | 14.56 |
| AD-60189.1 | 57.75 | 91.38 | 43.16 | 14.16 |
| AD-60190.1 | 29.40 | 94.84 | 41.57 | 7.55 |
| AD-1955 | 103.85 | 90.86 | 8.96 | 3.45 |
| AD-1955 | 71.27 | 115.36 | 36.17 | 13.40 |
| AD-1955 | 99.16 | 95.85 | 5.16 | 8.09 |
| AD-1955 | 112.29 | 104.37 | 3.65 | 12.88 |
| AD-1955 | 108.44 | 97.01 | 1.40 | 0.36 |
| AD-1955 | 118.26 | 109.90 | 2.10 | 12.76 |
| AD-1955 | 98.09 | 98.72 | 11.81 | 1.81 |

TABLE 15

| C3 Single dose screen in Hep 3B cells | | | | |
|---|---|---|---|---|
| Duplex ID | Avg 10 nM | Avg 0.1 nM | 10 nM SD | 0.1 nM SD |
| AD-60149.1 | 7.49 | 55.90 | 7.75 | 4.41 |
| AD-60151.1 | 24.05 | 101.65 | 14.22 | 8.27 |
| AD-60152.1 | 16.58 | 112.51 | 10.66 | 19.82 |
| AD-60153.1 | 20.13 | 22.40 | 22.87 | 3.76 |
| AD-60154.1 | 24.21 | 112.90 | 8.93 | 25.58 |
| AD-60155.1 | 20.48 | 68.97 | 2.10 | 1.73 |
| AD-60156.1 | 18.22 | 66.39 | 0.80 | 1.67 |
| AD-60157.1 | 29.07 | 125.72 | 5.80 | 8.08 |
| AD-60158.1 | 81.03 | 105.18 | 14.03 | 14.20 |
| AD-60159.1 | 27.58 | 92.91 | 4.77 | 2.22 |
| AD-60160.1 | 11.49 | 60.48 | 4.68 | 11.60 |
| AD-60161.1 | 27.49 | 80.57 | 10.88 | 16.13 |
| AD-60162.1 | 49.58 | 89.22 | 3.76 | 6.06 |
| AD-60163.1 | 91.18 | 99.19 | 5.14 | 21.40 |
| AD-60164.1 | 33.93 | 85.93 | 4.07 | 1.00 |
| AD-60165.1 | 5.54 | 13.05 | 0.43 | 2.69 |
| AD-60166.1 | 35.21 | 81.66 | 21.31 | 14.48 |
| AD-60167.1 | 106.64 | 115.02 | 8.09 | 39.17 |
| AD-60168.1 | 26.91 | 92.99 | 2.50 | 5.86 |
| AD-60169.1 | 10.66 | 49.63 | 6.66 | 17.36 |
| AD-60170.1 | 52.73 | 104.43 | 2.71 | 22.03 |
| AD-60171.1 | 23.77 | 60.35 | 7.94 | 7.27 |
| AD-60172.1 | 143.57 | 99.22 | 8.09 | 11.58 |
| AD-60173.1 | 100.25 | 108.80 | 12.25 | 44.49 |
| AD-60174.1 | 16.68 | 92.68 | 0.45 | 45.25 |
| AD-60175.1 | 24.94 | 42.14 | 4.74 | 7.68 |
| AD-60176.1 | 17.30 | 66.19 | 8.83 | 13.81 |
| AD-60177.1 | 50.71 | 116.18 | 20.19 | 1.49 |
| AD-60178.1 | 22.65 | 90.84 | 5.82 | 15.23 |
| AD-60179.1 | 15.21 | 85.30 | 3.55 | 23.07 |
| AD-60180.1 | 45.91 | 93.35 | 16.19 | 28.54 |
| AD-60181.1 | 63.50 | 109.82 | 10.07 | 14.56 |
| AD-60182.1 | 110.82 | 121.62 | 1.09 | 6.78 |
| AD-60183.1 | 13.82 | 69.24 | 8.64 | 3.35 |
| AD-60184.1 | 26.47 | 97.94 | 9.64 | 9.88 |
| AD-60185.1 | 41.42 | 103.45 | 7.77 | 2.47 |
| AD-60186.1 | 72.24 | 88.39 | 6.37 | 51.31 |
| AD-60187.1 | 9.49 | 51.15 | 3.28 | 11.65 |
| AD-60188.1 | 55.44 | 95.66 | 7.05 | 30.36 |
| AD-60189.1 | 52.59 | 89.41 | 4.25 | 20.79 |
| AD-60190.1 | 16.67 | 95.38 | 1.22 | 11.83 |

TABLE 16

| C3 Dose response screen in primary mouse hepatocytes | |
|---|---|
| Duplex ID | PMH IC50(nM) |
| AD-60149.1 | 0.03 |
| AD-60152.1 | 1.03 |
| AD-60156.1 | 0.19 |
| AD-60165.1 | 1.96 |
| AD-60169.1 | 0.04 |
| AD-60171.1 | 0.04 |
| AD-60174.1 | 0.01 |
| AD-60175.1 | 0.54 |
| AD-60176.1 | 0.05 |
| AD-60179.1 | 0.03 |
| AD-60183.1 | 0.03 |
| AD-60187.1 | 0.24 |

TABLE 17

| C3 Dose response screen in Hep3B cells | |
|---|---|
| Duplex ID | Hep3B IC50(nM) |
| AD-60149.1 | 0.88 |
| AD-60152.1 | 2.87 |
| AD-60156.1 | 2.06 |
| AD-60165.1 | 0.08 |
| AD-60169.1 | 0.41 |
| AD-60171.1 | 5.51 |
| AD-60174.1 | 2.60 |
| AD-60175.1 | 0.48 |
| AD-60176.1 | 2.29 |
| AD-60179.1 | 1.70 |
| AD-60183.1 | 0.94 |
| AD-60187.1 | 1.65 |

Example 3. In Vivo Screening

A subset of three CFB GalNAC conjugated iRNAs was selected for further in vivo evaluation, AD-60304, AD-60331, and AD-60344. The nucleotide sequences of the sense and antisens strands of these iRNA agents are provided in Table 18. As indicated in Table 19, the nucleotide sequence of AD-60304 is a perfect match to the mouse and rat nucleotide sequences. The nucleotide sequence of AD-60331 and the nucleotide sequence of AD-60344 have nucleotide mismatches ("MM"; see bolded, underlined nucleotides) to the mouse gene but have activity in mouse hepatocytes.

C57BL/6 mice (N=3 per group) were injected subcutaneously with either 1 mg/kg or 10 mg/kg of GalNAc conjugated duplexes or an equal volume of 1×Dulbecco's Phosphate-Buffered Saline (DPBS) (Life Technologies, Cat #14040133). Ninety-six hours later, mice were euthanized and the livers were dissected and flash frozen in liquid nitrogen. Livers were ground in a 2000 Geno/Grinder (SPEX SamplePrep, Metuchen N.J.). Approximately 10 mg of liver powder per sample was used for RNA isolation. Samples were first homogenized in a TissueLyserII (Qiagen Inc, Valencia, Calif.) and then RNA was extracted using a RNeasy 96 Universal Tissue Kit (Qiagen Inc, Cat #74881) following manufacturer's protocol using vacuum/spin technology. RNA concentration was measured by a NanoDrop 8000 (Thermo Scientific, Wilmington, Del.) and was adjusted to 100 ng/μl. cDNA was prepared and RT-PCR were performed as described above.

Figure 2:
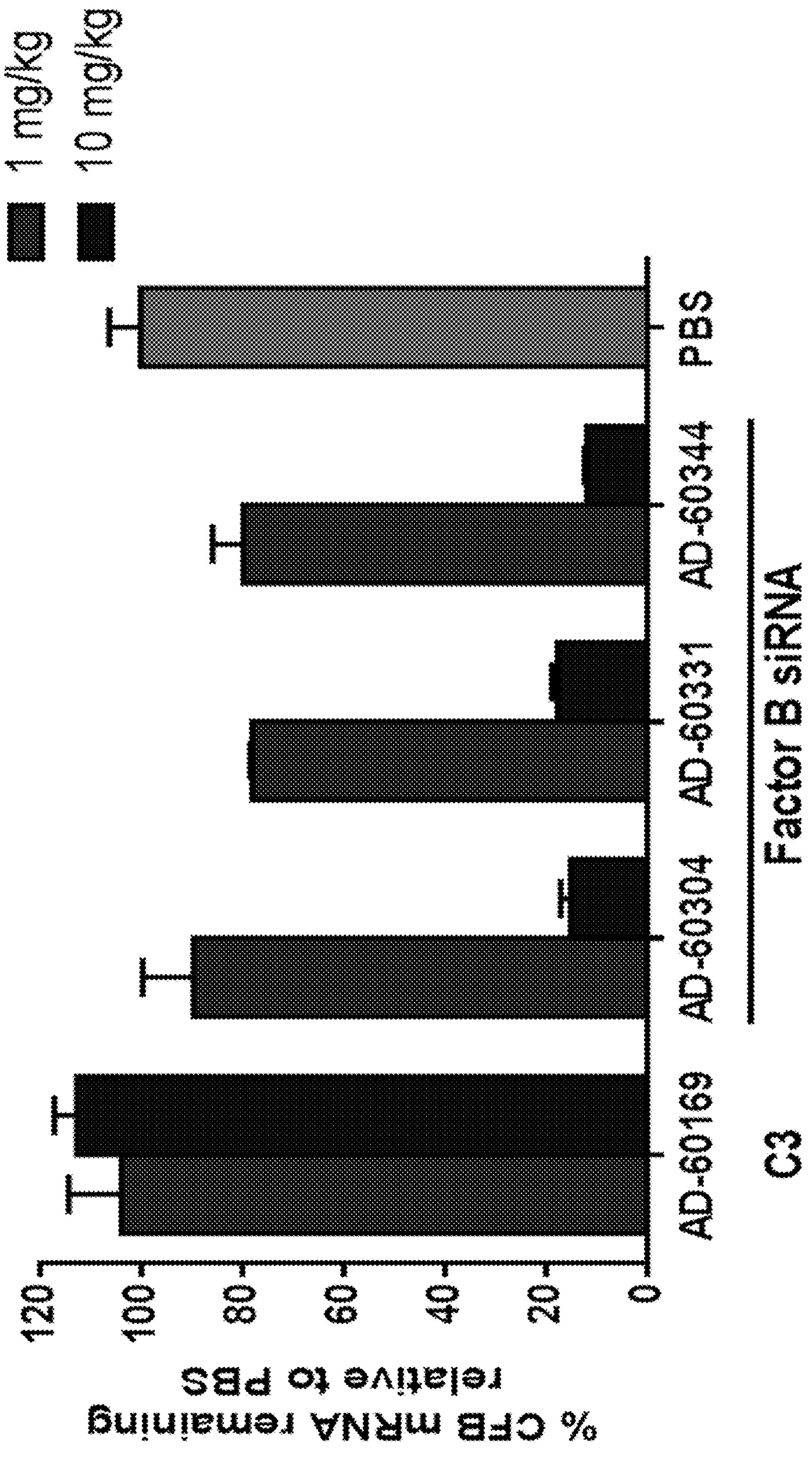
FIG. 2 is a graph showing the percentage of complement factor B (CFB) mRNA remaining in C57BL/6 mice 96 hours after a single 1 mg/kg or 10 mg/kg dose of the indicated iRNAs.

FIG. 2 demonstrates the efficacy of the CFB iRNAs to inhibit CFB mRNA at a dose of either 1 mg/kg or 10 mg/kg. At the 10 mg/kg dose, an average of about 80% silencing was observed for all three iRNAs tested. At the 1 mg/kg dose, an average of about 30% silencing was observed for AD-60331 and AD-60344.

Figure 3:
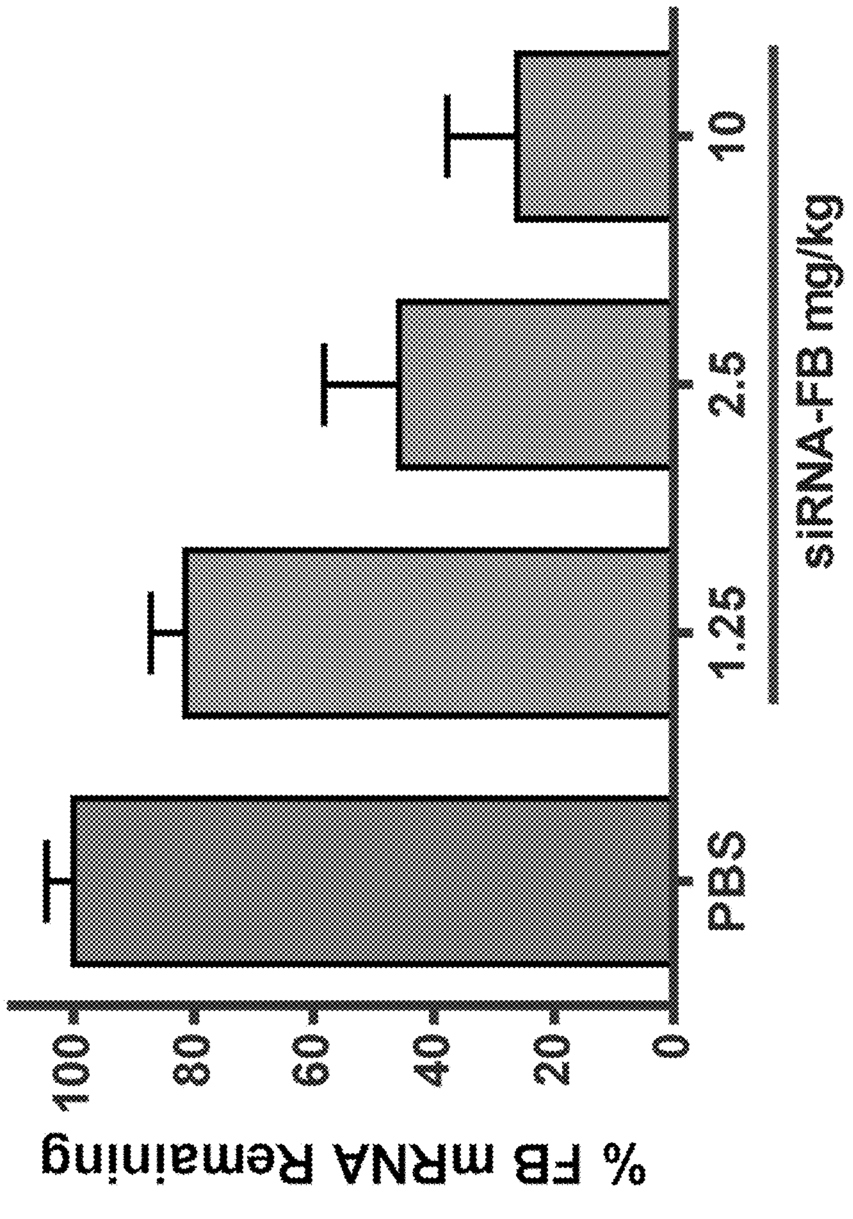
FIG. 3 is a graph showing the percentage of complement factor B (CFB) mRNA remaining in C57BL/6 mice 72 hours after a single 1.25 mg/kg, 2.5 mg/kg, or 10 mg/kg dose of AD-60331.

The ability of AD-60331 to suppress expression of CFB mRNA in vivo was also assessed using a single dose of 1.25 mg/kg, 2.5 mg/kg, and 10 mg/kg. C57BL/6 mice were injected subcutaneously with the foregoing doses and seventy hours later, mice were euthanized. RNA isolation form the livers of the animals, cDNA preparation, and RT-PCR were performed as described above. FIG. 3 demonstrates that AD-60331 reduces CFB mRNA in a dose responsive manner, with an $ED_{50}$ of about 2.5 mg/kg. It is expected that when introduced into human subjects, these iRNAs will be even more effective given the design of the sequences.

TABLE 18

| Duplex | Sense Sequence (SEQ ID NOS 481-483, respectively, in order of appearance) | Antisense Sequence (SEQ ID NOS 484-486, respectively, in order of appearance) | species |
|---|---|---|---|
| AD-60304.1 | GfsasUfuGfaGfaAfGfGfuGfgCfgAfgUfuAfL96 | usAfsaCfuCfgCfcAfccuUfcUfcAfaUfcsasa | MR |
| AD-60331.1 | AfsgsCfaAfcAfuGfUfGfuUfcAfaAfgUfcAfL96 | usGfsaCfuUfuGfaAfcacAfuGfuUfgCfuscsa | HC |
| AD-60344.1 | GfscsUfgUfgGfuGfUfCfuGfaGfuAfcUfuUfL96 | asAfsaGfuAfcUfcAfgacAfcCfaCfaGfcscsc | HC |

TABLE 19

| Duplex | Antisense MM to mouse (bold, underline) (SEQ ID NOS 487-489, respectively, in order of appearance) | Antisense MM to rat (bold, underline) (SEQ ID NOS 490-492, respectively, in order of appearance) | PrimaryMouse IC50 (nM) | Hep3b IC50 (nM) |
|---|---|---|---|---|
| AD-60304.1 | UAACUCGCCACCUUCUCAAUCAA | UAACUCGCCACCUUCUCAAUCAA | 0.028 | 2.876 |
| AD-60331.1 | UGACUUU**G**AACACAUG**U**UGCUCA | UGAC**U**UUGAACACAUG**U**UGCUCA | 0.031 | 0.225 |
| AD-60344.1 | **A**AAGUACUCAGACACCAC**A**GCCC | **A**AAGUACUC**A**GACACCAC**A**GCCC | 0.017 | 0.347 |

We claim:

1. A double stranded ribonucleic acid (dsRNA) agent for inhibiting expression of complement factor B (CFB) in a cell, wherein the dsRNA agent comprises a sense strand and an antisense strand forming a double stranded region, wherein said sense strand comprises the nucleotide sequence of 5'-GCUGUGGUGUCUGAGUACUUU-3' (SEQ ID NO:45), and said antisense strand comprises the nucleotide sequence of 5' AAAGUACUCA-GACACCACAGCCC-3' (SEQ ID NO:76), wherein substantially all of the nucleotides of said sense strand comprise a modification selected from the group consisting of a 2'-O-methyl modification and a 2'-fluoro modification, wherein said sense strand comprises two phosphorothioate internucleotide linkages at the 5'-terminus, wherein substantially all of the nucleotides of said antisense strand comprise a modification selected from the group consisting of a 2'-O-methyl modification and a 2'-fluoro modification, wherein said antisense strand comprises two phosphorothioate internucleotide linkages at the 5'-terminus and two phosphorothioate internucleotide linkages at the 3'-terminus, and wherein said sense strand is conjugated to one or more GalNAc derivatives attached through a branched bivalent or trivalent linker at the 3'-terminus.

2. The dsRNA agent of claim 1, wherein the ligand is

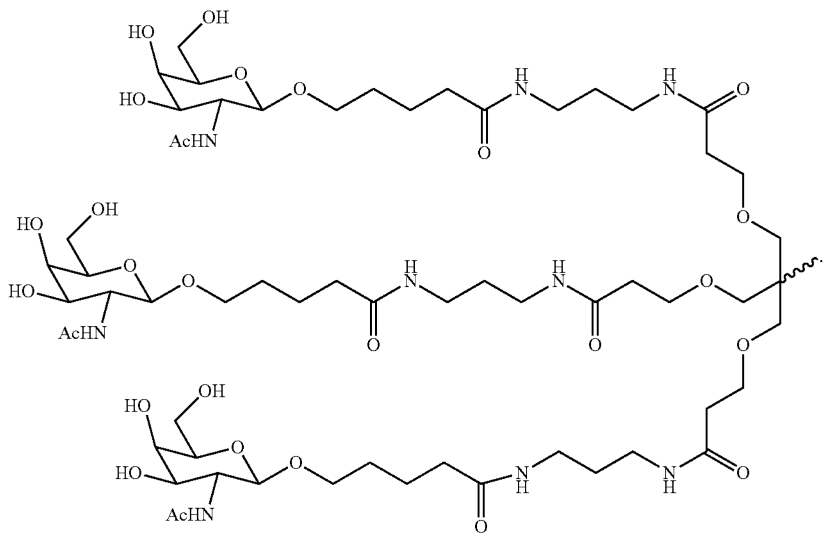 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

3. The dsRNA agent of claim 2, wherein the dsRNA agent is conjugated to the ligand as shown in the following schematic

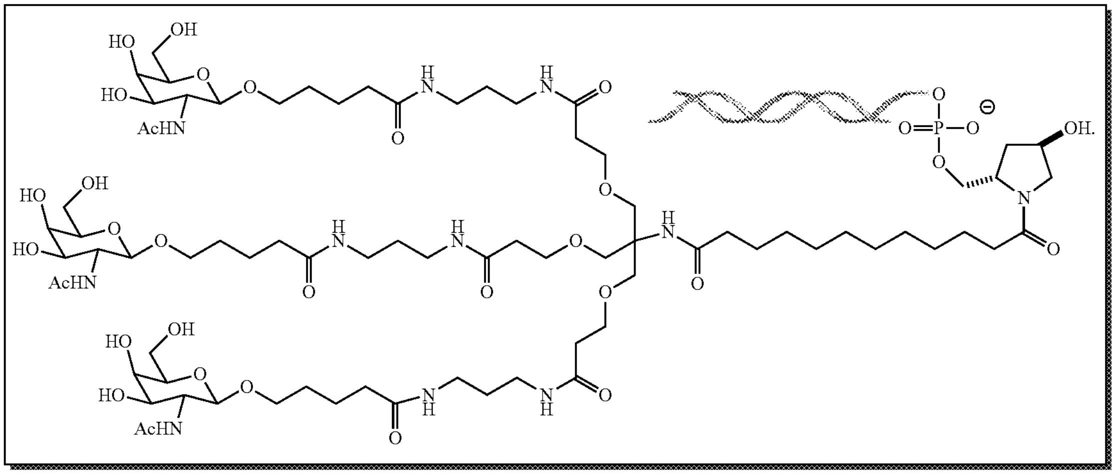

4. The dsRNA of claim 1, wherein all of the nucleotides of the sense strand and all of the nucleotides of the antisense strand comprise a nucleotide modification.

5. The dsRNA agent of claim 4, wherein all of the nucleotides of the sense strand and all of the nucleotides of the antisense strand comprise a 2'-O-methyl modification or a 2'-fluoro modification.

6. The dsRNA agent of claim 1, wherein the sense strand comprises 5'-GfscsUfgUfgGfuGfUfCfuGfaGfuAfcUfuUf-3' (SEQ ID NO:483) and the antisense strand comprises 5'-asAfsaGfuAfcUfcAfgacAfcCfaCfaGfcscsc-3' (SEQ ID NO:486), wherein a, c, g, and u are 2'-O-methyl (2'-OMe) A, C, G, and U; Af, Cf, Gf, and Uf are 2'-fluoro A, C, G, and U; and s is a phosphorothioate linkage.

7. The dsRNA agent of claim 1, wherein the sense strand consists of 5'-GfscsUfgUfgGfuGfUfCfuGfaGfuAfcU-fuUfL96-3' (SEQ ID NO:483) and the antisense strand consists of 5'-asAfsaGfuAfcUfcAfgacAfcCfaCfaGfcscsc-3' (SEQ ID NO:486), wherein a, c, g, and u are 2'-O-methyl (2'-OMe) A, C, G, and U; Af, Cf, Gf, and Uf are 2'-fluoro A, C, G, and U; s is a phosphorothioate linkage; and L96 is N-[tris (GalNAc-alkyl)-amidodecanoyl)]-4-hydroxyprolinol Hyp-(GalNAc-alkyl)3.

8. An isolated cell containing the dsRNA agent of claim 1.

9. A pharmaceutical composition for inhibiting expression of a complement component factor B gene comprising the dsRNA agent of claim 1.

10. The pharmaceutical composition of claim 9, wherein the dsRNA agent is formulated in an unbuffered solution.

11. The pharmaceutical composition of claim 9, wherein the dsRNA agent is formulated in a buffered solution.

12. A method of inhibiting complement factor B (CFB) expression in a cell, the method comprising:

(a) contacting the cell with the dsRNA agent of claim 1 or the pharmaceutical composition of claim 9; and (b) maintaining the cell in step (a) for a time sufficient to obtain degradation of the mRNA transcript of a CFB gene, thereby inhibiting expression of the CFB gene in the cell.

13. The method of claim 12, wherein said cell is within a human subject.

14. The method of claim 13, wherein the human subject suffers from a complement component-associated disease.

15. The method of claim 14, wherein the complement component-associated disease is selected from the group consisting of paroxysmal nocturnal hemoglobinuria (PNH), asthma, rheumatoid arthritis, systemic lupus erythmatosis, glomerulonephritis, psoriasis, dermatomyositis bullous pemphigoid, atypical hemolytic uremic syndrome, Shiga toxin *E. coli*-related hemolytic uremic syndrome, myasthenia gravis, neuromyelistis optica, dense deposit disease, C3 neuropathy, age-related macular degeneration, cold agglutinin disease, anti-neutrophil cytoplasmic antibody-associated vasculitis, humoral and vascular transplant rejection, graft dysfunction, myocardial infarction, a sensitized recipient of a transplant, and sepsis.

16. The method of claim 15, wherein the complement component-associated disease is paroxysmal nocturnal hemoglobinuria (PNH), atypical hemolytic uremic syndrome (aHUS), or rheumatoid arthritis.

17. The method of claim 14, wherein the dsRNA agent is administered at a dose of about 0.01 mg/kg to about 10 mg/kg or about 0.5 mg/kg to about 50 mg/kg.

18. The method of claim 14, wherein the dsRNA agent is administered subcutaneously; or intravenously.

* * * * *